(12) United States Patent
Feutrill et al.

(10) Patent No.: US 9,249,085 B2
(45) Date of Patent: Feb. 2, 2016

(54) ANILINE DERIVATIVES, THEIR PREPARATION AND THEIR THERAPEUTIC APPLICATION

(75) Inventors: John Feutrill, Rosanna (AU); Caroline Leriche, Paris, FL (US); David Middlemiss, Bishop's Storford Hertfordshire (GB)

(73) Assignee: FOVEA PHARMACEUTICALS, Paris (FR)

( * ) Notice: Subject to any disclaimer, the term of this patent is extended or adjusted under 35 U.S.C. 154(b) by 0 days.

(21) Appl. No.: 14/344,925

(22) PCT Filed: Sep. 7, 2012

(86) PCT No.: PCT/EP2012/067473
§ 371 (c)(1),
(2), (4) Date: Mar. 14, 2014

(87) PCT Pub. No.: WO2013/037705
PCT Pub. Date: Mar. 21, 2013

(65) Prior Publication Data
US 2014/0350019 A1    Nov. 27, 2014

(30) Foreign Application Priority Data

Sep. 16, 2011 (EP) .................................. 11306170
Feb. 3, 2012 (EP) .................................. 12305130
Jun. 4, 2012 (EP) .................................. 12305626

(51) Int. Cl.
*C07C 217/84* (2006.01)
*C07C 235/56* (2006.01)
*C07C 233/75* (2006.01)
(Continued)

(52) U.S. Cl.
CPC ............. *C07C 217/84* (2013.01); *A61K 31/165* (2013.01); *A61K 31/196* (2013.01); *A61K 31/216* (2013.01); *A61K 31/277* (2013.01); *A61K 31/5375* (2013.01); *A61K 45/06* (2013.01); *C07C 63/72* (2013.01); *C07C 65/105* (2013.01); *C07C 65/24* (2013.01); *C07C 213/02* (2013.01); *C07C 213/08* (2013.01); *C07C 215/76* (2013.01); *C07C 233/75* (2013.01); *C07C 235/20* (2013.01); *C07C 235/56* (2013.01); *C07C 237/30* (2013.01); *C07C 253/30* (2013.01); *C07C 255/57* (2013.01); *C07C 255/58* (2013.01); *C07C 255/59* (2013.01); *C07D 295/088* (2013.01)

(58) Field of Classification Search
CPC .. C07C 217/84; C07C 235/56; C07C 233/75; C07C 255/59; C07C 63/72; C07C 213/02; C07C 213/08; C07C 235/20; C07C 237/30; C07C 253/30; C07C 255/57; C07C 255/58; C07C 65/24; C07C 65/105; C07C 215/76; A61K 31/196; A61K 45/06; A61K 31/216; A61K 31/277; A61K 31/165; A61K 31/5375; C07D 295/088
See application file for complete search history.

(56) References Cited

U.S. PATENT DOCUMENTS 1,920,828 A    8/1933    Wyler et al.
1,969,354 A    8/1934    Chrisiansen et al.
(Continued)

FOREIGN PATENT DOCUMENTS

CN    101228169 A    7/2008
EP    0502784 A1     3/1992
(Continued)

OTHER PUBLICATIONS

Scientific Committee on Consumer Products, Opinion on M-Aminophenol, 2007, European Health and Consumer Directorate-General, p. 1-26.*
(Continued)

*Primary Examiner* — Samantha Shterengarts
*Assistant Examiner* — Matt Mauro
(74) *Attorney, Agent, or Firm* — Morrison & Foerster LLP

(57) ABSTRACT

The present invention relates to aniline derivatives of formula (I), to their preparation and to their therapeutic application, for example in treating glaucoma: Formula (I), R1a represents H, an halogen, a $(C_1-C_6)$alkyl or a CN; R1b represents H, an halogen or a $(C_1-C_6)$alkyl; R1c represents H or a $(C_1-C_6)$alkyl; R2 represents H, an halogen, an OH, an O—$(C_1-C_6)$alkyl or $(C_1-C_6)$alkyl; R3 represents H, an halogen, a $(C_1-C_6)$alkyl, an OH, an O—$(C_1-C_6)$alkyl, a $CONH_2$ or CN; R4 represents H, an halogen or a $(C_1-C_6)$alkyl; R5 represents H or F: R7 represents H or F; R8 represents H or F; R9 represents H or $(C_1-C_6)$alkyl, or one of its enantiomers.

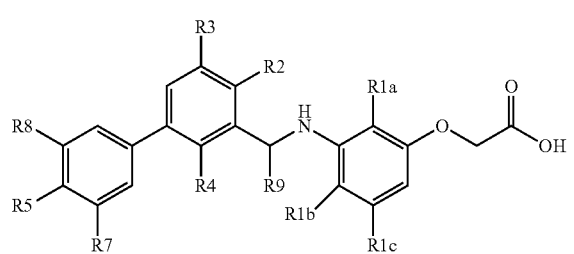

28 Claims, 1 Drawing Sheet

(51) Int. Cl.

| | |
|---|---|
| C07C 255/59 | (2006.01) |
| C07C 63/72 | (2006.01) |
| C07C 13/02 | (2006.01) |
| C07C 13/08 | (2006.01) |
| C07C 235/20 | (2006.01) |
| C07C 237/30 | (2006.01) |
| A61K 31/196 | (2006.01) |
| A61K 45/06 | (2006.01) |
| A61K 31/216 | (2006.01) |
| C07C 215/76 | (2006.01) |
| C07C 65/105 | (2006.01) |
| C07C 65/24 | (2006.01) |
| A61K 31/165 | (2006.01) |
| A61K 31/277 | (2006.01) |
| A61K 31/5375 | (2006.01) |
| C07C 213/02 | (2006.01) |
| C07C 213/08 | (2006.01) |
| C07C 253/30 | (2006.01) |
| C07C 255/57 | (2006.01) |
| C07C 255/58 | (2006.01) |
| C07D 295/088 | (2006.01) |

(56) References Cited

U.S. PATENT DOCUMENTS

| | | |
|---|---|---|
| 3,671,636 A | 6/1972 | Saari |
| 4,564,640 A | 1/1986 | Studt et al. |
| 5,261,926 A | 11/1993 | Lang et al. |
| 6,369,271 B1 | 4/2002 | Schneider |
| 6,376,524 B1 | 4/2002 | Barr et al. |
| 7,115,611 B2 | 10/2006 | Ackermann et al. |
| 7,115,662 B2 | 10/2006 | Fujimoto et al. |
| 7,700,628 B2 | 4/2010 | Argade et al. |
| 8,084,614 B2 | 12/2011 | Beaton et al. |
| 2005/0148633 A1 | 7/2005 | Xie et al. |
| 2006/0100245 A1 | 5/2006 | Bakthavatchalam et al. |
| 2007/0043035 A1 | 2/2007 | Gurram et al. |
| 2007/0072833 A1 | 3/2007 | Wendt et al. |
| 2008/0221175 A1 | 9/2008 | Yuan et al. |
| 2008/0249137 A1 | 10/2008 | Lin et al. |
| 2009/0163481 A1 | 6/2009 | Murphy et al. |
| 2009/0227566 A1 | 9/2009 | Argade et al. |
| 2010/0152207 A1 | 6/2010 | Beaton et al. |
| 2010/0197705 A1 | 8/2010 | Chen et al. |
| 2011/0195993 A1 | 8/2011 | Masson et al. |
| 2011/0275603 A1 | 11/2011 | Muthuppalaniappan et al. |
| 2012/0015978 A1 | 1/2012 | Old |
| 2012/0122891 A1 | 5/2012 | Beaton et al. |
| 2012/0225883 A1 | 9/2012 | Sun et al. |
| 2012/0316346 A1 | 12/2012 | Kang et al. |
| 2013/0029992 A1 | 1/2013 | Burk et al. |

FOREIGN PATENT DOCUMENTS

| | | |
|---|---|---|
| EP | 1575918 A2 | 9/2005 |
| EP | 1653968 A2 | 5/2006 |
| EP | 1678128 A1 | 7/2006 |
| EP | 1682508 A1 | 7/2006 |
| EP | 1817287 A1 | 8/2007 |
| EP | 1940767 A2 | 7/2008 |
| EP | 2155194 A1 | 2/2010 |
| EP | 2314576 A1 | 4/2011 |
| JP | 8333287 A | 12/1996 |
| JP | 2005179281 A | 7/2005 |
| JP | 2013166750 A | 8/2013 |
| KR | 2011/0097292 A | 8/2011 |
| KR | 101141556 B1 | 4/2012 |
| WO | 9606832 | 3/1996 |
| WO | WO-01/48314 A2 | 7/2001 |
| WO | WO-01/48314 A3 | 7/2001 |
| WO | WO-01/98245 A2 | 12/2001 |
| WO | WO-01/98245 A3 | 12/2001 |
| WO | 2004007439 A1 | 1/2004 |
| WO | WO-2004/010943 A2 | 2/2004 |
| WO | WO-2004/010943 A3 | 2/2004 |
| WO | WO-2004/056774 A2 | 7/2004 |
| WO | WO-2004/056774 A3 | 7/2004 |
| WO | WO-2005/009954 A2 | 2/2005 |
| WO | WO-2005/009954 A3 | 2/2005 |
| WO | 2005040104 A1 | 5/2005 |
| WO | WO-2005/049573 A1 | 6/2005 |
| WO | WO-2005/080367 A1 | 9/2005 |
| WO | WO-2005/111035 A1 | 11/2005 |
| WO | WO-2006/057845 A1 | 6/2006 |
| WO | 2007014926 A1 | 2/2007 |
| WO | WO-2007/014926 A1 | 2/2007 |
| WO | WO-2007/030567 A2 | 3/2007 |
| WO | WO-2007/030567 A3 | 3/2007 |
| WO | 2008024634 A1 | 2/2008 |
| WO | WO-2008/015517 A2 | 2/2008 |
| WO | WO-2008/015517 A3 | 2/2008 |
| WO | WO-2008/088540 A2 | 7/2008 |
| WO | WO-2008/088540 A4 | 7/2008 |
| WO | 2008092954 A2 | 8/2008 |
| WO | WO-2008/124610 A1 | 10/2008 |
| WO | 2009045479 A1 | 4/2009 |
| WO | WO-2009/078981 A2 | 6/2009 |
| WO | WO-2009/078981 A3 | 6/2009 |
| WO | 2009098457 A1 | 8/2009 |
| WO | WO-2009/098458 A2 | 8/2009 |
| WO | WO-2009/098458 A3 | 8/2009 |
| WO | 2009153496 A2 | 12/2009 |
| WO | 2010084050 A2 | 7/2010 |
| WO | 2010111449 A1 | 9/2010 |
| WO | 2010139481 A1 | 12/2010 |
| WO | WO-2011/094231 A1 | 8/2011 |
| WO | WO-2011/105643 A1 | 9/2011 |
| WO | WO-2011/138665 A1 | 11/2011 |
| WO | WO-2012/003145 A2 | 1/2012 |
| WO | WO-2012/003145 A3 | 1/2012 |
| WO | WO-2013/016677 A1 | 1/2013 |
| WO | WO-2013/079425 A1 | 6/2013 |
| WO | 2013128378 A1 | 9/2013 |
| WO | 2013150988 A1 | 10/2013 |

OTHER PUBLICATIONS

Carta, et al.; "Novel Therapies for Glaucoma: a patent review 2007-2011"; Expert Opin. Ther. Patents, vol. 22, No. 1, Jan. 1, 2012, pp. 79-88.

Herschhorn, et al.; "De Novo Parallel Design, Synthesis and Evaluation of Inhibitors against the Reverse Transcriptase of Human Immunodeficiency Virus Type-1 and Drug-Resistant Variants", Journal of Medicinal Chemistry, American Chemical Society, U.S., vol. 50, No. 10, May 17, 2007, pp. 2370-2384.

Adamski-Werner, et al.; Diflunisal Analogues Stabilize the Native State of Transthyretin, Potent Inhibition of Amyloidogenisis; Journal of Medicinal Chemistry, American Chemical Society, U.S., vol. 47, No. 2, Nov. 12, 2003, pp. 355-374.

Georgian, et al.; "Alicyclic Syntheses, I. The Diels—Alder Reaction of 2-Phenylbutadiene with Citraconic Anhydride and 5-p-Tolylthiotoluquinone"; The Journal of Organic Chemistry, vol. 29, No. 1, Jan. 1, 1964, pp. 40-44.

Lu, et al.; "Palladium Charcoal-catalyzed, ligandless Suzuki Reaction by Using Tetraarylborates in Water"; Tetrahedron Letters, Elsevier, Amsterdam, NL, vol. 46, No. 24, Jun. 13, 2005, pp. 4255-4259.

Shrestha, et al.; "Mono- and Disalicylic Acid Derivatives: PTP1B Inhibitors as Potential Anti-Obesity Drugs"; Bioorganic and Medicinal Chemistry, Pergamon, GB, vol. 15, No. 20, Aug. 25, 2007, pp. 6535-6548.

Hannah, et al.; "Novel Analgesic-Antiinflammatory Salicylates", Journal of Medicinal Chemistry, vol. 21, No. 11, Nov. 1, 1978, pp. 1093-1100.

Schultz, et al.,; "Sythesis of Momomeric and Oligmoeric Naphtho- and Biaryl-fused 1,8-Diaza-14-crown-4 Macrocycles", Tetradedron Letters, Elsevier, Amsterdam, NL, vol. 36, No. 5, Jan. 30, 1995, pp. 659-662.

(56) References Cited

OTHER PUBLICATIONS

El-Kabbani, et al.; "Structure-based optimization and biological evaluation of human 20alpha-hydroxysteroid dehydrogenase (AKR1C1) salicylic acid-based inhibitors", European Journal of Medicinal Chemistry Editions Scientifique Elsevier, Paris, FR, vol. 45, No. 11, Nov. 1, 2010, pp. 5309-5317.

Schlosser, et al.; "The Superbase Approach to Flurbiprofen: An Exercise in Optionally Site-Selective Metalation", Chemistry-A European Journal, vol. 4, No. 10, Jan. 1, 1998, pp. 1969-1973.

McDonald, et al.,; "Optimization of 1,3,4-Benzotriazepine-Based CCK 2 Antagonists to Obtain Potent, Orally Active Inhibitors of Gastrin-Mediated Gastric Acid Secretion"; Journal of Medicinal Chemistry, vol. 50, No. 13, Jun. 1, 2007, pp. 3101-3112.

Hirst, et al.; "Discovery of 1,5-benxodiazepines with Peripheral Cholecystokionin (CCK-A) Receptor Agonist Activity (II): Optimization of the C3 Amino Subsittuent"; Journal of Medicinal Chemistry; vol. 39, No. 26, 1996, pp. 5236-5245.

Jacobs, et la..; "On Nitro- and Aminophenoxyacetic Acids"; Journal of the American Chemical Society, ACS Publications, U.S.; vol. 39, No. 8, Jan. 1, 1917, pp. 2188-2224.

Takeda, et al.; "Synthesis of Phenoxyacetic Acid Derivatives as Highly Potent Antagonists of Gastrin/Cholecystokinin-B Receptors"; Chem. Pharm. Bull., vol. 46, No. 3, Jan. 1, 1998, pp. 434-444.

Fulmer Shealy, et al.; "Inhibition of Papilloma Formation by Analygues of 7,8-Dikyfroretinoic Acid"; Journal of Medicinal Chemistry, vol. 46, No. 10, May 1, 2003, pp. 1931-1939.

Romagnoli, et al.; "Synthesis and Biological Evaluation of 1-Methyl-2-(3', 4', 5'-trimethoxybenzoyl)-3-aminoinodoles as a New Class of Antimitotic Agents and Tubulin Inhibitors"; Journal of Medicinal Chemistry, vol. 51, No. 5, Mar. 1, 2008, pp. 1464-1468.

Nasipuri, et al.; "Synthetic STudies int heDieterpene Series, Part I, Synthesis of Some Degradation Products of Methyl Totaryl Ether", Journal of the Chemical Society, Jan. 1, 1958, p. 2579.

Attina, et al.; "Intramolecular Selectivity of the Alkylation of Substituted Anilines by Gaseous Cations"; Journal of the American Chemical Society, vol. 107, No. 6, Mar. 1, 1985, pp. 1556-1561.

Rodighiero, et al.; "Methyltriazolocoumarins: New Furocoumarin Isosters as Potential Photochemotherapeutic Agents"; Journal of Heterocyclic Chemistry, vol. 27, No. 4, May 1, 1990, pp. 1153-1158.

Buttelmann, et al.; "Arylmethoxypyridines as Novel, Potent and Orally Active mGlu5 Receptor Antagonists", Bioorganic and Medicinal Chemistry Letters Pergamon, Elsevier Science, GB, vol. 16, No. 7, Apr. 1, 2006, pp. 1892-1897.

Hansch, et al.; "Catalytic Synthesis of Heterocyles, VIII.I Dehydrocyclization of o-Ethylbenzenethiols to Thianaphenes", Journal of Organic Chemistry, vol. 21, No. 3, Mar. 29, 1956, pp. 265-270.

Arnold, et al.; "Thermal Rearrangement of m-Acetamidophenyl Allyl Ether", Journal of the American Chemical Society, vol. 64, No. 5, May 1, 1942, pp. 1023-1025.

International Search Report relative to PCT/EP2012/067473, dated Apr. 19, 2013.

Musso, et al.; "Uber Orceinfarbstoffe, XXII: Die Autoxydation des 5-tert.-Butyl-resorcins"; Chemische Berichte, vol. 98, No. 9, Sep. 1, 1965, pp. 2274-2796 (with English Translation).

Wesseley, et al., "Uber alkylierte p-Aminosalizylsauren"; Monatshefte Fur Chemie, vol. 83, Jan. 1, 1952, pp. 24-30 (with English Translation).

* cited by examiner

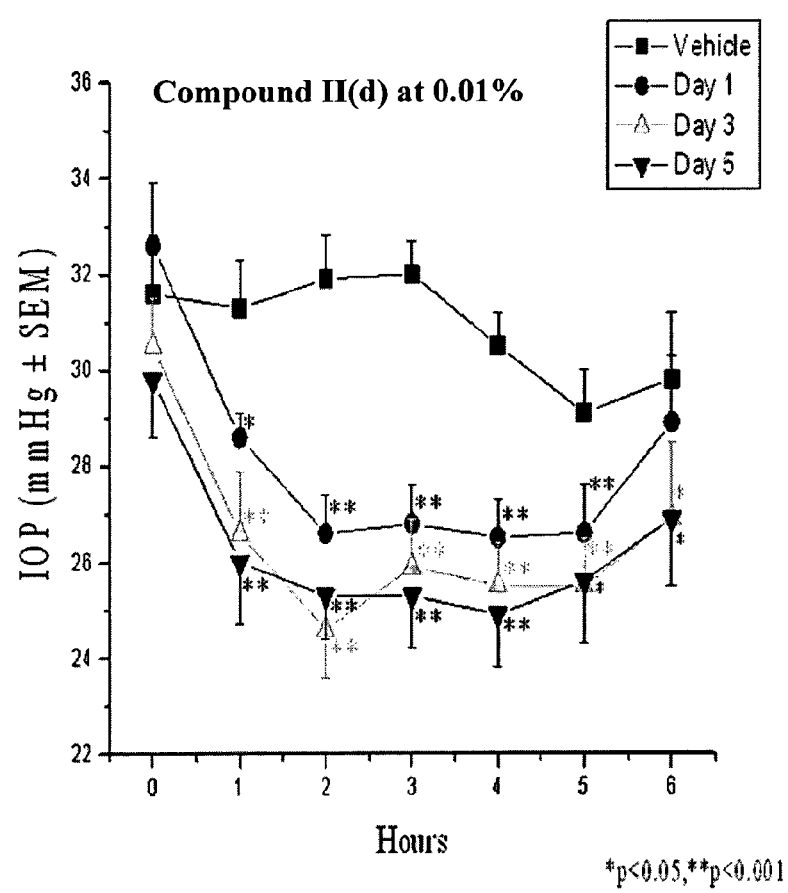

ANILINE DERIVATIVES, THEIR PREPARATION AND THEIR THERAPEUTIC APPLICATION

The present invention relates to aniline derivatives, to their preparation and to their therapeutic application.

Prostanoids comprise prostaglandins (PGs) and thromboxanes (Txs) and their receptors fall into five different classes (DP, EP, FP, IP and TP) based on their sensitivity to the five naturally occurring prostanoids, PGD2, PGE2, PGF2a, PGI2 and TxA2.

EP receptors (for which the endogenous ligand is PGE2) have been subdivided into four types termed EP1, EP2, EP3 and EP4. These four types of EP receptors have been cloned and are distinct at both molecular and pharmacological level. EP2 agonists have been shown to be effective in the treatment of a number of conditions, including (but not limited to) dysmenorrhoea, pre-term labour, glaucoma, ocular hypertension, immune disorders, osteoporosis, asthma, allergy, bone disease, fracture repair, male sexual dysfunction, female sexual dysfunction, periodontal disease, gastric ulcer, and renal disease.

EP2 agonists have also been described in the treatment of inflammatory and immune disorders such as psoriasis, dermatitis, rheumatoid arthritis, multiple sclerosis, scleroderma, transplant rejection, allergy, systemic lupus erythematosus, vasculitis, type 1 diabetes mellitus, and inflammatory lung diseases such as chronic obstructive pulmonary disease, asthma, acute respiratory distress syndrome and cystic fibrosis. In addition, EP2 agonists have also been described in the treatment of fibrosis, including, but not limited to, scleroderma and systemic sclerosis, post-operative fibrosis following trabulectomy, liver repair and regeneration following cirrhosis, hepatitis, toxicity, cancer or renal fibrosis. EP2 agonists can also be used in the prevention of fibroblast to myofibroblast conversion to treat asthma and other fibrotic lung diseases. EP2 agonists may also be used to maintain ductus arteriosus patency in infants with congenital heart disease.

Glaucoma is a disease of the eye. It is a multifactorial, progressive optic neuropathy with a characteristic loss of retinal ganglion cells that form the optic nerve. It is the second leading cause of blindness in the world. Prevalence models estimate that 8.4 millions individuals suffered from glaucoma-induced bilateral blindness in 2010, rising to 11.1 million in 2020. Glaucoma is asymptomatic in the early stages, which is why 50% of patients affected are undiagnosed. It then results in peripheral visual field loss and if untreated, can lead to irreversible blindness.

Primary glaucoma is a congenital glaucoma and secondary glaucoma results from pre-existing ocular diseases such as uveitis, intraocular tumor or enlarged cataract.

Primary Chronic Open-angle glaucoma is generally associated with increased pressure in the eye caused by trabecular blockage. Not all people with primary open-angle glaucoma show an elevated intra-ocular pressure, but decreasing the eye pressure has been shown to stop progression even in these cases. Primary open-angle glaucoma is characterized by progressive visual field loss and optic nerves changes.

In Primary Chronic or acute Closed-angle glaucoma, the iridocorneal angle is completely closed because of forward displacement of the final roll and root of the iris against the cornea. This can lead to acute crises characterized by sudden ocular pain, seeing halos around lights, red eye, very high intraocular pressure, nausea and vomiting, and sudden decreased vision. Acute angle closure is an ocular emergency.

The diagnosis of glaucoma is generally made by intraocular pressure measurements, visual field tests and by looking for changes in the optic nerve.

The different treatments of glaucoma aim to reduce intraocular pressure.

Several treatments are currently available: for example, beta-adrenergic antagonists, carbonic anhydrase inhibitors or topical prodrugs of prostaglandin FP receptor agonists (FP-agonists), like latanaprost, travoprost and bimatoprost. Applied in vivo, the marketed topical prodrugs release their active drug (FP-agonist), which mainly increase uveoscleral outflow.

The marketed drugs nevertheless have important side effects; for example, latanoprost induces a gradual change in the eye colour of the patient by increasing the amount of brown pigment in the coloured part of the eye known as the iris. This pigmentation is irreversible and usually appears within 8 months of treatment. Latanoprost further induces an eye irritation (a feeling of burning, grittiness, itching, stinging or the sensation of a foreign body in the eye), a gradual change to eyelashes of the treated eye and the fine hairs around the treated eye, irritation or disruption to the surface of the eye, eyelid inflammation (blepharitis) and eye pain amongst others.

Therefore, there is a need for new treatments that reduce intraocular pressure in order to treat and/or prevent ocular diseases involving EP2 receptors, such as glaucoma, for example.

The invention relates to EP2 agonists and their prodrugs, to their preparation and to their therapeutic applications.

FIG. 1 shows the effect of topical administration of compound II(d) on intraocular pressure (IOP) in laser-induced glaucomatous monkeys.

The present invention provides compounds of formula (I) as described in the present specification or one of its prodrugs.

Compounds of formula (I) are drugs, in which:

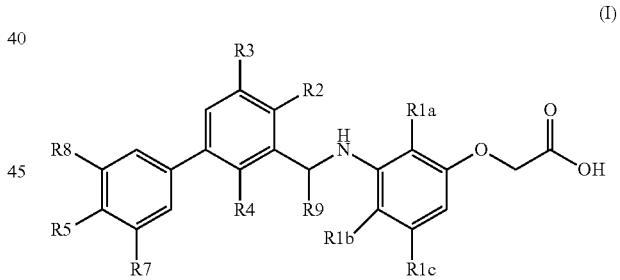

R1a represents H, an halogen, a $(C_1-C_6)$alkyl or a CN;
R1b represents H, an halogen or a $(C_1-C_6)$alkyl;
R1c represents H or a $(C_1-C_6)$alkyl;
R2 represents H, an halogen, an OH, an O—$(C_1-C_6)$alkyl or $(C_1-C_6)$alkyl;
R3 represents H, an halogen, a $(C_1-C_6)$alkyl, an OH, an O—$(C_1-C_6)$alkyl, a $CONH_2$ or CN;
R4 represents H, an halogen or a $(C_1-C_6)$alkyl;
R5 represents H or F:
R7 represents H or F;
R8 represents H or F;
R9 represents H or $(C_1-C_6)$alkyl, or one of its enantiomers.

The compounds of formula (I) may contain one or more asymmetric carbon atoms. They may therefore exist in the form of enantiomers or diastereoisomers. These enantiomers and diastereoisomers, and also mixtures thereof, including the racemic mixtures, form part of the invention.

The compounds of formula (I) may be present as well under tautomer forms and are part of the invention Compounds of formula (II) are prodrugs of compounds of formula (I), in which:

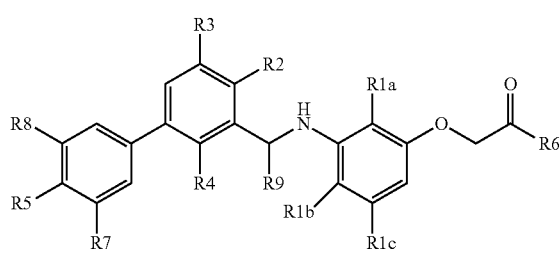

(II)

R1a represents H, an halogen, a $(C_1\text{-}C_6)$alkyl or a CN;
R1b represents H, an halogen or a $(C_1\text{-}C_6)$alkyl;
R1c represents H or a $(C_1\text{-}C_6)$alkyl;
R2 represents H, an halogen, an OH, an O—$(C_1\text{-}C_6)$alkyl or $(C_1\text{-}C_6)$alkyl;
R3 represents H, an halogen, a $(C_1\text{-}C_6)$alkyl, an OH, an O—$(C_1\text{-}C_6)$alkyl, a $CONH_2$ or a CN;
R4 represents H, an halogen or a $(C_1\text{-}C_6)$alkyl;
R5 represents H or F;
R6 represents an O—$(C_1\text{-}C_6)$alkyl, an O—$(C_1\text{-}C_6)$alkyl-heterocycloalkyl, a $NH_2$, a NH—$(C_1\text{-}C_6)$alkyl, an O—$(C_1\text{-}C_6)$alkyl optionally substituted by one to three hydroxyl groups, O—$(C_1\text{-}C_6)$alkyl-O—$CO(C_1\text{-}C_6)$alkyl);
R7 represents H or F;
R8 represents H or F;
R9 represents H or a $(C_1\text{-}C_6)$alkyl, or one of its enantiomers.

The compounds of formula (II) may contain one or more asymmetric carbon atoms. They may therefore exist in the form of enantiomers or diastereoisomers. These enantiomers and diastereoisomers, and also mixtures thereof, including the racemic mixtures, form part of the invention.

The compounds of formula (II) may be present as well under tautomer forms and are part of the invention In the context of the present invention, the following terms have to be understood as:
  enantiomers: Organic compounds that contain a chiral carbon usually have two non-superimposable structures.
  halogen: a fluorine, a chlorine, a bromine or an iodine atom;
  $(C_1\text{-}C_6)$alkyl: a linear or branched saturated hydrocarbon group. Examples include, but are not limited to the groups methyl, ethyl, propyl, isopropyl, butyl, isobutyl, tert-butyl, pentyl, etc. If a branched $(C_1\text{-}C_6)$alkyl is substituted, the substitution can occur, for example, on terminal hydrocarbon groups;
  heterocycloalkyl: a 5 to 8 membered saturated ring, comprising at least one of the following heteroatoms: O, N or S. The heterocycloalkyl can be linked to the rest of the molecule via a carbon or a heteroatom. If the heterocycloalkyl is substituted, substitution can occur on a carbon atom or on a heteroatom. Examples of heterocycloalkyl include morpholine;
  a prodrug: a compound that, on administration, must undergo conversion by chemical or metabolic processes before becoming an active pharmacological agent. Once administered, the prodrug is converted in vivo into a therapeutically active compound (drug). This conversion can take place in one or more steps. A prodrug is usually not a therapeutically active compound itself and will usually not elicit in vitro the biological response of the corresponding therapeutically active compound. For example, esters and amides can act as prodrugs of their corresponding carboxylic acids where the ester or amide bond can be hydrolysed either chemically or metabolically to provide the free carboxylic acid.

A major aim of prodrug design is to improve the safety and pharmacokinetic behaviour of active carboxylic acids. A carboxylic acid group, being ionized in the physiological pH range, contributes significantly to reduce the lipophilicity of compounds containing this moiety. As a result, a large number of pharmacologically active carboxylic acids display unfavorable pharmacokinetic properties such as low bioavailability, a problem of particular concern for compounds that contain other moieties of high polarity.

In the eye, the EP2 receptor has been identified in the plexiform and nerve fiber layers of the human retina and in the cornea, conjunctiva, sclera, and lens.

In addition, an EP2 receptor agonist may have an opportunity to enhance long term treatment outcomes following glaucoma filtration surgery. Scar formation is a major source of failure for glaucoma filtration surgery. Limiting fibrotic response is important for limiting scar formation and tissue fibrosis.

Among the compounds of formula (I) and (II) that are subject matter of the invention, mention may be made in particular of the compounds in table 1:

TABLE 1

| Compound number | Structure | Name |
|---|---|---|
| I(a) | 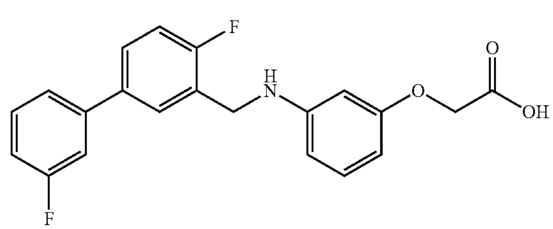 [SMILES: O=C(O)COc1cccc(NCc2cc(-c3cccc(F)c3)ccc2F)c1] | 2-[3-[[2-fluoro-5-(3-fluorophenyl)phenyl]methylamino]phenoxy]acetic acid |

TABLE 1-continued

| Compound number | Structure | Name |
| --- | --- | --- |
| I(b) | 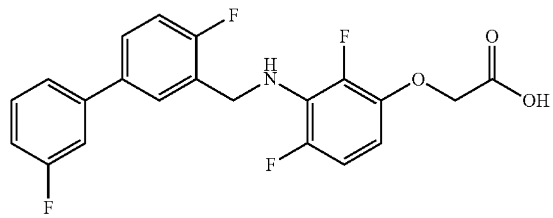 | 2-[2,4-difluoro-3-[[2-fluoro-5-(3-fluorophenyl)phenyl]methylamino]phenoxy]acetic acid |
| I(c) | 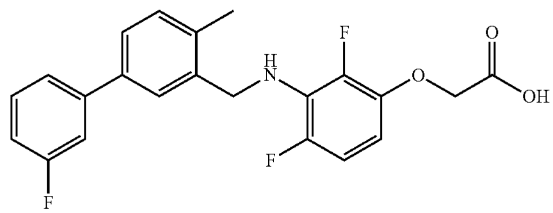 [SMILES: Cc1ccc(-c2cccc(F)c2)cc1CNc1c(F)ccc(OCC(=O)O)c1F] | 2-[2,4-difluoro-3-[[5-(3-fluorophenyl)-2-methyl-phenyl]methylamino]phenoxy]acetic acid |
| I(d) | 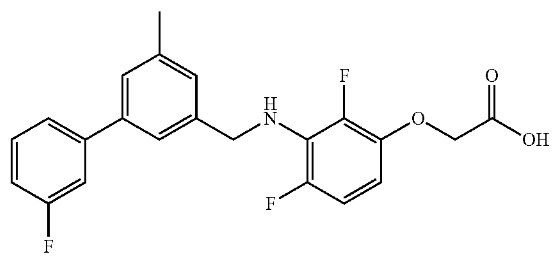 [SMILES: Cc1cc(CNc2c(F)ccc(OCC(=O)O)c2F)cc(-c2cccc(F)c2)c1] | 2-[2,4-difluoro-3-[[3-(3-fluorophenyl)-5-methyl-phenyl]methylamino]phenoxy]acetic acid |
| I(e) | 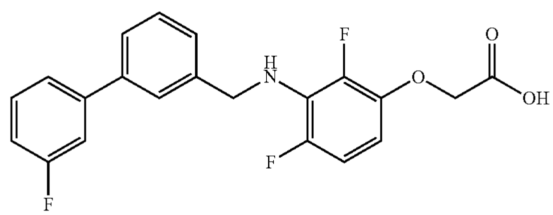 [SMILES: O=C(O)COc1ccc(F)c(NCc2cccc(-c3cccc(F)c3)c2)c1F] | 2-[2,4-difluoro-3-[[3-(3-fluorophenyl)phenyl]methylamino]phenoxy]acetic acid |
| I(f) | 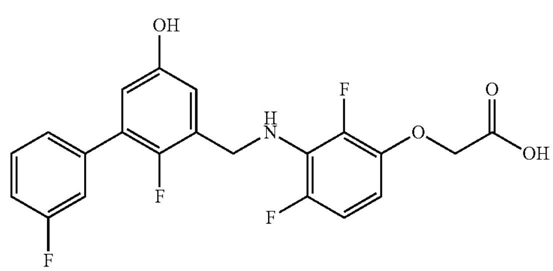 [SMILES: O=C(O)COc1ccc(F)c(NCc2cc(O)cc(-c3cccc(F)c3)c2F)c1F] | 2-[2,4-difluoro-3-[[2-fluoro-3-(3-fluorophenyl)-5-hydroxy-phenyl]methylamino]phenoxy]acetic acid |
| I(g) | 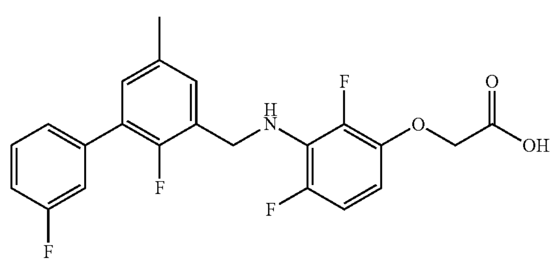 [SMILES: Cc1cc(CNc2c(F)ccc(OCC(=O)O)c2F)c(F)c(-c2cccc(F)c2)c1] | 2-[2,4-difluoro-3-[[2-fluoro-3-(3-fluorophenyl)-5-methyl-phenyl]methylamino]phenoxy]acetic acid |

TABLE 1-continued

| Compound number | Structure | Name |
|---|---|---|
| I(h) | 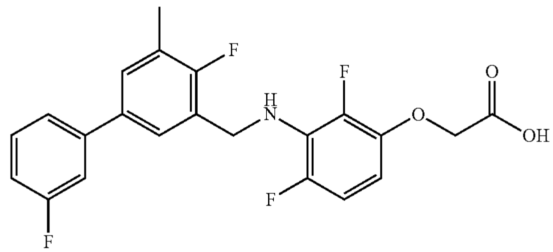 [SMILES: Cc1cc(-c2cccc(F)c2)cc(CNc2c(F)ccc(OCC(=O)O)c2F)c1F] | 2-[2,4-difluoro-3-[[2-fluoro-5-(3-fluorophenyl)-3-methyl-phenyl]methylamino]phenoxy]acetic acid |
| I(i) | 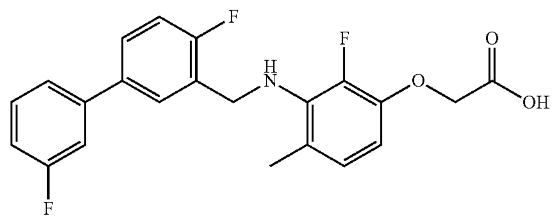 [SMILES: Cc1ccc(OCC(=O)O)c(F)c1NCc1cc(-c2cccc(F)c2)ccc1F] | 2-[2-fluoro-3-[[2-fluoro-5-(3-fluorophenyl)phenyl]methylamino]-4-methyl-phenoxy]acetic acid |
| I(j) | 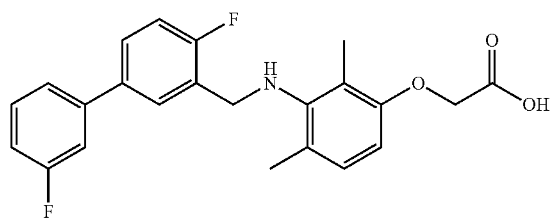 [SMILES: Cc1ccc(OCC(=O)O)c(C)c1NCc1cc(-c2cccc(F)c2)ccc1F] | 2-[3-[[2-fluoro-5-(3-fluorophenyl)phenyl]methylamino]-2,4-dimethyl-phenoxy]acetic acid |
| I(k) | 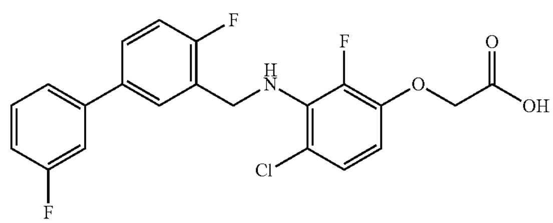 [SMILES: O=C(O)COc1ccc(Cl)c(NCc2cc(-c3cccc(F)c3)ccc2F)c1F] | 2-[4-chloro-2-fluoro-3-[[2-fluoro-5-(3-fluorophenyl)phenyl]methylamino]phenoxy]acetic acid |
| I(l) | 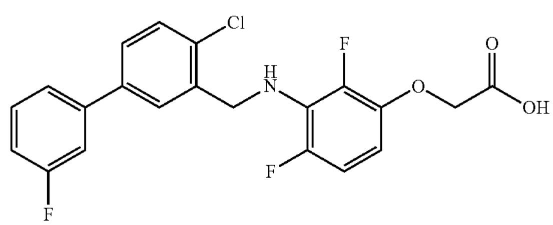 | 2-[3-[[2-chloro-5-(3-fluorophenyl)phenyl]methylamino]-2,4-difluoro-phenoxy]acetic acid |
| I(m) | 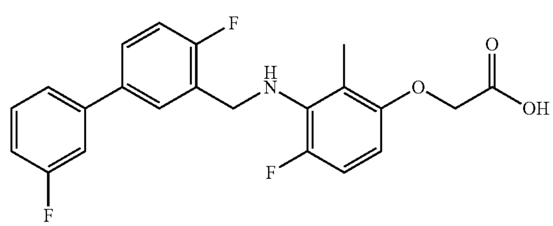 | 2-[4-fluoro-3-[[2-fluoro-5-(3-fluorophenyl)phenyl]methylamino]-2-methyl-phenoxy]acetic acid |

TABLE 1-continued

| Compound number | Structure | Name |
|---|---|---|
| I(n) | 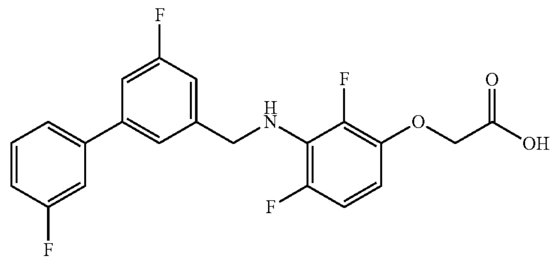 [SMILES: O=C(O)COc1ccc(F)c(NCc2cc(F)cc(-c3cccc(F)c3)c2)c1F] | 2-[2,4-difluoro-3-[[3-fluoro-5-(3-fluorophenyl)phenyl]methylamino]phenoxy]acetic acid |
| I(o) | 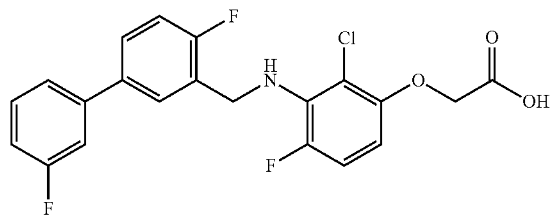 | 2-[2-chloro-4-fluoro-3-[[2-fluoro-5-(3-fluorophenyl)phenyl]methylamino]phenoxy]acetic acid |
| I(p) | 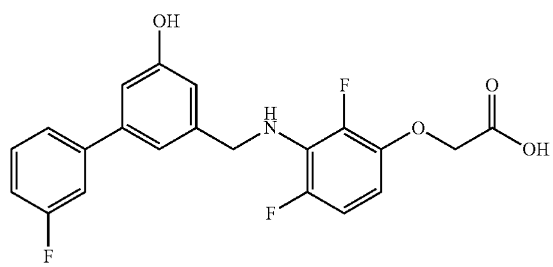 [SMILES: O=C(O)COc1ccc(F)c(NCc2cc(O)cc(-c3cccc(F)c3)c2)c1F] | 2-[2,4-difluoro-3-[[3-(3-fluorophenyl)-5-hydroxy-phenyl]methylamino]phenoxy]acetic acid |
| I(q) | 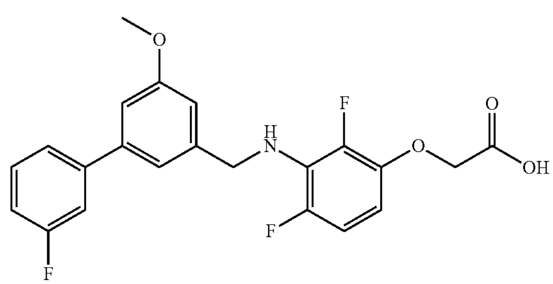 [SMILES: COc1cc(CNc2c(F)ccc(OCC(=O)O)c2F)cc(-c2cccc(F)c2)c1] | 2-[2,4-difluoro-3-[[3-(3-fluorophenyl)-5-methoxy-phenyl]methylamino]phenoxy]acetic acid |
| I(r) | 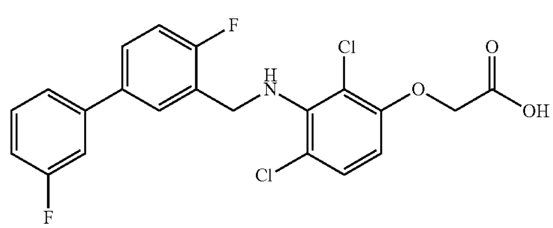 [SMILES: O=C(O)COc1ccc(Cl)c(NCc2cc(-c3cccc(F)c3)ccc2F)c1Cl] | 2-[2,4-dichloro-3-[[2-fluoro-5-(3-fluorophenyl)phenyl]methylamino]phenoxy]acetic acid |
| I(s) | 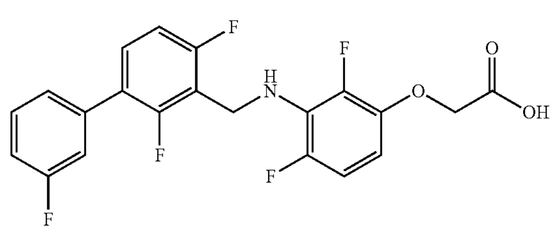 [SMILES: O=C(O)COc1ccc(F)c(NCc2c(F)ccc(-c3cccc(F)c3)c2F)c1F] | 2-[3-[[2,6-difluoro-3-(3-fluorophenyl)phenyl]methylamino]-2,4-difluoro-phenoxy]acetic acid |

TABLE 1-continued

| Compound number | Structure | Name |
|---|---|---|
| I(t) | 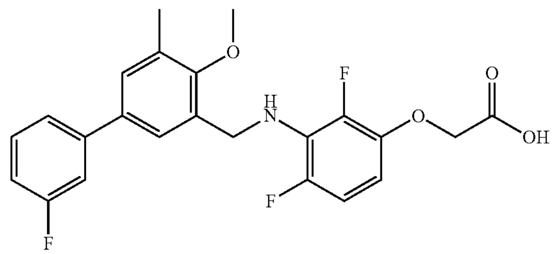 | 2-[2,4-difluoro-3-[[5-(3-fluorophenyl)-2-methoxy-3-methyl-phenyl]methylamino]phenoxy]acetic acid |
| I(u) | 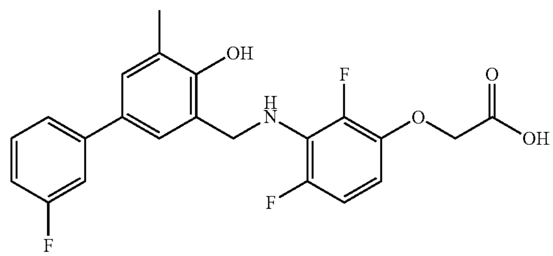 [SMILES: Cc1cc(-c2cccc(F)c2)cc(CNc2c(F)ccc(OCC(=O)O)c2F)c1O] | 2-[2,4-difluoro-3-[[5-(3-fluorophenyl)-2-hydroxy-3-methyl-phenyl]methylamino]phenoxy]acetic acid |
| I(v) | 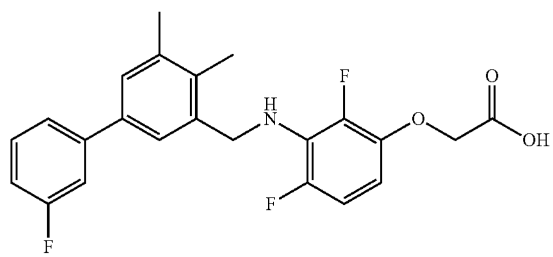 [SMILES: Cc1cc(-c2cccc(F)c2)cc(CNc2c(F)ccc(OCC(=O)O)c2F)c1C] | 2-[2,4-difluoro-3-[[5-(3-fluorophenyl)-2,3-dimethyl-phenyl]methylamino]phenoxy]acetic acid |
| I(w) | 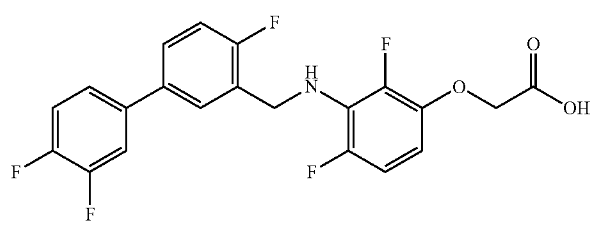 [SMILES: O=C(O)COc1ccc(F)c(NCc2cc(-c3ccc(F)c(F)c3)ccc2F)c1F] | 2-[3-[[5-(3,4-difluorophenyl)-2-fluoro-phenyl]methylamino]-2,4-difluoro-phenoxy]acetic acid |
| I(x) | 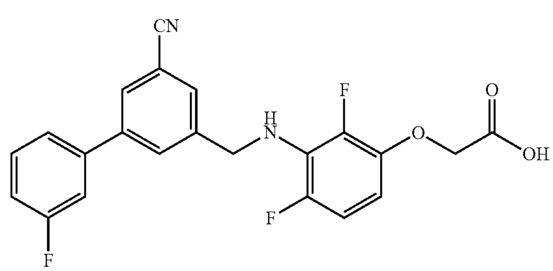 | 2-[3-[[3-cyano-5-(3-fluorophenyl)phenyl]methylamino]-2,4-difluoro-phenoxy]acetic acid |
| I(y) | 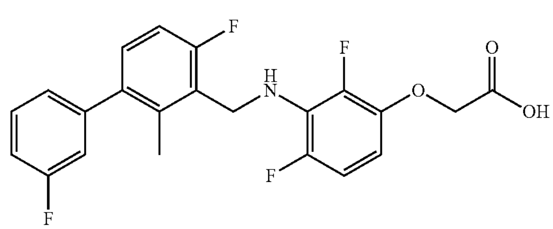 | 2-[2,4-difluoro-3-[[6-fluoro-3-(3-fluorophenyl)-2-methyl-phenyl]methylamino]phenoxy]acetic acid |

TABLE 1-continued

| Compound number | Structure | Name |
| --- | --- | --- |
| I(z) | 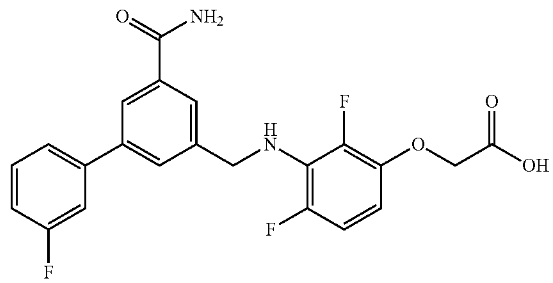 [SMILES: NC(=O)c1cc(CNc2c(F)ccc(OCC(=O)O)c2F)cc(-c2cccc(F)c2)c1] | 2-[3-[[3-carbamoyl-5-(3-fluorophenyl)phenyl]methylamino]-2,4-difluoro-phenoxy]acetic acid |
| I(aa) | 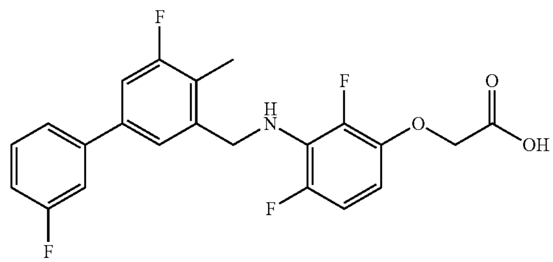 [SMILES: Cc1c(F)cc(-c2cccc(F)c2)cc1CNc1c(F)ccc(OCC(=O)O)c1F] | 2-[2,4-difluoro-3-[[3-fluoro-5-(3-fluorophenyl)-2-methyl-phenyl]methylamino]phenoxy]acetic acid |
| I(ab) | 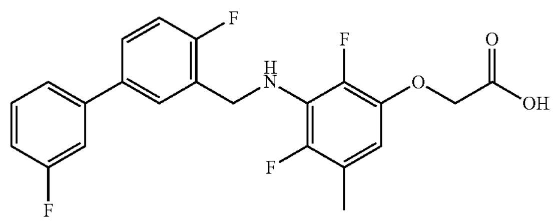 | 2-[2,4-difluoro-3-[[2-fluoro-5-(3-fluorophenyl)phenyl]methylamino]-5-methyl-phenoxy]acetic acid |
| I(ac) | 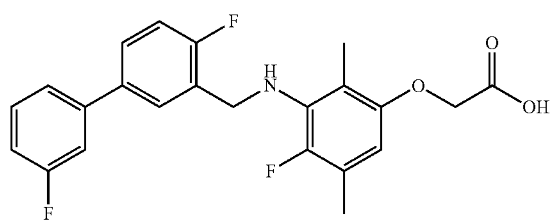 [SMILES: Cc1cc(OCC(=O)O)c(C)c(NCc2cc(-c3cccc(F)c3)ccc2F)c1F] | 2-[4-fluoro-3-[[2-fluoro-5-(3-fluorophenyl)phenyl]methylamino]-2,5-dimethyl-phenoxy]acetic acid |
| I(ad) | 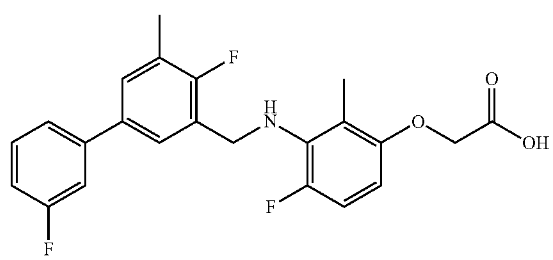 | 2-[4-fluoro-3-[[2-fluoro-5-(3-fluorophenyl)-3-methyl-phenyl]methylamino]-2-methyl-phenoxy]acetic acid |
| I(ae) | 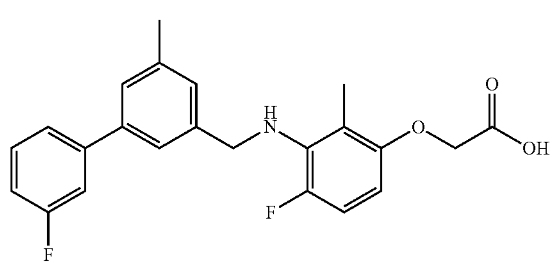 | 2-[4-fluoro-3-[[3-(3-fluorophenyl)-5-methyl-phenyl]methylamino]-2-methyl-phenoxy]acetic acid |

TABLE 1-continued

| Compound number | Structure | Name |
|---|---|---|
| I(af) | 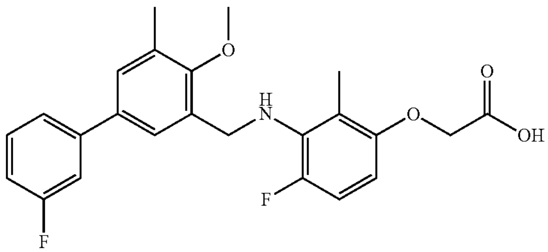 | 2-[4-fluoro-3-[[5-(3-fluorophenyl)-2-methoxy-3-methyl-phenyl]methylamino]-2-methyl-phenoxy]acetic acid |
| I(ag) | 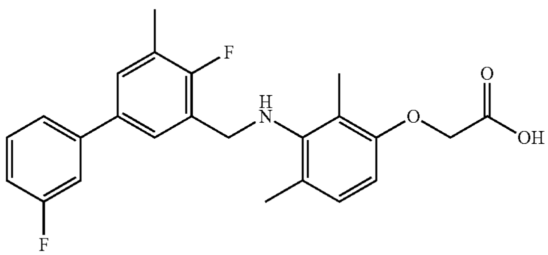 [SMILES: Cc1cc(-c2cccc(F)c2)cc(CNc2c(C)ccc(OCC(=O)O)c2C)c1F] | 2-[3-[[2-fluoro-5-(3-fluorophenyl)-3-methyl-phenyl]methylamino]-2,4-dimethyl-phenoxy]acetic acid |
| I(ah) | 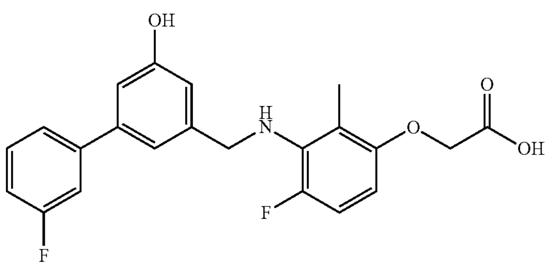 | 2-[4-fluoro-3-[[3-(3-fluorophenyl)-5-hydroxy-phenyl]methylamino]-2-methyl-phenoxy]acetic acid |
| I(ai) | 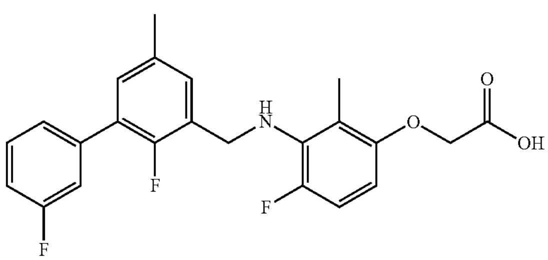 | 2-[4-fluoro-3-[[2-fluoro-3-(3-fluorophenyl)-5-methyl-phenyl]methylamino]-2-methyl-phenoxy]acetic acid |
| I(aj) | 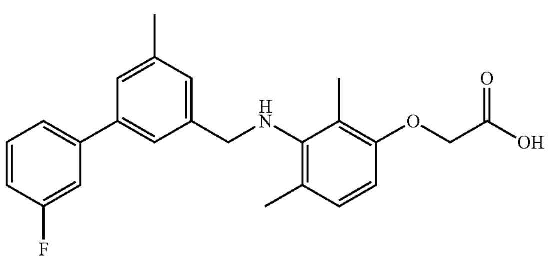 [SMILES: Cc1cc(CNc2c(C)ccc(OCC(=O)O)c2C)cc(-c2cccc(F)c2)c1] | 2-[3-[[3-(3-fluorophenyl)-5-methyl-phenyl]methylamino]-2,4-dimethyl-phenoxy]acetic acid |
| I(ak) | 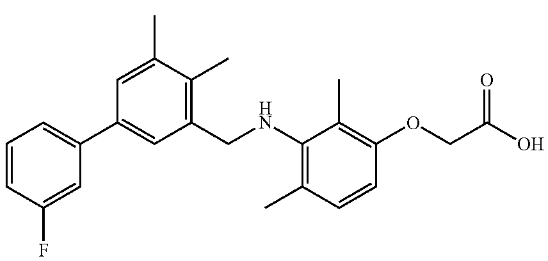 [SMILES: Cc1cc(-c2cccc(F)c2)cc(CNc2c(C)ccc(OCC(=O)O)c2C)c1C] | 2-[3-[[5-(3-fluorophenyl)-2,3-dimethyl-phenyl]methylamino]-2,4-dimethyl-phenoxy]acetic acid |

TABLE 1-continued

| Compound number | Structure | Name |
|---|---|---|
| I(al) | 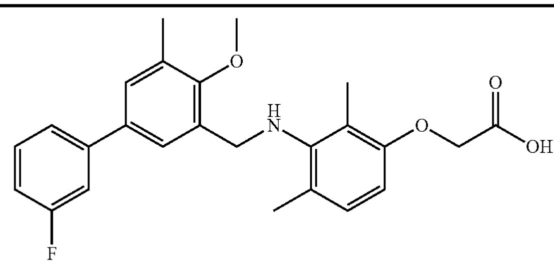 | 2-[3-[[5-(3-fluorophenyl)-2-methoxy-3-methyl-phenyl]methylamino]-2,4-dimethyl-phenoxy]acetic acid |
| I(am) | 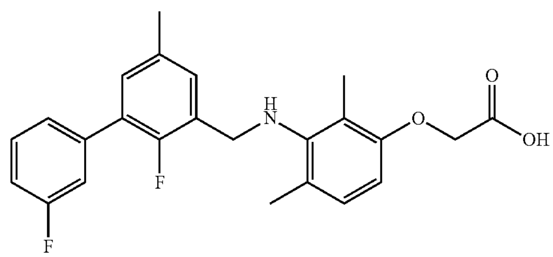 [SMILES: Cc1cc(CNc2c(C)ccc(OCC(=O)O)c2C)c(F)c(-c2cccc(F)c2)c1] | 2-[3-[[2-Fluoro-3-(3-fluorophenyl)-5-methyl-phenyl]methylamino]-2,4-dimethyl-phenoxy]acetic acid |
| I(an) | 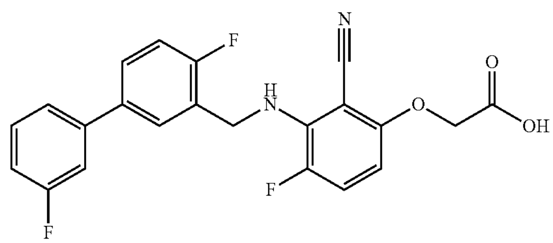 [SMILES: N#Cc1c(OCC(=O)O)ccc(F)c1NCc1cc(-c2cccc(F)c2)ccc1F] | 2-[2-cyano-4-fluoro-3-[[2-fluoro-5-(3-fluorophenyl)phenyl]methylamino]phenoxy]acetic acid |
| I(ao) | 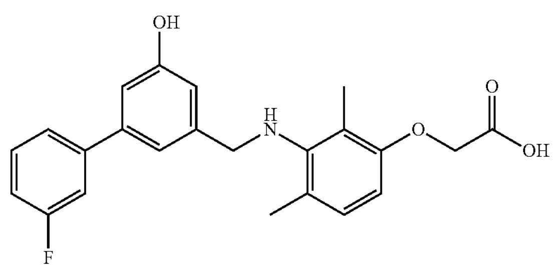 [SMILES: Cc1ccc(OCC(=O)O)c(C)c1NCc1cc(O)cc(-c2cccc(F)c2)c1] | 2-[3-[[3-(3-fluorophenyl)-5-hydroxy-phenyl]methylamino]-2,4-dimethyl-phenoxy]acetic acid |
| I(ap) | 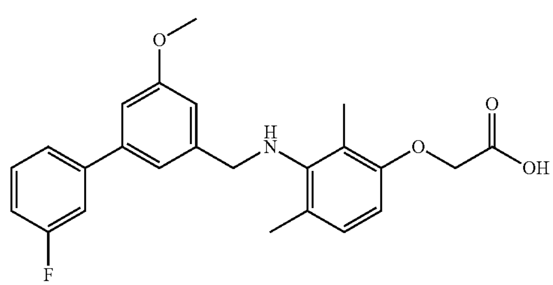 [SMILES: COc1cc(CNc2c(C)ccc(OCC(=O)O)c2C)cc(-c2cccc(F)c2)c1] | 2-[3-[[3-(3-fluorophenyl)-5-methoxy-phenyl]methylamino]-2,4-dimethyl-phenoxy]acetic acid |
| I(aq) | 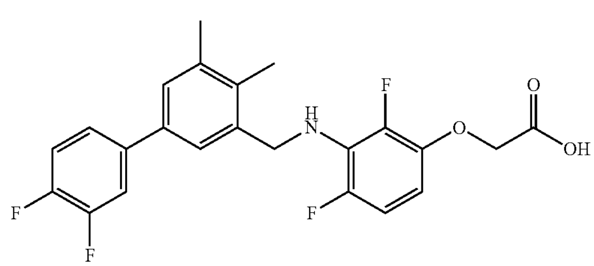 [SMILES: Cc1cc(-c2ccc(F)c(F)c2)cc(CNc2c(F)ccc(OCC(=O)O)c2F)c1C] | 2-[3-[[5-(3,4-difluorophenyl)-2,3-dimethyl-phenyl]methylamino]-2,4-difluoro-phenoxy]acetic acid |

TABLE 1-continued

| Compound number | Structure | Name |
|---|---|---|
| I(ar) | 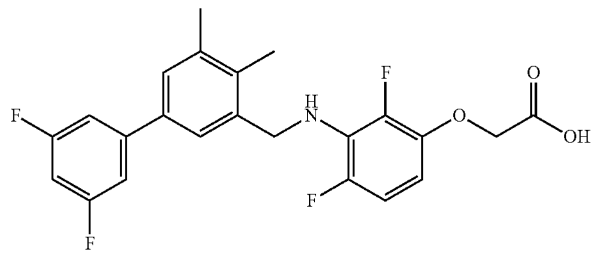 [SMILES: Cc1cc(-c2cc(F)cc(F)c2)cc(CNc2c(F)ccc(OCC(=O)O)c2F)c1C] | 2-[3-[[5-(3,5-difluorophenyl)-2,3-dimethyl-phenyl]methylamino]-2,4-difluoro-phenoxy]acetic acid |
| I(as) | 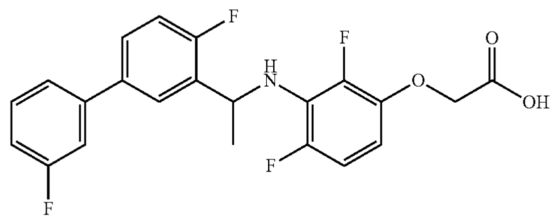 [SMILES: CC(Nc1c(F)ccc(OCC(=O)O)c1F)c1cc(-c2cccc(F)c2)ccc1F] | 2-[2,4-difluoro-3-[1-[2-fluoro-5-(3-fluorophenyl)phenyl]ethylamino]phenoxy]acetic acid |
| I(at) | 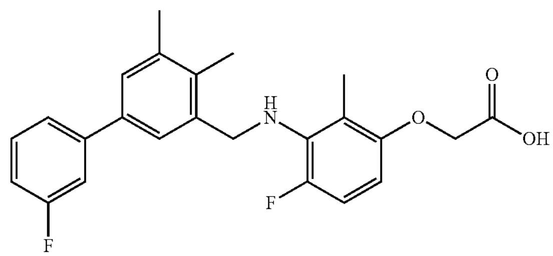 [SMILES: Cc1cc(-c2cccc(F)c2)cc(CNc2c(F)ccc(OCC(=O)O)c2C)c1C] | 2-[4-fluoro-3-[[5-(3-fluorophenyl)-2,3-dimethyl-phenyl]methylamino]-2-methyl-phenoxy]acetic acid |
| I(au) | 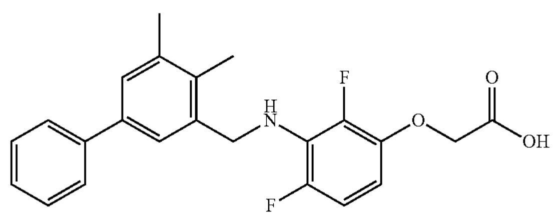 [SMILES: Cc1cc(-c2ccccc2)cc(CNc2c(F)ccc(OCC(=O)O)c2F)c1C] | 2-[3-[(2,3-dimethyl-5-phenyl-phenyl)methylamino]-2,4-difluoro-phenoxy]acetic acid |
| I(av) | 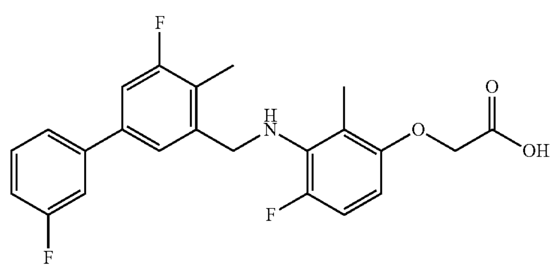 [SMILES: Cc1c(F)cc(-c2cccc(F)c2)cc1CNc1c(F)ccc(OCC(=O)O)c1C] | 2-[4-fluoro-3-[[3-fluoro-5-(3-fluorophenyl)-2-methyl-phenyl]methylamino]-2-methyl-phenoxy]acetic acid |
| I(aw) | 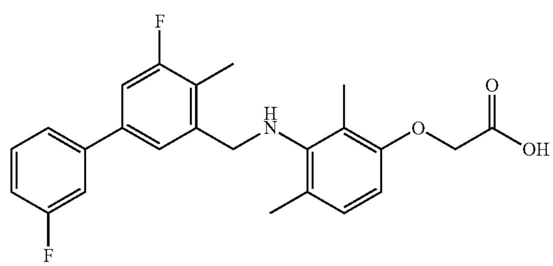 [SMILES: Cc1ccc(OCC(=O)O)c(C)c1NCc1cc(-c2cccc(F)c2)cc(F)c1C] | 2-[3-[[3-fluoro-5-(3-fluorophenyl)-2-methyl-phenyl]methylamino]-2,4-dimethyl-phenoxy]acetic acid |

TABLE 1-continued

| Compound number | Structure | Name |
|---|---|---|
| II(a) | 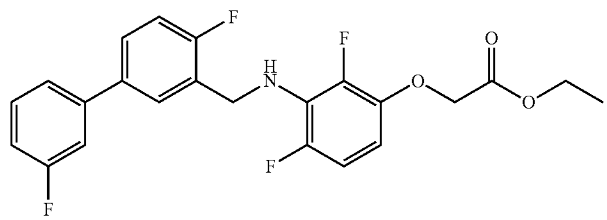 | ethyl 2-[2,4-difluoro-3-[[2-fluoro-5-(3-fluorophenyl)phenyl]methylamino]phenoxy]acetate |
| II(b) | 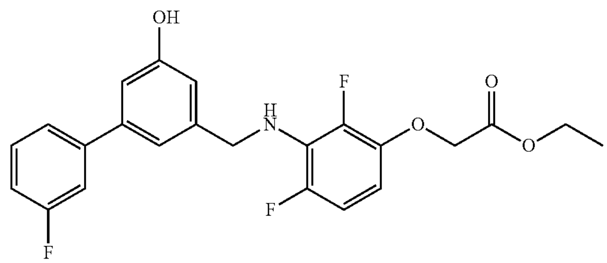 | ethyl 2-[2,4-difluoro-3-[[3-(3-fluorophenyl)-5-hydroxy-phenyl]methylamino]phenoxy]acetate |
| II(c) | 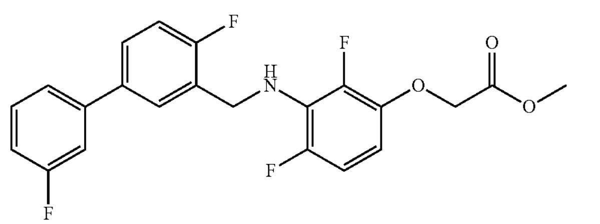 [SMILES: COC(=O)COc1ccc(F)c(NCc2cc(-c3cccc(F)c3)ccc2F)c1F] | methyl 2-[2,4-difluoro-3-[[2-fluoro-5-(3-fluorophenyl)phenyl]methylamino]phenoxy]acetate |
| II(d) | 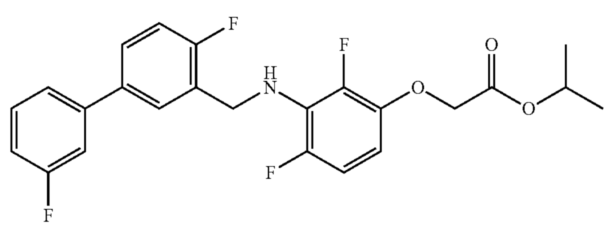 [SMILES: CC(C)OC(=O)COc1ccc(F)c(NCc2cc(-c3cccc(F)c3)ccc2F)c1F] | isopropyl 2-[2,4-difluoro-3-[[2-fluoro-5-(3-fluorophenyl)phenyl]methylamino]phenoxy]acetate |
| II(e) | 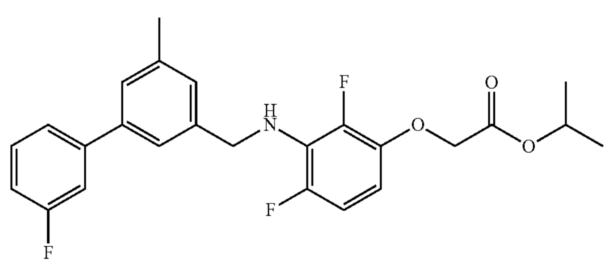 [SMILES: Cc1cc(CNc2c(F)ccc(OCC(=O)OC(C)C)c2F)cc(-c2cccc(F)c2)c1] | isopropyl 2-[2,4-difluoro-3-[[3-(3-fluorophenyl)-5-methyl-phenyl]methylamino]phenoxy]acetate |
| II(f) | 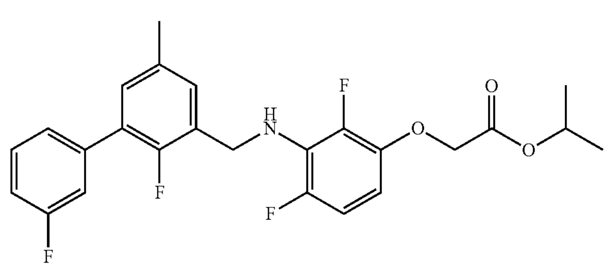 | isopropyl 2-[2,4-difluoro-3-[[2-fluoro-3-(3-fluorophenyl)-5-methyl-phenyl]methylamino]phenoxy]acetate |

TABLE 1-continued

| Compound number | Structure | Name |
|---|---|---|
| II(g) | 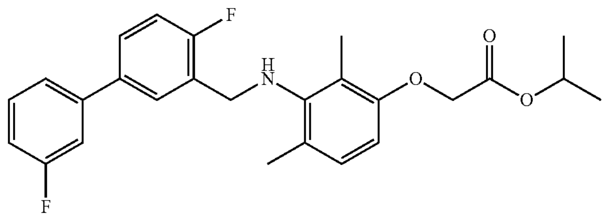 | isopropyl 2-[3-[[2-fluoro-5-(3-fluorophenyl)phenyl]methylamino]-2,4-dimethyl-phenoxy]acetate |
| II(h) | 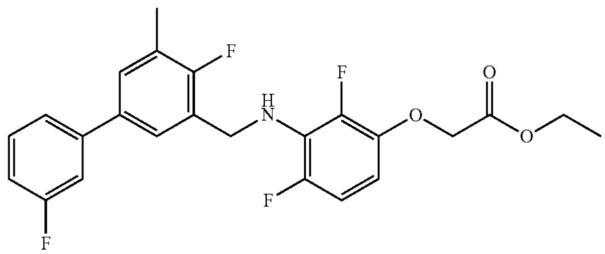 | ethyl 2-[2,4-difluoro-3-[[2-fluoro-5-(3-fluorophenyl)-3-methyl-phenyl]methylamino]phenoxy]acetate |
| II(i) | 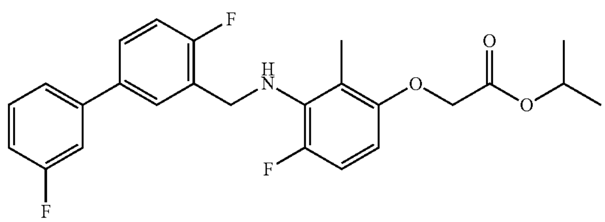 | isopropyl 2-[4-fluoro-3-[[2-fluoro-5-(3-fluorophenyl)phenyl]methylamino]-2-methyl-phenoxy]acetate |
| II(j) | 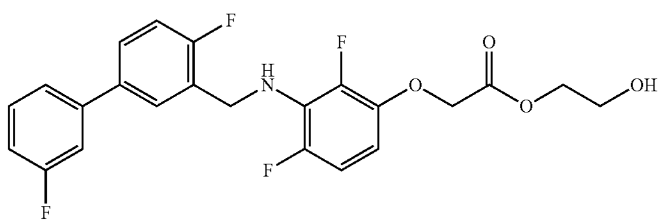 [SMILES: O=C(COc1ccc(F)c(NCc2cc(-c3cccc(F)c3)ccc2F)c1F)OCCO] | 2-hydroxyethyl 2-[2,4-difluoro-3-[[2-fluoro-5-(3-fluorophenyl)phenyl]methylamino]phenoxy]acetate |
| II(k) | 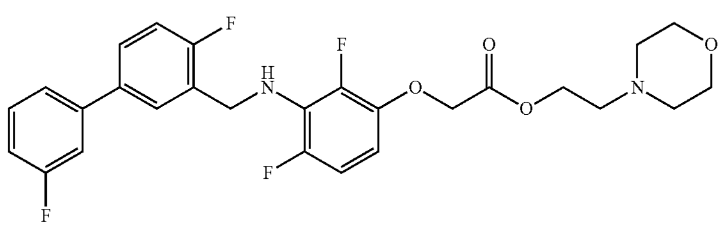 [SMILES: O=C(COc1ccc(F)c(NCc2cc(-c3cccc(F)c3)ccc2F)c1F)OCCN1CCOCC1] | 2-morpholinoethyl 2-[2,4-difluoro-3-[[2-fluoro-5-(3-fluorophenyl)phenyl]methylamino]phenoxy]acetate |
| II(l) | 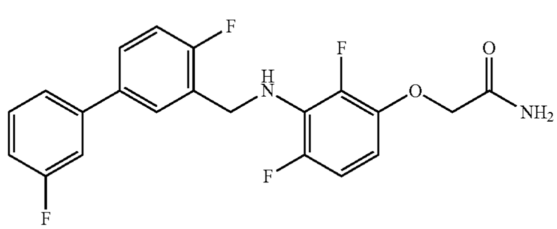 [SMILES: NC(=O)COc1ccc(F)c(NCc2cc(-c3cccc(F)c3)ccc2F)c1F] | 2-[2,4-difluoro-3-[[2-fluoro-5-(3-fluorophenyl)phenyl]methylamino]phenoxy]acetamide |
| II(m) | 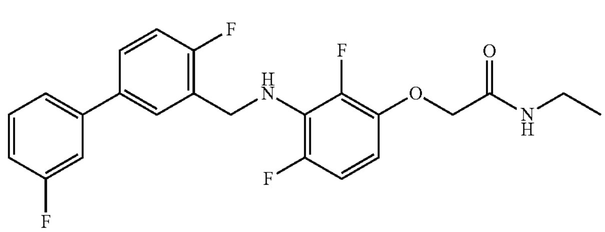 | 2-[2,4-difluoro-3-[[2-fluoro-5-(3-fluorophenyl)phenyl]methylamino]phenoxy]-N-ethyl-acetamide |

TABLE 1-continued

| Compound number | Structure | Name |
|---|---|---|
| II(n) | 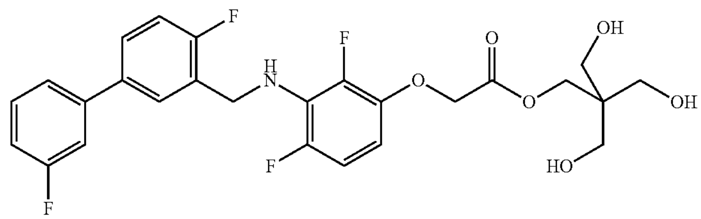 [SMILES: O=C(COc1ccc(F)c(NCc2cc(-c3cccc(F)c3)ccc2F)c1F)OCC(CO)(CO)CO] | [3-hydroxy-2,2-bis(hydroxymethyl)propyl] 2-[2,4-difluoro-3-[[2-fluoro-5-(3-fluorophenyl)phenyl]methylamino]phenoxy]acetate |
| II(o) | 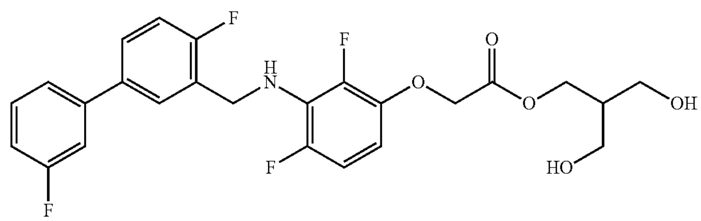 [SMILES: O=C(COc1ccc(F)c(NCc2cc(-c3cccc(F)c3)ccc2F)c1F)OCC(CO)CO] | [3-hydroxy-2-(hydroxymethyl)propyl] 2-[2,4-difluoro-3-[[2-fluoro-5-(3-fluorophenyl)phenyl]methylamino]phenoxy]acetate |
| II(p) | 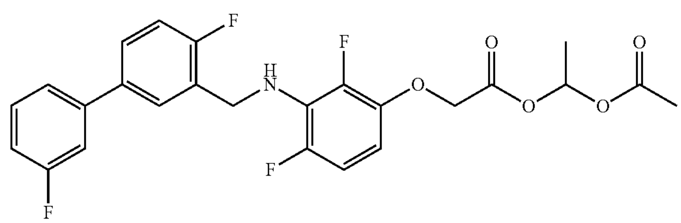 [SMILES: CC(=O)OC(C)OC(=O)COc1ccc(F)c(NCc2cc(-c3cccc(F)c3)ccc2F)c1F] | 1-acetoxyethyl 2-[2,4-difluoro-3-[[2-fluoro-5-(3-fluorophenyl)phenyl]methylamino]phenoxy]acetate |
| II(q) | 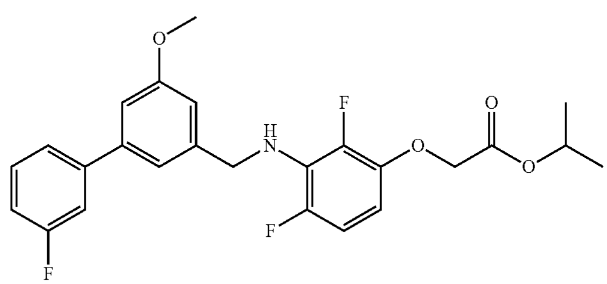 | isopropyl 2-[2,4-difluoro-3-[[3-(3-fluorophenyl)-5-methoxy-phenyl]methylamino]phenoxy]acetate |
| II(r) | 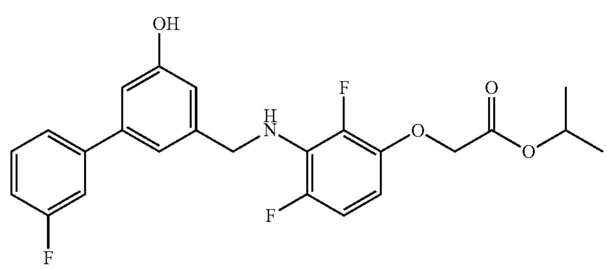 | isopropyl 2-[2,4-difluoro-3-[[3-(3-fluorophenyl)-5-hydroxy-phenyl]methylamino]phenoxy]acetate |
| II(s) | 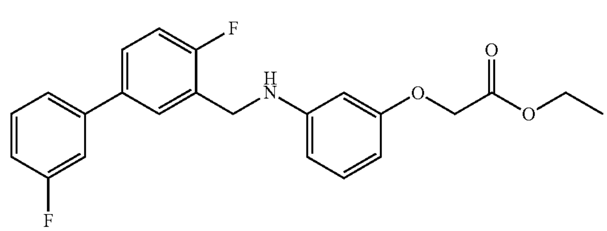 [SMILES: CCOC(=O)COc1cccc(NCc2cc(-c3cccc(F)c3)ccc2F)c1] | ethyl 2-[3-[[2-fluoro-5-(3-fluorophenyl)phenyl]methylamino]phenoxy]acetate |

TABLE 1-continued

| Compound number | Structure | Name |
|---|---|---|
| II(t) | 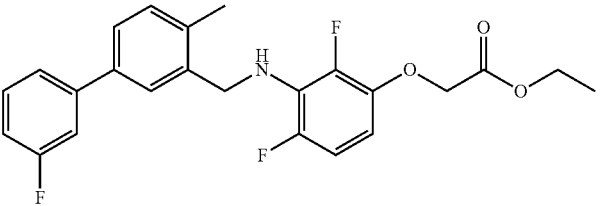 [SMILES: CCOC(=O)COc1ccc(F)c(NCc2cc(-c3cccc(F)c3)ccc2C)c1F] | ethyl 2-[2,4-difluoro-3-[[5-(3-fluorophenyl)-2-methyl-phenyl]methylamino]phenoxy]acetate |
| II(u) | 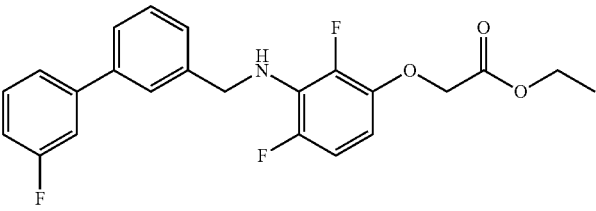 [SMILES: CCOC(=O)COc1ccc(F)c(NCc2cccc(-c3cccc(F)c3)c2)c1F] | ethyl 2-[2,4-difluoro-3-[[3-(3-fluorophenyl)phenyl]methylamino]phenoxy]acetate |
| II(v) | 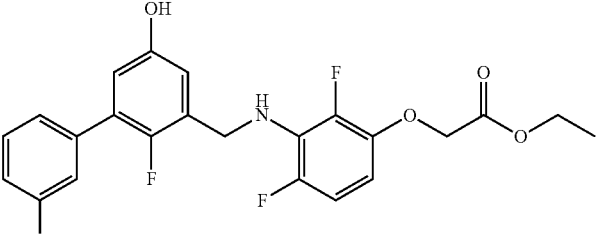 | ethyl 2-[2,4-difluoro-3-[[2-fluoro-3-(3-fluorophenyl)-5-hydroxy-phenyl]methylamino]phenoxy]acetate |
| II(w) | 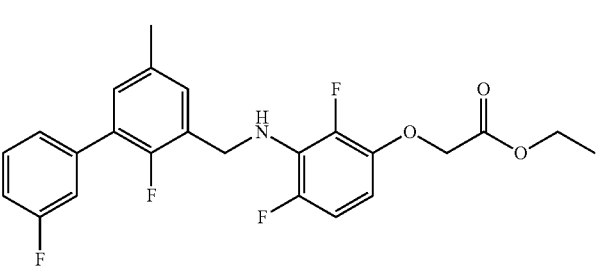 [SMILES: CCOC(=O)COc1ccc(F)c(NCc2cc(C)cc(-c3cccc(F)c3)c2F)c1F] | ethyl 2-[2,4-difluoro-3-[[2-fluoro-3-(3-fluorophenyl)-5-methyl-phenyl]methylamino]phenoxy]acetate |
| II(x) | 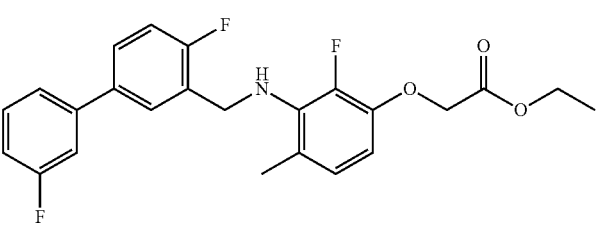 | ethyl 2-[2-fluoro-3-[[2-fluoro-5-(3-fluorophenyl)phenyl]methylamino]-4-methyl-phenoxy]acetate |
| II(y) | 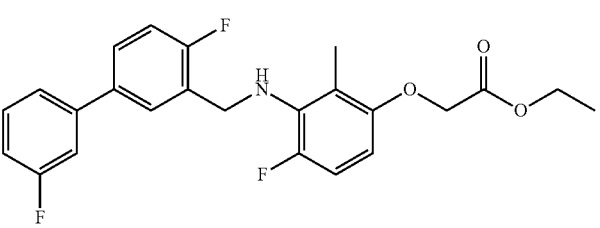 [SMILES: CCOC(=O)COc1ccc(F)c(NCc2cc(-c3cccc(F)c3)ccc2F)c1C] | ethyl 2-[4-fluoro-3-[[2-fluoro-5-(3-fluorophenyl)phenyl]methylamino]-2-methyl-phenoxy]acetate |

TABLE 1-continued

| Compound number | Structure | Name |
|---|---|---|
| II(z) | 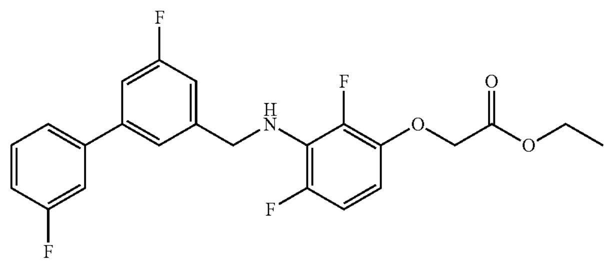 [SMILES: CCOC(=O)COc1ccc(F)c(NCc2cc(F)cc(-c3cccc(F)c3)c2)c1F] | ethyl 2-[2,4-difluoro-3-[[3-fluoro-5-(3-fluorophenyl)phenyl]methylamino]phenoxy]acetate |
| II(aa) | 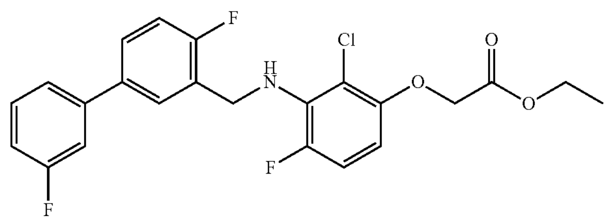 | ethyl 2-[2-chloro-4-fluoro-3-[[2-fluoro-5-(3-fluorophenyl)phenyl]methylamino]phenoxy]acetate |
| II(ab) | 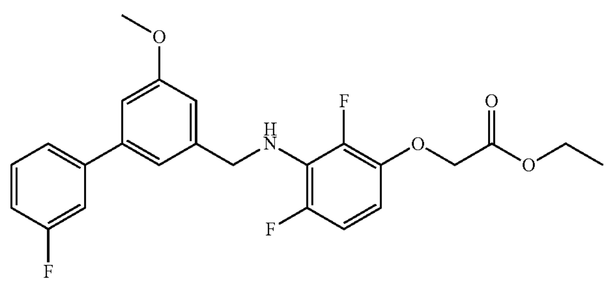 [SMILES: CCOC(=O)COc1ccc(F)c(NCc2cc(OC)cc(-c3cccc(F)c3)c2)c1F] | ethyl 2-[2,4-difluoro-3-[[3-(3-fluorophenyl)-5-methoxy-phenyl]methylamino]phenoxy]acetate |
| II(ac) | 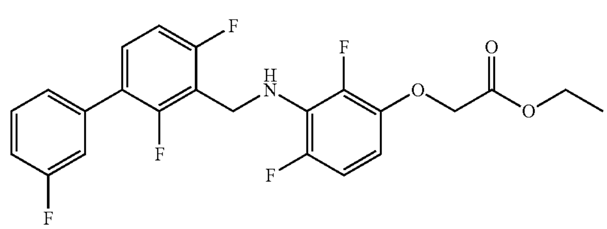 | ethyl 2-[3-[[2,6-difluoro-3-(3-fluorophenyl)phenyl]methylamino]-2,4-difluoro-phenoxy]acetate |
| II(ad) | 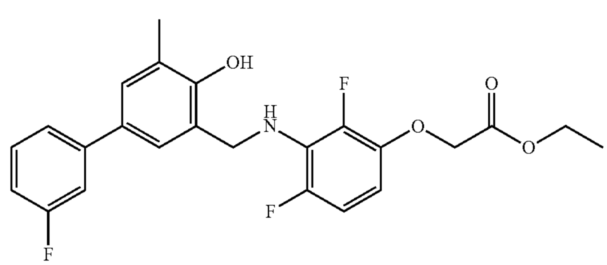 [SMILES: CCOC(=O)COc1ccc(F)c(NCc2cc(-c3cccc(F)c3)cc(C)c2O)c1F] | ethyl 2-[2,4-difluoro-3-[[5-(3-fluorophenyl)-2-hydroxy-3-methyl-phenyl]methylamino]phenoxy]acetate |
| II(ae) | 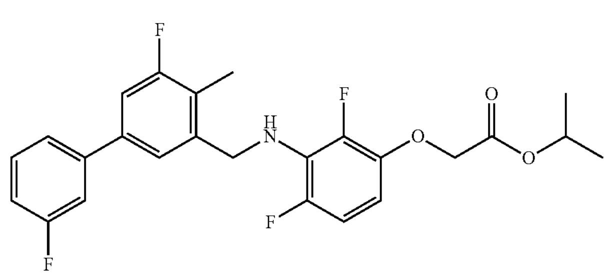 | isopropyl 2-[2,4-difluoro-3-[[3-fluoro-5-(3-fluorophenyl)-2-methyl-phenyl]methylamino]phenoxy]acetate |

TABLE 1-continued

| Compound number | Structure | Name |
|---|---|---|
| II(af) | 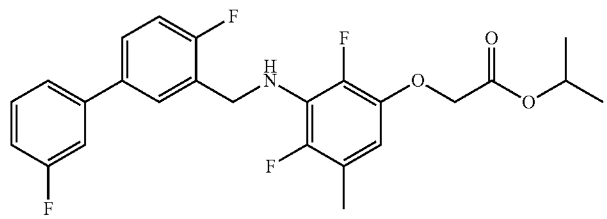 | isopropyl 2-[2,4-difluoro-3-[[2-fluoro-5-(3-fluorophenyl)phenyl]methylamino]-5-methyl-phenoxy]acetate |
| II(ag) | 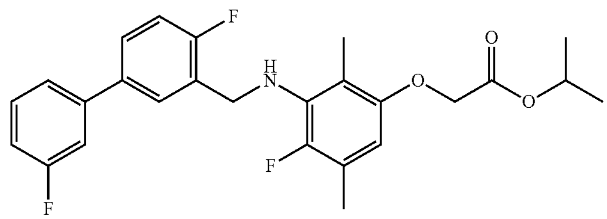 | isopropyl 2-[4-fluoro-3-[[2-fluoro-5-(3-fluorophenyl)phenyl]methylamino]-2,5-dimethyl-phenoxy]acetate |
| II(ah) | 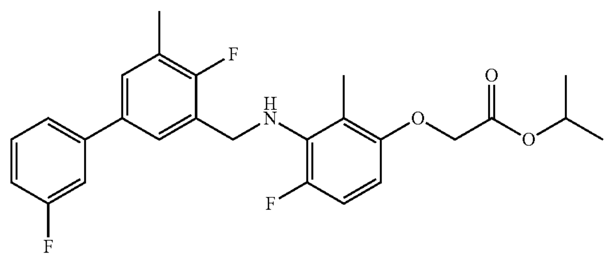 [SMILES: Cc1cc(-c2cccc(F)c2)cc(CNc2c(F)ccc(OCC(=O)OC(C)C)c2C)c1F] | isopropyl 2-[4-fluoro-3-[[2-fluoro-5-(3-fluorophenyl)-3-methyl-phenyl]methylamino]-2-methyl-phenoxy]acetate |
| II(ai) | 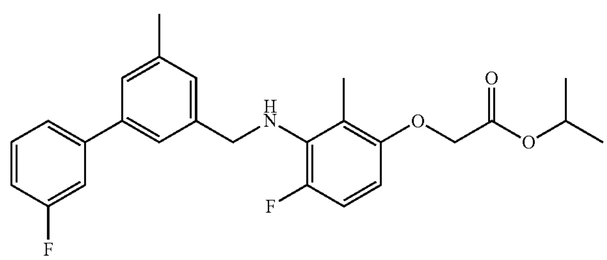 | isopropyl 2-[4-fluoro-3-[[3-(3-fluorophenyl)-5-methyl-phenyl]methylamino]-2-methyl-phenoxy]acetate |
| II(aj) | 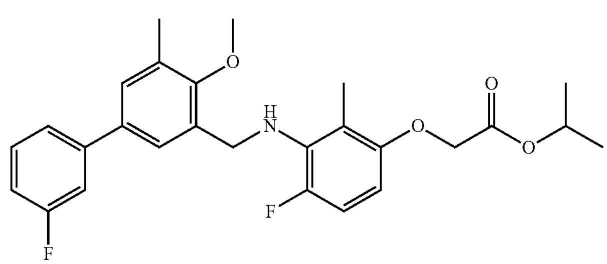 [SMILES: COc1c(C)cc(-c2cccc(F)c2)cc1CNc1c(F)ccc(OCC(=O)OC(C)C)c1C] | isopropyl 2-[4-fluoro-3-[[5-(3-fluorophenyl)-2-methoxy-3-methyl-phenyl]methylamino]-2-methyl-phenoxy]acetate |
| II(ak) | 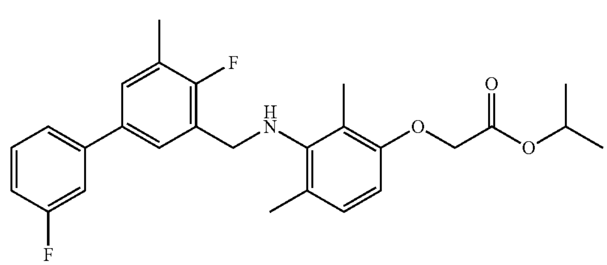 [SMILES: Cc1cc(-c2cccc(F)c2)cc(CNc2c(C)ccc(OCC(=O)OC(C)C)c2C)c1F] | isopropyl 2-[3-[[2-fluoro-5-(3-fluorophenyl)-3-methyl-phenyl]methylamino]-2,4-dimethyl-phenoxy]acetate |

TABLE 1-continued

| Compound number | Structure | Name |
|---|---|---|
| II(al) | 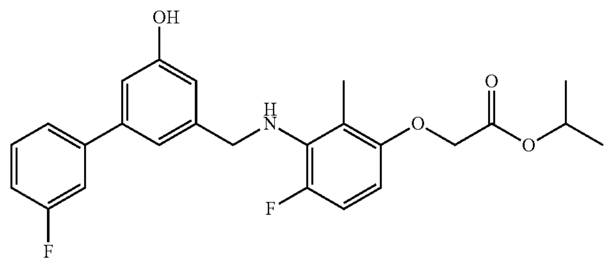 | isopropyl 2-[4-fluoro-3-[[3-(3-fluorophenyl)-5-hydroxy-phenyl]methylamino]-2-methyl-phenoxy]acetate |
| II(am) | 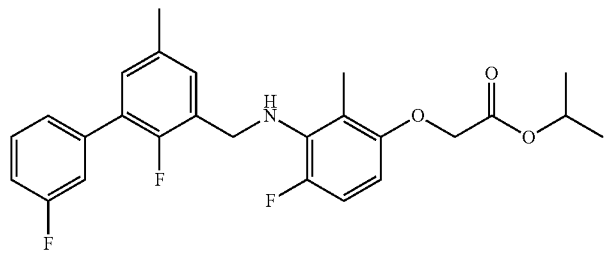 | isopropyl 2-[4-fluoro-3-[[2-fluoro-3-(3-fluorophenyl)-5-methyl-phenyl]methylamino]-2-methyl-phenoxy]acetate |
| II(an) | 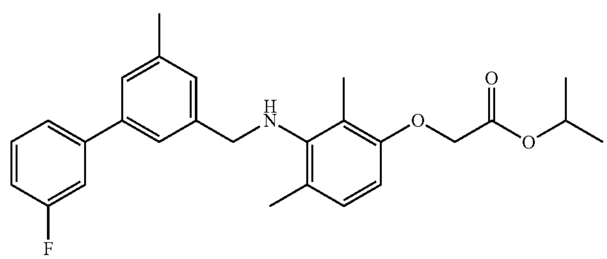 | isopropyl 2-[3-[[3-(3-fluorophenyl)-5-methyl-phenyl]methylamino]-2,4-dimethyl-phenoxy]acetate |
| II(ao) | 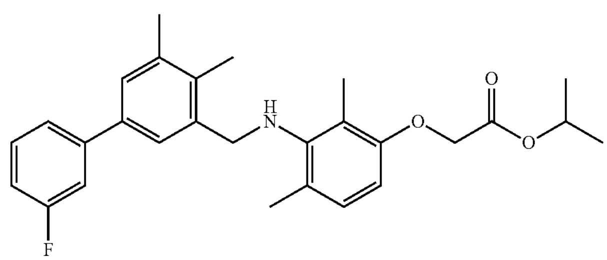 | isopropyl 2-[3-[[5-(3-fluorophenyl)-2,3-dimethyl-phenyl]methylamino]-2,4-dimethyl-phenoxy]acetate |
| II(ap) | 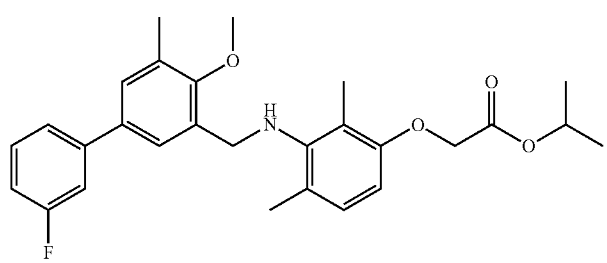 | isopropyl 2-[3-[[5-(3-fluorophenyl)-2-methoxy-3-methyl-phenyl]methylamino]-2,4-dimethyl-phenoxy]acetate |
| II(aq) | 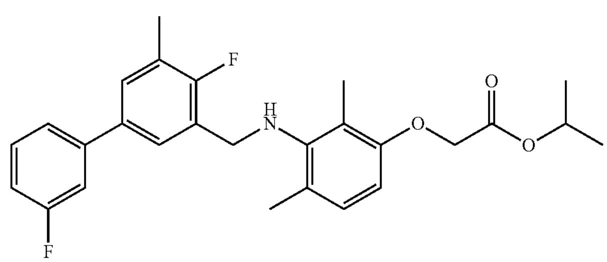 [SMILES: Cc1cc(-c2cccc(F)c2)cc(CNc2c(C)ccc(OCC(=O)OC(C)C)c2C)c1F] | isopropyl 2-[3-[[2-fluoro-5-(3-fluorophenyl)-3-methyl-phenyl]methylamino]-2,4-dimethyl-phenoxy]acetate |

TABLE 1-continued

| Compound number | Structure | Name |
| --- | --- | --- |
| II(ar) | 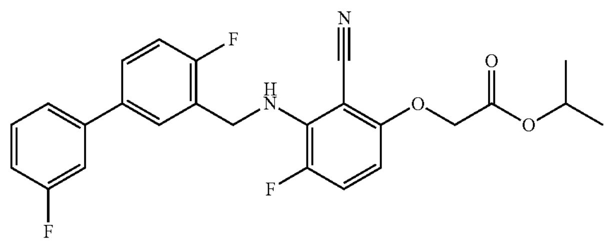 [SMILES: CC(C)OC(=O)COc1ccc(F)c(NCc2cc(-c3cccc(F)c3)ccc2F)c1C#N] | isopropyl 2-[2-cyano-4-fluoro-3-[[2-fluoro-5-(3-fluorophenyl)phenyl]methylamino]phenoxy]acetate |
| II(as) | 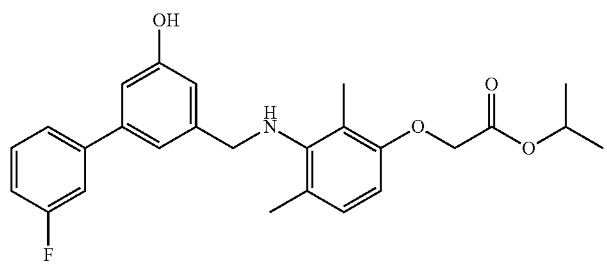 [SMILES: Cc1ccc(OCC(=O)OC(C)C)c(C)c1NCc1cc(O)cc(-c2cccc(F)c2)c1] | isopropyl 2-[3-[[3-(3-fluorophenyl)-5-hydroxy-phenyl]methylamino]-2,4-dimethyl-phenoxy]acetate |
| II(at) | 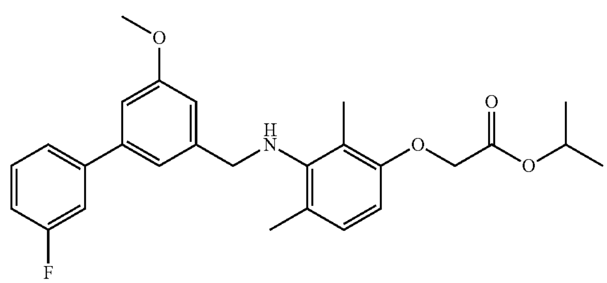 [SMILES: COc1cc(CNc2c(C)ccc(OCC(=O)OC(C)C)c2C)cc(-c2cccc(F)c2)c1] | isopropyl 2-[3-[[3-(3-fluorophenyl)-5-methoxy-phenyl]methylamino]-2,4-dimethyl-phenoxy]acetate |
| II(au) | 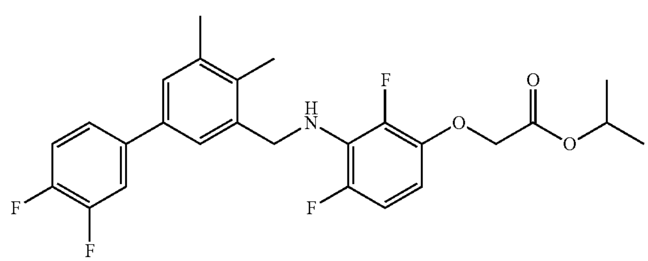 [SMILES: Cc1cc(-c2ccc(F)c(F)c2)cc(CNc2c(F)ccc(OCC(=O)OC(C)C)c2F)c1C] | isopropyl 2-[3-[[5-(3,4-difluorophenyl)-2,3-dimethyl-phenyl]methylamino]-2,4-difluoro-phenoxy]acetate |
| II(av) | 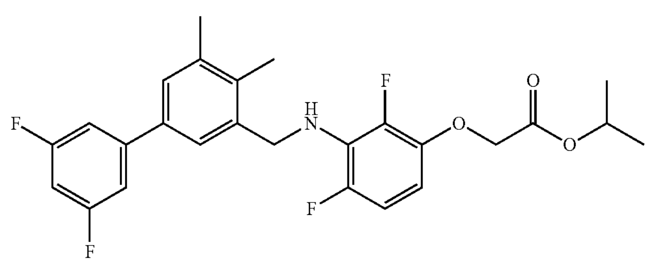 [SMILES: Cc1cc(-c2cc(F)cc(F)c2)cc(CNc2c(F)ccc(OCC(=O)OC(C)C)c2F)c1C] | isopropyl 2-[3-[[5-(3,5-difluorophenyl)-2,3-dimethyl-phenyl]methylamino]-2,4-difluoro-phenoxy]acetate |
| II(aw) | 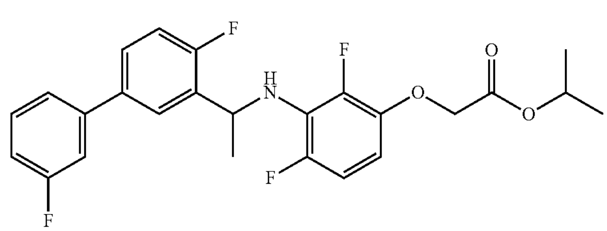 [SMILES: CC(C)OC(=O)COc1ccc(F)c(NC(C)c2cc(-c3cccc(F)c3)ccc2F)c1F] | isopropyl 2-[2,4-difluoro-3-[1-[2-fluoro-5-(3-fluorophenyl)phenyl]ethylamino]phenoxy]acetate |

TABLE 1-continued

| Compound number | Structure | Name |
|---|---|---|
| II(ax) | 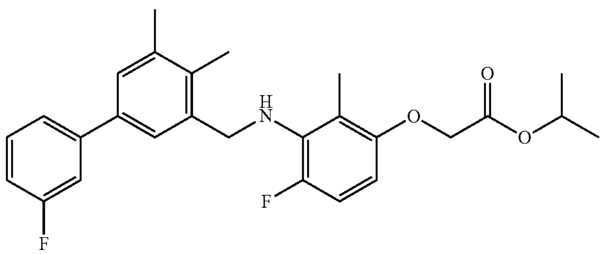 | isopropyl 2-[4-fluoro-3-[[5-(3-fluorophenyl)-2,3-dimethyl-phenyl]methylamino]-2-methyl-phenoxy]acetate |
| II(ay) | 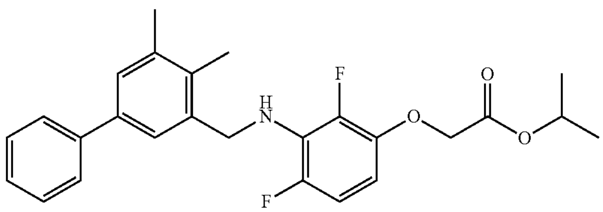 [SMILES: Cc1cc(-c2ccccc2)cc(CNc2c(F)ccc(OCC(=O)OC(C)C)c2F)c1C] | isopropyl 2-[3-[(2,3-dimethyl-5-phenyl-phenyl)methylamino]-2,4-difluoro-phenoxy]acetate |
| II(az) | 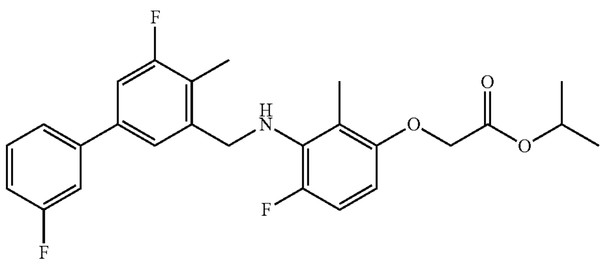 [SMILES: Cc1c(F)cc(-c2cccc(F)c2)cc1CNc1c(F)ccc(OCC(=O)OC(C)C)c1C] | isopropyl 2-[4-fluoro-3-[[3-fluoro-5-(3-fluorophenyl)-2-methyl-phenyl]methylamino]-2-methyl-phenoxy]acetate |
| II(ba) | 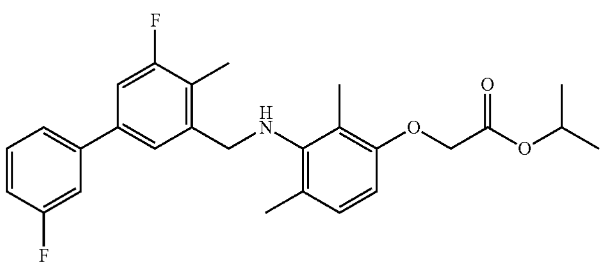 | isopropyl 2-[3-[[3-fluoro-5-(3-fluorophenyl)-2-methyl-phenyl]methylamino]-2,4-dimethyl-phenoxy]acetate |
| II(bb) | 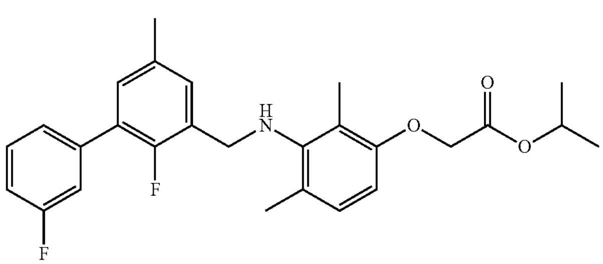 | isopropyl 2-[3-[[2-fluoro-3-(3-fluorophenyl)-5-methyl-phenyl]methylamino]-2,4-dimethyl-phenoxy]acetate |

(IUPAC chemical names have been attributed by the SymyxDraw program, version 3.2)

In another aspect of the present invention, the invention comprises compounds of formula (I) as described above with the provisio that compounds of formula (I) are not compounds of table 2:

TABLE 2

| Formula | Chemical name |
|---|---|
| | 2-[2,4-difluoro-3-[[2-fluoro-3-(3-fluorophenyl)phenyl]methylamino]phenoxy]acetic acid |
| | 2-[2,4-difluoro-3-[[3-(3-fluorophenyl)-2-methyl-phenyl]methylamino]phenoxy]acetic acid |
| | 2-[2-fluoro-3[[2-fluoro-5-(3-fluorophenyl)phenyl]methylamino]phenoxy]acetic acid |
| | 2-[4-fluoro-3[[2-fluoro-5-(3-fluorophenyl)phenyl]methylamino]phenoxy]acetic acid |
| | 2-[2,4-difluoro-3[[5-(3-fluorophenyl)-2-methoxy-phenyl]methylamino]phenoxy]acetic acid |
| | 2-[2,4-difluoro-3-[[5-(3-fluorophenyl)-2-hydroxy-phenyl]methylamino]phenoxy]acetic acid |

TABLE 2-continued

| Formula | Chemical name |
|---|---|
|  | 2-[2,4-difluoro-3-[[3-(3-fluorophenyl)-2,5-dimethyl-phenyl]methylamino]phenoxy]acetic acid |
|  | 2-[2,4-difluoro-3-[[5-fluoro-3-(3-fluorophenyl)-2-methyl-phenyl]methylamino]phenoxy]acetic acid |
|  | 2-[2,4-difluoro-3-[[2-fluoro-3-(3-fluorophenyl)-6-hydroxy-phenyl]methylamino]phenoxy]acetic acid |
|  | 2-[2,4-difluoro-3-[[2-fluoro-3-(3-fluorophenyl)-6-methoxy-phenyl]methylamino]phenoxy]acetic acid |
|  | 2-[2,4-difluoro-3-[[3-(3-fluorophenyl)-5-isopropyl-phenyl]methylamino]phenoxy]acetic acid |
|  | 2-[3-[[3-ethyl-5-(3-fluorophenyl)phenyl]methylamino]-2,4-difluoro-phenoxy]acetic acid |

TABLE 2-continued

| Formula | Chemical name |
|---|---|
| | 2-[2-ethyl-4-fluoro-3-[[2-fluoro-5-(3-fluorophenyl)phenyl]methylamino]phenoxy]acetic acid |
| | 2-[4-fluoro-3-[[2-fluoro-5-(3-fluorophenyl)phenyl]methylamino]-2-isopropyl-phenoxy]acetic acid |
| | 2-[2,4-difluoro-3-[[2-fluoro-5-(4-fluorophenyl)phenyl]methylamino]phenoxy]acetic acid |
| | 2-[2,4-difluoro-3-[[2-fluoro-5-phenyl-phenyl)methylamino]phenoxy]acetic acid |
| | 2-[2,4-difluoro-3-[[2-fluoro-3-(3-fluorophenyl)-6-methyl-phenyl)methylamino]phenoxy]acetic acid |
| | 2-[3-[[5-(3-fluorophenyl)-2,3-dimethyl-phenyl]methylamino]phenoxy]acetic acid |
| | 2-[4-fluoro-3-[[5-(3-fluorophenyl)-2,3-dimethyl-phenyl]methylamino]phenoxy]acetic acid |

TABLE 2-continued

| Formula | Chemical name |
|---|---|
|  | 2-[3-[[2-fluoro-5-(3-fluorophenyl)-3-methyl-phenyl]methylamino]phenoxy]acetic acid |

In another aspect, the invention comprises compounds of formula (I) as described above, where when R1a, R1b, R1c, R2, R3 and/or R9 represent a ($C_1$-$C_6$)alkyl, this ($C_1$-$C_6$)alkyl is a methyl, or one of its enantiomers.

In another aspect, the invention comprises compounds of formula (I) as described above, where halogen is fluorine or chlorine, or one of its enantiomers.

In another aspect, the invention comprises compounds of formula (I) as described above, where both R1a and R1b are fluorine, or one of its enantiomers.

In another aspect, the invention comprises compounds of formula (I) as described above, where two of R2, R3 and R4 are H, or one of its enantiomers.

In another aspect, the invention comprises compounds of formula (I) as described above, where one of R2, R3 and R4 is H, or one of its enantiomers.

In another aspect, the invention comprises compounds of formula (I) as described above, where R5 and R8 are hydrogen, or one of its enantiomers.

In another aspect, the invention comprises compounds of formula (I), or one of its prodrugs, as described above, where
R1a and R1b represent, independently from each other, H or an halogen,
R1c is H,
R2 represents H, an halogen or a ($C_1$-$C_6$)alkyl,
R3 represents H an halogen, an OH, or a ($C_1$-$C_6$)alkyl,
R4 represents H, an halogen, an OH or a ($C_1$-$C_6$)alkyl,
R5, R8 and R9 are H and,
R7 is F,
or one of its enantiomers.

In another aspect, the invention comprises compounds of formula (I), or one of its prodrugs, as described above, where
R1a and R1b represent, independently from each other, H or an halogen,
R1c is H,
R2 represents H, an halogen or a ($C_1$-$C_6$)alkyl,
R3 represents H, an halogen, an OH or a ($C_1$-$C_6$)alkyl,
R4 represents H, an halogen, or a ($C_1$-$C_6$)alkyl,
R5, R8 and R9 are H and,
R7 is F
or one of its enantiomers.

In another aspect, the invention comprises compounds of formula (I), or one of its prodrugs, as described above, where
R1a represents H, an halogen or a ($C_1$-$C_6$)alkyl,
R1b represents, H, an halogen or a ($C_1$-$C_6$)alkyl,
R1c is H or a ($C_1$-$C_6$)alkyl,
R2 represents H, an halogen, an OH, an O—($C_1$-$C_6$)alkyl or a ($C_1$-$C_6$)alkyl,
R3 represents H, an halogen, an OH, a ($C_1$-$C_6$)alkyl, an O—($C_1$-$C_6$)alkyl, a CONH$_2$ or a CN,
R4 represents H, an halogen or a ($C_1$-$C_6$)alkyl,
R5 represents H or F,
R8 and R9 are H, and
R7 is F,
or one of its enantiomers.

In another aspect, the invention comprises compounds of formula (II) as described above, where R1a and R1b represent, independently from each other, methyl and/or fluorine, or one of its enantiomers.

In another aspect, the invention comprises compounds of formula (II) as described above, where R1c, R5 and R8 represent H, or one of its enantiomers.

In another aspect, the invention comprises compounds of formula (II) as described above, where R2 and R4 represent, independently from each other, H and/or fluorine, or one of its enantiomers.

In another aspect, the invention comprises compounds of formula (II) as described above, where R6 is O-isopropyl, or one of its enantiomers.

In another aspect, the invention comprises compounds of formula (II) as described above, where
R1a and R1b represent, independently from each other, H or an halogen,
R1c is H,
R2 represents H, an halogen or a ($C_1$-$C_6$)alkyl,
R3 represents H, an halogen, an OH, or a ($C_1$-$C_6$)alkyl,
R4 represents H, an halogen, an OH, or a ($C_1$-$C_6$)alkyl,
R5, R8 and R9 are H,
R7 is F and
R6 is an O—($C_1$-$C_6$)alkyl, an O-ethyl-morpholine, an O—CH(CH$_3$)—OCOCH$_3$, an O—CH$_2$—CH$_2$—OH, an O—CH—(CH$_2$OH)$_2$, an O—CH$_2$—CH—(CH$_2$OH)$_2$ or an O—CH$_2$—C—(CH$_2$OH)$_3$, or one of its enantiomers.

In another aspect, the invention comprises compounds of formula (II) as described above, where
R1a and R1b represent, independently from each other, H or an halogen,
R1c is H,
R2 represents H, an halogen or a ($C_1$-$C_6$)alkyl,
R3 represents H, an halogen, an OH, or a ($C_1$-$C_6$)alkyl,
R4 represents H, an halogen or a ($C_1$-$C_6$)alkyl,
R5, R8 and R9 are H,
R7 is F and
R6 is an O—($C_1$-$C_6$)alkyl, an O-ethyl-morpholine, an O—CH(CH$_3$)—OCOCH$_3$, an O—CH$_2$—CH$_2$—OH, an O—CH—(CH$_2$OH)$_2$, an O—CH$_2$—CH—(CH$_2$OH)$_2$ or an O—CH$_2$—C—(CH$_2$OH)$_3$,
or one of its enantiomers.

In another aspect, the invention comprises compounds of formula (II) as described above, where
R1a represents H, an halogen or a ($C_1$-$C_6$)alkyl,
R1b represents H, an halogen or a ($C_1$-$C_6$)alkyl, R1c is H or a ($C_1$-$C_6$)alkyl, R2 represents H, an halogen, an OH, an O—($C_1$-$C_6$)alkyl or a ($C_1$-$C_6$)alkyl, R3 represents H, an halogen, an OH, a ($C_1$-$C_6$)alkyl, an O—($C_1$-$C_6$)alkyl, a $CONH_2$ or a CN, R4 represents H, an halogen or a ($C_1$-$C_6$)alkyl, R5 represents H or F;

R8 and R9 are H,

R7 is F, and

R6 represents O—($C_1$-$C_6$)alkyl, O—($C_1$-$C_6$)alkyl-heterocycloalkyl, $NH_2$, NH—($C_1$-$C_6$)alkyl, O—($C_1$-$C_6$)alkyl optionally substituted by one to three hydroxyl groups, O—($C_1$-$C_6$)alkyl—O—CO($C_1$-$C_6$)alkyl), or one of its enantiomers.

In another aspect, the invention comprises a process for preparing a compound of formula (I) or one of its prodrugs, characterized in that a compound of formula (XI):

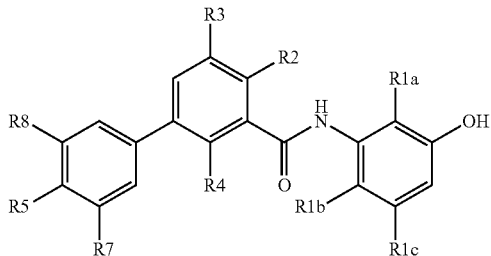

is reduced to give a compound of formula (IX):

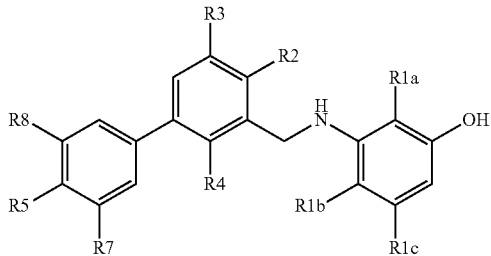

which is reacted with BrCH2COR6 to give a compound of formula (II), in which R1a, R1b, R1c, R2, R3, R4, R5, R7, R8 and R6 are as defined above.

In another aspect, the invention comprises a compound of formula (III):

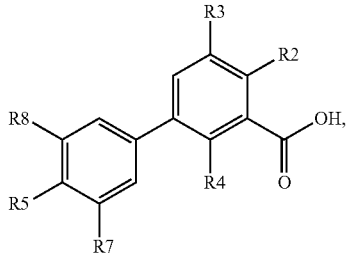

in which R2, R3, R4, R5, R7 and R8 are as defined above, or one of its enantiomers.

In another aspect, the invention comprises a compound of formula (IV):

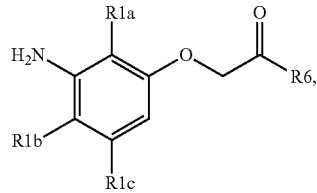

in which R1a, R1b, R1c and R6 are as defined above, or one of its enantiomers.

In another aspect, the invention comprises a compound of formula (VI):

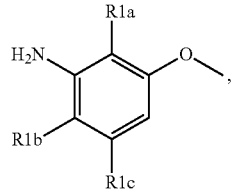

in which R1a, R1b and R1c are as defined above, or one of its enantiomers.

In another aspect, the invention comprises a compound of formula (X):

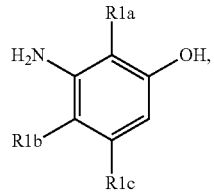

in which R1a, R1b and R1c are as defined above, or one of its enantiomers.

In another aspect, the invention comprises a medicament, characterized in that it comprises a compound of formula (I) or one of its prodrugs as defined above.

In another aspect, the invention comprises a pharmaceutical composition, characterized in that it comprises a compound of formula (I) or one of its prodrugs as defined above, and also at least one pharmaceutically acceptable excipient.

In another aspect, the invention comprises a use of a compound of formula (I) or one of its prodrugs as defined above, for preparing a medicament intended for the treatment of glaucoma.

In another aspect, the invention comprises a compound of formula (I) or one of its prodrugs as defined above, as EP2 agonist.

In another aspect, the invention comprises a method of treatment of glaucoma, which comprises administering to a patient an effective dose of a compound of formula (I) or one of its prodrugs as defined above.

In another aspect, the invention comprises a compound of formula (I) or one of its prodrugs as defined above, as a medicament.

In another aspect, the invention comprises a combination of a compound of formula (I) or one of its prodrugs, as defined above, with beta-blockers, prostaglandins, sympathomimetic collyres, inhibitors of carbonic anhydrase, or parasympathomimetic collyres.

In accordance with the invention the compounds of general formula (I) and (II) can be prepared by the following processes.

Acids of formula (I) according to the invention can be prepared by the route outlined in schemes 1 to 5, where R1a, R1b, R1c, R2, R3, R4, R5, R6, R7, R8 and R9 are as defined above. In a particular aspect, R6 is —O—($C_1$-$C_6$)alkyl.

Scheme 2:

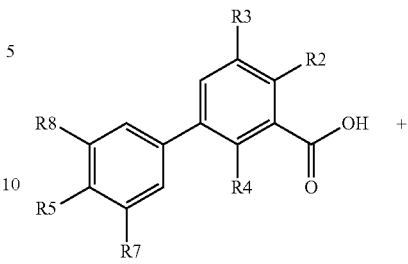

Scheme 1:

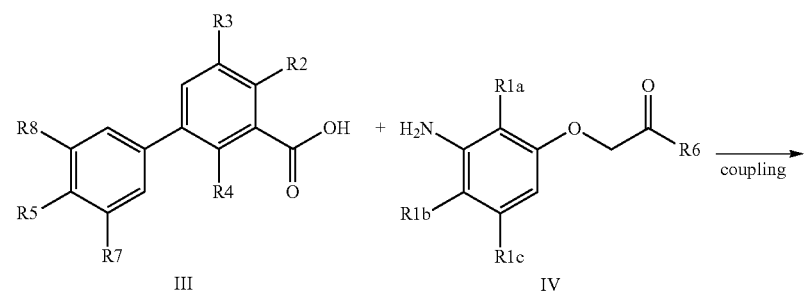

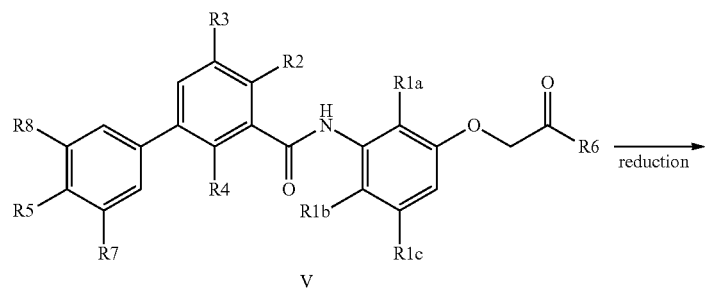

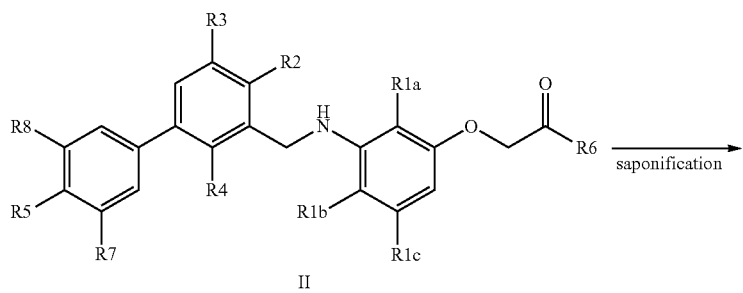

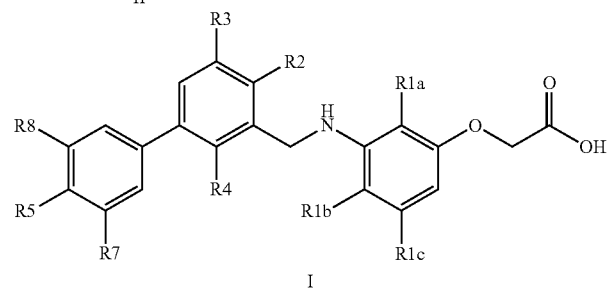

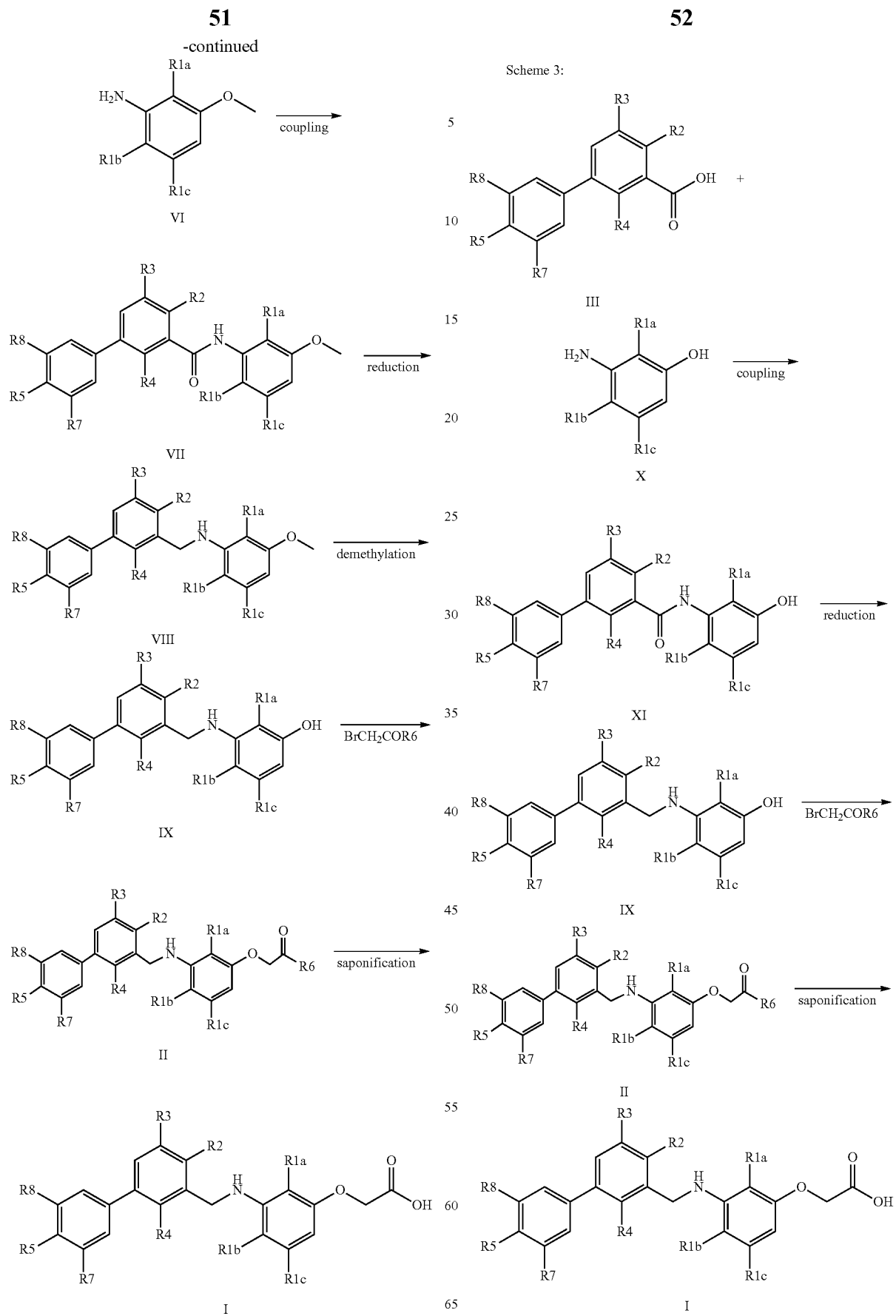

Scheme 4:
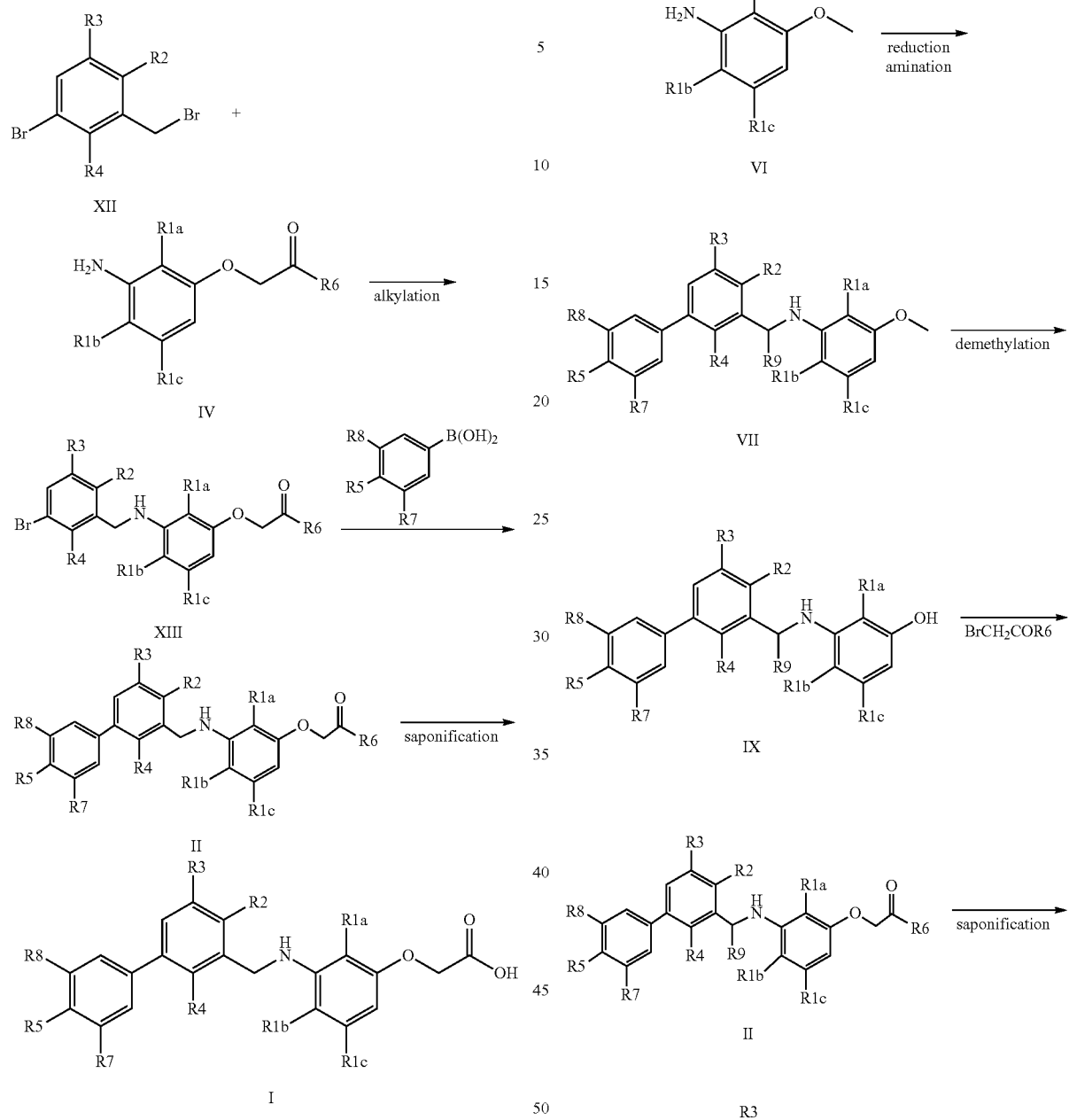
Scheme 5:
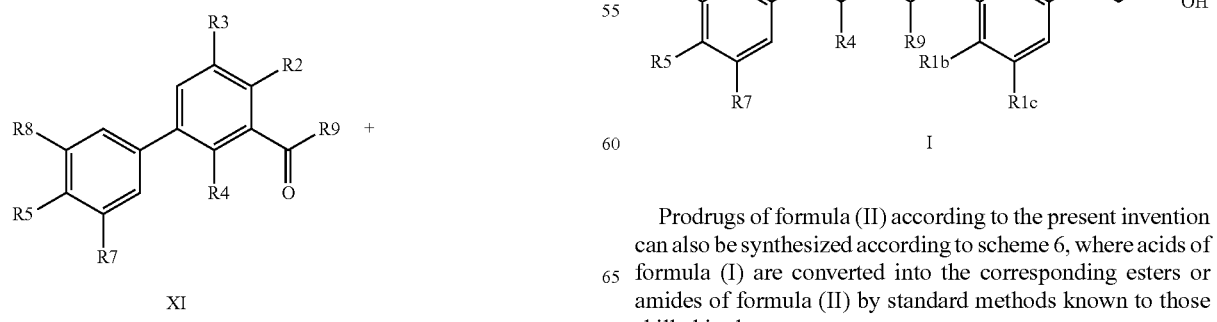
Prodrugs of formula (II) according to the present invention can also be synthesized according to scheme 6, where acids of formula (I) are converted into the corresponding esters or amides of formula (II) by standard methods known to those skilled in the art.

Scheme 6:

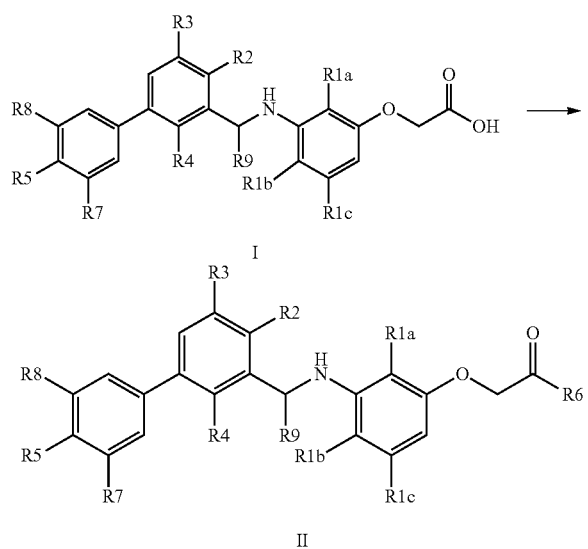

Prodrugs of formula (II) according to the present invention can also be synthesized according to scheme 7, where esters with R10 being a $(C_1-C_6)$alkyl, are converted into the corresponding esters or amides of formula (II) by standard methods known to those skilled in the art.

Scheme 7:

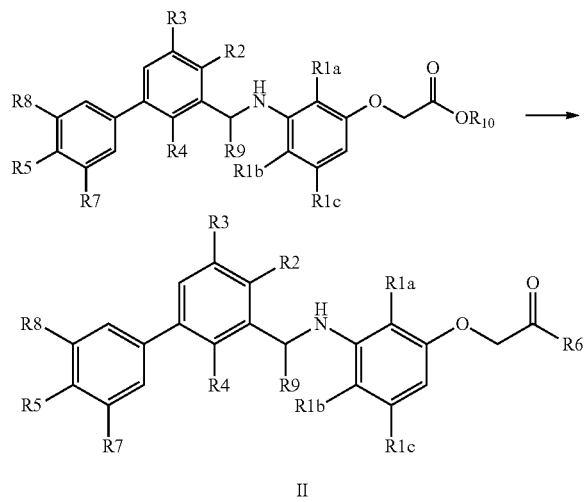

EXAMPLES

The following non-limiting preparations and examples illustrate the preparation of the compounds of the invention.

$^1$H Nuclear Magnetic Resonance (NMR) spectra were in all cases consistent with the proposed structures. We used a Fourier 300 MHz and 400MHz Bruker. Characteristic chemical shifts δ are given in parts-per-million downfield from tetramethylsilane using conventional abbreviations for designation of major peaks: e.g. s, singlet; d, doublet; t, triplet; q, quartet; m, multiplet; bb, broad band. The mass spectra (m/z) (Agilent MSD) were recorded using electrospray ionisation (ESI). The following abbreviations have been used for common solvents:

(Boc)$_2$O, di-tert-butyl dicarbonate,
CDCl$_3$, deuterochloroform,
DCM, dichloromethane,
DMA, N,N-dimethyl acetamide,
DMAP, 4-dimethylaminopyridine,
DMF, dimethylformamide,
DMSO-d$_6$, deuterodimethylsulphoxide,
Dppf, 1,1'-bis(diphenylphosphino)ferrocene,
EDC, 1-(3-Dimethylaminopropyl)-3-ethylcarbodiimide,
EtOAc, ethyl acetate,
EtOH, ethanol,
HATU, peptide coupling reagent (CAS nb. 148893-10-1),
HOBt, 1-hydroxybenzotriazole,
iPrOH, 2-propanol,
MeOD, deuterated methanol,
MeOH, methanol,
MTBE, methyl tertiary-butyl ether,
NBS, N-bromosuccinimide,
n-BuLi, n-butyllithium,
petroleum ether, that fraction of petroleum that boils between 60 and 80° C.,
PMDTA, N, N, N', N', N'''' pentamethyldiethylenetriamine,
sBuLi, sec-butyllithium,
tBuOH, tert-butylalcohol,
t-BuOK, Potassium tert-butoxid,
TEA, triethylamine,
TFA, trifluoroacetic acid,
THF, tetrahydrofuran,
TLC, thin layer chromatography,
TIPSCl, triisopropylsilylchloride, Where thin layer chromatography (TLC) has been used it refers to silica gel 60 F254 plates, R$_f$ is the distance traveled by a compound divided by the distance traveled by the solvent front on a TLC plate.

Example 1

Compound I(a) Synthesized According to Scheme 2

2-[3-[[2-Fluoro-5-(3-fluorophenyl)phenyl]methylamino]phenoxy]acetic acid (I(a))

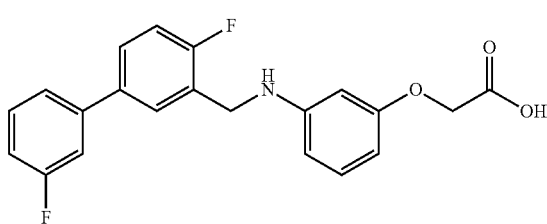 [SMILES: O=C(O)COc1cccc(NCc2cc(-c3cccc(F)c3)ccc2F)c1]

2-Fluoro-5-(3-fluorophenyl)benzoic acid (intermediate III(a))

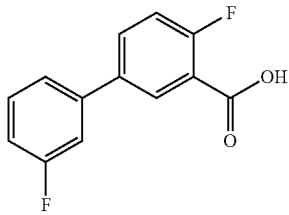 [SMILES: O=C(O)c1cc(-c2cccc(F)c2)ccc1F]

To a mixture of 5-bromo-2-fluorobenzoic acid (3 g, 13.2 mmol, 1.0 eq) and 3-fluorophenyl boronic acid (2.1 g, 15.1 mmol, 1.1 eq) in water (15 mL), EtOH (15 mL) and DMF (60 mL) was added Na$_2$CO$_3$ (5.81 g, 54.8 mmol, 4.1 eq) and Pd(PPh$_3$)$_4$ (1.58 g, 1.37 mmol, 0.1 eq). The reaction mixture was heated at 100° C. under nitrogen for 4 h, then cooled to room temperature. The resulting mixture was poured into water and extracted with ethyl acetate. The organic extracts were combined, dried (Na$_2$SO$_4$), filtered and evaporated in vacuo to give the title compound as a white powder (3 g, 97%).

LC-MS: m/z 235.1 [M+H]$^+$ , 257.0 [M+Na]$^+$ $^1$H NMR (400 MHz, DMSO-d$_6$) δ 8.10 (dd, J=6.9, 2.5 Hz, 1H), 7.96 (ddd, J=8.5, 4.5, 2.6 Hz, 1H), 7.59-7.48 (m, 3H), 7.42 (dd, J=10.6, 8.7 Hz, 1H), 7.22 (m, 1H).

2-Fluoro-5-(3-fluorophenyl)-N-(3-methoxyphenyl)benzamide

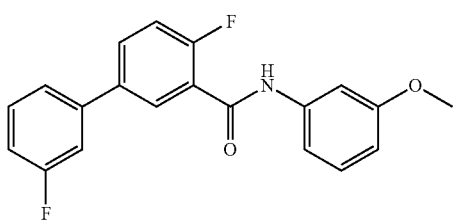 [SMILES: COc1cccc(NC(=O)c2cc(-c3cccc(F)c3)ccc2F)c1]

A mixture of 2-fluoro-5-(3-fluorophenyl)benzoic acid (intermediate III(a)) (500 mg, 2.10 mmol, 1.0 eq) in SOCl$_2$ (5 mL) was heated at 65° C. under N$_2$ for 1 h. The solution was then evaporated in vacuo and the remaining residue dissolved in CH$_2$Cl$_2$ and added dropwise to a mixture of 3-methoxyaniline (220 mg, 1.9 mmol, 0.9 eq) and K$_2$CO$_3$ (1.4 g, 10.1 mmol, 5.0 eq) in THF (10 mL) at 0° C. The reaction was allowed to warm to room temperature and stirred for 2 h. The reaction was quenched with water and the solution extracted with EtOAc. The combined organic extracts were washed with aqueous Na$_2$CO$_3$ and brine, dried (Na$_2$SO$_4$), filtered and evaporated in vacuo to give the title compound as a colourless oil (580 mg, 96%).

LC-MS: m/z 340.2 [M+H]$^+$

N-[[2-Fluoro-5-(3-fluorophenyl)phenyl]methyl]-3-methoxy-aniline

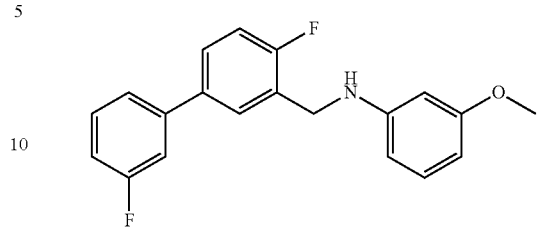

To a solution of 2-fluoro-5-(3-fluorophenyl)-N-(3-methoxyphenyl)benzamide (605 mg, 1.80 mmol, 1.0 eq) in THF (3 mL) was added dropwise a solution of BH$_3$ (1 M in THF, 5.3 mL, 5.3 mmol, 2.9 eq) at 0° C. The reaction was heated at reflux overnight, then cooled to room temperature and quenched by addition of methanol and water. The reaction was diluted with EtOAc and water and the aqueous layer extracted further with EtOAc. The combined organic extracts were washed with brine, dried (Na$_2$SO$_4$), filtered and evaporated in vacuo. The crude residue was purified by flash chromatography (petroleum ether: EtOAc, 10:1) to give the title compound as a colourless oil (512 mg, 88%).

LC-MS: m/z 326.1 [M+H]$^+$

3-[[2-Fluoro-5-(3-fluorophenyl)phenyl]methylamino]phenol

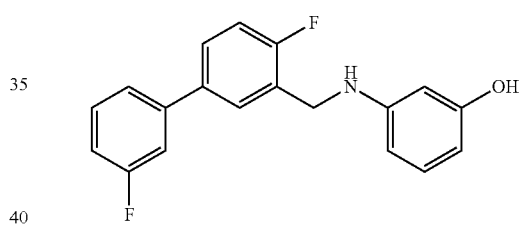

To a solution of N-[[2-fluoro-5-(3-fluorophenyl)phenyl]methyl]-3-methoxy-aniline (512 mg, 1.60 mmol, 1.0 eq) in CH$_2$Cl$_2$ (10 mL) at −70° C. was added BBr$_3$ (0.6 mL, 65.3 mmol, 40.8 eq). The reaction was warmed to room temperature and stirred for 1 h. The reaction was then cooled to 0° C. and quenched by addition of water. The pH of the solution was adjusted to pH 7 with aqueous Na$_2$CO$_3$, then extracted with EtOAc. The organic extract was washed with water and brine, dried (Na$_2$SO$_4$), filtered and evaporated in vacuo to give the title compound as a colourless oil (460 mg, 94%).

LC-MS: m/z 312.1 [M+H]$^+$

Ethyl 2-[3-[[2-fluoro-5-(3-fluorophenyl)phenyl]methylamino]phenoxy]acetate (II(s))

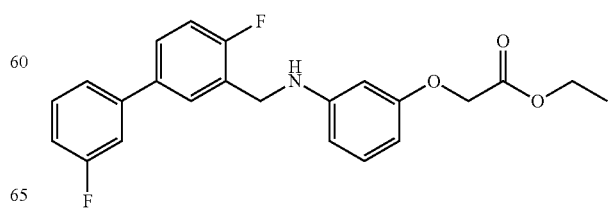

To a mixture of 3-[[2-fluoro-5-(3-fluorophenyl)phenyl]methylamino]phenol (300 mg, 0.96 mmol, 1.0 eq.) and t-BuOK (216 mg, 1.90 mmol, 2.0 eq) in DMF (3 mL) was added dropwise ethyl bromoacetate (193 mg, 128 uL, 1.20 mmol, 1.2 eq) at 0° C. The resulting mixture was stirred for 1 h at room temperature. The reaction was quenched with water and neutralized with 1 M HCl. The aqueous layer was extracted with EtOAc and the combined organic extracts were washed with brine, dried (Na$_2$SO$_4$), filtered and evaporated in vacuo. The residue obtained was purified by chromatography (petroleum ether: EtOAc, 4:1) to give the title compound as a colourless oil (200 mg, 52%).

LC-MS: m/z 398.1 [M+H]$^+$ $^1$H NMR (400 MHz, CDCl$_3$) δ 7.47-7.39 (m, 1H), 7.35-7.28 (m, 2H), 7.24 (t, J=7.9 Hz, 1H), 7.16-7.07 (m, 2H), 7.02 (d, J=7.6 Hz, 1H), 6.98 (s, 1H), 6.86-6.79 (m, 2H), 6.76 (dd, J=7.9, 2.4 Hz, 1H), 6.36 (m, 1H), 4.72 (s, 2H), 4.42 (d, J=6.2 Hz, 1H), 4.10 (q, J=7.1 Hz, 1H), 1.16 (t, J=7.1 Hz, 2H).

2-[3-[[2-Fluoro-5-(3-fluorophenyl)phenyl]methylamino]phenoxy]acetic acid (compound I(a))

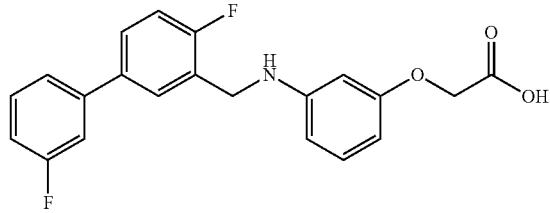 [SMILES: O=C(O)COc1cccc(NCc2cc(-c3cccc(F)c3)ccc2F)c1]

To a stirred solution of ethyl 2-[3-[[2-fluoro-5-(3-fluorophenyl)phenyl]methylamino]phenoxy]acetate (317.0 mg, 0.83 mmol, 1.0 eq) in a mixture of THF (6 mL) and H$_2$O (6 mL) was added LiOH.H$_2$O (134 mg, 3.19 mmol, 4.0 eq). The reaction was stirred at room temperature for 1 h, then diluted with water (30 mL) and the solution neutralized by addition of 1M HCl. The mixture was extracted with EtOAc, the combined organic extracts were washed with brine, dried (Na$_2$CO$_3$), filtered and evaporated in vacuo. The residue obtained was triturated with petroleum ether and EtOAc (2:1) and the solid that formed collected by filtration, washed with petroleum ether:EtOAc (2:1) and dried to give the title compound I(a) as an off-white solid (200 mg, 68%).

LC-MS: m/z 370.1 [M+H]$^+$ $^1$H NMR (400 MHz, DMSO-d$_6$) δ 7.77-7.60 (m, 1H), 7.57-7.47 (m, 1H), 7.44-7.35 (m, 1H), 7.35-7.29 (m, 2H), 7.27-7.14 (m, 1H), 7.11-7.01 (m, 1H), 6.85 (s, 1H), 6.22-6.11 (m, 2H), 6.11-6.03 (m, 1H), 6.02-5.87 (m, 1H), 4.42 (s, 2H), 4.22 (d, J=3.3 Hz, 2H)

Example 2

Compound I(b) Synthesized According to Scheme 1

2-[2,4-Difluoro-3-[[2-fluoro-5-(3-fluorophenyl)phenyl]methylamino]phenoxy]acetic acid (I(b))

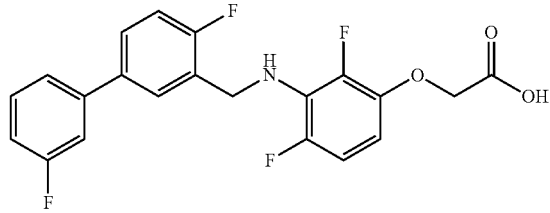 [SMILES: O=C(O)COc1ccc(F)c(NCc2cc(-c3cccc(F)c3)ccc2F)c1F]

(2,4-Difluorophenoxy)-triisopropyl-silane

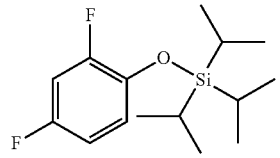

To a stirred solution of 2,4-difluorophenol (69.3 g, 0.53 mol, 1.0 eq) and imidazole (43.5 g, 0.64 mol, 1.2 eq) in DMF (300 mL) at 0° C. under N$_2$ was added TIPSCl (108 g, 0.56 mol, 1.05 eq) dropwise. After the addition was complete, the reaction mixture was allowed to warm to 25° C. and stirred for 1 h. The reaction was then poured into water and extracted with a mixture of EtOAc and petroleum ether (10:1). The combined organic extracts were washed with water and brine, dried and evaporated in vacuo. The crude residue was purified by column chromatography (petroleum ether) to give the title compound as a colourless oil (170 g, 86%).

$^1$H NMR (400 MHz, CDCl$_3$) δ 6.90 (td, J=9.2, 5.6 Hz, 1H), 6.87-6.80 (m, 1H), 6.76-6.69 (m, 1H), 1.35-1.21 (m, 3H), 1.11 (d, J=7.3 Hz, 18H)

2,6-Difluoro-3-triisopropylsilyloxy-benzoic acid

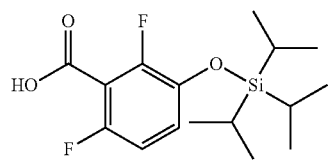 [SMILES: CC(C)[Si](Oc1ccc(F)c(C(=O)O)c1F)(C(C)C)C(C)C]

To a solution of ((2,4-difluorophenoxy)-triisopropyl-silane (50 g, 0.175 mol, 1.0 eq) in dry THF (500 mL) under N$_2$ at −60° C. was added a solution of s-BuLi (147.7 mL, 1.3 M in THF, 0.192 mol, 1.1 eq) over a period of 1 h. The reaction mixture was stirred at −60° C. for 2 h and then CO$_2$ (gas) was bubbled into the mixture. After 1 h, the reaction mixture was quenched with saturated NH$_4$Cl and extracted with EtOAc. The organic extract was washed with water and brine, dried (Na$_2$SO$_4$), filtered and evaporated in vacuo. The crude residue was purified by column chromatography (MeOH: DCM, 0:1 to 1:20) to give the title compound as a yellow oil (23.3 g, 37%).

LC-MS: m/z 329.1 [M−H]$^-$ $^1$H NMR (400 MHz, DMSO) δ 9.34 (s, 1H), 6.65 (ddd, J=11.0, 9.0, 2.2 Hz, 1H), 6.07 (td, J=9.2, 5.1 Hz, 1H), 5.04 (s, 2H)

3-Amino-2,4-difluoro-phenol (intermediate X(a))

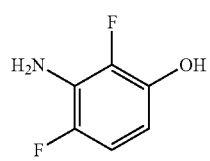

To a solution of 2,6-difluoro-3-triisopropylsilyloxy-benzoic acid (18.4 g, 0.056 mol, 1.0 eq) in DCM (180 mL) and DMF (3 drops) at 0° C. was added (COCl)$_2$ (21.19 g, 0.167 mmol, 3.0 eq) dropwise. The mixture was warmed to room temperature and stirred for 1 h. The reaction mixture was evaporated in vacuo and the residue obtained dissolved in acetone (100 mL). The resultant solution was added dropwise to a cooled solution of NaN$_3$ (14.5 g, 0.223 mol, 4.0 eq) in acetone (160 mL) and water (100 mL) at 0° C. The reaction was stirred for 1 h at 0° C. Further water was then added (200 mL) and the reaction heated at 70° C. overnight. The acetone was removed under reduced pressure and the aqueous layer extracted with EtOAc. The combined organic extracts were washed with water and brine, dried (Na$_2$SO$_4$), filtered and evaporated in vacuo. The residue obtained dissolved in EtOH (94 mL) and water (30 mL). Concentrated H$_2$SO$_4$ (30 mL) was added and the reaction heated at 110° C. overnight. The ethanol was removed under reduced pressure and the aqueous layer extracted with EtOAc. The combined organic extracts were dried (Na$_2$SO$_4$), filtered and evaporated in vacuo. The residue was purified by column chromatography (petroleum ether: EtOAc, 20:1 to 6:1) to give the title compound as a white solid (4.0 g, 50%).

LC-MS: m/z 146.1 [M+H]$^+$ $^1$H NMR (400 MHz, DMSO-d$_6$) δ 9.34 (s, 1H), 6.65 (ddd, J=11.0, 9.0, 2.2 Hz, 1H), 6.07 (ddd, J=9.2, 9.0, 5.1 Hz, 1H), 5.04 (s, 2H)

Ethyl 2-(3-amino-2,4-difluorophenoxy)acetate (intermediate IV(a))

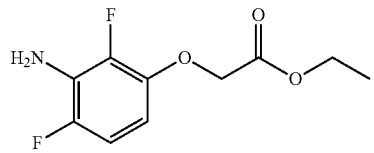 [SMILES: CCOC(=O)COc1ccc(F)c(N)c1F]

To a stirred solution of 3-amino-2,4-difluorophenol (intermediate X(a)) (713 mg, 4.9 mmol, 1.0 eq) in DMF (30 mL) was added Na$_2$CO$_3$ (1.56 g, 14.7 mmol, 3.0 eq). The resulting mixture was stirred for 40 min at room temperature. Ethyl bromoacetate (1 g, 5.90 mmol 1.2 eq) was added and the reaction stirred overnight. The reaction was diluted with water then extracted with EtOAc. The combined organic extracts were washed with brine, dried (Na$_2$SO$_4$), filtered and evaporated in vacuo. The residue was purified by chromatography (petroleum ether: EtOAc, 25:1) to give the title compound (intermediate IV(a)) as an oil (850 mg, 71%).

2-[2,4-Difluoro-3-[[2-fluoro-5-(3-fluorophenyl)benzoyl]amino]phenoxy]acetate

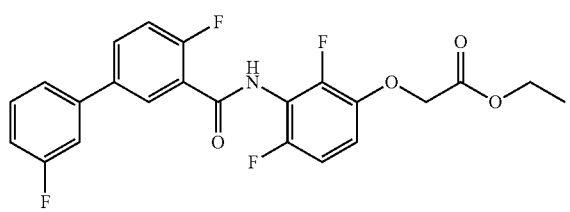 [SMILES: CCOC(=O)COc1ccc(F)c(NC(=O)c2cc(-c3cccc(F)c3)ccc2F)c1F]

2-Fluoro-5-(3-fluorophenyl)benzoic acid (intermediate III(a)) (330 mg, 1.4 mmol, 1.1 eq) was suspended in SOCl$_2$ (10 mL) and heated to reflux for 3 h. The solution was then concentrated in vacuo and the residue was dissolved in dry DCM (10 mL). Ethyl 2-(3-amino-2,4-difluoro-phenoxy)acetate (300 mg, 1.3 mmol, 1 eq) and TEA (260 mg, 2.6 mmol, 2 eq) were added and the mixture stirred at room temperature for 3 h. Water was added and the mixture extracted with CH$_2$Cl$_2$. The combined organic extracts were washed with brine, dried (Na$_2$SO$_4$), filtered and evaporated in vacuo. The residue was purified by chromatography (Hexane:ethyl acetate, 10:1 to 5:1) to give the title compound as a white solid (290 mg, 50%).

LC-MS: m/z 470.1 [M+Na]$^+$

Ethyl 2-[2,4-difluoro-3-[[2-fluoro-5-(3-fluorophenyl)phenyl]methylamino]phenoxy]acetate (II(a))

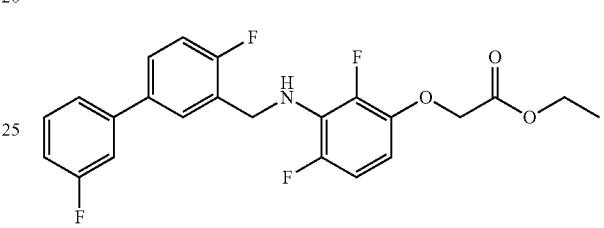

Ethyl 2-[2,4-difluoro-3-[[2-fluoro-5-(3-fluorophenyl)benzoyl]amino]phenoxy]acetate (250 mg, 0.56 mmol, 1.0 eq) was dissolved in dry THF (10 mL) and cooled to 0° C. A solution of BH$_3$ (1 M in THF, 2.8 mL, 2.8 mmol, 5.0 eq) was added dropwise. The solution was then heated at 60° C. for 2 h. The reaction was quenched by addition of methanol and evaporated in vacuo. The residue was purified by column chromatography (DCM:MeOH, 50:1 to 20:1) to give the title compound as a colourless oil (100 mg, 41%).

LC-MS: m/z 434.0 [M+H]$^+$ $^1$H NMR (300 MHz, DMSO-d$_6$) δ 7.73 (dd, J=7.2, 2.4 Hz, 1H), 7.65-7.56 (m, 1H), 7.54-7.44 (m, 1H), 7.42-7.35 (m, 2H), 7.24 (dd, J=9.9, 8.5 Hz, 1H), 7.22-7.13 (m, 1H), 6.80 (ddd, J=11.7, 9.3, 2.2 Hz, 1H), 6.35 (dt, J=9.1, 4.6 Hz, 1H), 5.88 (s, 1H), 4.74 (s, 2H), 4.52 (d, J=7.2 Hz, 2H), 4.11 (q, J=7.1 Hz, 2H), 1.15 (t, J=7.1 Hz, 3H)

2-[2,4-Difluoro-3-[[2-fluoro-5-(3-fluorophenyl)phenyl]methylamino]phenoxy]acetic acid (I(b))

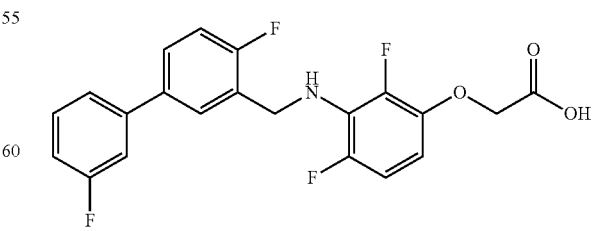

Ethyl 2-[2,4-difluoro-3-[[2-fluoro-5-(3-fluorophenyl)phenyl]methylamino]phenoxy]acetate (100 mg, 0.2 mmol, 1.0 eq) was dissolved in a mixture of THF (15 mL) and H$_2$O (10 mL). LiOH.2H₂O (55 mg, 0.8 mmol, 4.0 eq) was added and the solution heated at 60° C. overnight. The THF was removed under reduced pressure and the aqueous phase extracted with EtOAc. The organic extract was discarded and the aqueous layer acidified with 1M HCl and extracted with EtOAc. The combined organic extracts were washed with brine, dried (Na₂SO₄), filtered and evaporated in vacuo to give the title compound (I(b)) as a white solid (80 mg, 99%).

LC-MS: m/z 406.0 [M+H]⁺

¹H NMR (300 MHz, DMSO-d6) δ 13.02 (br. s., 1H, COOH), 7.74 (dd, J=7.2, 2.4 Hz, 1H), 7.64-7.55 (m, 1H), 7.54-7.44 (m, 1H), 7.43-7.34 (m, 2H), 7.24 (dd, J=8.5, 9.9 Hz, 1H), 7.22-7.13 (m, 1H), 6.80 (ddd, J=2.2, 9.3, 11.7 Hz, 1H), 6.32 (td, J=9.1, 4.6 Hz, 1H), 5.93-5.76 (m, 1H), 4.63 (s, 2H), 4.52 (d, J=7.0 Hz, 2H)

Example 3

Compound I(c) Synthesized According to Scheme 3

2-[2,4-Difluoro-3-[[5-(3-fluorophenyl)-2-methyl-phenyl]methylamino]phenoxy]acetic acid (I(c))

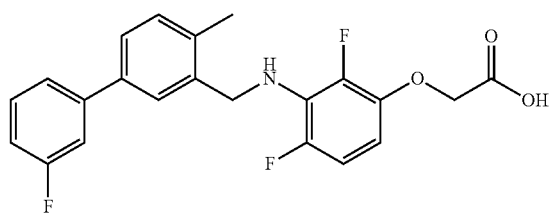 [SMILES: Cc1ccc(-c2cccc(F)c2)cc1CNc1c(F)ccc(OCC(=O)O)c1F]

5-(3-Fluorophenyl)-2-methyl-benzoic acid (intermediate III(b))

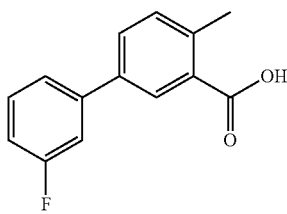 [SMILES: Cc1ccc(-c2cccc(F)c2)cc1C(=O)O]

To a solution of 5-bromo-2-methyl-benzoic acid (1 g, 5.12 mmol, 1.0 eq) and (3-fluorophenyl)boronic acid (720 mg, 4.65 mmol, 1.1 eq) in a mixture of EtOH (5 mL), DMF (20 mL) and H₂O (5 mL) were added Na₂CO₃ (1.98 g, 18.68 mmol, 4 eq) and Pd(PPh₃)₄ (270 mg, 0.23 mmol, 0.05 eq). The mixture was heated at 100° C. under N₂ for 4 h and the reaction quenched by addition of 1M HCl. The aqueous phase was extracted with EtOAc and the combined organic extracts washed with brine, dried (Na₂SO₄), filtered and evaporated in vacuo. The residue was purified by chromatography (petroleum ether:EtOAc, 20:1 to 1:1) to give the title compound as a white solid (780 mg, 68%).

LC-MS: m/z 229.0 [M−H]⁻

¹H NMR (400 MHz, DMSO-d₆) δ 13.01 (br s, 1H), 8.08 (d, J=1.9 Hz, 1H), 7.78 (dd, J=7.9, 1.9 Hz, 1H), 7.56-7.47 (m, 3H), 7.41 (d, J=8.0 Hz, 1H), 7.25-7.16 (m, 1H), 2.55 (s, 3H).

N-(2,6-Difluoro-3-hydroxy-phenyl)-5-(3-fluorophenyl)-2-methyl-benzamide

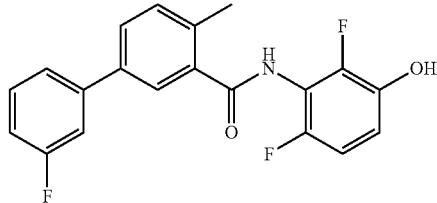 [SMILES: Cc1ccc(-c2cccc(F)c2)cc1C(=O)Nc1c(F)ccc(O)c1F]

To a solution of 5-(3-fluorophenyl)-2-methyl-benzoic acid (310 mg, 2.07 mmol, 1.0 eq) in CH₂Cl₂ (30 mL) at 0° C. was added (COCl)₂ (0.52 mL, 6.0 mmol, 3.0 eq) and DMF (2-3 drops). The reaction was stirred at 0° C. for 2 h, and then the solvent was removed in vacuo. The residue was taken up in THF (30 mL) and added to a suspension of 3-amino-2,4-difluoro-phenol (intermediate X(a)) (195.4 mg, 2.07 mmol, 1.0 eq) and NaHCO₃ (339.1 mg, 6.2 mmol, 3.0 eq) in THF (70 mL) at 0° C. The reaction was stirred for 3 h at 0° C. then quenched by addition of water and the aqueous layer extracted with EtOAc. The combined organic extracts were washed with brine, dried (Na₂SO₄), filtered and evaporated in vacuo. The crude residue was purified by chromatography (DCM:MeOH, 1:0 to 20:1) to give the title compound as a solid (230 mg, 48%).

LC-MS: m/z 358.1 [M+H]⁺ 380.1 [M+Na]⁺

2,4-Difluoro-3-[[5-(3-fluorophenyl)-2-methyl-phenyl]methylamino]phenol

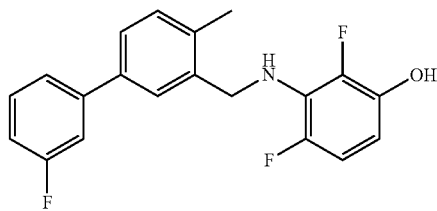 [SMILES: Cc1ccc(-c2cccc(F)c2)cc1CNc1c(F)ccc(O)c1F]

To a solution of N-(2,6-difluoro-3-hydroxy-phenyl)-5-(3-fluorophenyl)-2-methyl-benzamide (150 mg, 0.42 mmol, 1.0 eq) in THF (5 mL) was added dropwise a solution of BH₃ (1 M in THF, 3 mL, 3 mmol, 7 eq). The reaction was heated at 55° C. under N₂ for 2 h, and then quenched by the addition of 1M HCl. The aqueous layer was extracted with EtOAc and the combined organic extracts were washed with water and brine, dried (Na₂SO₄), filtered and evaporated in vacuo to give compound the title compound as a solid (124 mg, 86%).

LC-MS: m/z 344.1 [M+H]⁺

Ethyl 2-[2,4-difluoro-3-[[5-(3-fluorophenyl)-2-methyl-phenyl]methylamino]phenoxy]acetate (II(t))

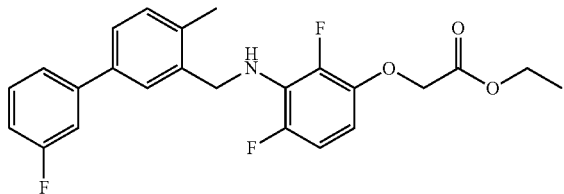 [SMILES: CCOC(=O)COc1ccc(F)c(NCc2cc(-c3cccc(F)c3)ccc2C)c1F]

To a stirred solution of 2,4-difluoro-3-[[5-(3-fluorophenyl)-2-methyl-phenyl]methyl amino]phenol (124 mg, 0.361 mmol, 1.0 eq) and $Cs_2CO_3$ (176.5 mg, 0.542 mmol, 1.5 eq) in 2-Butanone (10 mL) was added ethyl bromoacetate (72.4 mg, 0.433 mmol, 1.2 eq) and the reaction stirred 30 min. The reaction was filtered and the filtrate evaporated in vacuo. The residue obtained was purified by column chromatography (EtOAc:petroleum ether, 0:1 to 1:4) to give the title compound as an oil/gum (100 mg, 65%).

LC-MS: m/z 452.2 [M+Na]$^+$ $^1$H NMR (400 MHz, DMSO-$d_6$) δ 7.54 (s, 1H), 7.51-7.43 (m, 2H), 7.41-7.34 (m, 2H), 7.28 (d, J=7.7 Hz, 1H), 7.15 (br t, J=8.6 Hz, 1H), 6.42 (br s, 1H), 6.24-6.17 (m, 1H), 6.16-6.07 (m, 1H), 4.81 (s, 2H), 4.35 (d, J=5.8 Hz, 2H), 4.15 (q, J=7.1 Hz, 2H), 2.36 (s, 3H), 1.19 (t, J=7.1 Hz, 3H).

2-[2,4-Difluoro-3-[[5-(3-fluorophenyl)-2-methyl-phenyl]methylamino]phenoxy]acetic acid (I(c))

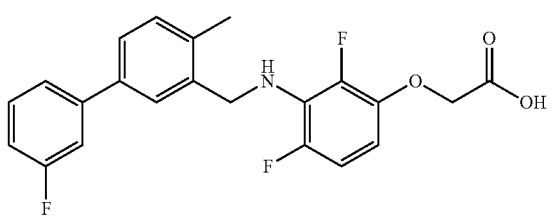 [SMILES: Cc1ccc(-c2cccc(F)c2)cc1CNc1c(F)ccc(OCC(=O)O)c1F]

To a stirred solution of ethyl 2-[2,4-difluoro-3-[[5-(3-fluorophenyl)-2-methyl-phenyl]methylamino]phenoxy]acetate (100 mg, 0.23 mmol, 1.0 eq) in THF (8 mL) was added NaOH (1M aqueous solution, 3 mL, 3 mmol, 13.0 eq) at room temperature. The reaction was stirred at room temperature for 2 h. The THF was evaporated in vacuo and the aqueous layer acidified to pH 3 by addition of 1M HCl. The resultant precipitate was collected by filtration and dried in vacuo to give the title compound (I(c)) as a white solid (85 mg, 91%).

LC-MS: m/z 401.9 [M+H]$^+$ $^1$H NMR (300 MHz, DMSO-$d_6$) δ (13.03, br. s., 1H, COOH), 7.59 (s, 1H), 7.54-7.32 (m, 4H), 7.24 (d, J=7.8 Hz, 1H), 7.15 (td, J=8.4, 1.7 Hz, 1H), 6.80 (ddd, J=11.6, 9.4, 2.1 Hz, 1H), 6.31 (td, J=9.1, 4.6 Hz, 1H), 5.74 (br. s., 1H), 4.64 (s, 2H), 4.46 (d, J=6.1 Hz, 2H), 2.32 (s, 3H)

Example 4

Compound I(d) Synthesized According to Scheme 4

2-[2,4-Difluoro-3-[[3-(3-fluorophenyl)-5-methyl-phenyl]methylamino]phenoxy]acetic acid (I(d))

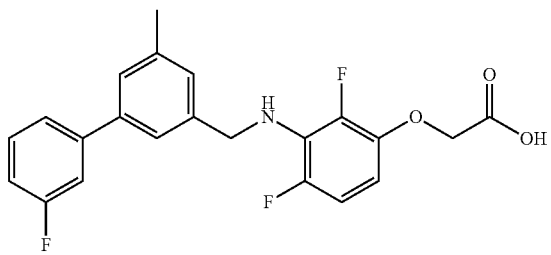 [SMILES: Cc1cc(CNc2c(F)ccc(OCC(=O)O)c2F)cc(-c2cccc(F)c2)c1]

Isopropyl 2-(3-amino-2,4-difluoro-phenoxy)acetate (intermediate IV(b))

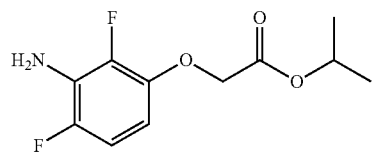 [SMILES: CC(C)OC(=O)COc1ccc(F)c(N)c1F]

To a stirred solution of 3-amino-2,4-difluoro-phenol (intermediate X(a)) (713 mg, 4.91 mmol, 1.0 eq) in DMF (20 mL) was added $Na_2CO_3$ (1.56 g, 14.8 mmol, 3.0 eq). The resulting mixture was stirred at room temperature for 35 min, then isopropyl bromoacetate (1.07 g, 5.90 mmol, 1.2 eq) was added and the reaction stirred at room temperature overnight. The reaction was diluted with water then extracted with EtOAc. The combined organic extracts were washed with brine, dried ($Na_2SO_4$), filtered and evaporated in vacuo. The residue was purified by chromatography (EtOAc:petroleum ether, 0:1 to 1:6) to give the title compound (intermediate IV(b)) as an oil (850 mg, 71%).

LC-MS: m/z 246.1 [M+H]$^+$ 268.1 [M+Na]$^+$

1-Bromo-3-(bromomethyl)-5-methyl-benzene

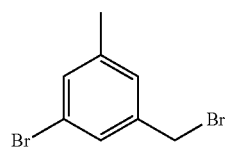

A solution of 1-bromo-3,5-dimethyl-benzene (1.0 g, 5.4 mmol, 1.0 eq), NBS (1.06 g, 5.94 mmol, 1.1 mmol) and AIBN (180 mg, 1.08 mmol, 0.2 eq) in $CCl_4$ (20 mL) was stirred at reflux overnight. The reaction was then diluted with water and extracted with $CH_2Cl_2$. The organic extracts were combined and washed with aqueous $NaHCO_3$, dried ($Na_2SO_4$), filtered and the solvent removed in vacuo. The residue was purified by flash chromatography (Petroleum ether:EtOAc, 1:0 to 10:1) to give the title compound as a light yellow oil (1.2 g, 84%).

$^1$H NMR (400 MHz, DMSO) δ 7.36 (s, 1H), 7.28 (s, 1H), 7.19 (s, 1H), 4.47 (s, 2H), 2.31 (s, 3H)

Isopropyl 2-[3-[(3-bromo-5-methyl-phenyl)methylamino]-2,4-difluoro-phenoxy]acetate

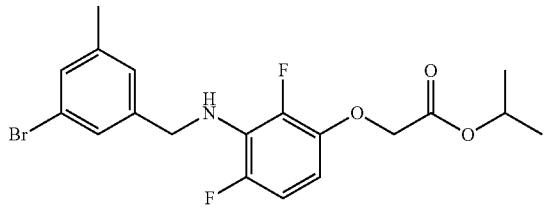 [SMILES: Cc1cc(Br)cc(CNc2c(F)ccc(OCC(=O)OC(C)C)c2F)c1]

To a solution of isopropyl 2-(3-amino-2,4-difluoro-phenoxy)acetate (intermediate IV(b)) (350 mg, 1.43 mmol, 1.0 eq) and 1-bromo-3-(bromomethyl)-5-methyl-benzene (528 mg, 1.99 mmol, 1.4 eq) in DMSO (15 mL) was added K$_2$CO$_3$ (593 mg, 4.29 mmol, 3.0 eq). The reaction was heated at 100° C. for 1 h in a microwave reactor, then diluted with water and extracted with EtOAc. The combined organic extracts were washed with brine, dried (Na$_2$SO$_4$), filtered and evaporated in vacuo. The residue was purified by chromatography (petroleum ether: EtOAc, 100:1 to 80:1) to give the title compound as a light yellow oil (192 mg, 16%).

LC-MS: m/z 428.1, 430.1 [M+H]$^+$

Isopropyl 2-[2,4-difluoro-3-[[3-(3-fluorophenyl)-5-methyl-phenyl]methylamino]phenoxy]acetate (II(e))

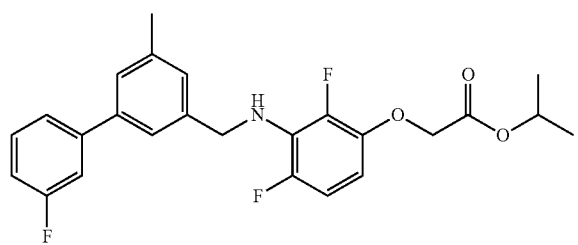 [SMILES: Cc1cc(CNc2c(F)ccc(OCC(=O)OC(C)C)c2F)cc(-c2cccc(F)c2)c1]

To a solution of isopropyl 2-[3-[(3-bromo-5-methyl-phenyl)methylamino]-2,4-difluoro-phenoxy]acetate (176 mg, 0.4 mmol, 1.0 eq) in acetonitrile (15 mL) was added 3-fluorophenylboronic acid (86 mg, 0.61 mmol, 1.5 eq), K$_2$CO$_3$ (142 mg, 1.03 mmol, 2.5 eq) and Pd(dppf)Cl$_2$ (15 mg, 0.02 mmol, 0.05 eq). The mixture was heated at reflux overnight then the solvent was removed in vacuo. The residue was diluted with CH$_2$Cl$_2$, washed with water, dried (MgSO$_4$), filtered and evaporated in vacuo. The residue was purified by chromatography (petroleum ether: EtOAc, 150:1 to 60:1) to give the title compound as an oil (140 mg, 77%).

LC-MS: m/z 443.9 [M+H]$^+$ $^1$H NMR (300 MHz, DMSO-d$_6$): δ 7.56-7.32 (m, 5H), 7.24-7.11 (m, 1H), 7.13 (s, 1H), 6.78 (ddd, J=11.6, 9.4, 2.1 Hz, 1H), 6.28 (td, J=9.0, 4.6 Hz, 1H), 6.03-5.87 (m, 1H), 4.93 (spt, J=6.3 Hz, 1H), 4.69 (s, 2H), 4.42 (d, J=7.2 Hz, 2H), 2.32 (s, 3H), 1.15 (d, J=6.2 Hz, 6H)

2-[2,4-Difluoro-3-[[3-(3-fluorophenyl)-5-methyl-phenyl]methylamino]phenoxy]acetic acid (I(d))

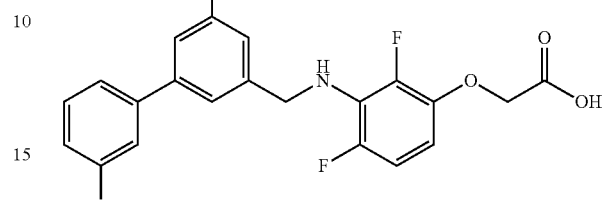

To a stirred solution of isopropyl 2-[2,4-difluoro-3-[[3-(3-fluorophenyl)-5-methylphenyl]methylamino]phenoxy]acetate (127 mg, 0.29 mmol, 1.0 eq) in THF (3 mL) was added NaOH (2M aqueous solution, 0.57 mL, 1.15 mmol, 4.0 eq) at room temperature. The reaction was stirred at room temperature for 1 h and then the THF removed in vacuo and the aqueous residue adjusted to pH 4 by addition of 1M HCl. The precipitate was collected by filtration, dried in vacuo and crystallized from CH$_2$Cl$_2$ and petroleum ether to give the title compound (I(d)) as a white solid (50 mg, 44%).

LC-MS: m/z 401.9 [M+H]$^+$ $^1$H NMR (300 MHz, DMSO-d$_6$) δ 13.05 (br. s., 1H), 7.58-7.28 (m, 5H), 7.24-7.04 (m, 2H), 6.77 (ddd, J=11.7, 9.4, 2.0 Hz, 1H), 6.27 (td, J=9.1, 4.6 Hz, 1H), 6.02-5.84 (m, 1H), 4.61 (s, 2H), 4.42 (d, J=6.9 Hz, 2H), 2.32 (s, 3H)

Example 5

Compound I(e) Synthesized According to Scheme 3

2-[2,4-Difluoro-3-[[3-(3-fluorophenyl)phenyl]methylamino]phenoxy]acetic acid (I(e))

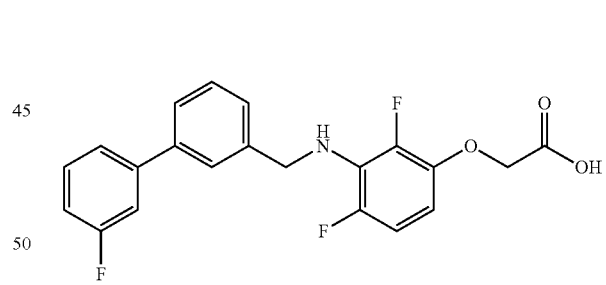

3-(3-Fluorophenyl)benzoic acid (intermediate III(c))

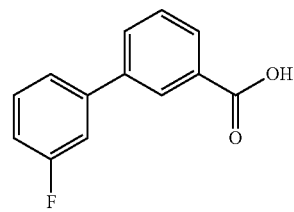 [SMILES: O=C(O)c1cccc(-c2cccc(F)c2)c1]

To a solution of (3-fluorophenyl)boronic acid (790 mg, 3.57 mmol, 1.0 eq), 3-bromobenzoic acid (790 mg, 3.93 mmol, 1.1 eq) and Na$_2$CO$_3$ (142 mg, 1.03 mmol, 2.5 eq) in a mixture of EtOH (2.5 mL), DMF (10 mL) and H$_2$O (2.5 mL) was added Pd(PPh$_3$)$_4$ (170 mg, 0.18 mmol, 0.05 eq). The mixture was stirred at 100° C. overnight. Water was added and the aqueous layer was extracted with EtOAc and the organic extract was discarded. The aqueous layer was acidified to pH 4-5 with 1M HCl and extracted with EtOAc. The combined organic extracts were filtered through silica gel and evaporated in vacuo to give the title compound as a white solid (440 mg, 56%).

LC-MS: m/z 239.1 [M+Na]$^+$

N-(2,6-Difluoro-3-hydroxy-phenyl)-3-(3-fluorophenyl)benzamide

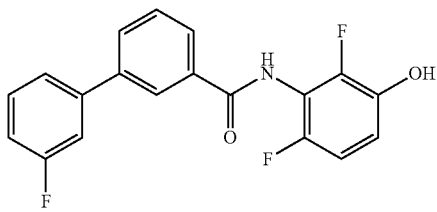 [SMILES: O=C(Nc1c(F)ccc(O)c1F)c1cccc(-c2cccc(F)c2)c1]

To a stirred solution of 3-(3-fluorophenyl)benzoic acid (430 mg, 1.99 mmol, 1.1 eq), in CH$_2$Cl$_2$ (10 mL) and DMF (0.15 mL) at 0° C. was added (COCl)$_2$ (760 mg, 5.97 mmol, 3.3 eq) dropwise. The reaction was stirred for 2 h, then the solvent removed. The residue dissolved in THF (6 mL) and added to a mixture of 3-amino-2,4-difluoro-phenol (intermediate X(a)) (262.5 mg, 1.81 mmol, 1.0 eq) and NaHCO$_3$ (760 mg, 9.05 mmol, 5 eq) in THF (6 mL) at 0° C. The reaction was stirred for 3 h then quenched by addition of water. The aqueous layer was extracted with EtOAc and the combined organic extracts were washed with Na$_2$CO$_3$, water and brine, dried (Na$_2$SO$_4$), filtered and evaporated in vacuo. The crude residue was crystallised from petroleum ether:EtOAc 3:1 to give the title compound (310 mg, 50%). Evaporation of the filtrate provided a further 180 mg of impure material.

LC-MS: m/z 344.1 [M+H]$^+$ 2,4-Difluoro-3-[[3-(3-fluorophenyl)phenyl]methylamino]phenol

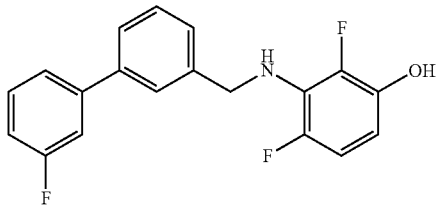 [SMILES: Oc1ccc(F)c(NCc2cccc(-c3cccc(F)c3)c2)c1F]

To a solution of N-(2,6-difluoro-3-hydroxy-phenyl)-3-(3-fluorophenyl)benzamide (310 mg, 0.9 mmol, 1.0 eq) in THF (5 mL) was added BH$_3$ (5.4 mL, 1M in THF, 5.4 mmol, 6.0 eq) and the reaction heated at 60° C. overnight. The reaction mixture was quenched with water and extracted with EtOAc. The organic extract was washed with water and brine, dried (Na$_2$SO$_4$) and evaporated in vacuo. The residue was purified by column chromatography (petroleum ether:EtOAc 1:0 to 10:1) to give the title compound as an oil (255 mg, 86%).

LC-MS: m/z 330.1 [M+H]$^+$

Ethyl 2-[2,4-difluoro-3-[[3-(3-fluorophenyl)phenyl]methylamino]phenoxy]acetate (II(u))

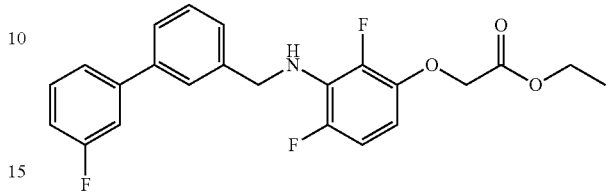

To a stirred solution of 2,4-difluoro-3-[[3-(3-fluorophenyl)phenyl]methylamino]phenol (250 mg, 0.76 mmol, 1.0 eq) in acetone (3 mL) was added Cs$_2$CO$_3$ (297 mg, 0.912 mmol, 1.2 eq). The resulting mixture was stirred for 40 min at room temperature then ethyl bromoacetate (139.4 mg, 0.84 mmol, 1.1 eq) was added. The resulting mixture was stirred overnight then partitioned against water and extracted with EtOAc. The combined organic extracts were washed with water and brine, dried (Na$_2$SO$_4$) and evaporated in vacuo. The residue was purified by column chromatography (petroleum ether:EtOAc 1:0 to 20:1) to give the title compound as an oil (270 mg, 86%).

LC-MS: m/z 438.1 [M+Na]$^+$ $^1$H NMR (400 MHz, DMSO-d$_6$) δ 7.65 (br s, 1H), 7.56-7.36 (m, 5H), 7.32 (d, J=7.4 Hz, 1H), 7.23-7.16 (m, 1H), 6.82-6.73 (m, 1H), 6.30 (td, J=9.2, 4.6 Hz, 1H), 6.06-5.97 (m, 1H), 4.73 (s, 2H), 4.47 (d, J=7.1 Hz, 2H), 4.12 (q, J=7.1 Hz, 2H), 1.16 (t, J=7.1 Hz, 3H).

2-[2,4-Difluoro-3-[[3-(3-fluorophenyl)phenyl]methylamino]phenoxy]acetic acid (I(e))

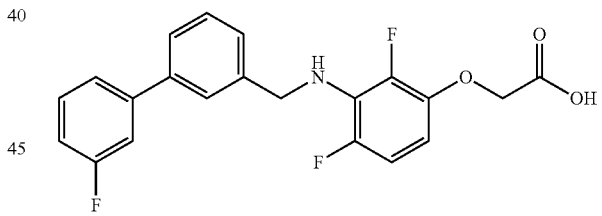

To a stirred solution of intermediate ethyl 2-[2,4-difluoro-3-[[3-(3-fluorophenyl)phenyl]methylamino]phenoxy]acetate (270 mg, 0.65 mmol, 1.0 eq) in THF (4 mL) was added NaOH (2 M aqueous solution, 2.5 mL, 5 mmol, 7.7 eq). The reaction was stirred at room temperature for 1 h. Water was added and the THF removed in vacuo. The aqueous layer was extracted with EtOAc and the combined organic extracts washed with water and brine, dried (Na$_2$SO$_4$), filtered and evaporated in vacuo. The crude material obtained was crystallised from CH$_2$Cl$_2$/petroleum ether, collected by filtration and dried in vacuo to give the title compound (I(e)) as a white solid (190 mg, 75%).

LC-MS: m/z 387.9 [M+H]$^+$ $^1$H NMR (300 MHz, DMSO-d$_6$) δ (13.03, br. s., 1H, COOH), 7.65 (s, 1H), 7.58-7.42 (m, 4H), 7.39 (t, J=7.7 Hz, 1H), 7.35-7.27 (m, 1H), 7.19 (dddd, J=8.9, 7.6, 2.6, 1.5 Hz, 1H), 6.77 (ddd, J=11.8, 9.3, 2.2 Hz, 1H), 6.27 (td, J=9.1, 4.5 Hz, 1H), 6.11-5.90 (m, 1H), 4.61 (s, 2H), 4.46 (d, J=7.0 Hz, 2H)

Example 6

Compound I(f) Synthesized According to Scheme 3

2-[2,4-Difluoro-3-[[2-fluoro-3-(3-fluorophenyl)-5-hydroxy-phenyl]methylamino]phenoxy]acetic acid (I(f))

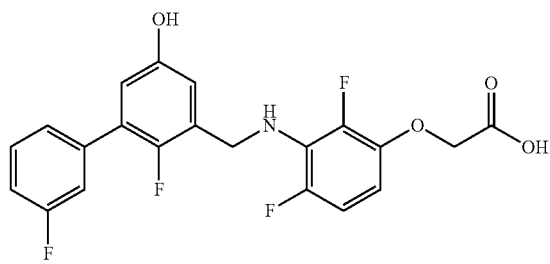

2-Fluoro-5-methoxy-benzoic acid

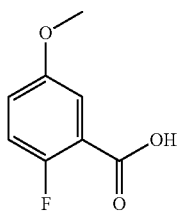

To a solution of 1-fluoro-4-methoxy-benzene (5 g, 39.6 mmol, 1.0 eq) and PMDTA (7.56 g, 43.62 mmol, 1.1 eq) in dry THF (100 mL) at −60° C. under $N_2$ was added a solution of s-BuLi (1.3 M, 36.6 mL, 47.5 mmol, 1.2 eq) over a period of 1 h. The reaction mixture was stirred at −60° C. for 2 h and then $CO_2$ (gas) was bubbled into the solution for 1 h. The reaction mixture was then warmed to room temperature, acidified by addition of 1M HCl and extracted with EtOAc. The combined organic extracts were washed with water and brine, dried ($Na_2SO_4$), filtered and evaporated in vacuo. The residue was purified by column chromatography (EtOAc:petroleum ether, 0:1 to 1:1) to give the title compound as a yellow solid (5.4 g, 80%).

LC-MS: m/z 171.1 [M+H]$^+$ 193.0 [M+Na]$^+$ $^1$H NMR (400 MHz, DMSO-$d_6$) δ 13.33 (s, 1H), 7.31 (m, 1H), 7.24 (m, 1H), 7.20-7.16 (m, 1H), 3.78 (s, 3H)

2-Fluoro-3-iodo-5-methoxy-benzoic acid

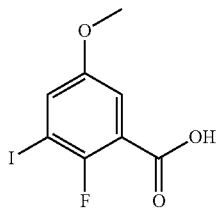

To a solution of 2,2,6,6-tetramethylpiperidine (42 g, 298 mmol, 2.5 eq) in THF at −60° C. under $N_2$ was added n-BuLi (2.2 M, 141 mL, 309.3 mmol, 2.6 eq) dropwise over a period of 30 min. The reaction mixture was stirred at −60° C. for 2 h, then a solution of 2-fluoro-5-methoxy-benzoic acid (15 g, 119 mmol, 1.0 eq) in THF (300 mL) was added dropwise with stirring. The reaction was stirred for a further 2 h at −60° C., then iodine (45 g, 179 mmol, 1.5 eq) was added in portions. The reaction was warmed to room temperature slowly and the resulting mixture acidified by addition of 1M HCl and extracted with EtOAc. The organic extract was washed with water and brine, dried ($Na_2SO_4$), filtered and evaporated in vacuo. The residue was purified by column chromatography (EtOAc:petroleum ether, 0:1 to 1:1) to give the title compound as a yellow solid (5.6 g, 16%).

2-Fluoro-3-(3-fluorophenyl)-5-methoxy-benzoic acid (intermediate III(d))

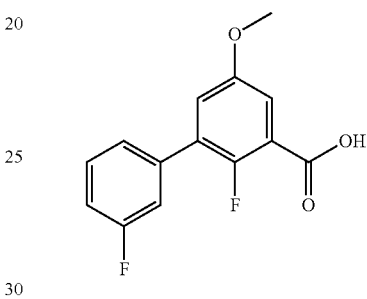

To a solution of 2-fluoro-3-iodo-5-methoxy-benzoic acid (3.0 g 10.14 mmol, 1.0 eq) in a mixture of water (30 mL), EtOH (30 mL) and DMF (60 mL), was added 3-fluorophenylboronic acid (1.56 g 11.15 mmol, 1.1 eq) and $Na_2CO_3$ (4.3 g, 40.56 mmol, 4.0 eq). The mixture was stirred at room temperature under $N_2$ for 10 mins then Pd(PPh$_3$)$_4$ (1.17 g, 1.01 mmol, 0.1 eq) was added. The mixture was heated at 100° C. for 5 h then cooled to room temperature and acidified with 1M HCl. The aqueous layer was extracted with EtOAc and the combined extracts were washed with water, dried ($Na_2SO_4$), filtered and evaporated in vacuo. The residue was purified by column chromatography (EtOAc:petroleum ether, 0:1 to 1:3) to give the title compound as a yellow solid (2.2 g, 81%).

LC-MS: m/z 219.1 [M−COOH]$^-$

N-(2,6-Difluoro-3-hydroxy-phenyl)-2-fluoro-3-(3-fluorophenyl)-5-methoxy-benzamide

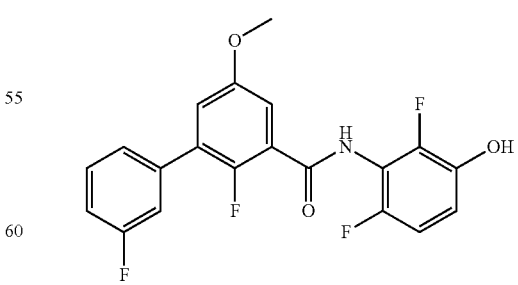

To a solution of 2-fluoro-3-(3-fluorophenyl)-5-methoxy-benzoic acid (402 mg, 1.52 mmol, 1.1 eq) in CH$_2$Cl$_2$ (20 mL) at 0° C. was added oxalylchloride (525 mg, 4.14 mmol, 3.0 eq) and DMF (5 drops). The solution was stirred at 0° C. for 2 h then the solvent removed in vacuo. The residue was taken up in THF (10 mL) and added dropwise to a mixture of 3-amino-2,4-difluorophenol (intermediate X(a)) (200 mg, 1.38 mmol, 1.0 eq) and NaHCO$_3$ (348 mg, 4.14 mmol, 3.0 eq) in THF (10 mL) at 0° C. The mixture was stirred at 0° C. for 4 h then poured into water and extracted with EtOAc. The organic extract was washed with water, brine, dried (Na$_2$SO$_4$) filtered and evaporated in vacuo. The residue was purified by column chromatography (EtOAc:petroleum ether, 0:1 to 1:3) to give the title compound as a white solid (300 mg, 50%).

LC-MS: m/z 392.1 [M+H]$^+$ 2,4-Difluoro-3-[[2-fluoro-3-(3-fluorophenyl)-5-methoxy-phenyl]methylamino]phenol

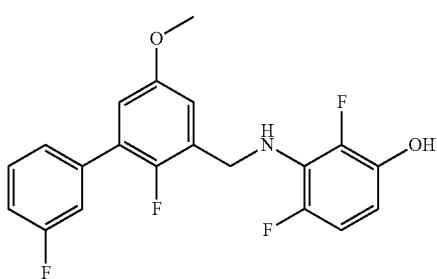 [SMILES: COc1cc(CNc2c(F)ccc(O)c2F)c(F)c(-c2cccc(F)c2)c1]

To a solution of N-(2,6-difluoro-3-hydroxy-phenyl)-2-fluoro-3-(3-fluorophenyl)-5-methoxy-benzamide (300 mg, 0.77 mmol, 1.0 eq) in THF (10 mL) at 0° C. under N$_2$ was added a solution of BH$_3$ (1M in THF, 4 mL, 4.0 mmol, 5.2 eq) dropwise. The reaction mixture was heated to 60° C. and stirred for 1.5 h. The reaction was cooled to room temperature then quenched by addition of 1M HCl. The mixture was stirred at room temperature for 1.5 h, then extracted with EtOAc. The organic extract was washed with water and brine, dried (Na$_2$SO$_4$), filtered and evaporated in vacuo. The residue was purified by column chromatography (EtOAc:petroleum ether, 0:1 to 1:4) to give the title compound as a yellow oil (180 mg, 62%).

LC-MS: m/z 378.1 [M+H]$^+$ 400.1 [M+Na]$^+$

Ethyl 2-[2,4-difluoro-3-[[2-fluoro-3-(3-fluorophenyl)-5-methoxy-phenyl]methylamino]phenoxy]acetate

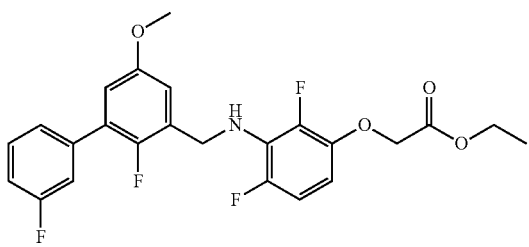 [SMILES: CCOC(=O)COc1ccc(F)c(NCc2cc(OC)cc(-c3cccc(F)c3)c2F)c1F]

To a stirred solution of 2,4-difluoro-3-[[2-fluoro-3-(3-fluorophenyl)-5-methoxy-phenyl]methylamino]phenol (180 mg, 0.48 mmol, 1.0 eq) in DMF (4 mL) was added Cs$_2$CO$_3$ (233 mg, 0.72 mmol, 1.5 eq). The resulting mixture was stirred for 40 min at room temperature then ethyl bromoacetate (96 mg, 0.57 mmol, 1.2 eq) was added. The resulting mixture was stirred at room temperature for 2 h then water added and the aqueous layer extracted with EtOAc. The combined organic extracts were washed with brine, dried (Na$_2$SO$_4$), filtered and evaporated in vacuo. The crude residue was purified by chromatography (EtOAc:petroleum ether, 0:1 to 1:10) to give the title compound as an oil (150 mg, 68%).

LC-MS: m/z 486.1 [M+Na]$^+$

Ethyl 2-[2,4-difluoro-3-[[2-fluoro-3-(3-fluorophenyl)-5-hydroxy-phenyl]methylamino]phenoxy]acetate (II(v))

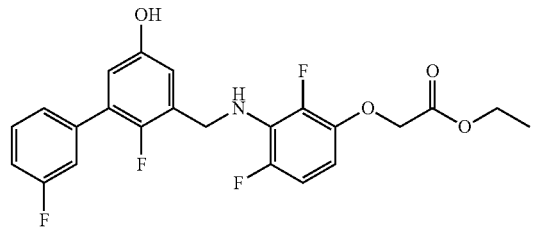 [SMILES: CCOC(=O)COc1ccc(F)c(NCc2cc(O)cc(-c3cccc(F)c3)c2F)c1F]

To a solution of 2-[2,4-difluoro-3-[[2-fluoro-3-(3-fluorophenyl)-5-methoxy-phenyl]methylamino]phenoxy]acetate (150 mg, 0.32 mmol, 1.0 eq) and AlCl$_3$ (259 mg, 1.94 mmol, 6.0 eq) in CH$_2$Cl$_2$ (5 mL) at 0° C. was added ethanethiol (120 mg, 1.94 mmol, 6.0 eq). The reaction mixture was stirred at 0° C. for 3 h. The resulting mixture was poured into water and extracted with CH$_2$Cl$_2$. The organic extract was dried (Na$_2$SO$_4$), filtered and evaporated in vacuo and the residue purified by column chromatography (EtOAc:petroleum ether, 0:1 to 1:2) to give the title as a yellow oil (120 mg, 82%).

LC-MS: m/z 472.1 [M+Na]$^+$

2-[2,4-Difluoro-3-[[2-fluoro-3-(3-fluorophenyl)-5-hydroxy-phenyl]methylamino]phenoxy]acetic acid (I(f))

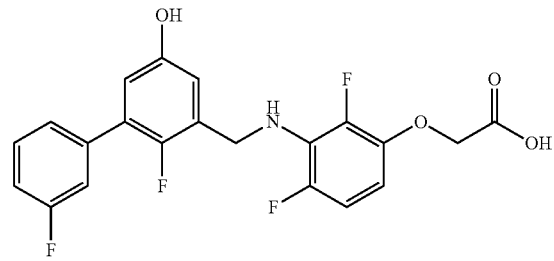

To a stirred solution of ethyl 2-[2,4-difluoro-3-[[2-fluoro-3-(3-fluorophenyl)-5-hydroxy-phenyl]methylamino]phenoxy]acetate (120 mg, 0.27 mmol, 1.0 eq) in THF (6 mL) at room temperature was added NaOH (1M aqueous solution, 3 mL, 3.0 mmol, 11.1 eq). The reaction was stirred at room temperature for 2 h. The solvent was then removed in vacuo and the solid obtained taken up in water and the aqueous layer acidified to pH 3-6 by addition of 1M HCl. The aqueous layer was extracted with EtOAc and the combined organic extracts were washed with water and brine, dried (Na$_2$SO$_4$) and evaporated in vacuo to give the title compound (I(f)) as a gummy solid (105 mg, 94%).

LC-MS: m/z 421.9 [M+H]$^+$ $^1$H NMR (300 MHz, DMSO-d$_6$) δ (13.08, bb, 1H, COOH); 9.44 (s, 1H); 7.50 (q, 1H); 7.39-7.20 (m, 3H); 6.89 (m, 1H); 6.79 (m, 1H); 6.68 (t, 1H); 6.19 (m, 1H); 5.72 (m, 1H); 4.68 (s, 2H); 4.47 (d, J=6 Hz, 2H)

Example 7

Compound I(g) Prepared According to Scheme 3

2-[2,4-Difluoro-3-[[2-fluoro-3-(3-fluorophenyl)-5-methyl-phenyl]methylamino]phenoxy]acetic acid (I(g))

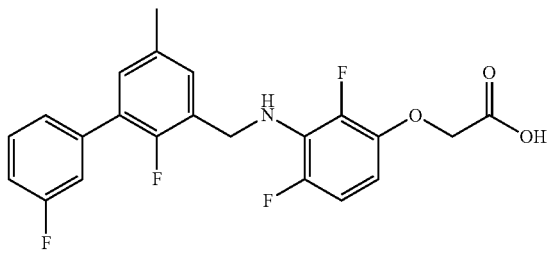

3-Bromo-2-fluoro-5-methyl-benzoic acid

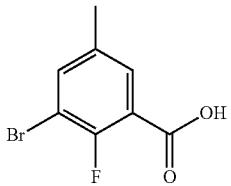

To a solution of diisopropylamine (590 mg, 5.8 mmol, 1.1 eq) in dry THF (15 mL) at −78° C. was added n-BuLi (2.6 mL, 5.8 mmol, 1.2 eq) dropwise. The solution was stirred at −78° C. for 30 min, then a solution of 2-bromo-1-fluoro-4-methyl-benzene (1 g, 5.3 mmol, 1.0 eq) in dry THF (5 mL) was added dropwise. After stirring for a further 1.5 h at −78° C., CO$_2$ gas was bubbled into the solution. The reaction was warmed to room temperature and allowed to stir for a further 1 h. The reaction was then quenched by addition of aqueous NH$_4$Cl and the THF removed under reduced pressure. The aqueous residue was acidified to pH 5 and the solid that formed collected by filtration, washed with water and dried to give the title compound as a solid (700 mg, 58%).

$^1$H NMR (400 MHz, DMSO-d$_6$) δ 7.78 (dd, J=6.0, 2.2 Hz, 1H), 7.66 (dd, J=6.4, 2.2 Hz, 1H), 2.33 (s, 3H)

2-Fluoro-3-(3-fluorophenyl)-5-methyl-benzoic acid (intermediate III(e))

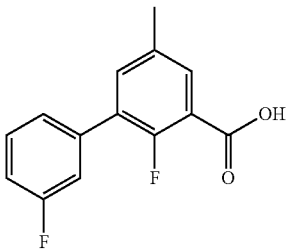 [SMILES: Cc1cc(C(=O)O)c(F)c(-c2cccc(F)c2)c1]

A mixture of 3-bromo-2-fluoro-5-methyl-benzoic acid (400 mg, 1.7 mmol, 1.0 eq), (3-fluorophenyl)boronic acid (720 mg, 5.2 mmol, 3.0 eq), K$_2$CO$_3$ (356 mg, 2.6 mmol, 1.5 eq) and Pd(PPh$_3$)$_4$ (396.0 mg, 0.40 mmol, 0.2 eq) in acetonitrile (5 mL) and H$_2$O (4 mL) was heated at reflux overnight. The reaction was acidified to pH 3 by addition of 1M HCl and extracted with EtOAc. The combined organic extracts were washed with water and brine, dried (Na$_2$SO$_4$), filtered and evaporated in vacuo. The residue was purified by chromatography (EtOAc:petroleum ether, 0:1 to 1:4) to give the title compound as a solid (160 mg, 75%).

LC-MS: m/z 249.0 [M+H]$^+$ 271.0 [M+Na]$^+$ $^1$H NMR (400 MHz, DMSO-d$_6$) δ 13.30 (br s, 1H), 7.67 (br d, J=6.3 Hz, 1H), 7.59-7.48 (m, 2H), 7.38 (d, J=7.5 Hz, 2H), 7.32-7.23 (m, 1H), 2.36 (s, 3H).

N-(2,6-Difluoro-3-hydroxy-phenyl)-2-fluoro-3-(3-fluorophenyl)-5-methyl-benzamide

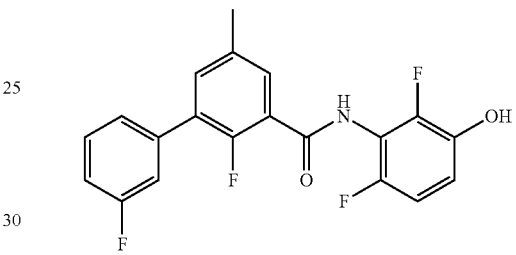

To a stirred solution of 2-fluoro-3-(3-fluorophenyl)-5-methyl-benzoic acid (400 mg, 1.65 mmol, 1.1 eq) in CH$_2$Cl$_2$ (10 mL) was added oxalylchloride (0.5 mL, 5.9 mmol, 4.0 eq) and DMF (2 drops). The reaction was stirred for 1 h, then the solvent removed in vacuo and the residue dissolved in THF (10 mL). The solution was then added dropwise to a mixture of 3-amino-2,4-difluoro-phenol (intermediate X(a)) (212 mg. 1.50 mmol, 1.0 eq) and NaHCO$_3$ (492 mg, 5.90 mmol, 4.0 eq) in THF (10 mL) at room temperature. The reaction was stirred overnight then poured into water and extracted with EtOAc. The combined organic extracts were washed with water and brine, dried (Na$_2$SO$_4$), filtered and evaporated in vacuo. The residue was purified by chromatography (EtOAc:petroleum ether, 0:1 to 1:3) to give the title compound as a solid (130 mg, 24%).

LC-MS: m/z 376.1 [M+H]$^+$ 398.1 [M+Na]$^+$ 2,4-Difluoro-3-[[2-fluoro-3-(3-fluorophenyl)-5-methyl-phenyl]methylamino]phenol

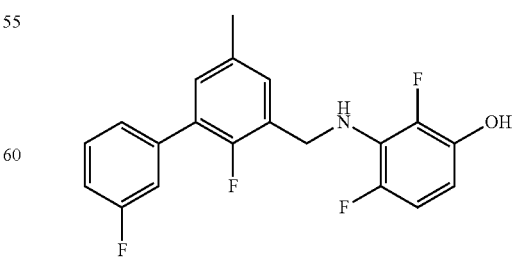

To a solution of N-(2,6-difluoro-3-hydroxy-phenyl)-2-fluoro-3-(3-fluorophenyl)-5-methyl-benzamide (130 mg, 0.30 mmol, 1.0 eq) in THF (25 mL) was added dropwise a solution of borane (1M in THF, 1.2 mL, 1.2 mmol, 4 eq) under N₂. The reaction was heated at 60° C. overnight. TLC showed the reaction was not complete so further borane (1 M in THF, 1.0 mL, 1 mmol) was added and heating continued at 60° C. for 2 h. The mixture was poured into water and extracted with EtOAc and the combined organic extracts washed with water and brine, dried (Na₂SO₄), filtered and evaporated in vacuo. The residue obtained was purified by chromatography (EtOAc:petroleum ether, 0:1 to 1:4) to give the title compound as an oil (100 mg, 80%).

LC-MS: m/z 362.1 [M+H]⁺

Ethyl 2-[2,4-difluoro-3-[[2-fluoro-3-(3-fluorophenyl)-5-methyl-phenyl]methylamino]phenoxy]acetate (II(w))

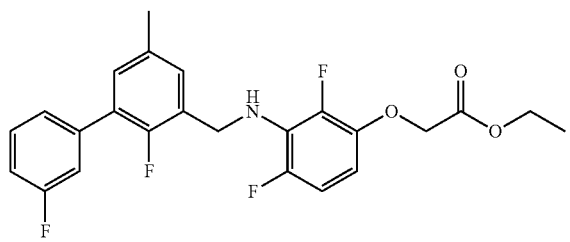 [SMILES: CCOC(=O)COc1ccc(F)c(NCc2cc(C)cc(-c3cccc(F)c3)c2F)c1F]

To a stirred solution of 2,4-difluoro-3-[[2-fluoro-3-(3-fluorophenyl)-5-methyl-phenyl]methylamino]phenol (100 mg, 0.30 mmol, 1.0 eq) and Na₂CO₃ (58 mg, 0.60 mmol, 2.0 eq) in 2-butanone (10 mL) was added ethyl bromoacetate (75.1 mg, 0.45 mmol, 1.5 eq). The mixture was stirred at room temperature for 3 h. TLC showed the reaction to be incomplete so Cs₂CO₃ (50 mg, 0.15 mmol, 0.5 eq) was added and the reaction stirred a further 3 h. TLC showed the reaction was still not finished so ethyl bromoacetate (0.2 mL) was added and the reaction stirred for a further 1 h. The solution was then poured into water and extracted with EtOAc. The combined organic extracts were washed with water and brine, dried (Na₂SO₄) and evaporated in vacuo. The residue was purified by chromatography (EtOAc:petroleum ether, 0:1 to 1:10) to give the title compound as a solid (100 mg, 81%).

LC-MS: m/z 448.2 [M+H]⁺ 470.1 [M+Na]⁺

¹H NMR (400 MHz, CDCl₃) δ 7.44-7.35 (m, 1H), 7.34-7.20 (m, 2H), 7.13 (dd, J=9.6, 7.0 Hz, 2H), 7.06 (td, J=8.3, 2.2 Hz, 1H), 6.75-6.65 (m, 1H), 6.29 (td, J=8.9, 4.6 Hz, 1H), 4.61 (s, 2H), 4.57 (s, 2H), 4.25 (q, J=7.1 Hz, 2H), 2.33 (s, 3H), 1.28 (t, J=7.1 Hz, 3H).

2-[2,4-Difluoro-3-[[2-fluoro-3-(3-fluorophenyl)-5-methyl-phenyl]methylamino]phenoxy]acetic acid (I(g))

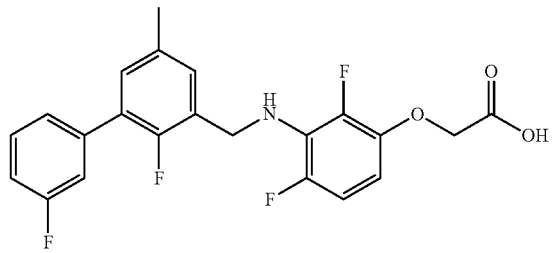

To a stirred solution of ethyl 2-[2,4-difluoro-3-[[2-fluoro-3-(3-fluorophenyl)-5-methyl-phenyl]methylamino]phenoxy]acetate (100 mg, 0.2 mmol, 1.0 eq) in a mixture of THF (20 mL) and water (20 mL) was added LiOH.H₂O (38 mg, 0.9 mmol, 4.0 eq). The reaction was stirred at room temperature for 2 h. The THF was then removed in vacuo and the aqueous residue acidified by addition of 1M HCl and extracted with EtOAc. The combined organic extracts were washed with water and brine, dried (Na₂SO₄), filtered and evaporated in vacuo. The residue obtained was washed with a mixture of petroleum ether: EtOAc, 10:1 to give the title compound (I(g)) as white solid (30 mg, 32%).

LC-MS: m/z 419.9 [M+H]⁺

1H NMR (300 MHz, DMSO-d6) δ 13.05 (br. s., 1H, COOH), 7.51 (td, J=8.0, 6.3 Hz, 1H), 7.41-7.29 (m, 2H), 7.28-7.12 (m, 3H), 6.80 (ddd, J=11.7, 9.4, 2.1 Hz, 1H), 6.31 (td, J=9.1, 4.6 Hz, 1H), 5.82 (s, 1H), 4.63 (s, 2H), 4.49 (d, J=7.0 Hz, 2H), 2.28 (s, 3H)

Example 8

Compound I(h) Synthesized According to Scheme 3

2-[2,4-difluoro-3-[[2-fluoro-5-(3-fluorophenyl)-3-methyl-phenyl]methylamino]phenoxy]acetic acid (I(h))

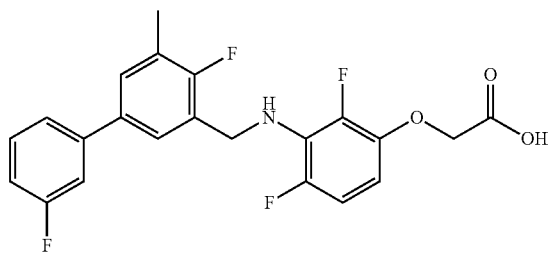

5-Bromo-2-fluoro-3-methyl-benzoic acid

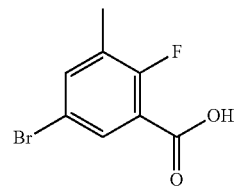

To a solution of diisopropylamine (1.77 g, 17.5 mmol, 1.1 eq) in THF (20 mL) was added n-BuLi (7.3 mL, 2.4 M in THF, 17.5 mmol, 1.1 eq) at −78° C. under N₂. The mixture was stirred at −78° C. for 1 h, then a solution of 4-bromo-1-fluoro-2-methyl-benzene (3 g, 15.8 mmol, 1.0 eq) in THF (20 mL) was added dropwise. The reaction was stirred a further 2 h at −78° C. then CO₂ gas was bubbled into the mixture for 30 min. The reaction was quenched by addition of water and acidified to pH 3 by addition of 1M HCl. The aqueous layer was extracted with EtOAc and the combined organic extracts were washed with brine, dried (Na₂SO₄), filtered and evaporated in vacuo. The residue obtained was purified by chromatography to give the title compound as a white solid (697 mg, 21%).

LC-MS: m/z 230.9, 232.9 [M−H]⁻

¹HNMR (400 MHz, DMSO-d₆) δ 7.94-7.59 (m, 2H), 2.26 (s, 3H)

2-Fluoro-5-(3-fluorophenyl)-3-methyl-benzoic acid (intermediate III(f))

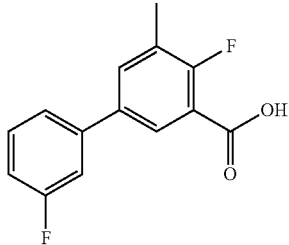 [SMILES: Cc1cc(-c2cccc(F)c2)cc(C(=O)O)c1F]

To a solution of 5-bromo-2-fluoro-3-methyl-benzoic acid (697 mg, 2.99 mmol, 1.0 eq) and (3-fluorophenyl)boronic acid (502 mg, 3.59 mmol, 1.2 eq) in a mixture of EtOH (10 mL), dioxane (20 mL) and H$_2$O (10 mL) were added K$_2$CO$_3$ (142 mg, 1.03 mmol, 2.5 eq) and Pd(PPh$_3$)$_4$ (345 mg, 0.30 mmol, 0.1 eq). The mixture was heated at 85° C. overnight. The reaction was quenched by addition of 1M HCl and the aqueous phase extracted with EtOAc. The organic extract was dried (MgSO$_4$), filtered and evaporated in vacuo. The residue was purified by chromatography to give the title compound as a solid (558 mg, 73%).

LC-MS: m/z 247.0 [M−H]$^-$ $^1$H NMR (400 MHz, DMSO-d$_6$) δ 7.95-7.86 (m, 2H), 7.58-7.47 (m, 3H), 7.27-7.18 (m, 1H), 2.34 (d, J=1.9 Hz, 3H)

N-(2,6-difluoro-3-hydroxy-phenyl)-2-fluoro-5-(3-fluorophenyl)-3-methyl-benzamide

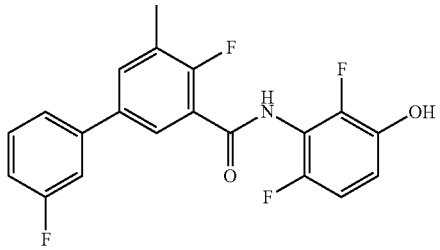

To a solution of 2-fluoro-5-(3-fluorophenyl)-3-methyl-benzoic acid (558 mg, 2.25 mmol, 1.0 eq) in DCM (30 mL) at 0° C. was added (COCl)$_2$ (856 mg, 0.57 mL, 6.74 mmol, 3 eq) and DMF (2 drops). The reaction was stirred at 0° C. for 2 h then the solvent was removed in vacuo. The residue was taken up in THF (30 mL) and added to a suspension of 3-amino-2,4-difluorophenol (intermediate X(a)) (330 mg, 2.36 mmol, 1.05 eq) and NaHCO$_3$ (566 mg, 6.74 mmol, 3.0 eq) in THF (30 mL) at 0° C. The reaction was stirred for 3 h at 0° C. then quenched by addition of 1 M HCl and the aqueous layer extracted with EtOAc. The combined organic extracts were washed with brine, dried (Na$_2$SO$_4$), filtered and evaporated in vacuo. The crude residue was purified by chromatography (MeOH:DCM, 0:1 to 1:50) to give the title compound as a solid (360 mg, 43%).

LC-MS: m/z 376.1 [M+H]$^+$ 398.1 [M+Na]$^+$

2,4-Difluoro-3-[[2-fluoro-5-(3-fluorophenyl)-3-methyl-phenyl]methylamino]phenol

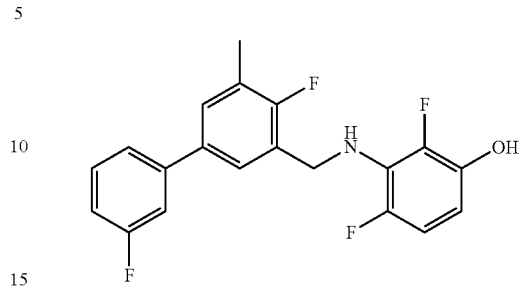

To a solution of N-(2,6-difluoro-3-hydroxy-phenyl)-2-fluoro-5-(3-fluorophenyl)-3-methyl-benzamide (200 mg, 0.53 mmol, 1.0 eq) in THF (8 mL) was added a solution of BH$_3$ (1M in THF, 5 mL, 5 mmol, 9.4 eq) dropwise. The reaction was heated at 55° C. for 2 h, then quenched by the addition of 1M HCl and EtOAc. The organic extract was separated, washed with water and brine, dried (Na$_2$SO$_4$), filtered and evaporated in vacuo to give the title compound (150 mg, 77%). This material was used without further purification.

LCMS: m/z 362.1 [M+H]$^+$ 384.1 [M+Na]$^+$

Ethyl 2-[2,4-difluoro-3-[[2-fluoro-5-(3-fluorophenyl)-3-methyl-phenyl]methylamino]phenoxy]acetate (II(h))

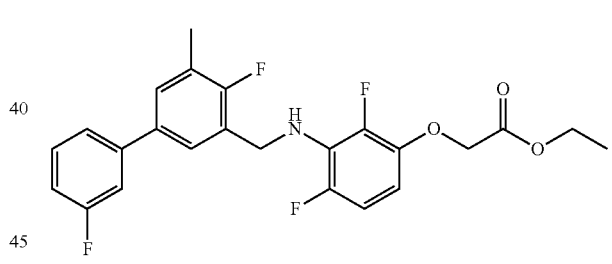

To a stirred solution of 2,4-difluoro-3-[[2-fluoro-5-(3-fluorophenyl)-3-methyl-phenyl]methylamino]phenol (150 mg, 0.42 mmol, 1.0 eq) in 2-butanone (10 mL) was added Cs$_2$CO$_3$ (203 mg, 0.62 mmol, 1.5 eq). The resulting mixture was stirred at room temperature for 30 min then ethyl bromoacetate (83 mg, 0.50 mmol, 1.2 eq) was added. The reaction was stirred at room temperature 30 min then filtered and concentrated. The crude residue was purified by chromatography (EtOAc:petroleum ether, 0:1 to 1:4) to give the title compound as a gum (150 mg, 81%).

LC-MS: m/z 448.2 [M+H]$^+$ 470.1 [M+Na]$^+$ $^1$H NMR (400 MHz, DMSO) δ 7.55-7.43 (m, 3H), 7.41-7.32 (m, 2H), 7.21-7.12 (m, 1H), 6.87-6.75 (m, 1H), 6.40-6.28 (m, 1H), 5.92-5.82 (m, 1H), 4.74 (s, 2H), 4.51 (d, J=7.0 Hz, 2H), 4.11 (q, J=7.1 Hz, 2H), 2.27 (s, 3H), 1.15 (t, J=7.2 Hz, 3H)

2-[2,4-Difluoro-3-[[2-fluoro-5-(3-fluorophenyl)-3-methyl-phenyl]methylamino]phenoxy]acetic acid (I(h))

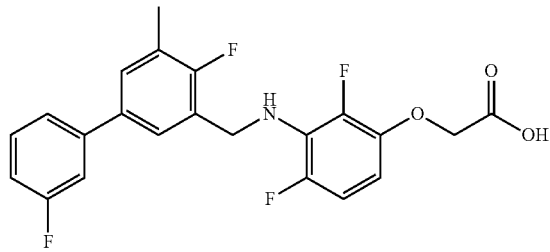

To a stirred solution of ethyl 2-[2,4-difluoro-3-[[2-fluoro-5-(3-fluorophenyl)-3-methyl-phenyl]methylamino]phenoxy]acetate (150 mg, 0.34 mmol, 1.0 eq) in THF (8 mL) was added NaOH (1M in water, 3.0 mL, 3.0 mmol) at room temperature. The reaction was stirred for 2 h, then the THF was removed in vacuo and the aqueous layer acidified to pH 4 by addition of 1M HCl. The resultant precipitate was collected by filtration and dried in vacuo to give the title compound (I(h)) (120 mg, 85%) as a white solid.

LC-MS: m/z 419.9 [M+H]$^+$ $^1$H NMR (300 MHz, DMSO-$d_6$) δ 13.04 (br. s., 1H), 7.62-7.42 (m, 3H), 7.40-7.31 (m, 2H), 7.24-7.10 (m, 1H), 6.80 (ddd, J=11.7, 9.4, 2.1 Hz, 1H), 6.32 (td, J=9.1, 4.5 Hz, 1H), 5.84 (br. s., 1H), 4.63 (s, 2H), 4.51 (d, J=7.1 Hz, 2H), 2.27 (d, J=1.6 Hz, 3H)

Example 9

Compound I(i) Synthesized According to Scheme 3

2-[2-Fluoro-3-[[2-fluoro-5-(3-fluorophenyl)phenyl]methylamino]-4-methyl-phenoxy]acetic acid (I(i))

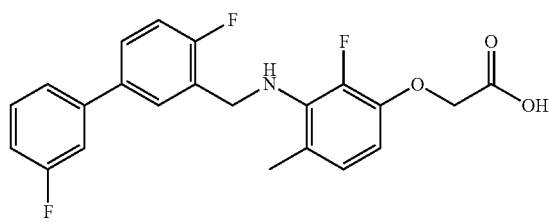

(2-Fluoro-4-methyl-phenoxy)-triisopropyl-silane

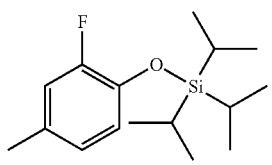 [SMILES: Cc1ccc(O[Si](C(C)C)(C(C)C)C(C)C)c(F)c1]

To a stirred solution of 2-fluoro-4-methyl-phenol (5 g, 39.6 mmol, 1.0 eq) and imidazole (3.24 g, 44.4 mmol, 1.2 eq) in DMF (50 mL) at 0° C. under N$_2$ was added TIPSCl (8.03 g, 41.6 mmol, 1.05 eq) dropwise. After the addition was complete, the reaction mixture was allowed to warm to room temperature and stirred for 1 h. The reaction was then poured into water and extracted with a mixture of EtOAc and petroleum ether (10:1). The combined organic extracts were washed with water and brine, dried (Na$_2$SO$_4$), filtered and evaporated in vacuo. The crude residue was purified by column chromatography (petroleum ether) to give the title compound as a colourless oil (8 g, 62%).

2-Fluoro-6-methyl-3-triisopropylsilyloxy-benzoic acid

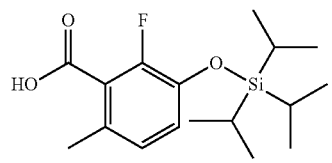

To a solution of (2-fluoro-4-methyl-phenoxy)-triisopropyl-silane (5 g, 17.7 mmol, 1.0 eq) and PMDTA (3.4 g, 19.5 mmol, 1.1 eq) in dry THF (70 mL) at −78° C. under N$_2$ was added a solution of n-BuLi (8 mL, 2.5 M in hexane, 20 mmol, 1.1 eq) over a period of 1 h. The reaction mixture was stirred at −78° C. for 2 h then CO$_2$ (gas) was bubbled into the mixture for 1 h. The reaction mixture was then quenched with saturated 1M HCl and extracted with EtOAc. The organic extract was washed with water and brine, dried (Na$_2$SO$_4$), filtered and evaporated in vacuo. The residue was purified by column chromatography (DCM:MeOH, 1:0 to 20:0) to give the title compound as a yellow oil (4 g, 69%).

$^1$H NMR (400 MHz, CDCl$_3$) δ 7.05-6.85 (m, 2H), 2.24 (s, 3H), 1.34-1.15 (m, 3H), 1.05 (d, J=7.4 Hz, 18H)

1,3-Bis(2-fluoro-6-methyl-3-triisopropylsilyloxy-phenyl)urea

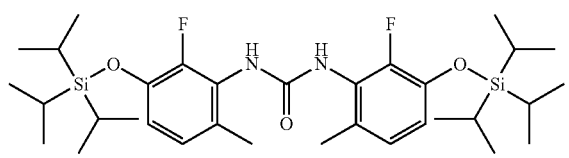 [SMILES: Cc1ccc(O[Si](C(C)C)(C(C)C)C(C)C)c(F)c1NC(=O)Nc1c(C)ccc(O[Si](C(C)C)(C(C)C)C(C)C)c1F]

To a solution of 2-fluoro-6-methyl-3-triisopropylsilyloxy-benzoic acid (4 g, 12.2 mmol, 1.0 eq) in a mixture of DCM (60 mL) and DMF (0.2 mL) at 0° C. was added (COCl)$_2$ (4.67 g, 36.75 mmol, 3.0 eq) dropwise. The mixture was warmed to room temperature and stirred for 1 h. The reaction mixture was concentrated to dryness, and the residue obtained dissolved in acetone (50 mL). The resultant solution was added dropwise to a cooled solution of NaN$_3$ (3.19 g, 49.0 mol) in acetone (50 mL) and water (50 mL) at 0° C. The reaction was stirred for 1 h at 0° C. Further water was then added (50 mL) and the reaction heated at 70° C. overnight. The acetone was evaporated in vacuo and the aqueous layer extracted with EtOAc. The combined organic extracts were washed with

3-Amino-2-fluoro-4-methyl-phenol (intermediate X(b))

To a solution of 1,3-bis(2-fluoro-6-methyl-3-triisopropylsilyloxy-phenyl)urea (3 g, 4.83 mmol, 1.0 eq) in dioxane (60 mL) was added KOH (30% aqueous solution, 30 mL) at room temperature. The reaction mixture was heated at reflux overnight, then cooled and the resulting mixture acidified by addition of 1M HCl and extracted with EtOAc. The organic extract was washed with water, brine, dried (Na$_2$SO$_4$), filtered and evaporated in vacuo. The crude residue was crystallized from DCM/petroleum ether (20 mL, 1/3, v/v) to give the title compound as a yellow solid (0.8 g, 59%).

$^1$H NMR (400 MHz, DMSO-d$_6$) δ 9.10 (s, 1H), 6.50 (d, J=8.1 Hz, 1H), 6.05 (app t, J=8.3 Hz, 1H), 4.67 (s, 2H), 1.99 (s, 3H)

2-Fluoro-N-(2-fluoro-3-hydroxy-6-methyl-phenyl)-5-(3-fluorophenyl)benzamide

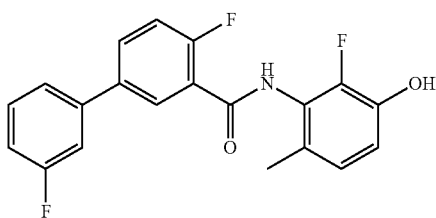 [SMILES: Cc1ccc(O)c(F)c1NC(=O)c1cc(-c2cccc(F)c2)ccc1F]

To a mixture of 2 fluoro-5-(3-fluorophenyl) benzoic acid (intermediate III(a)) (730 mg, 3.1 mmol, 1.1 eq) and (COCl)$_2$ (1.1 g, 8.49 mmol, 3 eq) in DCM (20 mL) was added DMF (5 drops). The reaction mixture was stirred at 0° C. for 1h and then concentrated in vacuo. The residue obtained was dissolved in THF (5 mL) and added dropwise to a solution of 3-amino-2-fluoro-4-methyl-phenol (400 mg, 2.83 mmol, 1 eq) 25 and NaHCO$_3$ (951 mg, 11.3 mmol, 4 eq) in THF (15 mL) at 0° C. After the addition, the reaction mixture was stirred at room temperature for 3h. The resulting mixture was poured into water and extracted with EtOAc. The organic extract was washed with water and brine, dried (Na$_2$SO$_4$), filtered and evaporated in vacuo. The residue was purified by column chromatography (EtOAc:petroleum ether, 0:1 to 1:4) to give the title compound as a yellow solid (600 mg, 60%).

LC-MS: m/z 358.1 [M+H]$^+$ 380.1 [M+Na]$^+$

2-Fluoro-3-[[2-fluoro-5-(3-fluorophenyl)phenyl]methylamino]-4-methyl-phenol

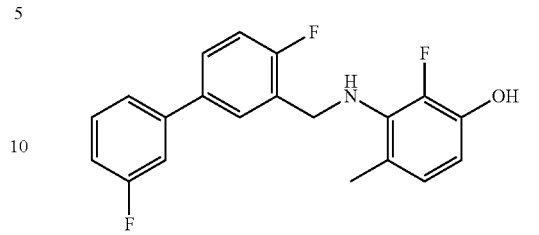

To a solution of 2-fluoro-N-(2-fluoro-3-hydroxy-6-methyl-phenyl)-5-(3-fluorophenyl)benzamide (500 mg, 1.4 mmol, 1 eq) in THF (10 mL) under N$_2$ was added dropwise a solution of BH$_3$ (1M in THF, 7 mL, 7.0 mmol, 5 eq). The reaction mixture was heated at 50° C. overnight. After cooling, the resulting mixture was quenched by addition of 1M HCl and extracted with EtOAc. The organic extract was washed with water and brine, dried (Na$_2$SO$_4$), filtered and evaporated in vacuo to give the title compound as an oil (300 mg, 42%).

LC-MS: m/z 344.1 [M+H]$^+$ 366.1 [M+Na]$^+$

Ethyl 2-[2-fluoro-3-[[2-fluoro-5-(3-fluorophenyl)phenyl]methylamino]-4-methyl-phenoxy]acetate (II(x))

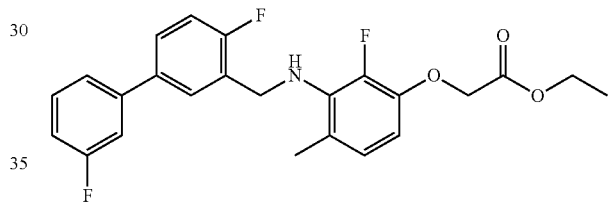

To a solution of 2-fluoro-3-[[2-fluoro-5-(3-fluorophenyl)phenyl]methylamino]-4-methyl-phenol (300 mg, 0.87 mmol, 1 eq) in DMF (6 mL) was added Cs$_2$CO$_3$ (425 mg, 1.31 mmol, 1.5 eq). The reaction mixture was stirred at room temperature for 1 h, then ethyl 2-bromoacetate (174 mg, 1.04 mmol, 1.2 eq) was added. The reaction mixture was stirred for 1 h then the reaction quenched by pouring into water. The mixture was extracted with EtOAc and the organic extract washed with water and brine, dried (Na$_2$SO$_4$), filtered and evaporated in vacuo. The residue obtained was purified by column chromatography (EtOAc:petroleum ether, 0:1 to 1:10) to give the title compound as an oil (260 mg, 70%).

LC-MS: m/z 430.2 [M+H]$^+$ 452.2 [M+Na]$^+$ $^1$H NMR (400 MHz, CDCl$_3$) δ 7.54 (dd, J=7.1, 2.3 Hz, 1H), 7.47-7.35 (m, 2H), 7.30-7.27 (m, 1H), 7.22-7.17 (m, 1H), 7.13 (dd, J=9.6, 8.6 Hz, 1H), 7.08-7.00 (m, 1H), 6.76 (dd, J=8.4, 1.0 Hz, 1H), 6.38 (app t, J=8.2 Hz, 1H), 4.63 (s, 2H), 4.53 (br s, 2H), 4.26 (q, J=7.1 Hz, 2H), 2.20 (s, 3H), 1.29 (t, J=7.1 Hz, 3H)

2-[2-Fluoro-3-[[2-fluoro-5-(3-fluorophenyl)phenyl]methylamino]-4-methyl-phenoxy]acetic acid (I(i))

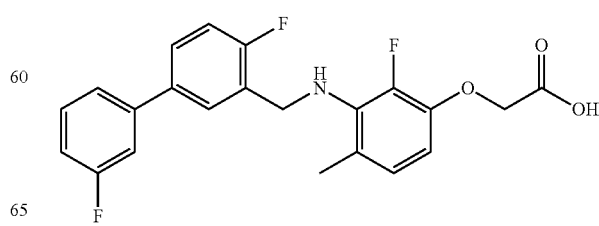

To a solution of ethyl 2-[2-fluoro-3-[[2-fluoro-5-(3-fluorophenyl)phenyl]methylamino]-4-methyl-phenoxy]acetate (260 mg, 0.61 mmol, 1.0 eq) in THF (10 mL) was added NaOH (1M aqueous solution, 5 mL, 5 mmol, 8.2 eq) at 0° C. The reaction mixture was allowed to warm to room temperature and stirred for 1 h. The organic solvent was evaporated in vacuo and the mixture that remained poured into water. The pH was adjusted to pH 4-6 with dilute HCl and the precipitate that formed was collected by filtration, washed with water and dried in vacuo to give title compound (I(i)) as a solid (200 mg, 82%).

LC-MS: m/z 402.0 [M+H]+

$^1$H NMR (300 MHz, DMSO-d$_6$) δ 7.72 (dd, J=7.2, 2.2 Hz, 1H), 7.63-7.54 (m, 1H), 7.53-7.44 (m, 1H), 7.40 (s, 1H), 7.39-7.34 (m, 1H), 7.30-7.18 (m, 1H), 7.21-7.09 (m, 1H), 6.67 (d, J=8.0 Hz, 1H), 6.25 (t, J=8.2 Hz, 1H), 4.48 (s, 2H), 4.44 (s, 2H), 2.12 (s, 3H)

Example 10

Compound I(j) Synthesized According to Scheme 3

2-[3-[[2-fluoro-5-(3-fluorophenyl)phenyl]methylamino]-2,4-dimethyl-phenoxy]acetic acid (I(j))

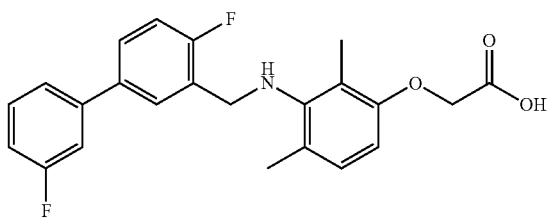 [SMILES: Cc1ccc(OCC(=O)O)c(C)c1NCc1cc(-c2cccc(F)c2)ccc1F]

N-(2,6-dimethylphenyl)acetamide

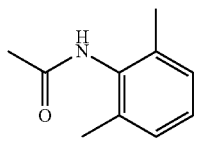

2,6-dimethylaniline (10 g, 82.5 mmol, 1.0 eq) was added to acetic anhydride (100 mL) at 0° C. The reaction mixture was then warmed to room temperature and stirred for 1 h. The reaction was poured into ice water and the precipitate that formed collected by filtration to give the title compound as a yellow solid (10 g, 74%).

N-(2,6-dimethyl-3-nitro-phenyl)acetamide

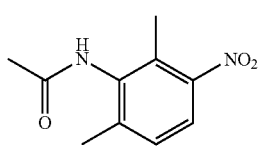

N-(2,6-dimethylphenyl)acetamide (10 g, 60 mmol, 1.0 eq) was dissolved in a mixture of H$_2$SO$_4$ (40 mL) and acetic acid (20 mL) at 0° C. A mixture of HNO$_3$ (10 mL) and H$_2$SO$_4$ (8 mL) was added dropwise with stirring. The reaction was allowed to warm to room temperature and stirred for a further 1 h. The reaction was quenched by pouring into ice water, and the solid that formed collected by filtration to give the title compound as a yellow solid (12 g, 94%).

LC-MS: 209.1 [M+H]+

$^1$H NMR (400 MHz, DMSO-d$_6$) δ 9.58 (s, 1H), 7.75 (d, J=8.4 Hz, 1H), 7.33 (d, J=8.4 Hz, 1H), 2.23 (s, 3H), 2.23 (s, 3H), 2.09 (s, 3H)

N-(3-amino-2,6-dimethyl-phenyl)acetamide

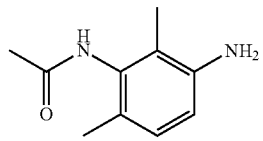

N-(2,6-dimethyl-3-nitro-phenyl)acetamide (12 g, 58 mmol, 1.0 eq) was dissolved in a mixture of MeOH (60 mL), EtOH (30 mL) and acetic acid (60 mL). Pd/C (1.6 g, 10%) was added and the reaction stirred at room temperature under H$_2$ for 36 h. The catalyst was removed by filtration through celite and the filtrate collected. Water was added and the pH adjusted to pH 8 by addition of aqueous NaHCO$_3$. The solution was concentrated in vacuo to remove methanol and ethanol. The aqueous layer was extracted with EtOAc and the combined organic extracts were dried (Na$_2$SO$_4$) filtered and evaporated in vacuo. The crude product was purified by column chromatography (EtOAc:petroleum ether, 1:10 to 1:1) to give the title compound as a yellow solid (2 g, 19%).

LC-MS: m/z 179.1 [M+H]+

N-(3-hydroxy-2,6-dimethyl-phenyl)acetamide

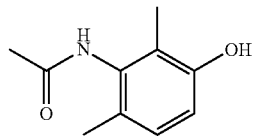

To a solution of N-(3-amino-2,6-dimethyl-phenyl)acetamide (2 g, 11 mmol, 1.1 eq) in a mixture of H$_2$SO$_4$ (10 mL) and H$_2$O (70 mL) at 0° C. was added a solution of NaNO$_2$ (1 g, 14.6 mmol, 1.3 eq) in H$_2$O (140 mL). The solution was stirred at 0° C. for 30 min then urea (425 mg, 7.1 mmol, 0.63 eq) was added. The reaction was poured into boiling water and the mixture stirred at 100° C. for 2 h. The aqueous phase was extracted with EtOAc, and the combined extracts were dried (Na$_2$SO$_4$), filtered and evaporated in vacuo. The residue was purified by column chromatography (MeOH:DCM, 0:1 to 1:20) to give the title compound as a white solid (800 mg, 40%).

LC-MS: m/z 180.1 [M+H]+

[3-(Acetyl(tert-butoxycarbonyl)amino)-2,4-dimethyl-phenyl]tert-butyl carbonate

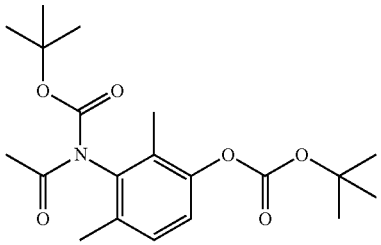 [SMILES: CC(=O)N(C(=O)OC(C)(C)C)c1c(C)ccc(OC(=O)OC(C)(C)C)c1C]

To a solution of N-(3-hydroxy-2,6-dimethyl-phenyl)acetamide (614 mg, 3.43 mmol, 1.0 eq) in DMF (50 mL) was added (Boc)₂O (3.74 g, 17.2 mmol, 5.0 eq), Et₃N (1.04 g, 10.3 mmol, 3.0 eq) and DMAP (1.26 g, 10.3 mmol, 5.0 eq) and the solution stirred at 50° C. overnight. The reaction was cooled to room temperature, water was added and the aqueous layer was extracted with EtOAc. The organic extract was dried (Na₂SO₄), filtered and evaporated in vacuo and the residue was purified by column chromatography (EtOAc:petroleum ether, 0:1 to 1:10) to give the title compound as a yellow solid (800 mg, 62%).

LC-MS: m/z 402.2 [M+Na]⁺

Tert-butyl N-(3-hydroxy-2,6-dimethyl-phenyl)carbamate

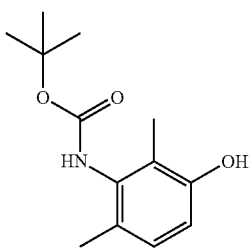 [SMILES: Cc1ccc(O)c(C)c1NC(=O)OC(C)(C)C]

A solution of [3-(acetyl(tert-butoxycarbonyl)amino)-2,4-dimethyl-phenyl]tert-butyl carbonate (800 mg, 2.11 mmol, 1.0 eq) and hydrazine hydrate (5 mL) in t-BuOH (5 mL) was stirred under N₂ at 110° C. overnight. The solution was adjusted to pH 6 by addition of diluted HCl and the aqueous layer extracted with EtOAc. The organic extract was dried (Na₂SO₄), filtered and evaporated in vacuo. The crude solid was used in the next step without further purification (657 mg, 100%).

LC-MS: m/z 260.1 [M+Na]⁺

3-Amino-2,4-dimethyl-phenol (intermediate X(c))

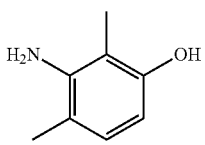

To a solution of tert-butyl N-(3-hydroxy-2,6-dimethyl-phenyl)carbamate (657 mg, 2.8 mmol, 1.0 eq) in DCM (5 mL) was added TFA (5 mL) and the reaction stirred at room temperature overnight. The solvent was removed in vacuo. The residue was taken up in water and solution adjusted to pH 7 by addition of aqueous NaHCO₃. The aqueous phase was extracted with EtOAc and the organic extract dried (Na₂SO₄), filtered and evaporated in vacuo to give the title compound as a yellow solid (370 mg, 97%) which was used without further purification.

LC-MS: 138.1 [M+H]⁺

¹H NMR (400 MHz, DMSO-d₆) δ 8.58 (s, 1H), 6.54 (d, J=8.0 Hz, 1H), 6.01 (d, J=8.0 Hz, 1H), 4.36 (s, 2H), 1.96 (s, 3H), 1.89 (s, 3H)

2-Fluoro-5-(3-fluorophenyl)-N-(3-hydroxy-2,6-dimethyl-phenyl)benzamide

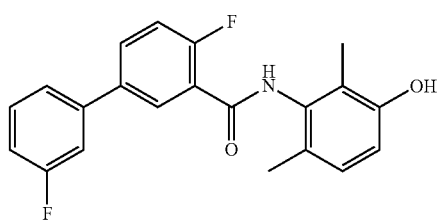 [SMILES: Cc1ccc(O)c(C)c1NC(=O)c1cc(-c2cccc(F)c2)ccc1F]

To a mixture of 2-fluoro-5-(3-fluorophenyl)benzoic acid (intermediate III(a)) (632 mg, 2.7 mmol, 1.0 eq) and oxalyl chloride (1.03 g, 8.1 mmol, 3.0 eq) in DCM (30 mL) was added DMF (0.3 mL). The reaction mixture was stirred at room temperature for 1 h. The resulting mixture was concentrated to remove the solvent and excess oxalyl chloride then the residue obtained was dissolved in THF (20 mL). This solution was added dropwise to a suspension of 3-amino-2,4-dimethyl-phenol (370 mg, 2.7 mmol, 1.0 eq) and NaHCO₃ (680 mg, 8.1 mmol, 3.0 eq) in THF (20 mL). After addition was complete, the reaction mixture was stirred at room temperature for 30 min. The resulting mixture was adjusted to pH 3 by addition of 1M HCl and the aqueous layer extracted with EtOAc. The organic extract was dried (Na₂SO₄), filtered, evaporated in vacuo and purified by column chromatography (EtOAc:petroleum ether, 0:1 to 1:1) to give the title compound as a yellow solid (400 mg, 42%).

LC-MS: m/z 354.1 [M+H]⁺ 376.1 [M+Na]⁺

3-[[2-Fluoro-5-(3-fluorophenyl)phenyl]methylamino]-2,4-dimethyl-phenol

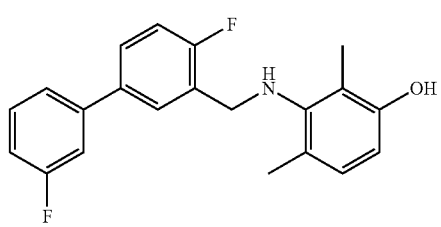

To a solution of 2-fluoro-5-(3-fluorophenyl)-N-(3-hydroxy-2,6-dimethyl-phenyl)benzamide (400 mg, 1.13 mmol, 1.0 eq) in THF under N₂ was added dropwise a solution of BH₃ (5.65 mL, 1M in THF, 5.65 mmol, 5.0 eq). The reaction mixture was heated to 60° C. and stirred under N₂ for 3 h. After cooling, the resulting mixture was quenched by addition of 1 M HCl and water and the aqueous layer extracted with EtOAc. The organic extract was dried (Na₂SO₄), filtered, evaporated in vacuo and purified by column chromatography (EtOAc:petroleum ether, 0:1 to 1:4) to give the title product as yellow oil (340 mg, 89%).

LC-MS: 340.2 [M+H]⁺ 362.1 [M+Na]⁺

Ethyl 2-[3-[[2-fluoro-5-(3-fluorophenyl)phenyl]methylamino]-2,4-dimethyl-phenoxy]acetate

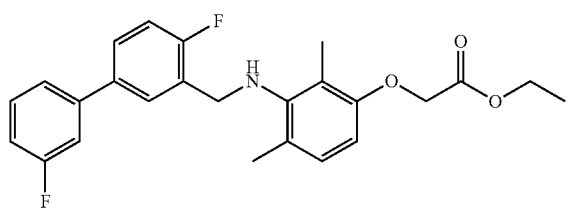 [SMILES: CCOC(=O)COc1ccc(C)c(NCc2cc(-c3cccc(F)c3)ccc2F)c1C]

A solution of 3-[[2-fluoro-5-(3-fluorophenyl)phenyl]methylamino]-2,4-dimethyl-phenol (340 mg, 1.0 mmol, 1.0 eq) and Cs₂CO₃ (489 mg, 1.5 mmol, 1.5 eq) in 2-butanone (20 mL) was stirred at room temperature for 30 min. Ethyl 2-bromoacetate (167 mg, 1.0 mmol, 1.0 eq) was added and the reaction mixture was stirred at for 3 h then quenched by addition of water. The aqueous layer was extracted with EtOAc and the organic extract dried (Na₂SO₄), filtered and evaporated in vacuo. The residue obtained was purified by column chromatography (EtOAc:petroleum ether, 0:1 to 1:4) to give the title compound as a gummy solid (300 mg, 70%).

LC-MS: 426.2 [M+H]⁺ 448.2 [M+Na]⁺

2-[3-[[2-Fluoro-5-(3-fluorophenyl)phenyl]methylamino]-2,4-dimethyl-phenoxy]acetic acid (I(j))

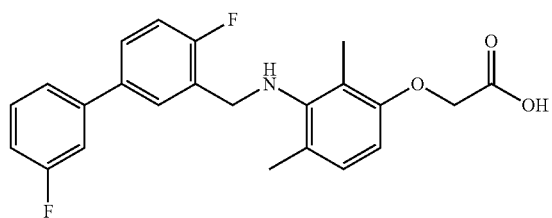 [SMILES: Cc1ccc(OCC(=O)O)c(C)c1NCc1cc(-c2cccc(F)c2)ccc1F]

To a solution of ethyl 2-[3-[[2-fluoro-5-(3-fluorophenyl)phenyl]methylamino]-2,4-dimethyl-phenoxy]acetate (300 mg, 0.71 mmol, 1.0 eq) in THF (8 mL) was added a solution of NaOH (1M aqueous solution, 3 mL, 3 mmol, 4.2 eq) at room temperature. The reaction mixture was stirred 1 h, then the THF was removed in vacuo. The remaining aqueous solution was poured into water and adjusted to pH 3 by addition of 1M HCl. The solid precipitate that formed was collected by filtration, washed with water and dried in vacuo to give the title compound (I(j)) as a solid (250 mg, 89%).

LC-MS: m/z 398.0 [M+H]⁺

¹H NMR (300 MHz, DMSO-d₆) δ 7.80 (dd, J=7.1, 2.3 Hz, 1H), 7.72-7.59 (m, 1H), 7.56-7.37 (m, 3H), 7.31-7.12 (m, 2H), 6.84 (d, J=8.3 Hz, 1H), 6.38 (d, J=8.3 Hz, 1H), 4.58 (s, 2H), 4.15 (s, 2H), 2.12 (d, 6H)

Example 11

Compound I(k) Synthesized According to Scheme 3

2-[4-Chloro-2-fluoro-3-[[2-fluoro-5-(3-fluorophenyl)phenyl]methylamino]phenoxy]acetic acid (I(k))

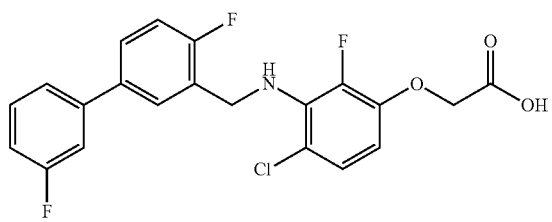 [SMILES: O=C(O)COc1ccc(Cl)c(NCc2cc(-c3cccc(F)c3)ccc2F)c1F]

6-Chloro-2-fluoro-3-methoxy-benzoic acid

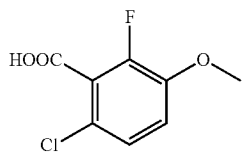

To a solution of 4-chloro-2-fluoro-1-methoxy-benzene (800 mg, 5 mmol, 1.0 eq) in THF (20 mL) at −78° C. was added n-BuLi (2.5M in THF, 3 mL, 7.5 mmol, 1.5 eq) dropwise under a nitrogen atmosphere. The mixture was stirred at this temperature for 30 min then CO₂ gas was bubbled through the solution for 1 h. The reaction was warmed to room temperature and quenched with water. The aqueous layer was acidified with 1M HCl and extracted with DCM. The combined organic extracts were washed with brine, dried (Na₂SO₄) and evaporated in vacuo to give the title compound as a white solid (800 mg, 80 %), which was used in the next step without further purification.

¹H NMR (400 MHz, DMSO-d₆) δ 7.72-6.90 (m, 1H), 3.87 (s, 2H)

1,3-Bis(6-chloro-2-fluoro-3-methoxy-phenyl)urea

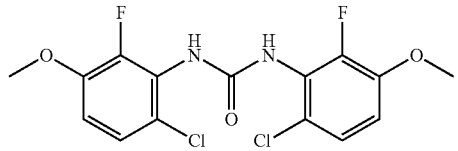

To a solution of 6-chloro-2-fluoro-3-methoxy-benzoic acid (600 mg, 2.93 mmol, 1.0 eq) in DCM (20 mL) at 0° C. was added (COCl)₂ (0.74 mL) and DMF (0.3 mL) and the reaction stirred for 2 h. The solvent was removed in vacuo and the residue dissolved in acetone (10 mL) and added to a solution of NaN₃ in a mixture of acetone (10 mL) and water (20 mL) at 0° C. The reaction was stirred at 0° C. for 30 min, then heated at 70° C. overnight. The reaction was partitioned

3-Amino-4-chloro-2-fluoro-phenol (intermediate X(d))

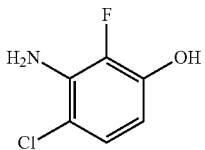

A solution of 1,3-bis(6-chloro-2-fluoro-3-methoxy-phenyl)urea (400 mg, 1.06 mmol, 1.0 eq) in HBr (48% aqueous solution, 20 mL) was stirred at 120° C. overnight. The solution was then adjusted to pH 7 by addition of dilute aqueous NaOH and extracted with EtOAc. The organic extract was dried (Na$_2$SO$_4$), filtered and evaporated in vacuo to give the title compound (330 mg, 87%) which was used without further purification.

LC-MS: m/z 162.0, 164.0 [M+H]$^+$

N-(6-chloro-2-fluoro-3-hydroxy-phenyl)-2-fluoro-5-(3-fluorophenyl)benzamide

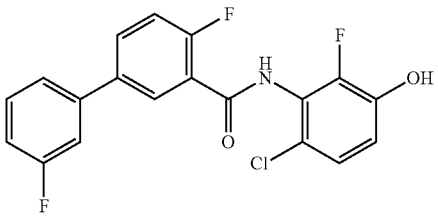

To a mixture of 2-fluoro-5-(3-fluorophenyl)benzoic acid (intermediate III(a)) (478 mg, 2.04 mmol, 1.0 eq) and (COCl)$_2$ (777 mg, 6.13 mmol, 3.0 eq) in DCM (20 mL) was added DMF (0.3 mL). The reaction mixture was stirred at 0° C. for 1 h, then the solvent removed in vacuo. The residue obtained was dissolved in THF (20 mL) and added dropwise to a solution of 3-amino-4-chloro-2-fluoro-phenol (intermediate X(d)) (330 mg, 2.04 mmol, 1.0 eq) and NaHCO$_3$ (515 mg, 6.13 mmol, 3.0 eq) in THF (20 mL). After the addition, the reaction mixture was stirred at room temperature for 30 min. The THF was evaporated in vacuo and the aqueous solution adjusted to pH 3 by addition of 1M HCl. The mixture was extracted with EtOAc and the combined organic extracts were dried (Na$_2$SO$_4$), filtered and evaporated in vacuo. The residue was purified by column chromatography (EtOAc: petroleum ether, 0:1 to 1:1) to give the title compound as a yellow solid (200 mg, 26%).

LC-MS: m/z 378.0, 380.0 [M+H]$^+$ 400.0, 402.0 [M+Na]$^+$

4-Chloro-2-fluoro-3-[[2-fluoro-5-(3-fluorophenyl)phenyl]methylamino]phenol

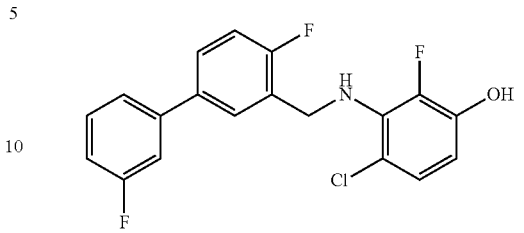

To a solution of N-(6-chloro-2-fluoro-3-hydroxy-phenyl)-2-fluoro-5-(3-fluorophenyl)benzamide (200 mg, 0.53 mmol, 1.0 eq) in THF under N$_2$ was added dropwise a solution of BH$_3$ (1M in THF, 2.65 mL, 2.65 mmol, 5.0 eq) at room temperature. The reaction mixture was heated at 60° C. for 3 h. After cooling, the resulting mixture was quenched by addition of 1M HCl and the mixture extracted with EtOAc. The combined organic extracts were dried (Na$_2$SO$_4$), filtered and evaporated in vacuo. The residue was purified by column chromatography (EtOAc:petroleum ether, 0:1 to 1:4) to give the title compound as an oil (130 mg, 68%).

LC-MS: m/z 364.0, 366.1 [M+H]$^+$

Ethyl 2-[4-chloro-2-fluoro-3-[[2-fluoro-5-(3-fluorophenyl)phenyl]methylamino]phenoxy]acetate

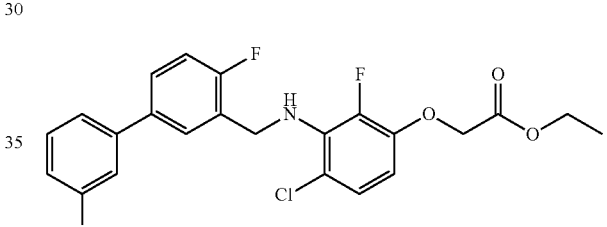

To a solution of 4-chloro-2-fluoro-3-[[2-fluoro-5-(3-fluorophenyl)phenyl]methylamino]phenol (130 mg, 0.36 mmol, 1.0 eq) and Cs$_2$CO$_3$ (175 mg, 0.54 mmol, 1.5 eq) in 2-butanone (20 mL) was added ethyl 2-bromoacetate (59.7 mg, 0.36 mmol, 1.0 eq). The reaction mixture was stirred at room temperature for 1 h. Water was then added and the aqueous layer extracted with EtOAc. The combined organic extracts were dried (Na$_2$SO$_4$), filtered and evaporated in vacuo. The residue was purified by column chromatography (EtOAc: petroleum ether, 0:1 to 1:10) to give the title compound as an oil (80 mg, 50%).

LC-MS: m/z 450.1, 452.1 [M+H]$^+$ 472.1, 474.1 [M+Na]$^+$

2-[4-Chloro-2-fluoro-3-[[2-fluoro-5-(3-fluorophenyl)phenyl]methylamino]phenoxy]acetic acid (I(k))

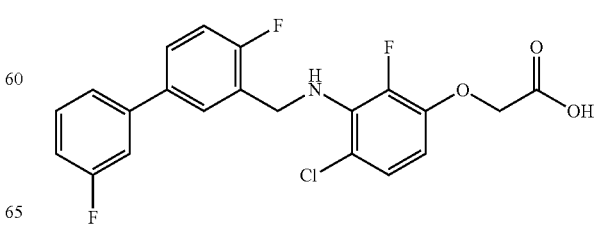

A solution of ethyl 2-[4-chloro-2-fluoro-3-[[2-fluoro-5-(3-fluorophenyl)phenyl]methylamino]phenoxy]acetate (80 mg, 0.18 mmol, 1.0 eq) in THF (6 mL) was added to a 1M solution of NaOH (2 mL, 2 mmol, 11.1 eq). The reaction mixture was stirred at room temperature for 2 h. The organic solvent was removed in vacuo and the aqueous solution diluted with water. The solution was adjusted to pH 3 by addition of diluted HCl and the precipitate that formed collected by filtration, washed with water and dried in vacuo to give the title compound (I(k)) as white solid (65 mg, 87%).

LC-MS: m/z 421.9, 423.9 [M+H]+

$^1$H NMR (300 MHz, DMSO-d$_6$) δ 7.70 (dd, J=7.2, 2.2 Hz, 1H), 7.64-7.55 (m, 1H), 7.53-7.42 (m, 1H), 7.42-7.32 (m, 2H), 7.30-7.19 (m, 1H), 7.23-7.12 (m, 1H), 7.03 (dd, J=8.9, 2.0 Hz, 1H), 6.41 (t, J=8.8 Hz, 1H), 5.67 (t, J=6.1 Hz, 1H), 4.65 (s, 2H), 4.60 (d, J=6.3 Hz, 2H)

Example 12

Compound I(l) Synthesized According to Scheme 3

2-[3-[[2-Chloro-5-(3-fluorophenyl)phenyl]methylamino]-2,4-difluoro-phenoxy]acetic acid (I(l))

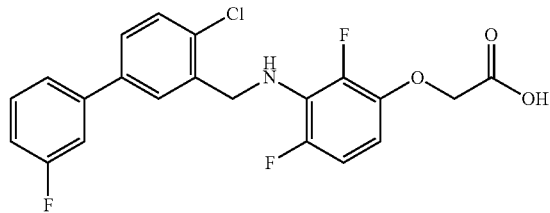 [SMILES: O=C(O)COc1ccc(F)c(NCc2cc(-c3cccc(F)c3)ccc2Cl)c1F]

2-Chloro-5-(3-fluorophenyl)benzoic acid (intermediate III(g))

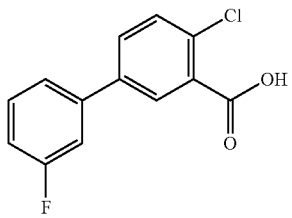 [SMILES: O=C(O)c1cc(-c2cccc(F)c2)ccc1Cl]

A solution of 3-fluorophenyl boronic acid (500 mg, 3.5 mmol, 1.2 eq), 5-bromo-2-chlorobenzoic acid (700 mg, 3.0 mmol, 1.0 eq), Pd(PPh$_3$)$_4$ (687 mg, 0.60 mmol, 0.2 eq) and Na$_2$CO$_3$ (2.52 g, 24 mmol, 8.0 eq) in a mixture of ethanol (5 mL), H$_2$O (5 mL) and DMF (20 mL) was stirred at 100° C. under N$_2$ overnight. The reaction was quenched by addition of diluted HCl (to pH 3) and the aqueous phase was extracted with EtOAc. The combined organic extracts were washed with brine, dried (Na$_2$SO$_4$) filtered and evaporated in vacuo. The residue was purified by chromatography (petroleum ether:EtOAc 20:1 to 1:1) to give the title compound as a white solid (500 mg, 67%).

LC-MS: m/z 249.0, 251.0 [M−H]−

$^1$H NMR (400 MHz, DMSO-d$_6$) δ 13.58 (br s, 1H), 8.06 (d, J=2.2 Hz, 1H), 7.88 (dd, J=8.3, 2.4 Hz, 1H), 7.65 (d, J=8.4 Hz, 1H), 7.63-7.50 (m, 3H), 7.26 (br t, J=8.2 Hz, 1H)

2-Chloro-N-(2,6-difluoro-3-hydroxy-phenyl)-5-(3-fluorophenyl)benzamide

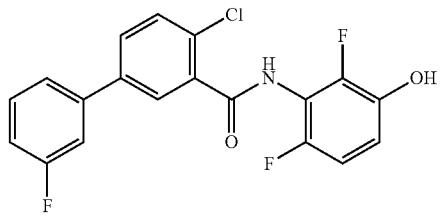

To a solution of 2-chloro-5-(3-fluorophenyl)benzoic acid (500 mg, 2.0 mmol, 1.0 eq) in DCM (20 mL) was added oxalyl chloride (761.6 mg, 6.0 mmol, 3.0 eq) and DMF (0.1 mL). The solution was stirred at room temperature for 1 h, then the solvent removed in vacuo. The resultant residue was dissolved in dry THF (30 mL) and added dropwise to a suspension of 3-amino-2,4-difluorophenol (intermediate X(a)) (290.2 mg, 2.0 mmol, 1.0 eq) and NaHCO$_3$ (504 mg, 6.0 mmol, 3.0 eq) in THF (30 mL). The mixture was warmed to room temperature and stirred for 30 min. The pH of the reaction was adjusted to pH 3 by addition of 1M HCl and the aqueous layer was extracted with EtOAc. The combined organic extracts were washed with brine, dried (Na$_2$SO$_4$) filtered and evaporated in vacuo. The residue was purified by chromatography to give the title compound as a white solid (200 mg, 27%).

LC-MS: m/z 378.0, 380.0 [M+H]+ 400.0, 402.0 [M+Na]+

3-[[2-Chloro-5-(3-fluorophenyl)phenyl]methylamino]-2,4-difluoro-phenol

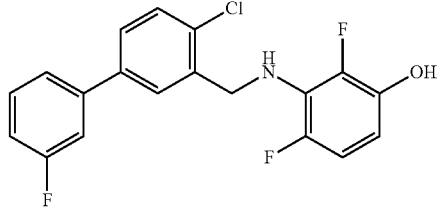 [SMILES: Oc1ccc(F)c(NCc2cc(-c3cccc(F)c3)ccc2Cl)c1F]

To a solution of 2-chloro-N-(2,6-difluoro-3-hydroxy-phenyl)-5-(3-fluorophenyl)benzamide (150 mg, 0.34 mmol, 1.0 eq) in THF (3 mL) was added a solution of BH$_3$ (1M in THF, 1.72 mL, 1.72 mmol, 5.0 eq). The reaction was heated at 60° C. for 3 h, then quenched by addition of 1M HCl. The aqueous layer was extracted with EtOAc and the organic extract was washed with water and brine, dried (Na$_2$SO$_4$) filtered and evaporated in vacuo. The residue obtained was purified by flash chromatography (petroleum ether:EtOAc, 100:1 to 30:1) to give the title compound as a colourless oil (128 mg, 89%).

LC-MS: m/z 364.0, 366.1 [M+H]+

Ethyl 2-[3-[[2-chloro-5-(3-fluorophenyl)phenyl]methylamino]-2,4-difluoro-phenoxy]acetate

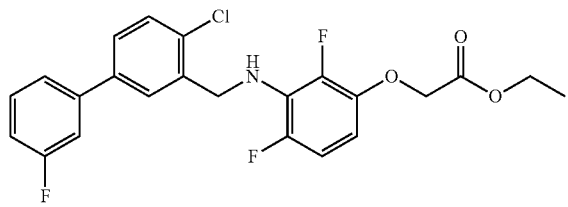 [SMILES: CCOC(=O)COc1ccc(F)c(NCc2cc(-c3cccc(F)c3)ccc2Cl)c1F]

To a solution of 3-[[2-chloro-5-(3-fluorophenyl)phenyl]methylamino]-2,4-difluoro-phenol (128 mg, 0.35 mmol, 1.0 eq) in DMF (10 mL) was added $Cs_2CO_3$ (172 mg, 0.53 mmol, 1.5 eq). The reaction was stirred at room temperature for 30 min then ethylbromoacetate (70.5 mg, 0.42 mmol, 1.2 eq) was added dropwise. The reaction was stirred at room temperature for further 3 h then water was added and the aqueous layer extracted with EtOAc. The organic extract was washed with water and brine, dried ($Na_2SO_4$), filtered, evaporated in vacuo and the residue obtained purified by chromatography (petroleum ether:EtOAc, 100:1 to 20:1) to give the title compound as a colourless oil (120 mg, 76%).

LC-MS: m/z 450.1, 452.1 $[M+H]^+$ 472.1, 474.1 $[M+Na]^+$

2-[3-[[2-Chloro-5-(3-fluorophenyl)phenyl]methylamino]-2,4-difluoro-phenoxy]acetic acid (I(l))

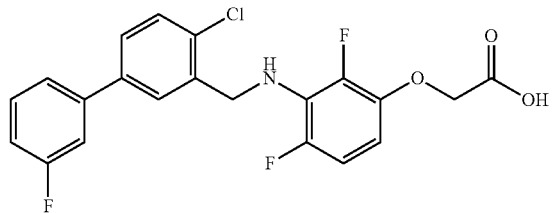 [SMILES: O=C(O)COc1ccc(F)c(NCc2cc(-c3cccc(F)c3)ccc2Cl)c1F]

To a solution of ethyl 2-[3-[[2-chloro-5-(3-fluorophenyl)phenyl]methylamino]-2,4-difluoro-phenoxy]acetate (120 mg, 0.27 mmol, 1.0 eq) in THF (8 mL) was added NaOH (1M aqueous solution, 3 mL, 3 mmol, 11.0 eq). The reaction was stirred at room temperature for 2 h. The THF was removed in vacuo and the residue acidified to pH 5 by addition of 1M HCl. The precipitate that formed was collected by filtration, washed with water and dried to give the title compound (I(l)) (100 mg, 88%).

LC-MS: m/z 421.9, 423.9 $[M+H]^+$ $^1$H NMR (300 MHz, DMSO-$d_6$) δ 7.74 (d, J=2.0 Hz, 1H), 7.65-7.56 (m, 1H), 7.55-7.45 (m, 2H), 7.43-7.35 (m, 2H), 7.31-7.09 (m, 1H), 6.82 (ddd, J=11.7, 9.4, 2.1 Hz, 1H), 6.33 (td, J=9.1, 4.6 Hz, 1H), 6.04-5.86 (m, 1H), 4.64 (s, 2H), 4.56 (d, J=6.8 Hz, 2H)

Example 13

Compound I(m) Synthesized According to Scheme 3

2-[4-Fluoro-3-[[2-fluoro-5-(3-fluorophenyl)phenyl]methylamino]-2-methyl-phenoxy]acetic acid (I(m))

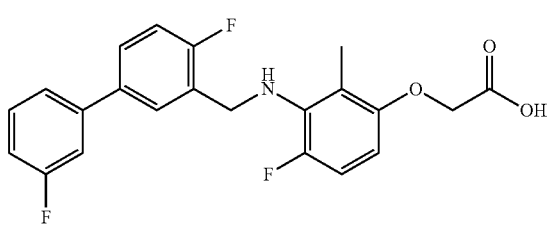

1-Bromo-4-fluoro-2-methyl-3-nitro-benzene

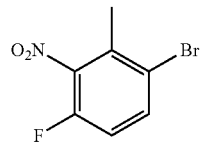

To a solution of 1-fluoro-3-methyl-2-nitro-benzene (5 g, 32.24 mmol, 1.0 eq) in TFA (25 mL) and conc.$H_2SO_4$ (10 mL) at 0° C. was added NBS (6.31 g, 35.46 mmol, 1.1 eq) in portions. After addition, the mixture was stirred at room temperature for 2 h. The resulting mixture was poured onto ice and the precipitate that formed collected by filtration, washed with water and dried in vacuo to give the title compound as a yellow solid (5 g, 67%).

$^1$H NMR (400 MHz, DMSO-$d_6$) δ 7.98 (dd, J=9.0, 5.2 Hz, 1H), 7.48 (app t, J=9.3 Hz, 1H), 2.36 (s, 3H)

1 Bromo-4-fluoro-3-amino-2-methyl-benzene

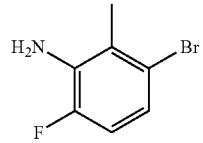

To a solution of 1-bromo-4-fluoro-2-methyl-3-nitro-benzene (3 g, 12.82 mmol, 1.0 eq) in EtOH (60 mL) was added $NH_4Cl$ (30 mL), water (30 mL) and iron powder (2.87 g, 51.28 mmol, 4.0 eq). The reaction mixture was heated at reflux for 3h, then filtered through Celite. The filtrate was evaporated in vacuo and purified by column chromatography (EtOAc:petroleum ether, 0:1 to 1:10) to give the title compound as a yellow solid (2 g, 77%).

LC-MS: m/z 204.0, 206.0 $[M+H]^+$ $^1$H NMR (400 MHz, CDCl$_3$) δ 6.91 (dd, J=8.7, 5.0 Hz, 1H), 6.80-6.71 (m, 1H), 3.78 (br s, 2H), 2.28 (s, 3H)

Tert-butyl N-(3-bromo-6-fluoro-2-methyl-phenyl)-N-tert-butoxycarbonyl-carbamate

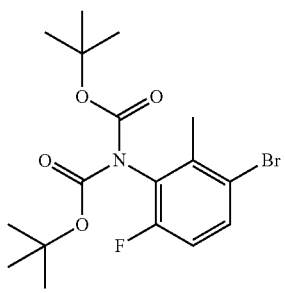 [SMILES: Cc1c(Br)ccc(F)c1N(C(=O)OC(C)(C)C)C(=O)OC(C)(C)C]

To a solution of 1-bromo-4-fluoro-2,3-dimethyl-benzene (6.09 g, 29.8 mmol, 1.0 eq) in DMF (60 mL) was added (Boc)$_2$O (32.5 g, 0.149 mol, 5.0 eq), TEA (6.14 g, 59.7 mmol, 2.0 eq) and DMAP (3.64 g, 29.8 mmol, 1.0 eq). The reaction mixture was stirred overnight then poured into water, and extracted with EtOAc. The organic extract was washed with water, brine, dried (Na$_2$SO$_4$), filtered and evaporated in vacuo. The residue obtained was purified by column chromatography, (EtOAc:petroleum ether, 0:1 to 5:100) and triturated with petroleum ether to give the title compound as a white solid (6 g, 50%).

Tert-butyl N-tert-butoxycarbonyl-N-[6-fluoro-2-methyl-3-(4,4,5,5-tetramethyl-1,3,2-dioxaborolan-2-yl)phenyl]carbamate

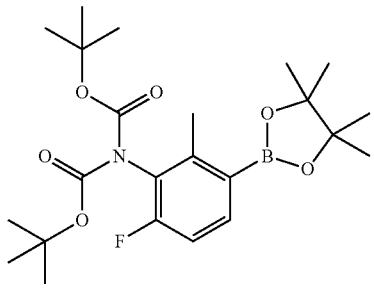 [SMILES: Cc1c(B2OC(C)(C)C(C)(C)O2)ccc(F)c1N(C(=O)OC(C)(C)C)C(=O)OC(C)(C)C]

A mixture of tert-butyl N-(3-bromo-6-fluoro-2-methyl-phenyl)-N-tert-butoxycarbonyl-carbamate (1 g, 2.47 mmol, 1.0 eq), KOAc (0.73 g, 7.42 mmol, 3.0 eq), bis(pinacolato)diboron (753 mg, 2.96 mmol, 1.2 eq) and Pd(dppf)Cl$_2$ (188 mg, 0.247 mmol, 0.1 eq) in DMSO (10 mL) under N$_2$ was heated at 80° C. for 4 h. After cooling, the resultant mixture was poured into water and extracted with EtOAc. The organic extract was washed with water and brine, dried (Na$_2$SO$_4$), filtered and evaporated in vacuo. The residue obtained was purified by column chromatography (EtOAc:petroleum ether, 0:1, 1:30) to give the title product as a colourless oil (700 mg, 64%).

Tert-butyl N-tert-butoxycarbonyl-N-(6-fluoro-3-hydroxy-2-methyl-phenyl)carbamate

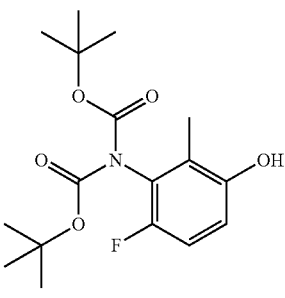 [SMILES: Cc1c(O)ccc(F)c1N(C(=O)OC(C)(C)C)C(=O)OC(C)(C)C]

To a solution of tert-butyl N-tert-butoxycarbonyl-N-[6-fluoro-2-methyl-3-(4,4,5,5-tetramethyl-1,3,2-dioxaborolan-2-yl)phenyl]carbamate (800 mg, 41.7 mmol, 1.0 eq) in a mixture of THF (10 mL) and NaOH (1M aqueous solution, 5.3 mL, 5.3 mmol, 3.0 eq) at 0° C. was added H$_2$O$_2$ (30% aqueous solution, 603 mg, 5.32 mmol, 3.0 eq). The reaction mixture was stirred at room temperature for 3 h. The resulting mixture was acidified to pH 5-7 by addition of diluted HCl, and extracted with EtOAc. The organic extract was washed with water and brine, dried (Na$_2$SO$_4$), filtered and evaporated in vacuo. The residue obtained was purified by column chromatography, (EtOAc:petroleum ether, 0:1 to 1:10) to give the title product as an oil (500 mg, 83%).

3-Amino-4-fluoro-2-methyl-phenol (intermediate X(e))

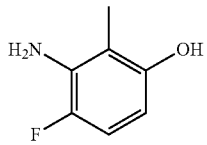

To a solution of tert-butyl N-tert-butoxycarbonyl-N-(6-fluoro-3-hydroxy-2-methyl-phenyl)carbamate (500 mg, 1.46 mmol, 1.0 eq) in DCM (6 mL) was added TFA (2 mL). The reaction was stirred at room temperature overnight, then the solvent was removed in vacuo, to give the title compound as yellow oil (200 mg, 97%).

LC-MS: m/z 141.6 [M+H]$^+$ $^1$H NMR (400 MHz, DMSO-d$_6$) δ 8.83 (s, 1H), 6.61 (dd, J=11.0, 8.7 Hz, 1H), 5.99 (dd, J=8.7, 4.2 Hz, 1H), 4.68 (br s, 2H), 1.91 (s, 3H)

2-Fluoro-N-(6-fluoro-3-hydroxy-2-methyl-phenyl)-5-(3-fluorophenyl)benzamide

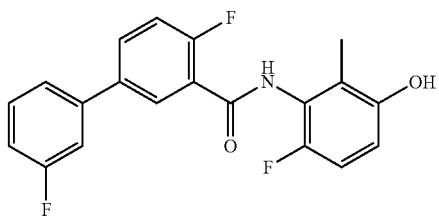 [SMILES: Cc1c(O)ccc(F)c1NC(=O)c1cc(-c2cccc(F)c2)ccc1F]

To a mixture of 2-fluoro-5-(3-fluorophenyl)benzoic acid (intermediate III(a)) (365 mg, 1.56 mmol, 1.1 eq) and (COCl)$_2$ (541 mg, 4.26 mmol, 3.0 eq) in DCM (10 mL) was added DMF (3 drops). The reaction mixture was stirred at room temperature for 2 h, then concentrated in vacuo. The residue obtained was dissolved in THF (5 mL) and added dropwise to a solution of 3-amino-4-fluoro-2-methyl-phenol (200 mg, 1.42 mmol, 1.0 eq) in THF (15 mL) at 0° C. After the addition was completed, the reaction mixture was allowed to warm to room temperature and stirred for 2 h. The resulting mixture was poured into water and extracted with EtOAc. The organic extract was washed with water and brine, dried (Na$_2$SO$_4$), filtered, evaporated in vacuo and purified by column chromatography (EtOAc:petroleum ether, 0:1 to 1:3) to give the title compound as a yellow solid (300 mg, 59%).

LC-MS: m/z 358.1 [M+H]$^+$ 380.1 [M+Na]$^+$

4-Fluoro-3-[[2-fluoro-5-(3-fluorophenyl)phenyl]methylamino]-2-methyl-phenol

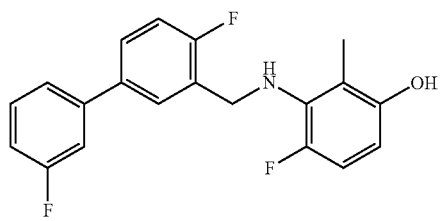

To a solution of 2-fluoro-N-(6-fluoro-3-hydroxy-2-methyl-phenyl)-5-(3-fluorophenyl)benzamide (300 mg, 0.84 mmol, 1.0 eq) in THF (10 mL) under N$_2$ was added dropwise a solution of BH$_3$ (1M in THF, 4.2 mL, 4.2 mmol, 5.0 eq). The reaction mixture was heated at 50° C. overnight, then cooled and the reaction quenched by addition of 1M HCl. The mixture was extracted with EtOAc and the organic extract was washed with water and brine, dried (Na$_2$SO$_4$), filtered and evaporated in vacuo to give the title product as an oil (200 mg, 69%).

LC-MS: m/z 344.1 [M+H]$^+$

Ethyl 2-[4-fluoro-3-[[2-fluoro-5-(3-fluorophenyl)phenyl]methylamino]-2-methyl-phenoxy]acetate (II(y))

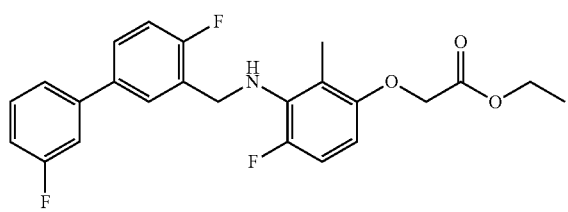 [SMILES: CCOC(=O)COc1ccc(F)c(NCc2cc(-c3cccc(F)c3)ccc2F)c1C]

To a solution of 4-fluoro-3-[[2-fluoro-5-(3-fluorophenyl)phenyl]methylamino]-2-methyl-phenol (200 mg, 0.58 mmol, 1.0 eq) in DMF (6 mL) was added Cs$_2$CO$_3$ (283 mg, 0.87 mmol, 1.5 eq). The reaction mixture was stirred for 1 h at room temperature, then ethyl 2-bromoacetate (117 mg, 0.70 mmol, 1.2 eq) was added. The reaction mixture was stirred for a further 1 h then poured into water and extracted with EtOAc. The organic extract was washed with water and brine, dried (Na$_2$SO$_4$), filtered and evaporated in vacuo. The residue obtained was purified by column chromatography to give the title compound as an oil (200 mg, 80%).

LC-MS: m/z 452.2 [M+Na]$^+$ $^1$H NMR (400 MHz, DMSO-d$_6$) δ 7.71 (dd, J=7.1, 2.2 Hz, 1H), 7.61-7.55 (m, 1H), 7.52-7.44 (m, 1H), 7.42-7.34 (m, 2H), 7.26-7.13 (m, 2H), 6.70 (d, J=8.5 Hz, 1H), 6.30 (app t, J=8.2 Hz, 1H), 4.68 (s, 2H), 4.49 (s, 2H), 4.11 (q, J=7.1 Hz, 2H), 2.13 (s, 3H), 1.15 (t, J=7.1 Hz, 3H)

2-[4-Fluoro-3-[[2-fluoro-5-(3-fluorophenyl)phenyl]methylamino]-2-methyl-phenoxy]acetic acid (I(m))

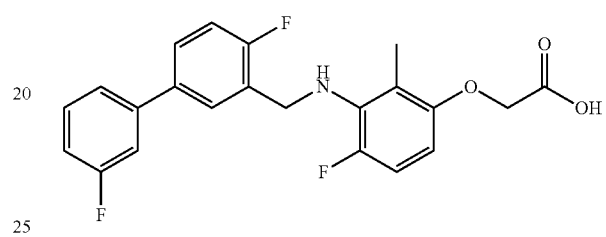

To a solution of ethyl 2-[4-fluoro-3-[[2-fluoro-5-(3-fluorophenyl)phenyl]methylamino]-2-methyl-phenoxy]acetate (200 mg, 0.466 mmol, 1.0 eq) in THF (8 mL) was added NaOH (1M aqueous solution, 4 mL, 4.0 mmol, 9.0 eq) at 0° C. The reaction mixture was stirred at room temperature for 1 h, then the organic solvent removed under reduced pressure and the aqueous solution diluted with water and adjusted to pH 4-6 by addition of diluted HCl. The precipitate that formed was collected by filtration, washed with water and dried in vacuo to give the title compound (I(m)) as a solid (150 mg, 80%).

LC-MS: m/z 402.0 [M+H]$^+$ $^1$H NMR (300 MHz, DMSO-d$_6$) δ 7.73 (dd, J=7.2, 2.3 Hz, 1H), 7.63-7.54 (m, 1H), 7.53-7.44 (m, 1H), 7.39 (d, J=7.7 Hz, 2H), 7.30-7.02 (m, 2H), 6.76 (dd, J=12.3, 9.0 Hz, 1H), 6.21 (dd, J=9.0, 3.7 Hz, 1H), 5.93 (m, 1H), 4.50-4.40 (m, 4H), 2.10 (s, 3H)

Example 14

Compound I(n) Synthesized According to Scheme 3

2-[2,4-Difluoro-3-[[3-fluoro-5-(3-fluorophenyl)phenyl]methylamino]phenoxy]acetic acid (I(n))

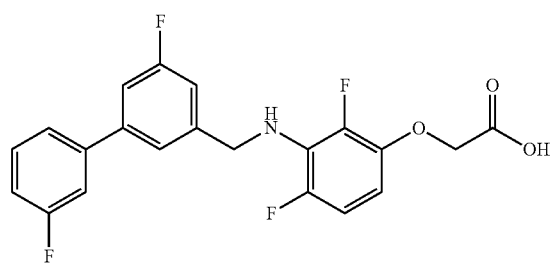

101

3-Fluoro-5-(3-fluorophenyl)benzoic acid (intermediate III(h))

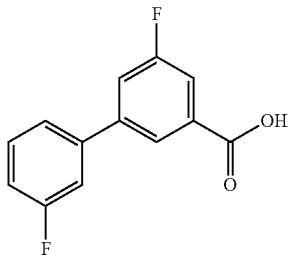 [SMILES: O=C(O)c1cc(F)cc(-c2cccc(F)c2)c1]

To a solution of 3-fluorophenyl boronic acid (0.7 g, 5.0 mmol, 1.0 eq), 3-bromo-5-fluoro-benzoic acid (1 g, 4.6 mmol, 1.1 eq) and $Na_2CO_3$ (1.45 g, 13.7 mmol, 3 eq) in a mixture of EtOH (5 mL), DMF (20 mL) and $H_2O$ (5 mL) under $N_2$ was added $Pd(PPh_3)_4$ (200 mg, 0.17 mmol, 0.05 eq). The mixture was stirred at 100° C. overnight then cooled to room temperature. Water and ethyl acetate were added and the reaction was filtered through Celite and the aqueous layer was extracted with EtOAc. The organic extract was discarded and the aqueous layer was acidified to pH 4-5 by addition of 1M HCl and extracted with EtOAc. The combined organic extracts were washed with water and brine, dried ($Na_2SO_4$), filtered and evaporated in vacuo to give the title compound as a white solid (970 mg, 90%).

LC-MS: m/z 233.0 [M−H]−

$^1$H NMR (400 MHz, MeOD/CDCl$_3$) δ 7.62 (t, J=1.5 Hz, 1H), 7.29-7.23 (m, 1H), 7.10-6.97 (m, 3H), 6.93-6.87 (m, 1H), 6.72-6.64 (m, 1H).

N-(2,6-difluoro-3-hydroxy-phenyl)-3-fluoro-5-(3-fluorophenyl)benzamide

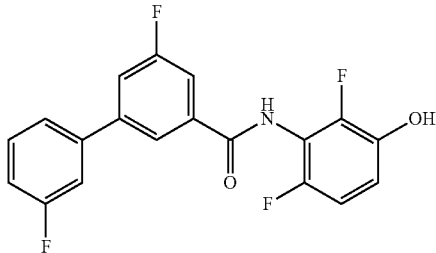 [SMILES: O=C(Nc1c(F)ccc(O)c1F)c1cc(F)cc(-c2cccc(F)c2)c1]

To a stirred solution of 3-fluoro-5-(3-fluorophenyl)benzoic acid (533 mg, 2.3 mmol, 1.1 eq) in DCM (10 mL) and DMF (3 drops) at 0° C. was added oxalylchloride (866 mg, 6.8 mmol, 3.3 eq) dropwise. The reaction was warmed to room temperature and stirred for 2 h, and then the solvent removed. The residue that remained was dissolved in THF (6 mL) and added to a solution of 3-amino-2,4-difluoro-phenol (intermediate X(a)) (300 mg, 2.07 mmol, 1.0 eq) and NaHCO$_3$ (868 mg, 10.34 mmol, 5.0 eq) in THF (6 mL) at 0° C. The reaction was warmed to room temperature and stirred for 1 h then quenched by addition of water. The aqueous layer was extracted with EtOAc and the combined organic extracts were washed with 5% Na$_2$CO$_3$, water and brine, dried (Na$_2$SO$_4$), filtered and evaporated in vacuo. The crude residue was recrystallised from DCM: petroleum ether (1:3) and collected by filtration to give the title compound as a solid (390 mg, 52%).

LC-MS: m/z 362.0 [M+H]+ 383.9 [M+Na]+

102

2,4-Difluoro-3-[[3-fluoro-5-(3-fluorophenyl)phenyl]methylamino]phenol

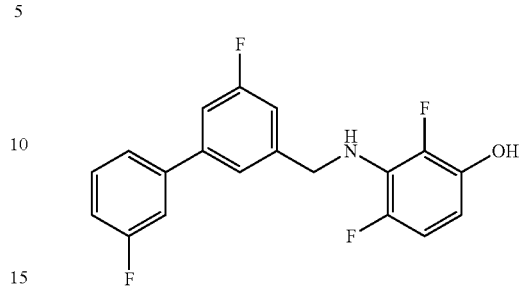

To a solution of N-(2,6-difluoro-3-hydroxy-phenyl)-3-fluoro-5-(3-fluorophenyl)benzamide (390 mg, 1.1 mmol, 1.0 eq) in THF (6 mL) at 0° C. was added a solution of BH$_3$ (1M in THF, 6.47 mL, 6.5 mmol, 6.0 eq). The reaction was heated to 60° C. and stirred overnight. The reaction mixture was quenched with water and extracted with EtOAc. The organic extract was washed with 5% NaHCO$_3$, water and brine, dried (Na$_2$SO$_4$) and the solvent removed in vacuo to afford a crude residue which was purified by column chromatography (petroleum ether:EtOAc 1:0 to 10:1) to give the title compound as an oil (353 mg, 94%).

LC-MS: m/z 348.1 [M−H]+

Ethyl 2-[2,4-difluoro-3-[[3-fluoro-5-(3-fluorophenyl)phenyl]methylamino]phenoxy]acetate (II(z))

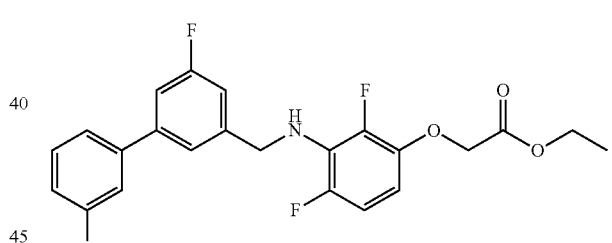

To a stirred solution of 2,4-difluoro-3-[[3-fluoro-5-(3-fluorophenyl)phenyl]methylamino]phenol (350 mg, 1.0 mmol, 1.0 eq) in acetone (5 mL) was added Cs$_2$CO$_3$ (492.5 mg, 1.5 mmol, 1.5 eq). The resulting mixture was stirred for 30 min at room temperature then ethyl bromoacetate (202 mg, 1.21 mmol, 1.2 eq) was added. The resulting mixture was stirred 1 h then water added and the mixture extracted with EtOAc. The combined organic extracts were washed with water and brine, dried (Na$_2$SO$_4$), filtered and evaporated in vacuo to give the title compound as an oil (385 mg, 88%).

LC-MS: m/z calculated for C$_{23}$H$_{19}$F$_4$NO$_3$ [M+H]+ 434.14, [M+Na]+ 456.13. found 433.9, 456.0

$^1$H NMR (400 MHz, DMSO) δ 7.56-7.47 (m, 4H), 7.43 (d, J=10.1 Hz, 1H), 7.29-7.19 (m, 1H), 7.14 (d, J=9.8 Hz, 1H), 6.85-6.75 (m, 1H), 6.33 (td, J=9.2, 4.7 Hz, 1H), 6.09 (br t, J=7.1 Hz, 1H), 4.75 (s, 2H), 4.47 (br d, J=7.0 Hz, 2H), 4.15 (q, J=6.9 Hz, 2H), 1.16 (t, J=7.1 Hz, 3H)

2-[2,4-difluoro-3-[[3-fluoro-5-(3-fluorophenyl)phenyl]methylamino]phenoxy]acetic acid (I(n))

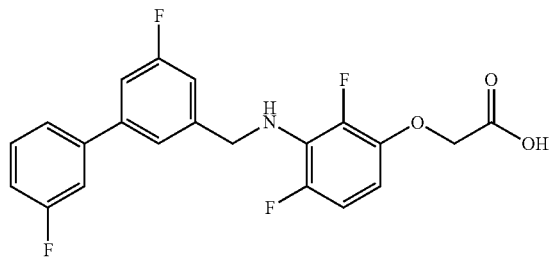 [SMILES: O=C(O)COc1ccc(F)c(NCc2cc(F)cc(-c3cccc(F)c3)c2)c1F]

To a stirred solution of Ethyl 2-[2,4-difluoro-3-[[3-fluoro-5-(3-fluorophenyl)phenyl]methylamino]phenoxy]acetate (385 mg, 0.89 mmol, 1.0 eq) in THF (4 mL) was added an aqueous solution of LiOH (2M aqueous solution, 3 mL, 6 mmol, 6.7 eq). The reaction was stirred at room temperature for 1 h. Water was added and the THF removed in vacuo. The aqueous residue was extracted with EtOAc and the combined organic extracts were washed with water and brine, dried (Na$_2$SO$_4$), filtered and evaporated in vacuo. The crude material obtained was recrystallised from DCM/petroleum ether, collected by filtration and dried in vacuo to give (I(n)) (60 mg, 17%) as a white solid.

LC-MS: m/z calculated for C$_{21}$H$_{15}$F$_4$NO$_3$ [M+H]$^+$ 406.11. found 406.0

$^1$H NMR (300 MHz, DMSO-d$_6$) δ 7.63-7.46 (m, 4H), 7.40 (d, J=10.1 Hz, 1H), 7.29-7.17 (m, 1H), 7.13 (d, J=9.7 Hz, 1H), 6.70 (ddd, J=11.7, 9.4, 2.1 Hz, 1H), 6.15 (td, J=9.2, 4.7 Hz, 1H), 5.96-5.80 (m, 1H), 4.45 (d, J=7.3 Hz, 2H), 4.05 (s, 2H)

Example 15

Compound I(o) Synthesized According to Scheme 3

2-[2-Chloro-4-fluoro-3-[[2-fluoro-5-(3-fluorophenyl)phenyl]methylamino]phenoxy]acetic acid (I(o))

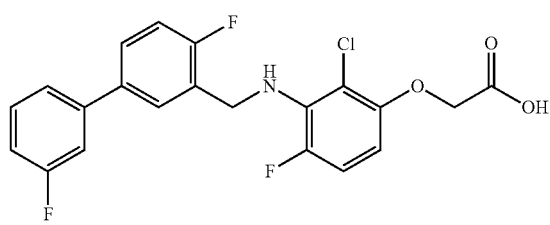 [SMILES: O=C(O)COc1ccc(F)c(NCc2cc(-c3cccc(F)c3)ccc2F)c1Cl]

2-Chloro-6-fluoro-3-methoxy-benzoic acid

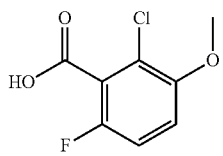

To a solution of 2-chloro-4-fluoro-1-methoxy-benzene (2.5 g, 15.6 mmol, 1 eq) in THF (25 mL) at −65° C. under N$_2$ was added a solution of n-BuLi (2.5 M, 17.1 mmol, 1.1 eq) dropwise. The reaction mixture was stirred at −65° C. for 1.5 h then CO$_2$ (gas) was bubbled into the solution for 10 min. The reaction mixture was then stirred at −60 to −20° C. for 30 min, then acidified with diluted HCl and extracted with EtOAc. The combined organic extracts were washed with water and brine, dried (Na$_2$SO$_4$), filtered and evaporated in vacuo to give the title compound (2.7 g, 85%) as a yellow solid which was used for next step without further purification.

LC-MS: m/z 203.0, 205.0 [M−H]$^-$ 159.0, 161.0. [M−COOH]$^-$ $^1$H NMR (400 MHz, DMSO-d$_6$) δ 14.06 (s, 1H), 7.31 (app t, J=8.9 Hz, 1H), 7.24 (dd, J=9.3, 5.0 Hz, 1H), 3.86 (s, 3H)

2-Chloro-6-fluoro-3-methoxy-aniline

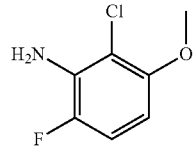

To a solution of 2-chloro-6-fluoro-3-methoxy-benzoic acid (2.7 g, 13.2 mmol, 1.0 eq) in a mixture of DCM (20 mL) and DMF (3 drops) at 0° C. was added (COCl)$_2$ (5.0 g, 39.6 mmol, 3.0 eq) dropwise. The reaction mixture was stirred at room temperature for 1 h, and then concentrated to dryness; the residue was dissolved in acetone (20 mL) and added dropwise to a solution of NaN$_3$ (2.6 g, 39.6 mmol, 3.0 eq) in water (15 mL) at 0° C. The reaction was stirred 1 h at 0° C., water (50 mL) was added, then the reaction heated at 70° C. overnight. The acetone was removed by distillation and the aqueous residue extracted with EtOAc. The combined organic extracts were washed with water and brine, dried (Na$_2$SO$_4$), filtered and evaporated in vacuo to give a residue, which was purified by column chromatography (EtOAc:petroleum ether, 0:1 to 1:30) to give the title compound as a yellow oil (0.85 g, 37%).

LC-MS: m/z 176.0, 178.0 [M+H]$^+$

3-Amino-2-chloro-4-fluoro-phenol (intermediate X(f))

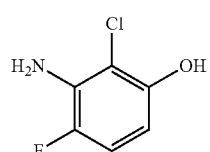

To a solution of 2-chloro-6-fluoro-3-methoxy-aniline (0.85 g, 4.84 mmol, 1.0 eq) in DCM (8 mL) at 0° C. was added BBr$_3$ (6.06 g, 24.2 mmol, 5.0 eq). The mixture was stirred at room temperature under N$_2$ overnight, then poured into ice-water. The pH of the solution was adjusted to pH 6 by addition of sat.NaHCO$_3$. The dichloromethane was removed under reduced pressure and the aqueous residue was extracted with EtOAc. The combined organic extracts were washed with brine, dried (Na$_2$SO$_4$), filtered and evaporated in vacuo to give the title compound as a pale yellow solid (0.74 g, 95%).

LC-MS: m/z 162.0, 164.0 [M+H]$^+$

¹H NMR (400 MHz, DMSO-d₆) δ 9.67 (s, 1H), 6.80 (dd, J=10.9, 8.9 Hz, 1H), 6.12 (dd, J=8.9, 4.6 Hz, 1H), 5.20 (br s, 2H)

N-(2-chloro-6-fluoro-3-hydroxy-phenyl)-2-fluoro-5-(3-fluorophenyl)benzamide

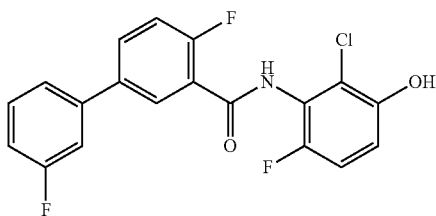

To a solution of 2-fluoro-5-(3-fluorophenyl)benzoic acid (intermediate III(a)) (478 mg, 2.04 mmol, 1.1 eq) in DCM (9 mL) and DMF (3 drops) at 0° C. was added (COCl)₂ (779 mg, 6.14 mmol, 3.3 eq) dropwise. The reaction mixture was stirred at room temperature for 1.5 h, then the solvent removed in vacuo. The residue obtained was dissolved in THF (7 mL) and added dropwise to a mixture of 3-amino-2-chloro-4-fluoro-phenol (intermediate X(f)) (300 mg, 1.86 mmol, 1.0 eq) and NaHCO₃ (781 mg, 9.3 mmol, 5.0 eq) in THF (7 mL) at 0° C. After addition was completed, the reaction mixture was warmed to room temperature and stirred overnight. Water was added and the aqueous mixture was extracted with EtOAc. The organic extract was washed with 5% Na₂CO₃, water and brine, dried (Na₂SO₄), filtered, evaporated in vacuo and purified by column chromatography (EtOAc:petroleum ether, 3:20 to 1:4) to give the title as a yellow solid compound (180 mg, 26%).

LC-MS: m/z 378.0 [M+H]⁺ 400.04, 402.04 [M+Na]⁺

2-Chloro-4-fluoro-3-[[2-fluoro-5-(3-fluorophenyl)phenyl]methylamino]phenol

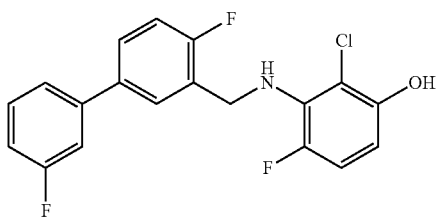 [SMILES: Oc1ccc(F)c(NCc2cc(-c3cccc(F)c3)ccc2F)c1Cl]

To a solution of N-(2-chloro-6-fluoro-3-hydroxy-phenyl)-2-fluoro-5-(3-fluorophenyl) benzamide (180 mg, 0.48 mmol, 1.0 eq) in THF (2.5 mL) at 0° C. under N₂ was added dropwise a solution of BH₃ (1M in THF, 2.86 mL, 2.86 mmol, 6.0 eq). The reaction mixture was heated at 60° C. for 3 h, then cooled and quenched by addition of water. The mixture was extracted with EtOAc and the organic extract was washed with NaHCO₃, water and brine, dried (Na₂SO₄), filtered, evaporated in vacuo and purified by column chromatography (EtOAc:petroleum ether, 1:10, 1.2:10) to give the title compound as an oil (144 mg, 83%).

LC-MS: m/z 364.1, 366.1 [M+H]⁺

Ethyl 2-[2-chloro-4-fluoro-3-[[2-fluoro-5-(3-fluorophenyl)phenyl]methylamino]phenoxy]acetate (II (aa))

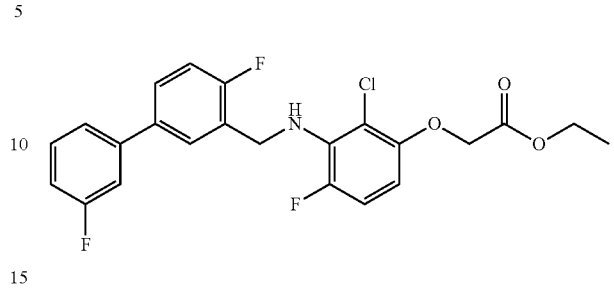

To a solution of 2-chloro-4-fluoro-3-[[2-fluoro-5-(3-fluorophenyl)phenyl]methylamino]phenol (144 mg, 0.40 mmol, 1.0 eq) in acetone (3 mL) was added Cs₂CO₃ (193.5 mg, 0.59 mmol, 1.5 eq). The reaction mixture was stirred for 30 min, then ethyl 2-bromoacetate (79.3 mg, 0.48 mmol, 1.2 eq) was added. The reaction mixture was stirred at room temperature for 1 h and the resulting mixture poured into water and extracted with EtOAc. The organic extract was washed with water and brine, dried (Na₂SO₄), filtered, and evaporated in vacuo. The residue obtained was purified by column chromatography (EtOAc:petroleum ether, 1:20 to 1:10) to give the title compound as an oil (155 mg, 87%).

LC-MS: m/z 450.1, 452.1 [M+H]⁺ 472.1, 474.1 [M+Na]⁺

¹H NMR (400 MHz, DMSO-d₆) δ 7.68 (dd, J=7.1, 2.4 Hz, 1H), 7.62-7.55 (m, 1H), 7.49 (td, J=7.9, 6.4 Hz, 1H), 7.40-7.32 (m, 2H), 7.26-7.14 (m, 2H), 6.95 (dd, J=12.8, 9.2 Hz, 1H), 6.34 (dd, J=9.2, 3.8 Hz, 1H), 5.83-5.74 (m, 1H), 4.79 (s, 2H), 4.61 (br d, J=7.2 Hz, 2H), 4.11 (q, J=7.1 Hz, 2H), 1.15 (t, J=7.1 Hz, 3H)

2-[2-Chloro-4-fluoro-3-[[2-fluoro-5-(3-fluorophenyl)phenyl]methylamino]phenoxy]acetic acid (I(o))

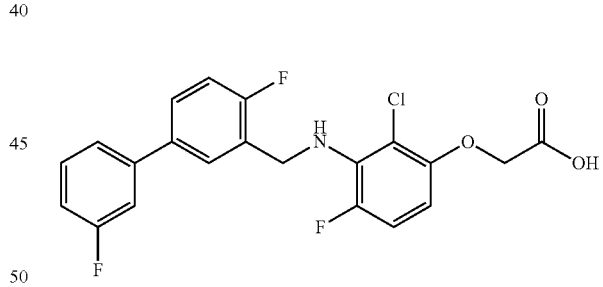

To a solution of ethyl 2-[2-chloro-4-fluoro-3-[[2-fluoro-5-(3-fluorophenyl)phenyl]methylamino]phenoxy]acetate (155 mg, 0.34 mmol) in THF (2 mL) was added LiOH (2M aqueous solution, 2.5 mL, 2.5 mmol, 7.4 eq). The reaction mixture was stirred at room temperature for 2 h, then the organic solvent was removed in vacuo. The residue that remained was diluted with water and adjusted to pH 4-6 by addition of diluted HCl. The solid precipitate that formed was collected by filtration, washed with water and dried in vacuo to afford a crude product which was crystallized from DCM (1 mL) and hexane (20 mL) to give the title compound (I(o)) as a white solid (100 mg, 69%).

LC-MS: m/z 421.9, 423.9 [M+H]⁺

¹H NMR (300 MHz, DMSO-d₆) δ 7.69 (dd, J=7.2, 2.2 Hz, 1H), 7.63-7.55 (m, 1H), 7.53-7.43 (m, 1H), 7.43-7.32 (m,

2H), 7.23 (dd, J=9.8, 8.6 Hz, 1H), 7.22-7.10 (m, 1H), 6.94 (dd, J=12.6, 9.2 Hz, 1H), 6.30 (dd, J=9.2, 3.8 Hz, 1H), 5.73 (t, J=7.1 Hz, 1H), 4.85-4.43 (m, 4H)

Example 16

Compound I(p) Synthesized According to Scheme 3 (Amended by Addition of Hydrolysis Step Before Last Step)

2-[2,4-Difluoro-3-[[3-(3-fluorophenyl)-5-hydroxy-phenyl]methylamino]phenoxy]acetic acid (I(p))

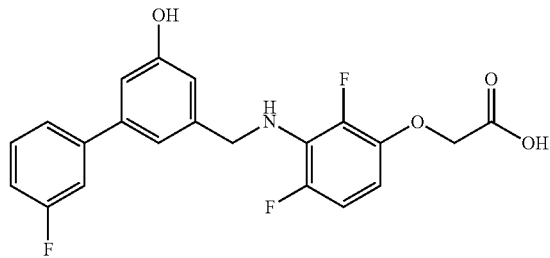

Methyl 3-bromo-5-methoxy-benzoate

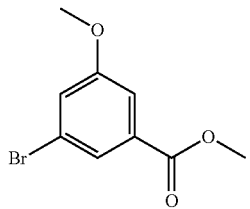

A mixture of 3-bromo-5-hydroxy-benzoic acid (3 g, 13.8 mmol, 1.0 eq) and Cs$_2$CO$_3$ (13.5 g, 41.5 mmol, 3.0 eq) in DMF (60 mL) was stirred at room temperature for 1 h. Methyl iodide (4.9 g, 34.6 mmol, 2.5 eq) was added and the reaction was stirred at room temperature overnight. The resulting mixture was poured into water and extracted with EtOAc. The organic extract was washed with water and brine, dried (Na$_2$SO$_4$), filtered and evaporated in vacuo to give the title compound as a colourless oil (3 g, 88%).
LCMS: m/z 245.0, 247.0 [M+H]$^+$ 266.9, 269.0 [M+Na]$^+$ Methyl 3-(3-fluorophenyl)-5-methoxy-benzoate

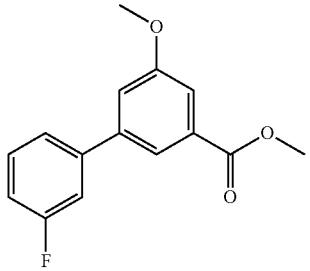 [SMILES: COC(=O)c1cc(OC)cc(-c2cccc(F)c2)c1]

A suspension of methyl 3-bromo-5-methoxy-benzoate (3.2 g, 13.1 mmol, 1.0 eq), 3-fluorophenylboronic acid (2.0 g, 14.4 mmol, 1.1 eq) K$_2$CO$_3$ (7.2 g, 52.2 mmol, 4.0 eq) and Pd(PPh$_3$)$_4$ (754 mg, 0.65 mmol, 0.05 eq) in a mixture of methanol (10 mL) and dioxane (50 mL) was heated at 70° C. for 4 h under N$_2$. After cooling, the resulting mixture was concentrated and purified by column chromatography (EtOAc:petroleum ether, 0:1 to 1:20) to give the title compound as an oil (3.0 g, 88%).
LCMS: m/z 261.1 [M+H]$^+$ 283.1 [M+Na]$^+$ 3-(3-Fluorophenyl)-5-methoxy-benzoic acid (intermediate III(i))

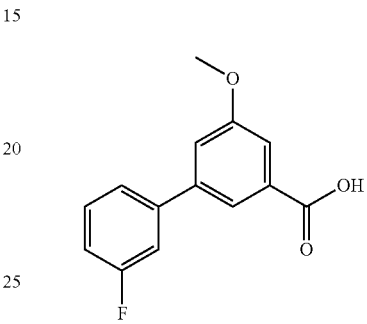

To a solution of methyl 3-(3-fluorophenyl)-5-methoxy-benzoate (3 g, 11.5 mmol, 1.0 eq) in a mixture of methanol (20 mL) and THF (20 mL) at 0° C. was added a solution of aqueous KOH (2M aqueous solution, 20 mL, 40 mmol, 3.5 eq). The reaction mixture was stirred at room temperature for 2 h. The resulting mixture was concentrated to remove the methanol and THF then poured into water and the pH adjusted to pH 3-4 by addition of 1M HCl. The precipitate that formed was collected by filtration, washed with water and dried in vacuo to give the title compound as a white solid (2.5 g, 88%).
LC-MS: m/z 247.1 [M+H]$^+$ 269.0 [M+Na]$^+$
$^1$H NMR (400 MHz, DMSO-d$_6$) δ 13.20 (br. s., 1H), 7.78 (s, 1H), 7.62-7.50 (m, 3H), 7.50-7.44 (m, 2H), 7.28-7.20 (m, 1H), 3.89 (s, 3H)

N-(2,6-difluoro-3-hydroxy-phenyl)-3-(3-fluorophenyl)-5-methoxy-benzamide

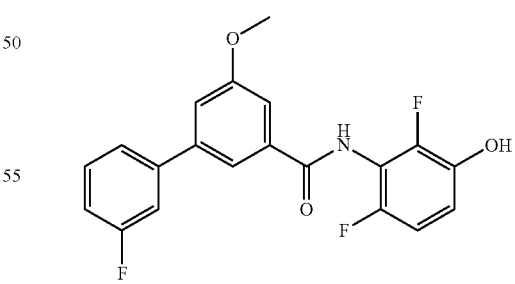

To a solution of 3-(3-fluorophenyl)-5-methoxy-benzoic acid (747 mg, 3.0 mmol, 1.1 eq) in DCM (20 mL) was added oxalyl chloride (1.05 g, 8.3 mmol, 3.0 eq) and DMF (3 drops). The reaction mixture was stirred at room temperature for 2 h, then concentrated. The oil obtained was dissolved in THF (5 mL) and added dropwise to a cooled solution of 3-Amino-2, 4-difluoro-phenol (intermediate X(a)) (400 mg, 2.76 mmol, 1.0 eq) in THF (25 mL) at 0° C. After addition, the reaction mixture was stirred at room temperature for 2 h. The resulting mixture was poured into water and extracted with EtOAc. The organic extract was washed with water and brine, dried (Na$_2$SO$_4$), filtered, evaporated in vacuo and purified by column chromatography (EtOAc:petroleum ether, 0:1 to 1:3) to give the title compound as a yellow solid (700 mg, 68%).

LC-MS: m/z 374.1 [M+H]$^+$ 396.1 [M+Na]$^+$ 2,4-Difluoro-3-[[3-(3-fluorophenyl)-5-methoxy-phenyl]methylamino]phenol

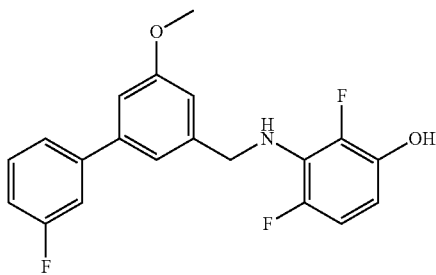 [SMILES: COc1cc(CNc2c(F)ccc(O)c2F)cc(-c2cccc(F)c2)c1]

To a solution of N-(2,6-difluoro-3-hydroxy-phenyl)-3-(3-fluorophenyl)-5-methoxy-benzamide (600 mg, 1.6 mmol, 1.0 eq) in THF under N$_2$ was added dropwise a solution of BH$_3$ (1M in THF, 8 mL, 8.0 mmol, 8.0 eq) at room temperature. The reaction mixture was heated at reflux for 4 h, then cooled and the reaction quenched by addition of 1M HCl. The aqueous layer was extracted with EtOAc and the combined organic extracts were washed with water and brine, dried (Na$_2$SO$_4$), filtered and evaporated in vacuo to give the product (550 mg, 95%) as yellow oil which was used directly to the next step without further purification.

LC-MS: m/z 360.1 [M+H]$^+$

Ethyl 2-[2,4-difluoro-3-[[3-(3-fluorophenyl)-5-methoxy-phenyl]methylamino]phenoxy]acetate (II(ab))

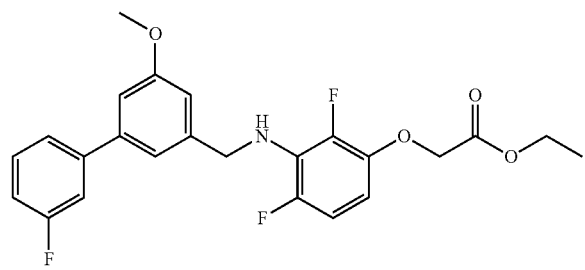 [SMILES: CCOC(=O)COc1ccc(F)c(NCc2cc(OC)cc(-c3cccc(F)c3)c2)c1F]

To a solution of 2,4-difluoro-3-[[3-(3-fluorophenyl)-5-methoxy-phenyl]methylamino]phenol (500 mg, 1.4 mmol, 1.0 eq) in DMF (10 mL) was added Cs$_2$CO$_3$ (634 mg, 1.9 mmol, 1.4 eq). The reaction mixture was stirred for 1 h, then ethyl 2-bromoacetate (279 mg, 1.7 mmol, 1.2 eq) was added. The reaction mixture was stirred for a further 1 h, then poured into water and extracted with EtOAc. The organic extract was washed with water and brine, dried (Na$_2$SO$_4$), filtered and evaporated in vacuo. The crude residue obtained was purified by column chromatography (EtOAc:petroleum ether, 0:1 to 1:10) to give the title compound as an oil (500 mg, 80%).

LC-MS: m/z 446.2 [M+H]$^+$ 468.2 [M+Na]$^+$ $^1$H NMR (400 MHz, CDCl$_3$) δ 7.42-7.32 (m, 2H), 7.28-7.22 (m, 1H), 7.13 (br s, 1H), 7.08-7.01 (m, 1H), 7.01-6.97 (m, 1H), 6.91 (br s, 1H), 6.70 (ddd, J=11.3, 9.2, 2.2 Hz, 1H), 6.28 (ddd, J=13.8, 9.1, 4.7 Hz, 1H), 4.61 (s, 2H), 4.54 (br s, 2H), 4.25 (q, J=7.1 Hz, 2H), 3.85 (s, 3H), 1.28 (t, J=7.1 Hz, 3H)

Ethyl 2-[2,4-difluoro-3-[[3-(3-fluorophenyl)-5-hydroxy-phenyl]methylamino]phenoxy]acetate (II(b))

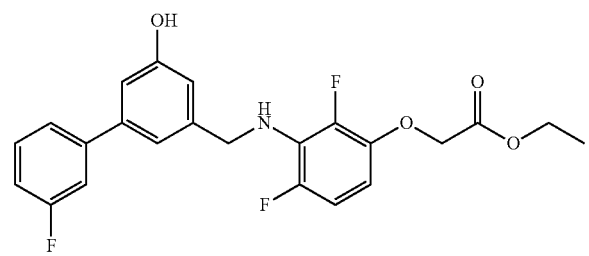

To a solution of ethyl 2-[2,4-difluoro-3-[[3-(3-fluorophenyl)-5-methoxy-phenyl]methylamino]phenoxy]acetate (400 mg, 0.9 mmol, 1.0 eq) and AlCl$_3$ (718 mg, 5.4 mmol, 6.0 eq) in DCM (10 mL) at 0° C. was added ethanethiol (315 mg, 5.4 mmol, 6.0 eq) under N$_2$. The reaction mixture was stirred at 0° C. for 30 min. The resulting mixture was poured into water and extracted with EtOAc. The organic extract was washed with brine, dried (Na$_2$SO$_4$), filtered, evaporated in vacuo and the crude residue obtained purified by column chromatography (EtOAc:petroleum ether, 0:1 to 1:4) to give the title compound as an oil (260 mg, 67%).

LC-MS: m/z 432.1 [M+H]$^+$ 454.1 [M+Na]$^+$ $^1$H NMR (400 MHz, CDCl$_3$) δ 7.44-7.32 (m, 2H), 7.28-7.22 (m, 1H), 7.11 (br s, 1H), 7.08-7.02 (m, 1H), 6.96 (br s, 1H), 6.85 (br s, 1H), 6.72 (ddd, J=11.3, 9.2, 2.2 Hz, 1H), 6.31 (td, J=9.0, 4.7 Hz, 1H), 4.66 (s, 2H), 4.53 (br s, 2H), 4.27 (q, J=7.1 Hz, 2H), 1.31 (t, J=7.1 Hz, 3H)

2-[2,4-Difluoro-3-[[3-(3-fluorophenyl)-5-hydroxy-phenyl]methylamino]phenoxy]acetic acid (I(p))

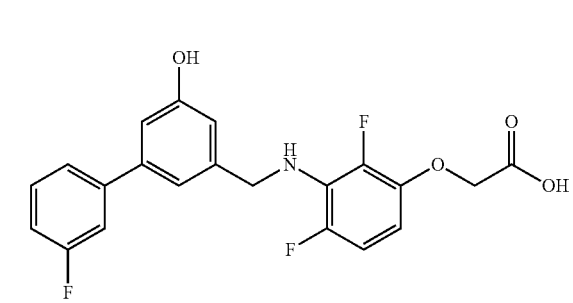 [SMILES: O=C(O)COc1ccc(F)c(NCc2cc(O)cc(-c3cccc(F)c3)c2)c1F]

To a solution of ethyl 2-[2,4-difluoro-3-[[3-(3-fluorophenyl)-5-hydroxy-phenyl]methylamino]phenoxy]acetate (II(b)) (200 mg, 0.46 mmol, 1.0 eq) in THF (10 mL) was added NaOH (1M, 6 mL, 6 mmol, 13.0 eq) at 0° C. The reaction mixture was allowed to warm room temperature and was stirred for 3 h. The THF was removed in vacuo and the remaining solution diluted with water and adjusted to pH 4-6 by addition of diluted HCl. The precipitate that formed was collected by filtration and dried in vacuo to give the title compound (I(p)) as a solid (170 mg, 91%).

LC-MS: m/z 404.0 [M+H]$^+$ $^1$H NMR (300 MHz, CDCl$_3$) δ 7.59-7.42 (m, 1H), 7.41-7.27 (m, 2H), 7.25-7.09 (m, 1H), 7.05 (s, 1H), 6.86 (s, 1H), 6.82-6.75 (m, 1H), 6.74 (s, 1H), 6.27 (td, J=9.0, 4.5 Hz, 1H), 5.92 (s, 1H), 4.62 (s, 2H), 4.38 (d, J=6.9 Hz, 2H)

Example 17

Compound I(q) Synthesized According to Scheme 3

2-[2,4-Difluoro-3-[[3-(3-fluorophenyl)-5-methoxy-phenyl]methylamino]phenoxy]acetic acid (I(q))

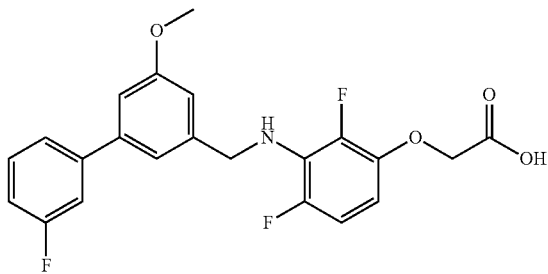

To a solution of ethyl 2-[2,4-difluoro-3-[[3-(3-fluorophenyl)-5-methoxy-phenyl]methylamino]phenoxy]acetate (see example 16) (200 mg, 0.45 mmol, 1.0 eq) in THF (10 mL) was added an aqueous solution of NaOH (1 M aqueous solution, 4 mL, 4 mmol, 8.9 eq) at 0° C. The reaction mixture was stirred at room temperature for 3 h. The organic solvent was removed water added and the pH adjusted to pH 4-6 by addition of 1M HCl. The solid that precipitated was collected by filtration and dried in vacuo to give the title compound as a solid (150 mg, 80%).

LC-MS: m/z 417.9 [M+H]$^+$ $^1$H NMR (400 MHz, DMSO-d$_6$) δ 7.61-7.36 (m, 3H), 7.36-7.14 (m, 2H), 7.05 (s, 1H), 6.89 (s, 1H), 6.85-6.64 (m, 1H), 6.28 (td, J=9.1, 4.6 Hz, 1H), 5.96 (s, 1H), 4.62 (s, 2H), 4.42 (d, J=6.9 Hz, 2H), 3.78 (s, 3H)

Example 18

Compound I(r) Synthesized According to Scheme 2

2-[2,4-Dichloro-3-[[2-fluoro-5-(3-fluorophenyl)phenyl]methylamino]phenoxy]acetic acid (I(r))

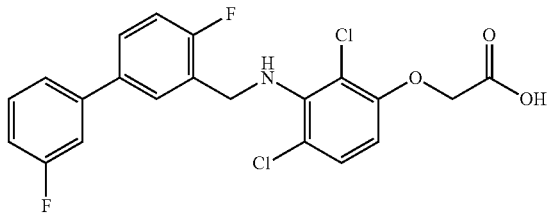

1,3-Dichloro-4-methoxy-2-nitro-benzene

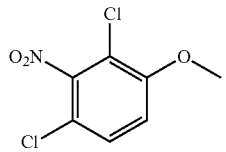

To a solution of 2,4-dichloro-3-nitro-phenol (600 mg, 2.9 mmol, 1.0 eq) in acetone (30 mL), was added K$_2$CO$_3$ (1.2 g, 8.7 mmol, 3.0 eq) and the solution was stirred at room temperature for 30 min. Methyl iodide (1.2 g, 8.7 mmol, 3.0 eq) was added and the reaction was stirred at room temperature overnight. The reaction was filtered to remove the inorganic salts and the organic phase was evaporated in vacuo to give the title compound (550 mg, 86%).

$^1$H NMR (400 MHz, DMSO-d$_6$) δ 7.78 (d, J=9.3 Hz, 1H), 7.47 (d, J=9.2 Hz, 1H), 3.97 (s, 3H)

2,6-Dichloro-3-methoxy-aniline (intermediate VI(a))

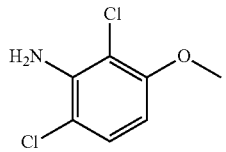

To a solution of 1,3-dichloro-4-methoxy-2-nitro-benzene (550 mg, 2.5 mmol, 1.0 eq) in EtOAc (20 mL) was added Pd/C (10% Pd, 50 mg) and the reaction was stirred under a hydrogen atmosphere overnight. The catalyst was removed by filtration and the filtrate was evaporated in vacuo to give the title compound (500 mg, 100%).

LC-MS: m/z 192.0, 194.0, 196.0 [M+H]$^+$

N-(2,6-dichloro-3-methoxy-phenyl)-2-fluoro-5-(3-fluorophenyl)benzamide

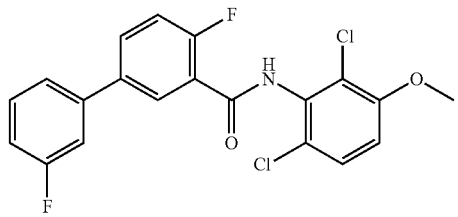 [SMILES: COc1ccc(Cl)c(NC(=O)c2cc(-c3cccc(F)c3)ccc2F)c1Cl]

A solution of 2-fluoro-5-(3-fluorophenyl)benzoic acid (intermediate III(a)) (1.6 g, 7 mmol, 3.0 eq) in SOCl$_2$ (20 mL) was heated at reflux for 3 h. The excess thionyl chloride was removed in vacuo and the residue obtained dissolved in THF (10 mL) and added dropwise to a solution of 2,6-dichloro-3-methoxy-aniline (450 mg, 2.3 mmol, 1.0 eq) and NaH (85 mg, 3.4 mmol, 1.5 eq) in THF (10 mL). The reaction was stirred at room temperature for 2 h then quenched by addition of aqueous NH$_4$Cl. The mixture was extracted with EtOAc and the combined organic extracts were dried (Na$_2$SO$_4$), filtered and evaporated in vacuo. The residue obtained was purified by column chromatography (EtOAc:petroleum ether, 0:1 to 1:4) to give the title compound (200 mg, 21%).

LC-MS: m/z 430.0, 432.0, 434.0 [M+Na]$^+$

2,6-Dichloro-N-[[2-fluoro-5-(3-fluorophenyl)phenyl]methyl]-3-methoxy-aniline

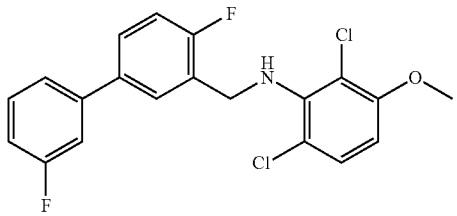

To a solution of N-(2,6-dichloro-3-methoxy-phenyl)-2-fluoro-5-(3-fluorophenyl)benzamide (200 mg, 0.5 mmol, 1.0 eq) in dry THF (10 mL) was added a solution of $BH_3$ (1M in THF, 2 mL, 2 mmol, 4.0 eq) dropwise. The solution was then heated at 60° C. overnight. The reaction was quenched by addition of MeOH, then concentrated and the residue obtained was purified by column chromatography (Petroleum ether:EtOAc, 10:1) to give the title compound (150 mg, 77%).

LC-MS: m/z 394.0, 396.0 $[M+H]^+$

2,4-Dichloro-3-[[2-fluoro-5-(3-fluorophenyl)phenyl]methylamino]phenol

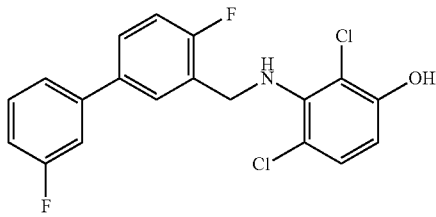

To a solution of 2,6-dichloro-N-[[2-fluoro-5-(3-fluorophenyl)phenyl]methyl]-3-methoxy-aniline (200 mg, 0.5 mmol, 1.0 eq) in DCM (15 mL) at 0° C. was added borontribromide (640 mg, 2.5 mmol, 5.0 eq) portion-wise. The reaction was stirred at room temperature overnight then poured into ice. The mixture was extracted with EtOAc and the combined organic extracts were dried, $(Na_2SO_4)$ filtered and evaporated in vacuo. The residue obtained was purified by column chromatography (Petroleum ether:EtOAc, 20:1) to give the title compound (150 mg, 77%).

LC-MS: m/z 380.1, 382.0, 384.1 $[M+H]^+$

Ethyl 2-[2,4-dichloro-3-[[2-fluoro-5-(3-fluorophenyl)phenyl]methylamino]phenoxy]acetate

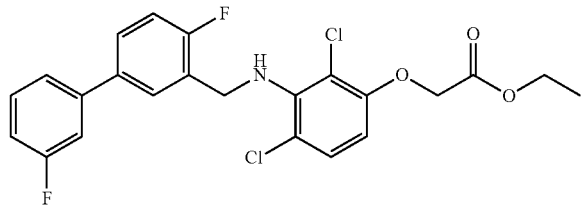 [SMILES: CCOC(=O)COc1ccc(Cl)c(NCc2cc(-c3cccc(F)c3)ccc2F)c1Cl]

To a solution of 2,4-dichloro-3-[[2-fluoro-5-(3-fluorophenyl)phenyl]methylamino]phenol (150 mg, 0.4 mmol, 1.0 eq) in DMF (50 mL), was added $K_2CO_3$ (220 mg, 0.6 mmol, 1.5 eq) and the solution was stirred at room temperature for 30 min. $BrCH_2CO_2Et$ (100 mg, 1.6 mmol, 4.0 eq) was added dropwise and the reaction was stirred overnight. The reaction was quenched by addition of water (200 mL) and extracted with EtOAc. The combined organic extracts were dried $(Mg_2SO_4)$, filtered and evaporated under reduced pressure and the residue obtained purified by column chromatography (EtOAc:petroleum ether, 0:1 to 1:10) to give the title compound (130 mg, 70%).

LC-MS: m/z 466.1, 468.1, 470.1 $[M+H]^+$ 488.1, 490.1, 490.0 $[M+Na]^+$

2-[2,4-Dichloro-3-[[2-fluoro-5-(3-fluorophenyl)phenyl]methylamino]phenoxy]acetic acid (I(r))

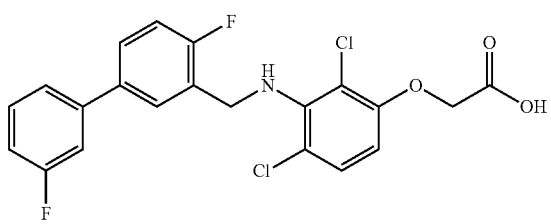 [SMILES: O=C(O)COc1ccc(Cl)c(NCc2cc(-c3cccc(F)c3)ccc2F)c1Cl]

To a solution of ethyl 2-[2,4-dichloro-3-[[2-fluoro-5-(3-fluorophenyl)phenyl]methylamino]phenoxy]acetate (130 mg, 0.28 mmol, 1.0 eq) in THF (20 mL), $LiOH.H_2O$ (50 mg, 1.1 mmol, 4.0 eq) was added. After the addition of water (10 mL), the mixture was heated to 60° C. overnight. The THF was then removed in vacuo and the water phase was adjusted to pH 6 by addition of 1M HCl. The precipitate was collected by filtration, washed with water and dried in vacuo to give the title compound as a solid (80 mg, 65%).

LC-MS: m/z 437.9, 439.1, 441.1 $[M+H]^+$ $^1$H NMR (300 MHz, DMSO-$d_6$) δ 7.96-7.73 (m, 1H), 7.59 (td, J=5.4, 2.4 Hz, 1H), 7.54-7.45 (m, 1H), 7.44-7.33 (m, 2H), 7.31-7.00 (m, 3H), 6.49 (d, J=9.0 Hz, 1H), 5.52-5.18 (m, 1H), 4.62 (d, J=5.6 Hz, 2H), 4.58 (s, 2H)

Example 19

Compound I(s) Synthesized According to Scheme 3

2-[3-[[2,6-Difluoro-3-(3-fluorophenyl)phenyl]methylamino]-2,4-difluoro-phenoxy]acetic acid (I(s))

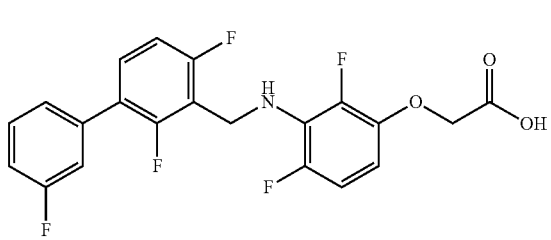

Methyl 2,6-difluoro-3-hydroxy-benzoate

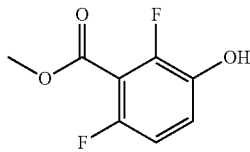

To a solution of 2,6-difluoro-3-triisopropylsilyloxy-benzoic acid (see example 2) (7 g, 21.1 mmol, 1.0 eq) in MeOH (100 mL) was added SOCl$_2$ (10 mL) dropwise. The reaction mixture was heated at reflux for 3 h, then cooled and the solvent removed in vacuo. Water was added and the aqueous layer was extracted with EtOAc. The organic extract was washed with water and brine, dried (Na$_2$SO$_4$), filtered and evaporated in vacuo to give the title compound as a solid (3 g, 75%) which was used in the next step without further purification.

LC-MS: m/z 189.0 [M+H]$^+$ 211.0 [M+Na]$^+$

Methyl 2,6-difluoro-3-(trifluoromethylsulfonyloxy)benzoate

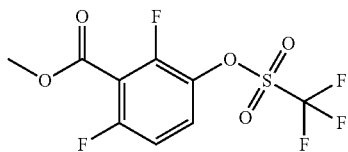 [SMILES: COC(=O)c1c(F)ccc(OS(=O)(=O)C(F)(F)F)c1F]

To a solution of Methyl 2,6-difluoro-3-hydroxy-benzoate (2 g, 10.6 mmol, 1.0 eq) and pyridine (2.1 g, 26.8 mmol, 2.5 eq) in DCM (30 mL) at 0° C. under N$_2$ was added dropwise triflic anhydride (4.5 g, 15.95 mmol, 1.5 eq). After addition was completed, the reaction was allowed to warm to room temperature and stirred at room temperature for 4 h. The resulting mixture was poured into water and adjusted to pH 5-6 by addition of 1M HCl. The aqueous layer was extracted with EtOAc and the organic extract washed with water and brine, dried (Na$_2$SO$_4$), filtered, evaporated in vacuo and purified by flash column chromatography (EtOAc:petroleum ether, 0:1 to 1:20) to give the title compound as a colourless oil (3 g, 88%).

Methyl 2,6-difluoro-3-(3-fluorophenyl)benzoate

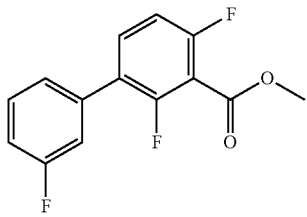 [SMILES: COC(=O)c1c(F)ccc(-c2cccc(F)c2)c1F]

A mixture of methyl 2,6-difluoro-3-(trifluoromethylsulfonyloxy)benzoate (3.0 g, 9.4 mmol, 1.0 eq), 3-fluorophenyl-boronic acid (1.57 g, 11.2 mmol, 1.2 eq), K$_2$CO$_3$ (5.2 g, 37.6 mmol, 4.0 eq) and Pd(PPh$_3$)$_4$ (543 mg, 0.47 mmol, 0.05 eq) in a mixture of MeOH (10 mL) and dioxane (30 mL) was heated to 80° C. under N$_2$ overnight. After cooling, the resulting mixture was concentrated in vacuo and purified by flash column chromatography (EtOAc:petroleum ether, 0:1 to 1:10) to give the title compound as an oil (1.7 g, 68%).

LC-MS: m/z 267.1 [M+H]$^+$ 289.1 [M+Na]$^+$

2,6-difluoro-3-(3-fluorophenyl)benzoic acid (intermediate III(j))

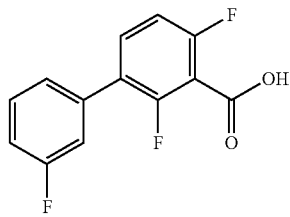 [SMILES: O=C(O)c1c(F)ccc(-c2cccc(F)c2)c1F]

To a solution of methyl 2,6-difluoro-3-(3-fluorophenyl)benzoate (1.7 g, 6.4 mmol, 1.0 eq) in mixture of MeOH (20 mL) and THF (20 mL) was added a solution of aqueous NaOH (1M aqueous solution, 20 mL, 20 mmol, 3.1 eq) at room temperature. The reaction mixture was heated to reflux for 30 mins, then cooled and the resulting mixture concentrated in vacuo to remove the organic solvent. The residue was diluted with water and adjusted to pH 5-6, by addition of 1M HCl. The precipitate that formed was collected by filtration, washed with water and dried in vacuo to give the title compound as a white solid (1.4 g, 87%).

LC-MS: m/z 253.0 [M+H]$^+$ 275.0 [M+Na]$^+$ $^1$H NMR (400 MHz, DMSO-d6) δ 14.15 (br s, 1H), 7.77-7.68 (m, 1H), 7.58-7.50 (m, 1H), 7.43-7.36 (m, 2H), 7.36-7.24 (m, 2H)

N-(2,6-difluoro-3-hydroxy-phenyl)-2,6-difluoro-3-(3-fluorophenyl)benzamide

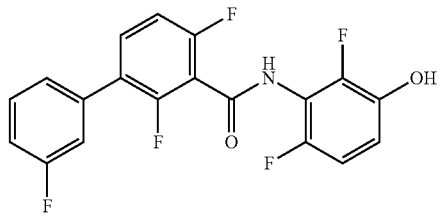 [SMILES: O=C(Nc1c(F)ccc(O)c1F)c1c(F)ccc(-c2cccc(F)c2)c1F]

To a solution of 2,6-difluoro-3-(3-fluorophenyl)benzoic acid (765 mg, 3.03 mmol, 1.1 eq) and oxalyl chloride (1.05 g, 8.5 mmol, 3.0 eq) in DCM (20 mL) was added DMF (0.1 mL). The reaction mixture was stirred at room temperature for 2 h, then concentrated in vacuo. The residue obtained was dissolved in THF (5 mL) and added dropwise to a solution of 3-amino-2,4-difluoro-phenol (intermediate X(a)) (400 mg, 2.76 mmol, 1.0 eq) in THF (25 mL) at 0° C. over 10 min. After addition, the reaction mixture was allowed to warm to room temperature and stirred for 3 h. The resulting mixture was poured into water and extracted with EtOAc. The organic extract was washed with water and brine, dried (Na$_2$SO$_4$), filtered, evaporated in vacuo and purified by column chromatography (EtOAc:petroleum ether, 0:1 to 1:4) to give the title compound as a yellow solid (600 mg, 61%).

3-[[2,6-Difluoro-3-(3-fluorophenyl)phenyl]methylamino]-2,4-difluoro-phenol

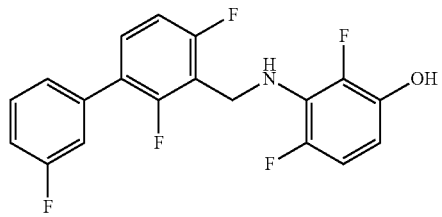 [SMILES: Oc1ccc(F)c(NCc2c(F)ccc(-c3cccc(F)c3)c2F)c1F]

To a solution of N-(2,6-difluoro-3-hydroxy-phenyl)-2,6-difluoro-3-(3-fluorophenyl)benzamide (500 mg, 1.32 mmol, 1.0 eq) in THF (10 mL) under N₂ was added dropwise a solution of BH₃ (1M in THF, 7 mL, 7.0 mmol, 5.3 eq) at room temperature. The reaction mixture was heated at reflux for 4 h then cooled and the reaction was quenched by addition of 1M HCl. The aqueous layer was extracted with EtOAc and the organic extract was washed with water and brine, dried (Na₂SO₄), filtered and evaporated in vacuo to give the title compound (400 mg, 83%) as an oil which was used in the next step without purification.

Ethyl 2-[3-[[2,6-difluoro-3-(3-fluorophenyl)phenyl]methylamino]-2,4-difluoro-phenoxy]acetate (II(ac))

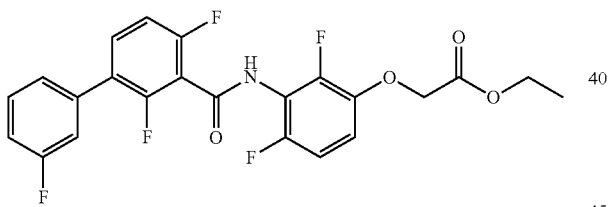

To a solution of 3-[[2,6-difluoro-3-(3-fluorophenyl)phenyl]methylamino]-2,4-difluoro-phenol (300 mg, 0.82 mmol, 1.0 eq) in DMF (5 mL) was added Cs₂CO₃ (375 mg, 1.15 mmol, 1.4 eq) at room temperature. The reaction mixture was stirred for 1 h, then ethyl 2-bromoacetate (151 mg, 0.90 mmol, 1.1 eq) was added. The reaction mixture was stirred for a further 1 h and the resulting mixture was poured into water and extracted with EtOAc. The organic extract was washed with water and brine, dried (Na₂SO₄), filtered, evaporated in vacuo and purified by column chromatography (EtOAc:petroleum ether, 0:1 to 1:10) to give the title compound as an oil (240 mg, 65%).

LC-MS: m/z 452.1 [M+H]⁺ 474.1 [M+Na]⁺

¹H NMR (400 MHz, CDCl₃) δ 7.43-7.36 (m, 1H), 7.35-7.27 (m, 1H), 7.26-7.22 (m, 1H), 7.18 (br d, J=10.0 Hz, 1H), 7.10-7.03 (m, 1H), 6.98-6.92 (m, 1H), 6.73-6.66 (m, 1H), 6.34 (td, J=9.0, 4.7 Hz, 1H), 4.66 (s, 2H), 4.60 (s, 2H), 4.24 (q, J=7.1 Hz, 2H), 1.27 (t, J=7.2 Hz, 3H)

2-[3-[[2,6-difluoro-3-(3-fluorophenyl)phenyl]methylamino]-2,4-difluoro-phenoxy]acetic acid (I(s))

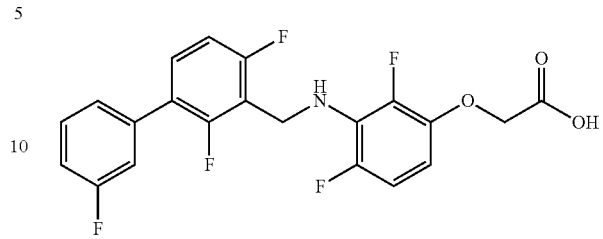

To a solution of ethyl 2-[3-[[2,6-difluoro-3-(3-fluorophenyl)phenyl]methylamino]-2,4-difluoro-phenoxy]acetate (240 mg, 0.53 mmol, 1.0 eq) in THF (10 mL) was added a solution of aqueous NaOH (1M aqueous solution, 5 mL, 5 mmol, 9.4 eq). The reaction mixture was stirred at room temperature for 3 h. The organic solvent was removed in vacuo and the residue diluted with water and adjusted to pH 5-6 by addition of diluted HCl. The precipitate that formed was collected by filtration, washed with water and dried in vacuo to give the title compound as a solid (180 mg, 80%).

LC-MS: m/z 423.9 [M+H]⁺

¹H NMR (300 MHz, DMSO-d₆) δ 7.63-7.43 (m, 2H), 7.39-7.29 (m, 2H), 7.29-7.21 (m, 1H), 7.16 (td, J=8.9, 1.3 Hz, 1H), 6.82 (ddd, J=11.5, 9.3, 2.2 Hz, 1H), 6.39 (td, J=9.1, 4.7 Hz, 1H), 5.56-5.21 (m, 1H), 4.64 (s, 2H), 4.55 (d, J=6.5 Hz, 2H)

Example 20

Compound I(t) Synthesized According to Scheme 3

2-[2,4-Difluoro-3-[[5-(3-fluorophenyl)-2-methoxy-3-methyl-phenyl]methylamino]phenoxy]acetic acid (I(t))

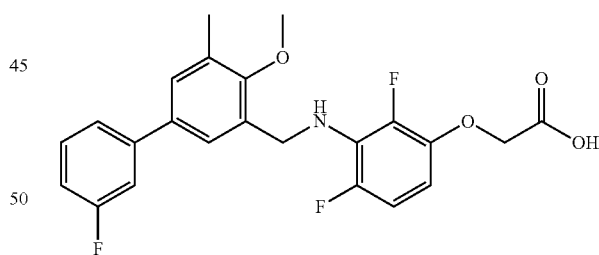

5-Bromo-2-hydroxy-3-methyl-benzoic acid

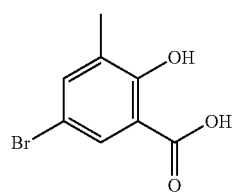

To a solution of 2-hydroxy-3-methyl-benzoic acid (10 g, 66.7 mmol, 1.0 eq) in acetic acid (100 mL) was added bromine (10.66 g, 66.7 mmol, 1.0 eq) slowly over 5 min. The mixture was stirred at room temperature for 24 h, then water was added slowly and the mixture was stirred for a further 30 min. The precipitate was collected by filtration and was washed with water and dried to give the title compound as a white solid (13.7 g, 90%).

LC-MS: m/z 229.0, 231.0 [M−H]+

$^1$H NMR (400 MHz, DMSO-d$_6$) δ 7.71 (dd, J=2.6, 0.6 Hz, 1H), 7.60 (dd, J=2.6, 0.8 Hz, 1H), 2.18 (s, 3H)

Methyl 5-bromo-2-methoxy-3-methyl-benzoate

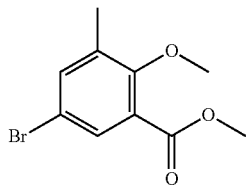

To a solution of 5-bromo-2-hydroxy-3-methyl-benzoic acid (3 g, 12.9 mmol, 1.0 eq) and K$_2$CO$_3$ (5.38 g, 38.9 mmol, 3.0 eq) in acetone (15 mL) was added MeI (5.53 g, 38.9 mmol, 3.0 eq). The mixture was stirred at 58° C. overnight. TLC indicated that the reaction was not completed. Water was added and the aqueous layer extracted with EtOAc. The organic extract was washed with water and brine, dried (Na$_2$SO$_4$) filtered and evaporated in vacuo. The crude solid obtained was dissolved in DMF (20 mL) and Cs$_2$CO$_3$ (6 g, 18.4 mmol, 1.4 eq) added. To the mixture was added MeI (2 mL, 38.95 mmol, 3 eq). The mixture was stirred for 1 h at room temperature, water was added and the aqueous layer was extracted with EtOAc. The combined organic extracts were washed with water and brine, dried (Na$_2$SO$_4$), filtered and evaporated in vacuo to give the title compound as a white solid (2.6 g, 77%).

LC-MS: m/z 259.0, 260.9 [M+H]+ 280.9, 282.9 [M+Na]+

5-Bromo-2-methoxy-3-methyl-benzoic acid

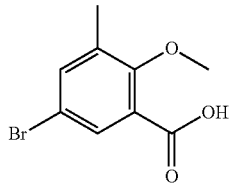

To a solution of methyl 5-bromo-2-methoxy-3-methyl-benzoate (2.6 g, 10.0 mmol, 1.0 eq) in THF (20 mL) was added an aqueous solution of NaOH (2M, 20 mL, 40 mmol, 4.0 eq). The mixture was stirred at room temperature for 5 h. Water was added and the aqueous layer was acidified to pH 9 by addition of 1M HCl. The THF was removed in vacuo and the aqueous layer was further acidified to pH 4-5 with 1M HCl. The solid that precipitated from the reaction was collected by filtration and dried to give the title compound as a white solid (1.8 g, 73%).

LC-MS: m/z 245.0, 247.0 [M+H]+ 267.0, 269.0 [M+Na]+

5-(3-Fluorophenyl)-2-methoxy-3-methyl-benzoic acid (intermediate III(k))

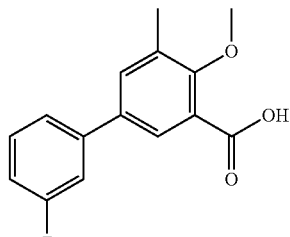

To a solution of 3-fluorophenylboronic acid (0.75 g, 5.39 mmol, 1.1 eq), 5-bromo-2-methoxy-3-methyl-benzoic acid (1.2 g, 4.90 mmol, 1.0 eq) and Na$_2$CO$_3$ (1.56 g, 14.69 mmol, 3 eq) in a mixture of EtOH (6 mL), DMF (24 mL) and H$_2$O (6 mL) was added Pd(PPh$_3$)$_4$ (300 mg, 0.26 mmol, 0.05 eq). The mixture was stirred at 100° C. overnight. Water was added, the reaction was filtered and the filtrate was extracted with EtOAc. The organic extract was discarded and the aqueous phase was acidified to pH 4-5 with 1M HCl and extracted with EtOAc. The combined organic extracts were washed with water and brine, dried (Na$_2$SO$_4$), filtered and evaporated in vacuo to provide the title compound as a white solid (1.09 g, 86%).

LC-MS: m/z 261.1 [M+H]+ 283.1 [M+Na]+

$^1$H NMR (400 MHz, DMSO-d6) δ 13.02 (s, 1H), 7.77 (d, J=5.0 Hz, 2H), 7.56-7.45 (m, 3H), 7.25-7.15 (m, 1H), 3.78 (s, 2H), 2.33 (s, 2H)

N-(2,6-Difluoro-3-hydroxy-phenyl)-5-(3-fluorophenyl)-2-methoxy-3-methyl-benzamide

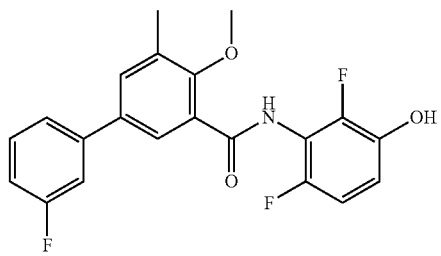 [SMILES: COc1c(C)cc(-c2cccc(F)c2)cc1C(=O)Nc1c(F)ccc(O)c1F]

To 5-(3-fluorophenyl)-2-methoxy-3-methyl-benzoic acid (1.09 g, 4.19 mmol, 1.1 eq) was added SOCl$_2$ (10 mL, 12.6 mmol, 3.0 eq). The reaction was heated to 70° C. and stirred for 6 h, then the solvent was removed. The residue obtained was dissolved in THF (10 mL) and added to a mixture of 3-amino-2,4-difluorophenol (intermediate X(a)) (0.405 g, 2.8 mmol, 1.0 eq) and NaHCO$_3$ (1.17 g, 13.9 mmol, 5 eq) in THF (8 mL) at 0° C. The reaction was warmed to room temperature, stirred for 2 h then quenched by addition of water. The aqueous layer was extracted with EtOAc and the combined organic extracts were washed with water and brine dried (Na$_2$SO$_4$) and evaporated in vacuo. The crude residue obtained was purified by column chromatography (petroleum ether:EtOAc 1:0 to 10:1) to give the title compound as a white solid (209 mg, 19%).

LC-MS: m/z 388.1 [M+H]+ 410.1 [M+Na]+

2,4-Difluoro-3-[[5-(3-fluorophenyl)-2-methoxy-3-methyl-phenyl]methylamino]phenol

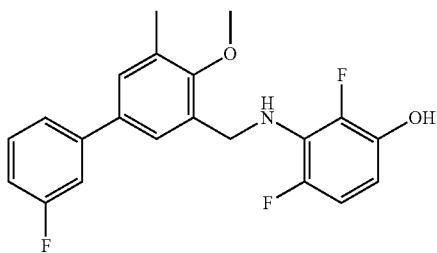

To a solution of N-(2,6-difluoro-3-hydroxy-phenyl)-5-(3-fluorophenyl)-2-methoxy-3-methyl-benzamide (150 mg, 0.39 mmol, 1.0 eq) in THF (3 mL) at 0° C. was added a solution of BH$_3$ (1M in THF, 2.32 mL, 2.32 mmol, 5.9 eq). The reaction was heated at 60° C. overnight, then quenched by addition of water. The aqueous layer was extracted with EtOAc and the organic extract was washed with 5% Na$_2$CO$_3$, water and brine, dried (Na$_2$SO$_4$), filtered and evaporated in vacuo. The crude residue was purified by column chromatography (petroleum ether:EtOAc, 1:0 to 10:1) to give the title compound as an oil (47 mg, 33%).

LC-MS: m/z 374.2 [M+H]$^+$ 396.1, [M+Na]$^+$

Ethyl 2-[2,4-difluoro-3-[[5-(3-fluorophenyl)-2-methoxy-3-methyl-phenyl]methylamino]phenoxy]acetate

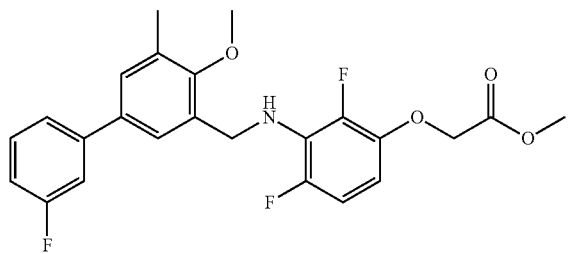 [SMILES: COC(=O)COc1ccc(F)c(NCc2cc(-c3cccc(F)c3)cc(C)c2OC)c1F]

To a stirred solution of 2,4-difluoro-3-[[5-(3-fluorophenyl)-2-methoxy-3-methyl-phenyl]methylamino]phenol (47 mg, 0.13 mmol, 1.0 eq) in acetone (5 mL) was added Cs$_2$CO$_3$ (61.5 mg, 0.19 mmol, 1.5 eq). The resulting mixture was stirred for 30 min at room temperature then ethyl bromoacetate (25.2 mg, 0.15 mmol, 1.2 eq) was added. The resulting mixture was stirred for 1 h then diluted with water and extracted with EtOAc. The combined organic extracts were washed with water and brine, dried (Na$_2$SO$_4$) and evaporated in vacuo. The residue was purified by column chromatography (petroleum ether:EtOAc, 1:0 to 20:1) to give the title compound as an oil (64 mg, 86%).

2-[2,4-Difluoro-3-[[5-(3-fluorophenyl)-2-methoxy-3-methyl-phenyl]methylamino]phenoxy]acetic acid (I(t))

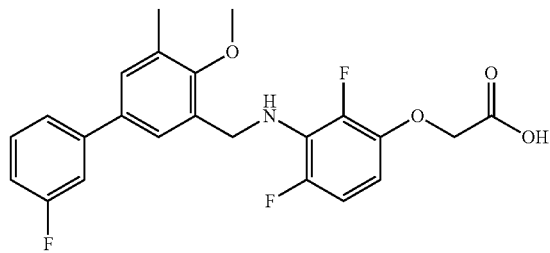

To a stirred solution of ethyl 2-[2,4-difluoro-3-[[5-(3-fluorophenyl)-2-methoxy-3-methyl-phenyl]methylamino]phenoxy]acetate (64 mg, 0.14 mmol, 1.0 eq) in THF (3 mL) was added an aqueous solution of LiOH (2M aqueous solution, 2 mL, 4 mmol). The reaction was stirred at room temperature for 1 h. Water was added and the THF removed in vacuo. The aqueous layer was extracted with EtOAc and the combined organic extracts were washed with water and brine, dried (Na$_2$SO$_4$), filtered and evaporated in vacuo give the title compound as a white solid (32 mg, 53%).

LC-MS: m/z 431.9 [M+H]$^+$ $^1$H NMR (400 MHz, DMSO-d$_5$) δ=7.47 (s, 2H), 7.42 (s, 1H), 7.38-7.27 (m, 2H), 7.20-7.09 (m, 1H), 6.87-6.72 (m, 1H), 6.28 (d, J=4.9 Hz, 1H), 5.66 (s, 1H), 4.70-4.38 (m, 4H), 3.71 (s, 3H), 2.29 (s, 3H)

Example 21

Compound I(u) Synthesized According to Scheme 3 (Amended by Addition of Hydrolysis Step Before Last Step)

2-[2,4-Difluoro-3-[[5-(3-fluorophenyl)-2-hydroxy-3-methyl-phenyl]methylamino]phenoxy]acetic acid (I(u))

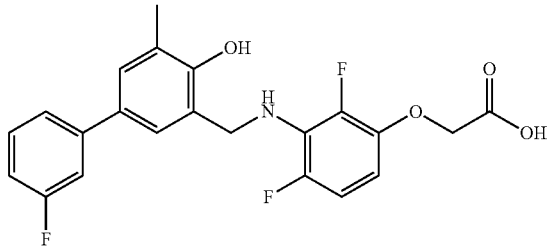 [SMILES: Cc1cc(-c2cccc(F)c2)cc(CNc2c(F)ccc(OCC(=O)O)c2F)c1O]

Ethyl 2-[2,4-difluoro-3-[[5-(3-fluorophenyl)-2-hydroxy-3-methyl-phenyl]methylamino]phenoxy]acetate (II(ad))

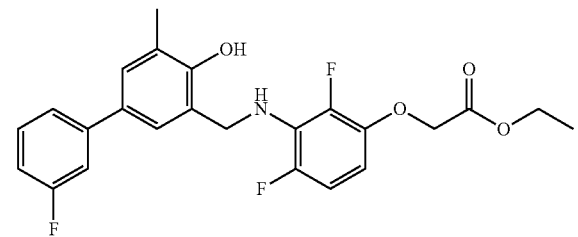 [SMILES: CCOC(=O)COc1ccc(F)c(NCc2cc(-c3cccc(F)c3)cc(C)c2O)c1F]

To a stirred solution of ethyl 2-[2,4-difluoro-3-[[5-(3-fluorophenyl)-2-methoxy-3-methyl-phenyl]methylamino]phenoxy]acetate (see example 20) (190 mg, 0.414 mmol, 1.0 eq) in DCM (5 mL) at 0° C. under N$_2$ was added AlCl$_3$ (330.8 mg, 2.48 mmol, 6.0 eq) and EtSH (154.2 mg, 2.48 mmol, 6.0 eq). The resulting mixture was stirred for 1.5 h at room temperature then the reaction was quenched by dropwise addition of water. The aqueous layer was extracted with EtOAc and the combined organic extracts were washed with water and brine, dried (Na$_2$SO$_4$) filtered and evaporated in vacuo. The residue obtained was purified by column chromatography (petroleum ether:EtOAc 1:0 to 10:1 v/v) to give the title compound as an oil (90 mg, 49%).

LC-MS: m/z 468.2 [M+Na]+

$^1$H NMR (400 MHz, DMSO-d$_6$) δ 8.81 (br s, 1H), 7.46-7.38 (m, 1H), 7.36-7.25 (m, 4H), 7.12-7.05 (m, 1H), 6.82 (t, J=10.3 Hz, 1H), 6.34 (td, J=8.9, 4.1 Hz, 1H), 5.58 (br s, 1H), 4.75 (s, 2H), 4.47 (d, J=6.8 Hz, 2H), 4.12 (q, J=7.1 Hz, 2H), 2.24 (s, 3H), 1.16 (t, J=7.1 Hz, 3H)

2-[2,4-Difluoro-3-[[5-(3-fluorophenyl)-2-hydroxy-3-methyl-phenyl]methylamino]phenoxy]acetic acid (I(u))

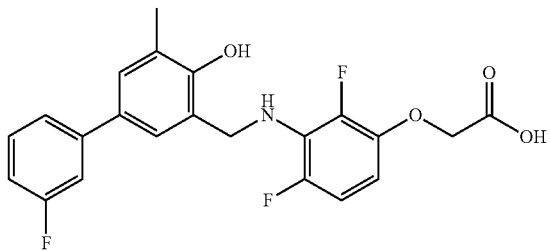 [SMILES: Cc1cc(-c2cccc(F)c2)cc(CNc2c(F)ccc(OCC(=O)O)c2F)c1O]

To a stirred solution of ethyl 2-[2,4-difluoro-3-[[5-(3-fluorophenyl)-2-hydroxy-3-methyl-phenyl]methylamino]phenoxy]acetate (90 mg, 0.20 mmol, 1.0 eq) in THF (3 mL) was added a solution of LiOH (2M aqueous solution, 3 mL, 6 mmol, 30 eq). The reaction was stirred at room temperature for 3 h. Water was added and the mixture acidified to pH 4-5 with diluted HCl then extracted with EtOAc. The combined organic extracts were washed with water and brine, dried and evaporated in vacuo to give the title compound (as a white solid (73 mg, 86%).

LC-MS: m/z 417.9 [M+H]+

$^1$H NMR (300 MHz, DMSO-d$_6$) δ=8.77 (s, 1H), 7.52-7.36 (m, 1H), 7.36-7.23 (m, 4H), 7.18-6.97 (m, 1H), 6.89-6.67 (m, 1H), 6.30 (dt, 0.1=4.6, 9.1 Hz, 1H), 4.59 (s, 2H), 4.46 (d, J=6.7 Hz, 2H), 2.23 (s, 3H)

Example 22

Compound I(v) Synthesized According to Scheme 3

2-[2,4-Difluoro-3-[[5-(3-fluorophenyl)-2,3-dimethyl-phenyl]methylamino]phenoxy]acetic acid (I(v))

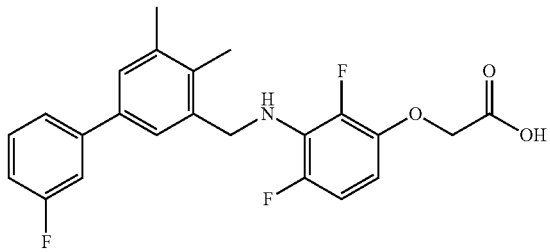

5-Bromo-2,3-dimethyl-benzoic acid

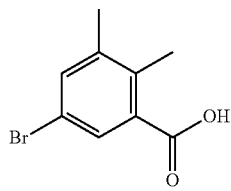

To a solution of 2,3-dimethylbenzoic acid (5 g, 33.3 mmol, 1.0 eq) in acetic acid (167 mL) at room temperature was added a solution of conc. nitric acid (25.2 g, 399 mmol, 12 eq), water (15 g, 0.83 mmol, 25 eq) and bromine (5.85 g, 36.6 mmol, 1.1 eq). A solution of silver nitrate (7.35 g, 43 mmol, 1.3 eq) in water (43 mL) was then added dropwise over 30 min. Once addition was completed, the reaction was stirred at room temperature for 1 h, then quenched by addition of water and EtOAc. The aqueous layer was extracted with EtOAc and the combined organic extracts were washed with water and brine, dried (Na$_2$SO$_4$), filtered and evaporated in vacuo to give the title compound as a yellow solid (6.4 g, 83%).

LC-MS: m/z 228.4 [M+H]+

5-(3-Fluorophenyl)-2,3-dimethyl-benzoic acid (intermediate III(m))

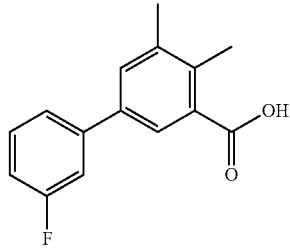 [SMILES: Cc1cc(-c2cccc(F)c2)cc(C(=O)O)c1C]

To a solution of 3-fluorophenylboronic acid (2.20 g, 15.7 mmol, 1.2 eq) 5-bromo-2,3-dimethyl-benzoic acid (3 g, 13.1 mmol, 1.0 eq) in DMF (30 mL) and H$_2$O (15 mL) was added Na$_2$CO$_3$ (5.56 g, 52.3 mmol, 4.0 eq) and Pd(PPh$_3$)$_4$ (0.76 g, 0.66 mmol, 0.05 eq). The reaction was heated at 95° C. overnight under N$_2$. Water was added and the aqueous layer extracted with EtOAc. The combined organic extracts were washed with water and brine, dried (Na$_2$SO$_4$), filtered and evaporated in vacuo to give the title compound as a white solid (3.82 g, 100%).

LC-MS: m/z 245.1 [M+H]+ 267.1 [M+Na]+

$^1$H NMR (400 MHz, DMSO-d$_6$) δ 12.99 (br s, 1H), 7.80 (d, J=1.7 Hz, 1H), 7.70 (d, J=1.4 Hz, 1H), 7.55-7.45 (m, 3H), 7.23-7.15 (m, 1H), 2.41 (s, 3H), 2.35 (s, 3H)

N-(2,6-difluoro-3-hydroxy-phenyl)-5-(3-fluorophenyl)-2,3-dimethyl-benzamide

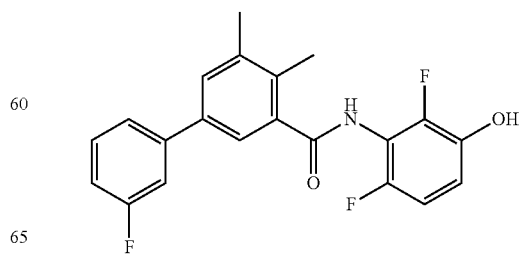

To a solution of 5-(3-fluorophenyl)-2,3-dimethyl-benzoic acid (3.82 g, 15.6 mmol, 5.8 eq) in DCM (30 mL) was added (COCl)$_2$ (5.96 g, 46.8 mmol, 17.0 eq) and DMF (0.5 mL). The mixture was stirred at room temperature under N$_2$ for 2 h then the solvent removed in vacuo. The residue obtained was dissolved in THF (10 mL) and added to a mixture of 3-amino-2,4-difluoro-phenol (intermediate X(a)) (0.4 g, 2.75 mmol, 1.0 eq) and Na$_2$CO$_3$ (0.87 g, 8.26 mmol, 3.0 eq) in THF. The reaction was stirred at room temperature overnight then water and EtOAc were added. The organic extract was washed with water, dried (Na$_2$SO$_4$), filtered and evaporated in vacuo. The residue obtained was purified by column chromatography (DCM:MeOH, 0:1 to 1:50) to give the title compound as a solid (0.16 g, 15%).

LC-MS: m/z 372.1 [M+H]$^+$ 394.1 [M+Na]$^+$ 2,4-Difluoro-3-[[5-(3-fluorophenyl)-2,3-dimethyl-phenyl]methylamino]phenol

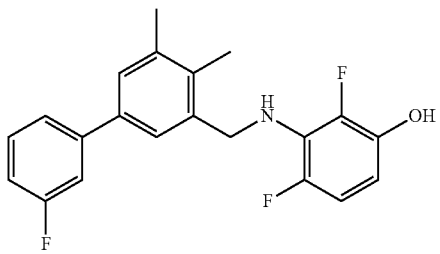 [SMILES: Cc1cc(-c2cccc(F)c2)cc(CNc2c(F)ccc(O)c2F)c1C]

To a solution of N-(2,6-difluoro-3-hydroxy-phenyl)-5-(3-fluorophenyl)-2,3-dimethyl-benzamide (160 mg, 0.4 mmol, 1.0 eq) in THF (15 mL) was added a solution of BH$_3$ (1M in THF, 180 mg, 2.1 mmol, 5.0 eq). The solution was stirred for 30 min then heated at 60° C. overnight. The reaction was quenched by addition of 1M HCl and the aqueous layer extracted with EtOAc. The organic extract was washed with brine, dried (Na$_2$SO$_4$), filtered and evaporated in vacuo to give the title compound as a white solid (137 mg, 89%).

LC-MS: m/z 358.2 [M+H]$^+$ 380.1 [M+Na]$^+$

Ethyl 2-[2,4-difluoro-3-[[5-(3-fluorophenyl)-2,3-dimethyl-phenyl]methylamino]phenoxy]acetate

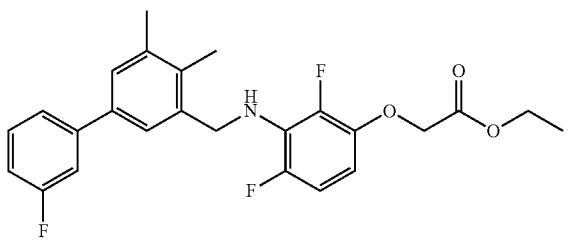 [SMILES: CCOC(=O)COc1ccc(F)c(NCc2cc(-c3cccc(F)c3)cc(C)c2C)c1F]

To a stirred solution of 2,4-difluoro-3-[[5-(3-fluorophenyl)-2,3-dimethyl-phenyl]methylamino]phenol (137 mg, 0.38 mmol, 1.0 eq) in DMF (10 mL) was added Cs$_2$CO$_3$ (170 mg, 0.5 mmol, 1.4 eq). The resulting mixture was stirred for 30 min at room temperature, then ethyl 2-bromoacetate (77 mg, 0.46 mmol, 1.2 eq) was added. The mixture was stirred at room temperature for 2.5 h and then diluted in water and extracted with EtOAc. The combined organic extracts were washed with water and brine, dried (Na$_2$SO$_4$), filtered and evaporated in vacuo to give the title compound as an oil (120 mg, 70%).

LC-MS: m/z 444.1 [M+H]$^+$ 466.2 [M+Na]$^+$

2-[2,4-Difluoro-3-[[5-(3-fluorophenyl)-2,3-dimethyl-phenyl]methylamino]phenoxy]acetic acid (I(v))

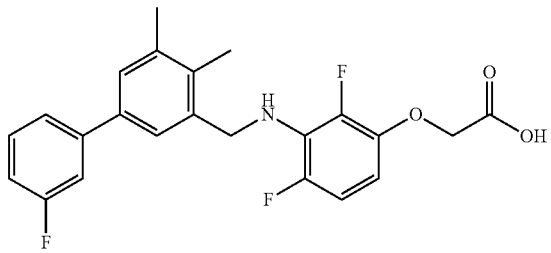

To a stirred solution of ethyl 2-[2,4-difluoro-3-[[5-(3-fluorophenyl)-2,3-dimethyl-phenyl]methylamino]phenoxy]acetate (120 mg, 0.27 mmol, 1.0 eq.) in a mixture of THF (5 mL) and MeOH (5 mL) at room temperature was added NaOH (2M aqueous solution, 5 mL, 10 mmol). The reaction was stirred at room temperature for 3 h. The reaction was then diluted with EtOAc and the aqueous layer was extracted with EtOAc. The combined organic extracts were washed with water and brine, dried (Na$_2$SO$_4$) filtered and evaporated in vacuo to give the title compound as a gummy solid (112 mg, 94%).

LC-MS: m/z 415.9 [M+H]$^+$ $^1$H NMR (300 MHz, DMSO-d$_6$) δ 7.59-7.27 (m, 6H), 7.21-7.03 (m, 1H), 6.79 (t, J=10.6 Hz, 1H), 6.29 (td, J=9.0, 4.7 Hz, 1H), 4.58 (s, 2H), 4.48 (d, J=6.2 Hz, 2H), 2.31 (s, 3H), 2.22 (s, 3H)

Example 23

Compound I(w) Synthesized According to Scheme 4

2-[3-[[5-(3,4-difluorophenyl)-2-fluoro-phenyl]methylamino]-2,4-difluoro-phenoxy]acetic acid (I(w))

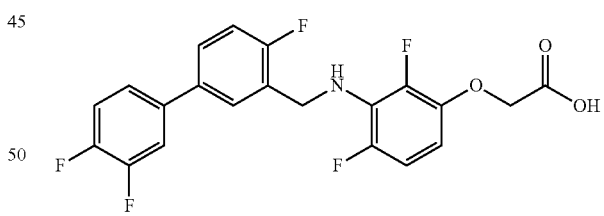

5-Bromo-N-(2,6-difluoro-3-hydroxy-phenyl)-2-fluoro-benzamide

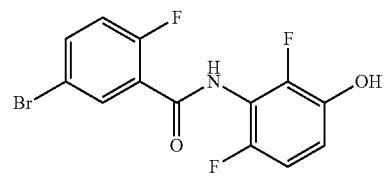 [SMILES: O=C(Nc1c(F)ccc(O)c1F)c1cc(Br)ccc1F]

To a solution of 5-bromo-2-fluoro-benzoic acid (5.1 g, 23.3 mmol, 1.0 eq) in CH$_2$Cl$_2$ (50 mL) were added (COCl)$_2$ (8.8 g, 69.9 mmol, 3.0 eq) and DMF (0.07 mL). The reaction mixture was stirred at room temperature for 1.5 h then the solvent and excess reagent were removed under reduced pressure. The residue obtained was dissolved in THF (30 mL) and added dropwise to a mixture of 3-amino-2,4-difluorophenol (intermediate X(a)) (3.0 g, 20.9 mmol, 1.0 eq) and NaHCO$_3$ (5.3 g, 62.9 mmol, 3.0 eq) in THF (3 mL) at 0° C. The reaction was allowed to warm to room temperature and stirred for 1 h then poured into water and extracted with EtOAc. The combined organic extracts were washed with water and brine, dried (Na$_2$SO$_4$), filtered and evaporated in vacuo. The residue obtained was purified by column chromatography (CH$_2$Cl$_2$: MeOH, 500:1 to 300:1) to give the title compound as a white solid (5.78 g 79%).

LC-MS: m/z 346.0, 348.0 [M+H]$^+$

3-[(5-Bromo-2-fluoro-phenyl)methylamino]-2,4-difluoro-phenol

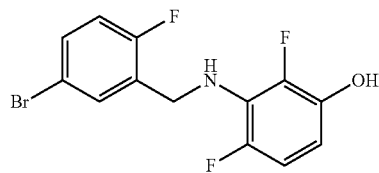 [SMILES: Oc1ccc(F)c(NCc2cc(Br)ccc2F)c1F]

To a solution of 5-bromo-N-(2,6-difluoro-3-hydroxy-phenyl)-2-fluoro-benzamide (5.78 g, 7.1 mmol, 1.0 eq) in THF (100 mL) at 0° C. under N$_2$ was added a solution of BH$_3$ (1M in THF, 83.5 mL, 83.5 mmol, 5.0 eq) dropwise. The reaction mixture was heated at 60° C. overnight then cooled to room temperature and quenched with water. The aqueous layer was extracted with EtOAc and the combined organic extracts were washed with water and brine, dried (Na$_2$SO$_4$), filtered and evaporated in vacuo. The residue was purified by column chromatography (petroleum ether:EtOAc, 30:1 to 20:1) to give the title compound as a brown oil (5.26 g, 94%).

LC-MS: m/z 332.0, 334.0 [M+H]$^+$

Ethyl 2-[3-[(5-bromo-2-fluoro-phenyl)methylamino]-2,4-difluoro-phenoxy]acetate

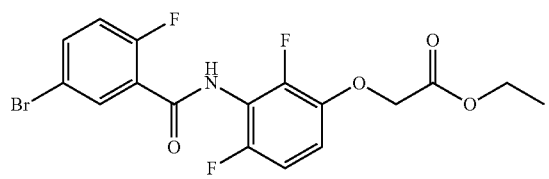 [SMILES: CCOC(=O)COc1ccc(F)c(NC(=O)c2cc(Br)ccc2F)c1F]

To a solution of 3-[(5-bromo-2-fluoro-phenyl)methylamino]-2,4-difluoro-phenol (5.26 g, 15.8 mmol, 1.0 eq) in DMF (50 mL) was added Na$_2$CO$_3$ (2.35 g, 22.2 mmol, 1.4 eq). The reaction was stirred at room temperature for 30 min then ethyl bromoacetate (2.91 g, 17.4 mmol, 1.1 eq) was added. The reaction mixture was stirred at room temperature for 1 h then poured into water and extracted with EtOAc. The combined organic extracts were washed with water and brine, dried (Na$_2$SO$_4$), filtered and evaporated in vacuo. The residue obtained was purified by column chromatography (petroleum ether:EtOAc, 40:1 to 30:1) to give the title compound as a colorless oil (5 g, 75%).

LC-MS: m/z 418.0, 420.0 [M+H]$^+$

2-[3-[[5-(3,4-Difluorophenyl)-2-fluoro-phenyl]methylamino]-2,4-difluoro-phenoxy]acetic acid (I(w))

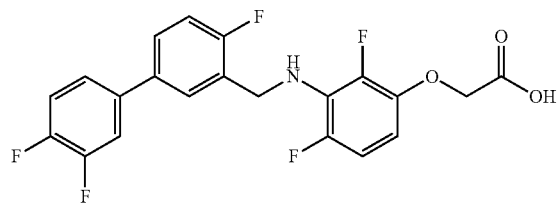 [SMILES: O=C(O)COc1ccc(F)c(NCc2cc(-c3ccc(F)c(F)c3)ccc2F)c1F]

To a solution of ethyl 2-[3-[(5-bromo-2-fluoro-phenyl)methylamino]-2,4-difluoro-phenoxy]acetate (100 mg, 0.24 mmol, 1.0 eq) in acetonitrile (3 mL) and water (1 mL) under N$_2$ was added Na$_2$CO$_3$ (100 mg, 0.96 mmol, 4.0 eq) and Pd(PPh$_3$)$_4$ (14 mg, 0.012 mmol, 0.05 eq). The reaction was heated at 90° C. overnight then diluted HCl was added and the aqueous layer extracted with EtOAc. The combined organic extracts were washed with water and brine, dried (Na$_2$SO$_4$), filtered and evaporated in vacuo. The residue obtained was purified by column chromatography (CH$_2$Cl$_2$:MeOH, 1:0 to 80:1) to give the title compound as a white solid (20 mg, 44%).

LC-MS: m/z 451.3 [M−H]$^-$ $^1$H NMR (400 MHz, DMSO) δ 7.73 (dd, J=7.1, 2.2 Hz, 1H), 7.64 (ddd, J=9.9, 7.5, 1.9 Hz, 1H), 7.60-7.47 (m, 2H), 7.45-7.34 (m, 1H), 7.28-7.17 (m, 1H), 6.72 (t, J=10.1 Hz, 1H), 6.20 (td, J=8.9, 4.6 Hz, 1H), 5.70 (br s, 1H), 4.49 (d, J=7.1 Hz, 2H), 4.16 (s, 2H).

Example 24

Compound I(x) Synthesized According to Scheme 3

2-[3-[[3-cyano-5-(3-fluorophenyl)phenyl]methylamino]-2,4-difluoro-phenoxy]acetic acid (I(x))

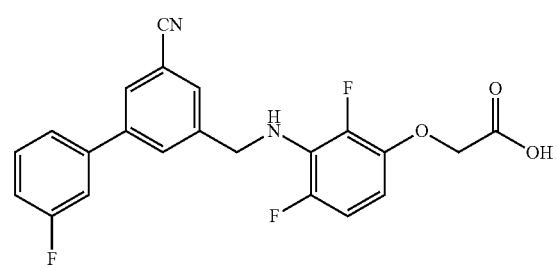

Dimethyl 5-bromobenzene-1,3-dicarboxylate

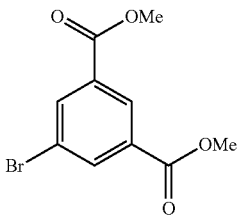 [SMILES: COC(=O)c1cc(Br)cc(C(=O)OC)c1]

5-bromobenzene-1,3-dicarboxylic acid (5 g, 20.4 mmol, 1.0 eq) was dissolved in DMF (150 mL). $Cs_2CO_3$ (33.2 g, 102 mmol, 5.0 eq) was added and the reaction stirred for 30 min. MeI (7.2 g, 51 mmol, 2.5 eq) was added dropwise and the solution was stirred at room temperature overnight. Water was added and the aqueous layer was extracted with EtOAc. The combined organic extracts were dried ($Na_2SO_4$), filtered and evaporated in vacuo to give the title compound as a colourless oil (5 g, 90%).

LC-MS: m/z 274.9 [M+H]$^+$

3-Bromo-5-methoxycarbonyl-benzoic acid

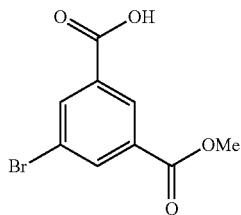

Dimethyl 5-bromobenzene-1,3-dicarboxylate (5 g, 18.3 mmol, 1.0 eq) was dissolved in THF (50 mL) and LiOH.$H_2O$ (1.1 g, 27.5 mmol, 1.5 eq) and $H_2O$ (10 mL) were added. The mixture was stirred at room temperature overnight. The THF was removed in vacuo and the aqueous phase acidified with diluted HCl. The aqueous phase was extracted with EtOAc, dried ($Na_2SO_4$), filtered and evaporated in vacuo. The residue obtained was purified by column chromatography ($CH_2Cl_2$:MeOH, 50:1) to give the title compound as a white solid (3 g, 63%).

LC-MS: m/z 259.0, 261.0 [M+H]$^+$

Methyl 3-bromo-5-carbamoyl-benzoate

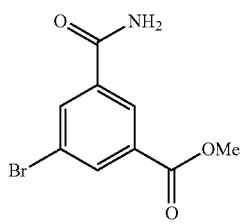

To 3-bromo-5-methoxycarbonyl-benzoic acid (3 g, 11.6 mmol, 1 eq) was added $SOCl_2$ (20 mL) and the reaction heated at reflux overnight. The excess $SOCl_2$ was removed in vacuo and the residue obtained was dissolved in THF (15 mL) and added dropwise to a solution of $NH_3$ (38% aqueous, 30 mL). The precipitate that formed was collected by filtration, washed with water and dried to give the title compound as a white solid (2.8 g, 94%).

LC-MS: m/z 255.9, 257.9 [M−H]$^−$

3-Bromo-5-cyano-benzoic acid

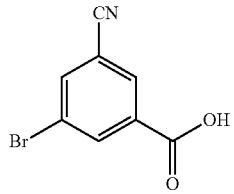 [SMILES: N#Cc1cc(Br)cc(C(=O)O)c1]

To methyl 3-bromo-5-carbamoyl-benzoate (2.8 g, 10.8 mmol, 1.0 eq) was added $POCl_3$ (30 mL) and the reaction heated at 100° C. overnight. The $POCl_3$ was removed under reduced pressure, water was added and the aqueous layer extracted with EtOAc. The combined organic extracts were dried ($Na_2SO_4$), filtered and evaporated in vacuo to afford a crude residue which was purified by column chromatography (petroleum ether:EtOAc, 20:1) to give methyl 3-bromo-5-cyano-benzoate (2.5 g, 96%). This material was dissolved in THF (30 mL) and LiOH.$H_2O$ (1.7 g, 41.6 mmol, 1.54 eq) and $H_2O$ (10 mL) were added. The mixture was stirred at room temperature overnight. The THF was removed under reduced pressure and the aqueous phase acidified with diluted HCl and extracted with EtOAc. The combined organic extracts were dried ($Na_2SO_4$), filtered and evaporated in vacuo. The residue obtained was purified by column chromatography ($CH_2Cl_2$: MeOH, 50:1) to give the title compound as a white solid (2 g, 85%).

LC-MS: m/z 248.0, 249.9 [M+Na]$^+$ $^1$H NMR (400 MHz, DMSO) δ 13.67 (br s, 1H), 8.40 (s, 1H), 8.24 (s, 1H), 8.24 (s, 1H).

3-Cyano-5-(3-fluorophenyl)benzoic acid (III(n))

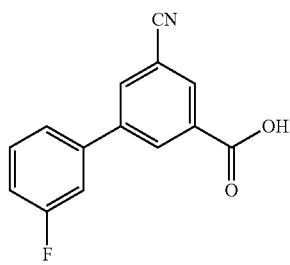 [SMILES: N#Cc1cc(C(=O)O)cc(-c2cccc(F)c2)c1]

To a solution of 3-Bromo-5-cyano-benzoic acid (2 g, 8.8 mmol, 1 eq) and 3-fluorophenylboronic acid (1.6 g, 11.5 mmol, 1.3 eq) in DMF (100 mL) under nitrogen were added Pd(PPh$_3$)$_4$ (500 mg, 0.44 mmol, 0.05 eq) and $K_2CO_3$ (3.6 g, 26.4 mmol, 3 eq). The solution was heated at 100° C. overnight, then water and EtOAc were added. The aqueous layer was acidified by addition of diluted HCl and extracted with EtOAc. The combined organic extracts were dried ($Na_2SO_4$), filtered and evaporated in vacuo. The residue obtained was purified by column chromatography ($CH_2Cl_2$:MeOH, 25:1) to give the title compound as a white solid (1.2 g, 56%).

LC-MS: m/z 264.1 [M+Na]$^+$

3-Cyano-N-(2,6-difluoro-3-hydroxy-phenyl)-5-(3-fluorophenyl)benzamide

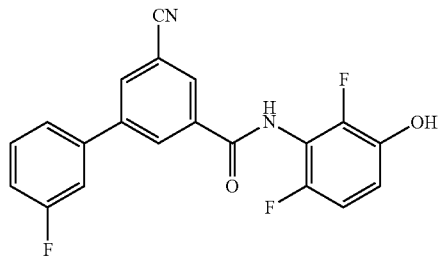 [SMILES: N#Cc1cc(C(=O)Nc2c(F)ccc(O)c2F)cc(-c2cccc(F)c2)c1]

3-Cyano-5-(3-fluorophenyl)benzoic acid (500 mg, 2.1 mmol, 1 eq) was dissolved in SOCl$_2$ (15 mL) and heated at reflux overnight. The excess SOCl$_2$ was removed under reduced pressure and the residue that remained dissolved in THF (10 mL) and added dropwise to a mixture of 3-amino-2,4-difluorophenol (280 mg, 2 mmol, 0.95 eq) and NaHCO$_3$ (880 mg, 10.5 mmol, 5 eq) in THF (40 mL). The reaction was stirred at room temperature for 3 h, then filtered and the filtrate concentrated in vacuo. The residue was purified by column chromatography (petroleum ether: EtOAc, 10:1) to give the title compound as a white solid (500 mg, 64%).

LC-MS: m/z 369.1 [M+H]$^+$ 391.1 [M+Na]$^+$

3-[(2,6-Difluoro-3-hydroxy-anilino)methyl]-5-(3-fluorophenyl)benzonitrile

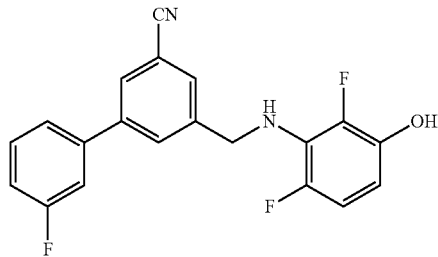 [SMILES: N#Cc1cc(CNc2c(F)ccc(O)c2F)cc(-c2cccc(F)c2)c1]

To a solution of 3-Cyano-N-(2,6-difluoro-3-hydroxy-phenyl)-5-(3-fluorophenyl)benzamide (500 mg, 2.7 mmol, 1.0 eq) in THF (30 mL) at 0° C. was added a solution of BH$_3$ (1M in THF, 10.8 mL, 10.8 mmol, 4.0 eq) dropwise. The reaction was then heated at 50° C. for 6 h. The reaction was cooled to room temperature and quenched by addition of aqueous NH$_4$Cl. The aqueous layer was extracted with EtOAc and the combined organic extracts dried (Na$_2$SO$_4$), filtered and evaporated in vacuo. The residue obtained was purified by column chromatography (petroleum ether:EtOAc, 7:1) to give the title compound as white solid (280 g, 58%).

LC-MS: m/z 355.1 [M+H]$^+$, 377.1 [M+Na]$^+$

Ethyl 2-[3-[[3-cyano-5-(3-fluorophenyl)phenyl]methylamino]-2,4-difluoro-phenoxy]acetate

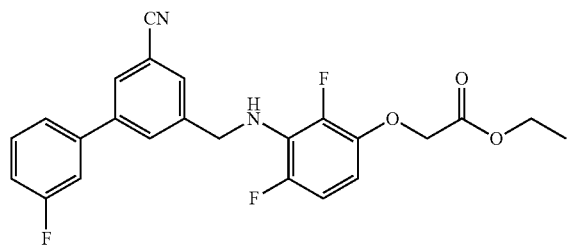 [SMILES: CCOC(=O)COc1ccc(F)c(NCc2cc(C#N)cc(-c3cccc(F)c3)c2)c1F]

To a solution of 3-[(2,6-Difluoro-3-hydroxy-anilino)methyl]-5-(3-fluorophenyl)benzonitrile (280 mg, 0.8 mmol, 1 eq) in DMF (10 mL) was added K$_2$CO$_3$ (550 mg, 4 mmol, 5 eq). The solution was stirred at room temperature for 30 min, then ethyl bromoacetate (200 mg, 1.2 mmol, 1.5 eq) was added dropwise. The reaction was stirred overnight, then water was added and the aqueous phase extracted with EtOAc. The combined organic extracts were dried (Na$_2$SO$_4$), filtered and evaporated in vacuo. The residue obtained was purified by column chromatography (petroleum ether: EtOAc, 15:1) to give the title compound as colorless oil (300 mg, 86%).

LC-MS: m/z 441.1 [M+H]$^+$ 463.1 [M+Na]$^+$

2-[3-[[3-Cyano-5-(3-fluorophenyl)phenyl]methylamino]-2,4-difluoro-phenoxy]acetic acid (I(x))

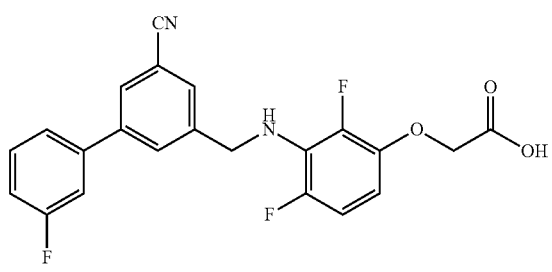

Ethyl 2-[3-[[3-cyano-5-(3-fluorophenyl)phenyl]methylamino]-2,4-difluoro-phenoxy]acetate (300 mg, 0.68 mmol, 1.0 eq) was dissolved in THF (20 mL). Water (10 mL) and LiOH.H$_2$O (110 mg, 2.7 mmol, 4 eq) were added and the solution heated at 40° C. overnight. The THF was removed in vacuo and the aqueous phase acidified to pH 6 by addition of diluted HCl. The precipitate that formed was collected by filtration, washed with water and dried to give the title compound as a white solid (70 mg, 25%).

LC-MS: m/z 413.1 [M+H]$^+$ 435.1 [M+Na]$^+$ $^1$H NMR (400 MHz, DMSO) δ 8.06 (s, 1H), 8.01 (s, 1H), 7.75 (s, 1H), 7.62-7.49 (m, 3H), 7.30-7.21 (m, 1H), 6.83-6.74 (m, 1H), 6.30 (td, J=9.1, 4.4 Hz, 1H), 6.09 (br t, J=7.2 Hz, 1H), 4.60 (s, 2H), 4.50 (d, J=6.8 Hz, 2H).

Example 25

Compound I(y) Synthesized According to Scheme 3

2-[2,4-difluoro-3-[[6-fluoro-3-(3-fluorophenyl)-2-methyl-phenyl]methylamino]phenoxy]acetic acid (I(y))

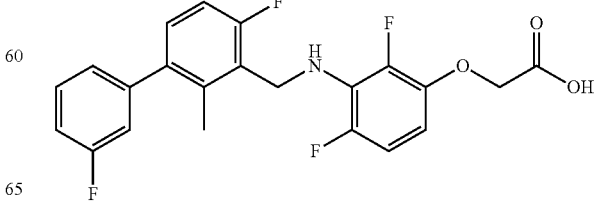

3-Bromo-6-fluoro-2-methyl-benzoic acid

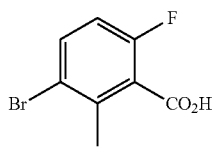

To a stirred solution of 2-fluoro-6-methyl-benzoic acid (1 g, 6.4 mmol, 1.0 eq) in acetic acid (32 mL) was added nitric acid (3.27 mL), water (3 mL) and bromine (0.36 mL). A solution of silver nitrate (1.43 g, 8.4 mmol 1.3 eq) in water (10 mL) was then added dropwise over a period of 15 min. After the addition was completed, stirring was continued a further 1.5 h at room temperature. The reaction was diluted with water and extracted with EtOAc. The combined organic extracts were washed with brine, dried ($Na_2SO_4$), filtered and evaporated in vacuo to afford a crude product, which was triturated with hexane to give the title compound as a yellow solid (1.35 g, 90%).

LC-MS: m/z 232.9 [M−H]⁻

¹H NMR (400 MHz, $CDCl_3$) δ 7.72 (dd, J=8.9, 5.4 Hz, 1H), 7.15 (app t, J=8.9 Hz, 1H), 2.34 (s, 3H).

6-Fluoro-3-(3-fluorophenyl)-2-methyl-benzoic acid (III(o))

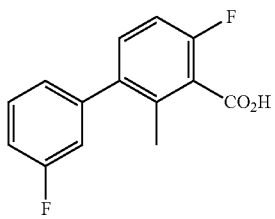 [SMILES: Cc1c(-c2cccc(F)c2)ccc(F)c1C(=O)O]

To a solution of 3-bromo-6-fluoro-2-methylbenzoic acid (1.35 g, 5.8 mmol, 1.0 eq) and 3-fluorophenyl boronic acid (970 mg, 6.9 mmol, 1.2 eq) in DMF (25 mL) under $N_2$ were added $Na_2CO_3$ (2.45 g, 23.1 mmol, 4 eq) and $Pd(PPh_3)_4$ (0.33 g, 0.29 mmol, 0.05 eq). The reaction was heated at 95° C. overnight, then the reaction acidified by addition of 4M HCl to a final pH of 4. The reaction mixture was filtered through celite and extracted with EtOAc. The organic extract was washed with brine, dried ($Na_2SO_4$), filtered and evaporated in vacuo to give the title compound (680 mg, 48%). This material was used without further purification.

LC-MS: m/z 247.0 [M−H]⁻

N-(2,6-Difluoro-3-hydroxy-phenyl)-6-fluoro-3-(3-fluorophenyl)-2-methyl-benzamide

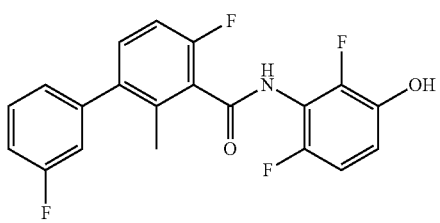 [SMILES: Cc1c(-c2cccc(F)c2)ccc(F)c1C(=O)Nc1c(F)ccc(O)c1F]

To 6-fluoro-3-(3-fluorophenyl)-2-methyl-benzoic acid (3 g, 12.0 mmol, 1 eq) was added $SOCl_2$ (60 mL) and the reaction heated at 80° C. overnight. The resulting mixture was concentrated in vacuo and the residue that remained dissolved in THF (20 mL) and added dropwise to a mixture of 3-amino-2,4-difluoro-phenol (1.93 g, 13.2 mmol, 1.1 eq) and $NaHCO_3$ (2.32 g, 36.2 mmol, 3 eq) in THF (5 mL). After the addition, the reaction mixture was stirred at room temperature for 30 min. Water was added and the aqueous layer was extracted with EtOAc. The combined organic extracts were dried ($Na_2SO_4$), filtered and evaporated in vacuo to give the title compound (500 mg, 11%) which was used without further purification.

LC-MS: m/z 376.1 [M+H]⁺, 398.1 [M+Na]⁺

2,4-Difluoro-3-[[6-fluoro-3-(3-fluorophenyl)-2-methyl-phenyl]methylamino]phenol

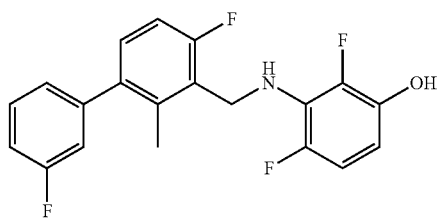 [SMILES: Cc1c(-c2cccc(F)c2)ccc(F)c1CNc1c(F)ccc(O)c1F]

To a solution of N-(2,6-difluoro-3-hydroxy-phenyl)-6-fluoro-3-(3-fluorophenyl)-2-methyl-benzamide (400 mg, 1.06 mmol, 1.0 eq) in THF (5 mL) under $N_2$ was added a solution of $BH_3$ (1M in THF, 5.3 mL, 5.3 mmol, 5.0 eq). The reaction mixture was heated at 60° C. overnight, then quenched by addition of methanol and concentrated in vacuo. The residue was purified by column chromatography (petroleum ether: EtOAc, 50:1 to 20:1) to give title compound as colorless oil (230 mg, 59%).

LC-MS: m/z 362.1 [M+H]⁺ 384.1 [M+Na]⁺

Ethyl 2-[2,4-difluoro-3-[[6-fluoro-3-(3-fluorophenyl)-2-methyl-phenyl]methylamino]phenoxy]acetate

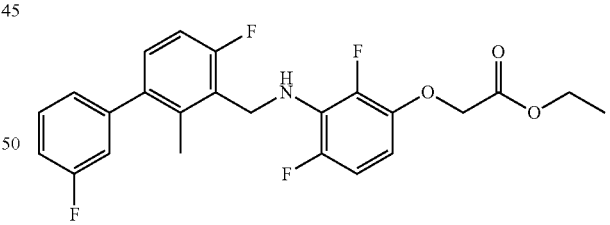

To a solution of 2,4-difluoro-3-[[6-fluoro-3-(3-fluorophenyl)-2-methyl-phenyl]methylamino]phenol (230 mg, 0.63 mmol, 1.0 eq) in DMF (4 mL) was added $Cs_2CO_3$ (420 mg, 1.2 mmol, 2 eq). The reaction was stirred for 10 min, then ethyl bromoacetate (130 mg, 0.76 mmol, 1.2 eq) was added. The reaction mixture was stirred for a further 30 min, then water was added and the aqueous layer was extracted with EtOAc. The combined organic extracts were washed with water, dried ($Na_2SO_4$), filtered and evaporated in vacuo. The residue was purified by column chromatography (petroleum ether: EtOAc, 25:1) to give title compound as a colourless oil (240 mg, 85%).

LC-MS: m/z 448.2 [M+H]⁺ 470.2 [M+Na]⁺

2-[2,4-Difluoro-3-[[6-fluoro-3-(3-fluorophenyl)-2-methyl-phenyl]methylamino]phenoxy]acetic acid (I(y))

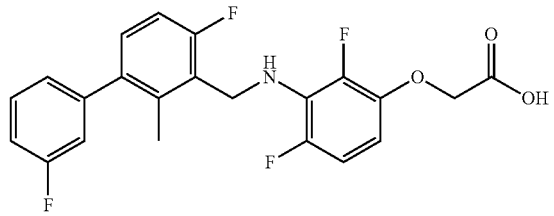 [SMILES: Cc1c(-c2cccc(F)c2)ccc(F)c1CNc1c(F)ccc(OCC(=O)O)c1F]

To a solution of ethyl 2-[2,4-difluoro-3-[[6-fluoro-3-(3-fluorophenyl)-2-methyl-phenyl]methylamino]phenoxy]acetate (240 mg, 0.53 mmol, 1.0 eq) in a mixture of THF (2 mL) and MeOH (2 mL) was added NaOH (2M aqueous solution, 2 mL, 4.0 mmol). The reaction mixture was stirred at room temperature for 3 h. The THF and MeOH were evaporated in vacuo and the pH of the aqueous phase adjusted to pH 3 by addition of diluted HCl. The solid that formed was collected by filtration, washed with water and dried to give the title compound as a white solid (150 mg, 68%).

LC-MS: m/z 418.1 [M−H]$^-$ $^1$H NMR (400 MHz, DMSO) δ 7.54-7.44 (m, 1H), 7.26-7.15 (m, 2H), 7.15-7.05 (m, 3H), 6.83-6.72 (m, 1H), 6.26 (td, J=9.2, 5.0 Hz, 1H), 4.70 (br s, 1H), 4.47 (d, J=5.3 Hz, 2H), 4.08 (s, 2H), 2.27 (s, 3H).

Example 26

2-[3-[[3-carbamoyl-5-(3-fluorophenyl)phenyl]methylamino]-2,4-difluoro-phenoxy]acetic acid (I(z))

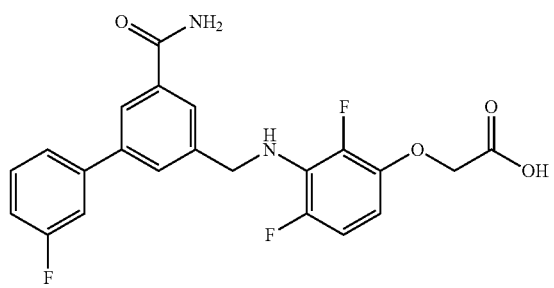 [SMILES: NC(=O)c1cc(CNc2c(F)ccc(OCC(=O)O)c2F)cc(-c2cccc(F)c2)c1]

To a mixture of ethyl 2-[3-[[3-cyano-5-(3-fluorophenyl)phenyl]methylamino]-2,4-difluoro-phenoxy]acetate (see example 24) (200 mg, 0.45 mmol, 1 eq) and K$_2$CO$_3$ (310 mg, 2.3 mmol, 5 eq) in DMSO (10 mL) at 40° C. was added H$_2$O$_2$ (30% aqueous solution, 10 mL) dropwise. The mixture was stirred for 20 min then cooled to room temperature. Water was added, and the reaction neutralised by addition of diluted HCl. The solid precipitate that formed was collected by filtration, washed with water and dried to give the title compound as white solid (90 mg, 46%).

LC-MS: m/z 431.1 [M+H]$^+$ 453.1 [M+Na]$^+$ $^1$H NMR (400 MHz, DMSO) δ 8.10 (s, 1H), 8.04 (s, 1H), 7.86 (s, 1H), 7.82 (s, 1H), 7.62-7.48 (m, 3H), 7.44 (s, 1H), 7.30-7.18 (m, 1H), 6.78 (t, J=10.0 Hz, 1H), 6.28 (td, J=9.1, 4.8 Hz, 1H), 6.05 (br t, J=7.4 Hz, 1H), 4.60 (s, 2H), 4.50 (d, J=6.4 Hz, 2H).

Example 27

Compound I(aa) Synthesized According to Scheme 3

2-[2,4-difluoro-3-[[3-fluoro-5-(3-fluorophenyl)-2-methylphenyl]methylamino]phenoxy]acetic acid (I(aa))

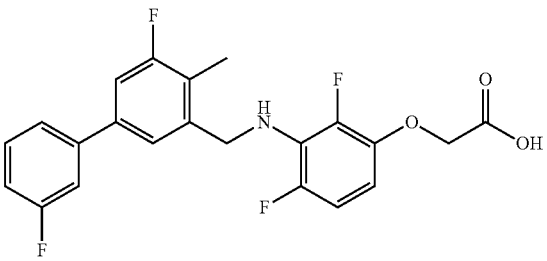

1-Fluoro-5-(3-fluorophenyl)-2-methyl-3-nitro-benzene

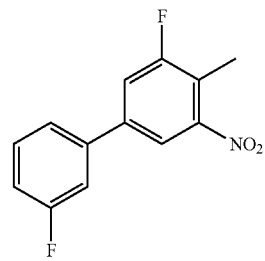

A mixture of 5-bromo-1-fluoro-2-methyl-3-nitro-benzene (5.0 g, 21.31 mmol, 1.0 eq), 3-fluorophenylboronic acid (3.29 g, 23.8 mmol, 1.1 eq), Pd(PPh$_3$)$_4$ (1.2 g, 1.07 mmol, 0.05 eq) and K$_2$CO$_3$ (11.8 g, 85.5 mmol, 4 eq) in a mixture of dioxane (150 mL) and EtOH (50 mL) was heated at 80° C. under N$_2$ overnight. After cooling to room temperature the reaction was poured into water and extracted with EtOAc. The combined organic extracts were washed with water and brine, dried (Na$_2$SO$_4$), filtered and evaporated in vacuo to give the title compound as an oil (4.0 g, 75%). This material was used without further purification.

3-Fluoro-5-(3-fluorophenyl)-2-methyl-aniline

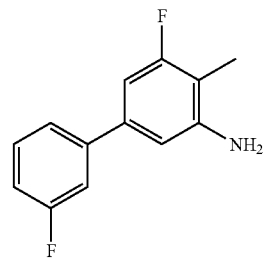 [SMILES: Cc1c(F)cc(-c2cccc(F)c2)cc1[N+](=O)[O-]]

A solution of 1-fluoro-5-(3-fluorophenyl)-2-methyl-3-nitro-benzene (4.0 g, 16.0 mmol, 1.0 eq) in EtOH (80 mL) was added to Pd/C (10%, 0.8 g) and the mixture stirred under hydrogen for 48 h. The catalyst was removed by filtration through celite and the compound purified by silica gel chromatography (petroleum ether:EtOAc, 20:1 to 10:1) to give the title compound as a white solid (1.54 g, 44%).

LC-MS: m/z, 220.1 [M+1]$^+$

1-Bromo-3-fluoro-5-(3-fluorophenyl)-2-methyl-benzene

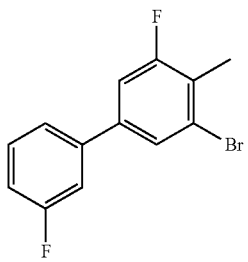 [SMILES: Cc1c(F)cc(-c2cccc(F)c2)cc1Br]

Copper(II)bromide (1.88 g, 8.4 mmol, 1.2 eq) and tert-butyl nitrite (1.81 g, 17.5 mmol, 2.5 eq) were suspended in acetonitrile (15 mL), the mixture was cooled to 0° C. and a solution of 3-fluoro-5-(3-fluorophenyl)-2-methyl-aniline (1.54 g, 7.0 mmol, 1 eq) in acetonitrile was added dropwise. The solution was stirred at 0° C. for 1 h, water was added and the aqueous layer extracted with EtOAc. The organic phase was dried (Na$_2$SO$_4$), filtered and evaporated in vacuo to give an oil which was purified by column chromatography (petroleum ether:EtOAc, 1:0 to 50:1) to give the title compound as a colourless oil (1.88 g, 94%).

LC-MS: m/z No target MS observed by LCMS.

Methyl 3-fluoro-5-(3-fluorophenyl)-2-methyl-benzoate

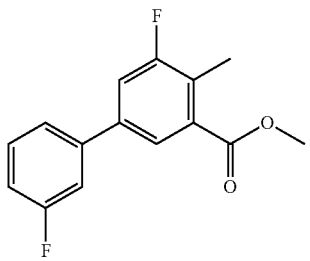 [SMILES: COC(=O)c1cc(-c2cccc(F)c2)cc(F)c1C]

A mixture of 1-bromo-3-fluoro-5-(3-fluorophenyl)-2-methyl-benzene (1.88 g, 6.6 mmol, 1 eq), potassium acetate (3.25 g, 33.2 mmol, 5 eq), palladium (II) acetate (0.12 g, 0.5 mmol, 0.075 eq) and dppf (0.41 g, 0.9 mmol, 0.15 eq) in a mixture of MeOH (50 mL) and THF (50 mL) was placed in a high pressure reactor and pressurized with carbon monoxide gas to 50 bar. The reaction mixture was heated at 125° C. for 16 h, then cooled, filtered and the solvent evaporated in vacuo. The residue was partitioned between water and CH$_2$Cl$_2$ and extracted with CH$_2$Cl$_2$. The combined organic extracts were dried (MgSO$_4$), filtered and evaporated in vacuo. The residue obtained was purified by column chromatography (petroleum ether:EtOAc 1:0 to 50:1) to give the title compound as a white solid (1 g, 57%).

LC-MS: m/z 263.1 [M+1]$^-$ 285.1 [M+Na]$^+$

3-Fluoro-5-(3-fluorophenyl)-2-methyl-benzoic acid
(III(p))

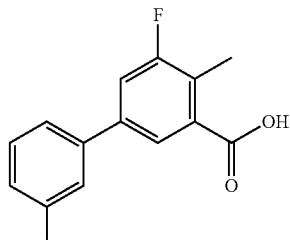

To a solution of methyl 3-fluoro-5-(3-fluorophenyl)-2-methyl-benzoate (1.0 g, 3.1 mmol, 1.0 eq) in a mixture of THF (4 mL) and MeOH (4 mL) was added NaOH (2 M aqueous solution, 10 mL, 20 mmol). The reaction mixture was stirred at room temperature for 3 h. The THF and MeOH were evaporated in vacuo and the pH of the aqueous phase was adjusted to pH 4-6 by addition of diluted HCl. The solid precipitate that formed was collected by filtration, washed with water and dried to give the title compound as a white solid (1.1 g, 100%).

LC-MS: m/z, 247.1 [M−1]$^-$ $^1$H NMR (400 MHz, DMSO) δ 7.93-7.85 (m, 2H), 7.56-7.48 (m, 3H), 7.25-7.18 (m, 1H), 2.33 (d, J=1.9 Hz, 3H).

N-(2,6-Difluoro-3-hydroxy-phenyl)-3-fluoro-5-(3-fluorophenyl)-2-methyl-benzamide

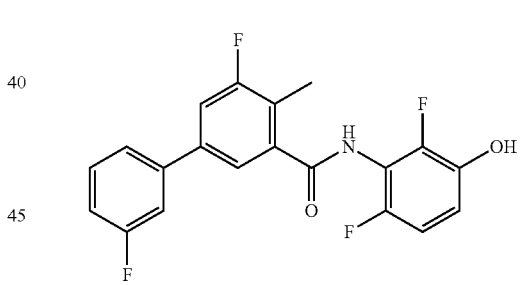

To a solution of 3-fluoro-5-(3-fluorophenyl)-2-methyl-benzoic acid (1.1 g, 4.4 mmol, 1 eq) in CH$_2$Cl$_2$ (15 mL) at 0° C. was added DMF (0.05 mL), and (COCl)$_2$ (1.68 g, 13.2 mmol, 3 eq). The reaction mixture was stirred at room temperature for 3 h. The resulting mixture was concentrated to dryness under reduced pressure and the residue obtained dissolved in THF (10 mL) and added dropwise to a solution of 3-amino-2,4-difluoro-phenol (intermediate X(a)) (770 mg, 5.3 mmol, 1.2 eq) and K$_2$CO$_3$ (3 g, 22.1 mmol, 5 eq) in THF (20 mL) at 0° C. After the addition, the reaction mixture was stirred for 2 h and then water added and the aqueous layer extracted with EtOAc. The combined organic extracts were dried (Na$_2$SO$_4$), filtered and evaporated in vacuo. The residue obtained was purified by column chromatography (petroleum ether:EtOAc, 10:1 to 3:1) to give the title compound as a white solid (0.9 g, 54%).

LC-MS: m/z, 376.1 [M+H]$^+$ 398.1 [M+Na]$^+$

2,4-Difluoro-3-[[3-fluoro-5-(3-fluorophenyl)-2-methyl-phenyl]methylamino]phenol

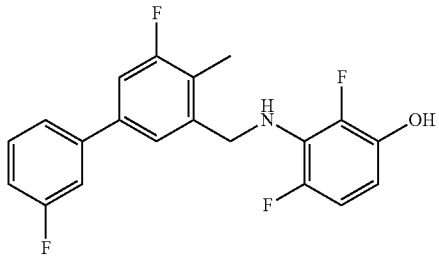 [SMILES: Cc1c(F)cc(-c2cccc(F)c2)cc1CNc1c(F)ccc(O)c1F]

To a solution of N-(2,6-difluoro-3-hydroxy-phenyl)-3-fluoro-5-(3-fluorophenyl)-2-methyl-benzamide (0.9 g, 2.4 mmol, 1.0 eq) in THF (20 mL) under $N_2$ was added a solution of $BH_3$ (1 M in THF, 11.9 mL, 11.9 mmol, 5.0 eq). The reaction mixture was heated at reflux overnight. Methanol was added to quench the reaction and the solution was then concentrated in vacuo to give the title compound (900 mg, 100%) which was used without further purification.

LC-MS: m/z, 362.1 [M+H]$^+$ 384.1 [M+Na]$^+$

Isopropyl 2-[2,4-difluoro-3-[[3-fluoro-5-(3-fluorophenyl)-2-methyl-phenyl]methylamino]phenoxy]acetate (II(ae))

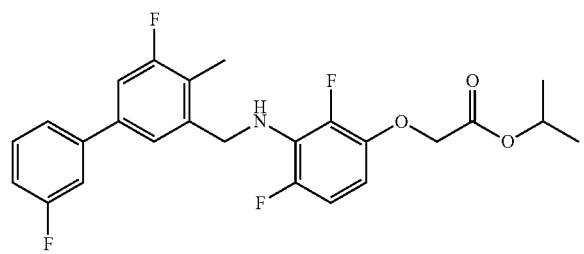

To a solution 2,4-difluoro-3-[[3-fluoro-5-(3-fluorophenyl)-2-methyl-phenyl]methylamino]phenol (900 mg, 2.5 mmol, 1.0 eq) in DMF (10 mL) was added $Cs_2CO_3$ (1.62 g, 4.9 mmol, 2 eq). The reaction mixture was stirred for 30 min, then isopropyl bromoacetate (540 mg, 2.9 mmol, 1.2 eq) was added dropwise. The reaction was stirred at room temperature for 30 min, then water was added and the aqueous layer was extracted with EtOAc. The organic extract was washed with water, dried ($Na_2SO_4$), filtered and evaporated in vacuo. The residue obtained was purified by column chromatography (petroleum ether:EtOAc 20:1 to 5:1) to give the title compound (300 mg, 26%).

LC-MS: m/z 462.2 [M+H]$^+$, 484.1 [M+Na]$^+$ $^1$H NMR (400 MHz, DMSO) δ 8.30-8.22 (m), 8.20 (d, J=7.8 Hz), 8.16-8.05 (m), 7.92 (td, J=8.5, 2.3 Hz), 7.66-7.56 (m), 7.18 (td, J=9.0, 4.7 Hz), 6.06-5.94 (m), 5.47 (s), 5.44 (br d, J=3.2 Hz), 4.69 (br s), 3.21 (d, J=1.5 Hz), 2.14 (d, J=6.3 Hz).

2-[2,4-Difluoro-3-[[3-fluoro-5-(3-fluorophenyl)-2-methyl-phenyl]methylamino]phenoxy]acetic acid (I(aa))

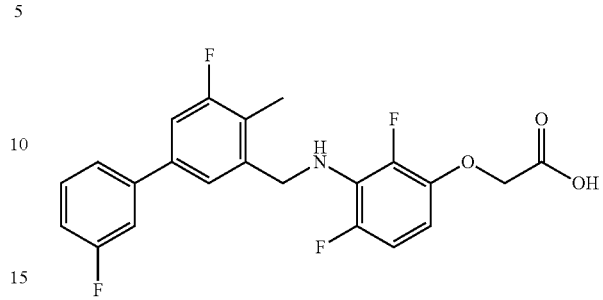

To a solution of isopropyl 2-[2,4-difluoro-3-[[3-fluoro-5-(3-fluorophenyl)-2-methyl-phenyl]methylamino]phenoxy]acetate (300 mg, 0.65 mmol, 1.0 eq) in a mixture of THF (10 mL) and MeOH (10 mL) was added NaOH (2M aqueous solution, 10 mL). The reaction mixture was stirred at room temperature for 3 h. The THF was evaporated in vacuo and the pH of the aqueous phase adjusted pH 3 with diluted HCl. The solid precipitate that formed was collected by filtration, washed with water and dried to give the title compound as a white solid (104 mg, 38%).

LC-MS: m/z 417.2 [M–1]$^-$ $^1$H NMR (400 MHz, DMSO) δ 7.54-7.36 (m, 5H), 7.23-7.14 (m, 1H), 6.86-6.74 (m, 1H), 6.30 (td, J=9.1, 4.6 Hz, 1H), 5.79 (br t, J=5.9 Hz, 1H), 4.59 (s, 2H), 4.48 (d, J=6.2 Hz, 2H), 2.22 (s, 3H).

Example 28

Compound I(ab) Synthesized According to Scheme 3

2-[2,4-difluoro-3-[[2-fluoro-5-(3-fluorophenyl)phenyl]methylamino]-5-methyl-phenoxy]acetic acid (I(ab))

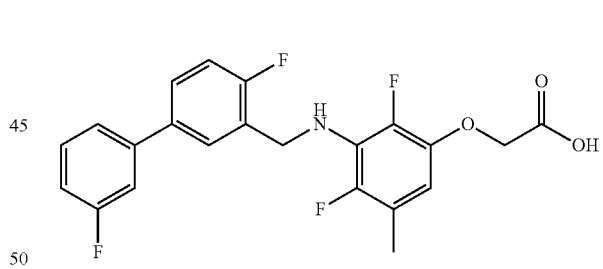

2-(2,4-Difluoro-5-methyl-phenyl)-4,4,5,5-tetramethyl-1,3,2-dioxaborolane

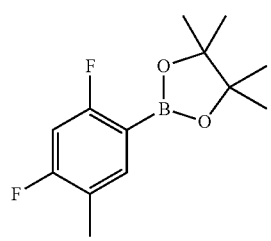 [SMILES: Cc1cc(B2OC(C)(C)C(C)(C)O2)c(F)cc1F]

A mixture of 1-bromo-2,4-difluoro-5-methylbenzene (5 g, 24.15 mmol, 1.0 eq), Pd(dppf)Cl₂ (844 mg, 1.22 mmol, 0.05 eq), KOAc (7.11 g, 72.46 mmol, 3 eq) and bis(pinacolato)diboron (7.36 g, 29 mmol, 1.2 eq) in DMSO (30 mL) under $N_2$ was stirred at 90° C. overnight. The reaction was then poured into water and extracted with EtOAc. The combined organic extracts were washed with water and brine, dried ($Na_2SO_4$), filtered and evaporated in vacuo to give the title compound as colorless oil (2.24 g, 36%).

LC-MS: m/z 277.1 [M+Na]⁺

2,4-Difluoro-5-methyl-phenol

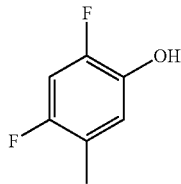

To a solution of 2-(2,4-difluoro-5-methyl-phenyl)-4,4,5,5-tetramethyl-1,3,2-dioxaborolane (2.24 g, 8.82 mmol, 1.0 eq) in a mixture of NaOH (1M aqueous solution, 26.4 mL, 26.4 mmol, 3.0 eq) and THF (20 mL) at 0° C. was added $H_2O_2$ (3 g, 26.4 mmol, 3 eq). The reaction mixture was stirred at room temperature for 4 h, then the pH of the reaction mixture was adjusted to pH 5 by addition of 1M HCl. The aqueous layer was extracted with EtOAc and the combined organic extracts were washed with water and brine, dried ($Na_2SO_4$), filtered and evaporated in vacuo. The crude residue obtained was purified by column chromatography (petroleum ether: EtOAc, 100:1 to 50:1) to give the title compound as a colorless oil (850 mg, 65%).

LC-MS: m/z 143.1 [M−H]⁻

(2,4-Difluoro-5-methyl-phenoxy)-triisopropyl-silane

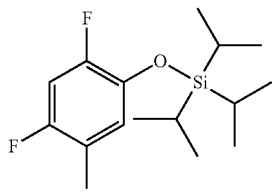 [SMILES: Cc1cc(O[Si](C(C)C)(C(C)C)C(C)C)c(F)cc1F]

To a stirred solution of 2,4-difluoro-5-methylphenol (780 mg, 5.41 mmol, 1.0 eq) and imidazole (442 mg, 6.5 mmol, 1.2 eq) in DMF (10 mL) at 0° C. was added TIPSCl (1.15 g, 5.95 mmol, 1.1 eq) dropwise. After the addition, the reaction mixture was allowed to warm to room temperature and stirred overnight. The reaction was then poured into water and extracted with EtOAc. The combined organic extracts were washed with water and brine, dried ($Na_2SO_4$), filtered and evaporated in vacuo to give a crude residue, which was purified by column chromatography (petroleum ether: EtOAc, 100:1) to give the title compound as a colorless oil (1.2 g, 80%).

¹H NMR (400 MHz, DMSO) δ 7.16 (t, J=10.2 Hz, 1H), 6.91-6.85 (m, 1H), 2.15 (s, 3H), 1.31-1.15 (m, 3H), 1.04 (d, J=7.4 Hz, 18H).

2,6-Difluoro-3-methyl-5-triisopropylsilyloxy-benzoic acid

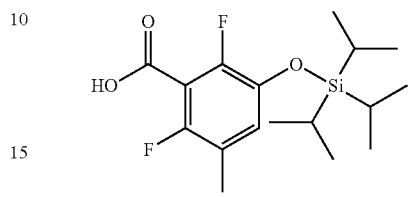

To a solution of (2,4-difluoro-5-methyl-phenoxy)-triisopropyl-silane (1.15 g, 3.83 mmol, 1.0 eq) in dry THF (20 mL) under $N_2$ at −60° C. was added a solution of n-BuLi (1.7 mL, 2.5 M in hexane, 4.21 mmol, 1.1 eq) over a period of 5 min. The reaction mixture was stirred at −60° C. for 2 h, then $CO_2$ (gas) was bubbled into the mixture. The reaction was warmed to room temperature and stirred for 1 h, then quenched with water. The aqueous layer was extracted with EtOAc and the organic extract was discarded. The aqueous layer was then acidified to pH 5 with diluted HCl and extracted with ethyl acetate. The combined organic extracts were dried ($Na_2SO_4$), filtered and evaporated in vacuo to give the title compound as a white solid (1.08 g, 82%).

¹H NMR (400 MHz, DMSO) δ 13.87 (br s, 1H), 7.07-6.98 (m, 1H), 2.18 (s, 3H), 1.31-1.18 (m, 3H), 1.05 (d, J=7.4 Hz, 18H).

3-Amino-2,4-difluoro-5-methyl-phenol (X(g))

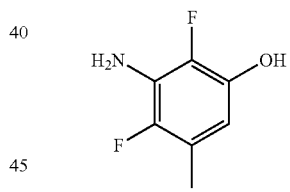

To a solution of 2,6-difluoro-3-methyl-5-triisopropylsilyloxy-benzoic acid (1.08 g, 3.14 mmol, 1.0 eq) in $CH_2Cl_2$ (15 mL) was added (COCl)₂ (1.19 g, 9.40 mmol, 3.0 eq) dropwise at 0° C. DMF (3 drops) was added and the mixture warmed to room temperature and stirred for 1 h. The reaction mixture was concentrated to dryness, and the residue obtained was dissolved in acetone (20 mL) and added dropwise to a cooled solution of $NaN_3$ (815 mg, 12.5 mol, 4 eq) in a mixture of acetone (10 mL) and water (10 mL) at 0° C. The reaction was stirred for 1 h at 0° C., further water (20 mL) was then added and the reaction heated at 70° C. overnight. The reaction was partitioned between EtOAc and water and extracted with EtOAc, the combined organic extracts were washed with water and brine, dried ($Na_2SO_4$), filtered and evaporated in vacuo. The residue obtained was dissolved in dioxane (25 mL), aqueous KOH (25% aqueous solution, 12 mL) was added and the reaction heated at reflux overnight. The reaction was then cooled to room temperature and acidified to pH 5-6 with 1M HCl. The aqueous layer was extracted with EtOAc and the combined organic extracts washed with water, brine, dried (Na$_2$SO$_4$), filtered and evaporated in vacuo. The residue obtained was purified by column chromatography (petroleum Ether: EtOAc, 50:1 to 20:1) to give the title compound as a white solid (270 mg, 87%).

LC-MS: m/z 160.1 [M+H]$^+$

N-(2,6-Difluoro-3-hydroxy-5-methyl-phenyl)-2-fluoro-5-(3-fluorophenyl)benzamide

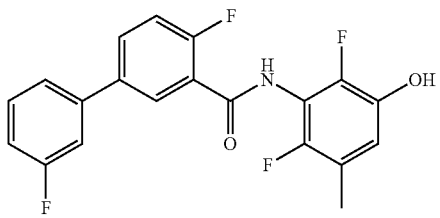 [SMILES: Cc1cc(O)c(F)c(NC(=O)c2cc(-c3cccc(F)c3)ccc2F)c1F]

To a solution of 2-fluoro-5-(3-fluorophenyl)benzoic acid (Intermediate III(a)) (437 mg, 1.87 mmol, 1.1 eq) in CH$_2$Cl$_2$ (10 mL) and DMF (3 drops) was added SOCl$_2$ (15 mL) dropwise at 0° C. The solution was stirred at room temperature for 1 h, then concentrated in vacuo. The residue obtained was dissolved in THF (20 mL) and added dropwise to a solution of 3-amino-2,4-difluoro-5-methyl-phenol (270 mg, 1.70 mmol, 1.0 eq) in THF (10 mL) at 0° C. After addition was completed, the reaction mixture was stirred at room temperature for 2 h, then poured into water and extracted with EtOAc. The combined organic extracts were washed with water and brine, dried (Na$_2$SO$_4$), filtered, and evaporated in vacuo. The residue obtained was purified by column chromatography (petroleum ether: EtOAc, 10:1 to 3:1) to give the title compound as a white solid (285 mg, 45%).

LC-MS: m/z 376.1 [M+H]$^+$ 398.1 [M+Na]$^+$

2,4-Difluoro-3-[[2-fluoro-5-(3-fluorophenyl)phenyl]methylamino]-5-methyl-phenol

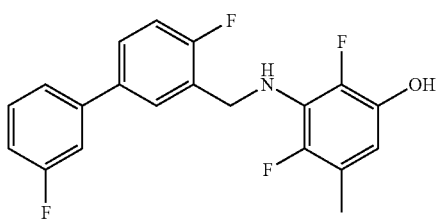 [SMILES: Cc1cc(O)c(F)c(NCc2cc(-c3cccc(F)c3)ccc2F)c1F]

N-(2,6-difluoro-3-hydroxy-5-methyl-phenyl)-2-fluoro-5-(3-fluorophenyl)benzamide (285 mg, 0.76 mmol, 1.0 eq) was dissolved in THF (20 mL). A solution of BH$_3$ (1M in THF, 4.56 mL, 4.56 mmol, 6.0 eq) was added and the reaction mixture heated at 60° C. under nitrogen for 2 h. After cooling, the reaction was quenched with water and extracted with EtOAc. The combined organic extracts were washed with water and brine, dried (Na$_2$SO$_4$), filtered and evaporated in vacuo. The residue was purified by column chromatography (petroleum ether: EtOAc, 30:1 to 20:1) to give the title compound as a colorless oil (206 mg, 75%).

LC-MS: m/z 362.1 [M+H]$^+$ 384.1 [M+Na]$^+$

Isopropyl 2-[2,4-difluoro-3-[[2-fluoro-5-(3-fluorophenyl)phenyl]methylamino]-5-methyl-phenoxy]acetate (II(af))

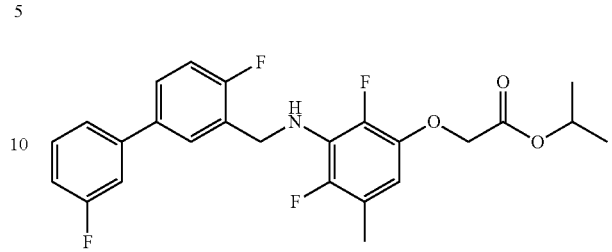

2,4-difluoro-3-[[2-fluoro-5-(3-fluorophenyl)phenyl]methylamino]-5-methyl-phenol (206 mg, 0.57 mmol, 1.0 eq) was dissolved in DMF (15 mL). Cs$_2$CO$_3$ (279 mg, 0.86 mmol, 1.5 eq) was added and the reaction mixture stirred for 30 min at room temperature. Isopropyl bromoacetate (124 mg, 0.68 mmol, 1.2 eq) was added and the reaction stirred a further 1 h at room temperature. The resulting mixture was poured into water and extracted with EtOAc. The organic extract was washed with water and brine, dried (Na$_2$SO$_4$), filtered and evaporated in vacuo. The residue was purified by column chromatography (petroleum ether: EtOAc, 50:1 to 30:1) to give the title compound as a colorless oil (200 mg, 76%).

LC-MS: m/z 462.2 [M+H]$^+$ 484.2 [M+Na]$^+$ $^1$H NMR (400 MHz, DMSO) δ 7.72 (d, J=5.3 Hz, 1H), 7.58 (br s, 1H), 7.54-7.45 (m, 1H), 7.44-7.33 (m, 2H), 7.29-7.13 (m, 2H), 6.26 (t, J=7.1 Hz, 1H), 5.80 (br s, 1H), 5.01-4.87 (m, 1H), 4.66 (s, 2H), 4.51 (d, J=6.6 Hz, 2H), 2.07 (s, 3H), 1.14 (d, J=5.9 Hz, 6H).

2-[2,4-Difluoro-3-[[2-fluoro-5-(3-fluorophenyl)phenyl]methylamino]-5-methyl-phenoxy]acetic acid (I(ab))

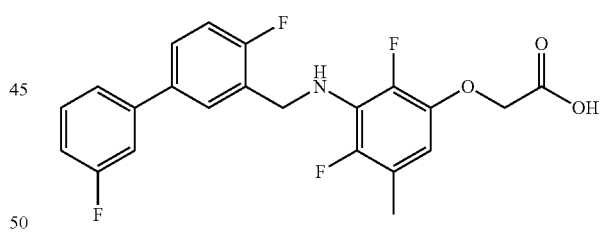

To a solution of isopropyl 2-[2,4-difluoro-3-[[2-fluoro-5-(3-fluorophenyl)phenyl]methylamino]-5-methyl-phenoxy]acetate (194 mg, 0.42 mmol, 1.0 eq) in THF (10 mL) was added LiOH (2M aqueous solution, 5 mL, 5 mmol). The reaction mixture was stirred at room temperature overnight. The THF was removed under reduced pressure and the pH of the aqueous phase adjusted to pH 5 by addition of diluted HCl. The solid that formed was collected by filtration, washed with water and dried in vacuo to give the title compound as a white solid (61 mg, 91%).

LC-MS: m/z 420.1 [M+H]$^+$ 442.1 [M+Na]$^+$ $^1$H NMR (400 MHz, DMSO) δ 7.74 (dd, J=7.1, 2.2 Hz, 1H), 7.62-7.54 (m, 1H), 7.54-7.46 (m, 1H), 7.43-7.35 (m, 2H), 7.27-7.14 (m, 2H), 6.12 (t, J=7.8 Hz, 1H), 5.65 (br s, 1H), 4.50 (d, J=7.0 Hz, 2H), 4.20 (s, 2H), 2.04 (s, 3H)

Example 29

Compound I(ac) Synthesized According to Scheme 3

2-[4-fluoro-3-[[2-fluoro-5-(3-fluorophenyl)phenyl]methylamino]-2,5-dimethyl-phenoxy]acetic acid (I(ac))

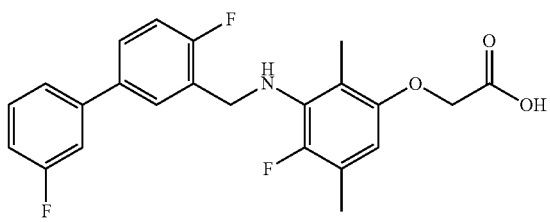

Tert-butyl N-tert-butoxycarbonyl-N-(3-bromo-6-fluoro-2,5-dimethylphenyl)carbamate

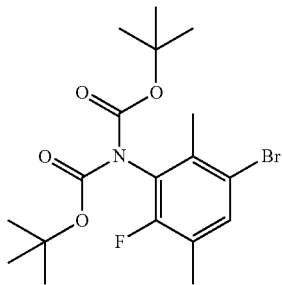 [SMILES: Cc1cc(Br)c(C)c(N(C(=O)OC(C)(C)C)C(=O)OC(C)(C)C)c1F]

To a stirred solution of 2,2,6,6-tetramethylpiperidine (699 mg, 4.9 mmol, 2.0 eq) in THF (7.5 mL) at −50° C. was added sec-BuLi (3.8 mL, 1.3 M, 4.9 mmol, 2.0 eq) dropwise. The reaction was stirred for 20 min at −15° C. to −10° C., then cooled to −65° C. and a solution of tert-butyl N-tert-butoxycarbonyl-N-(3-bromo-6-fluoro-2-methylphenyl)carbamate (See example 13) (1 g, 2.47 mmol, 1.0 eq) in THF (7.5 mL) added dropwise. The reaction was stirred a further 2 h at −65° C. Iodomethane (1.05 g, 7.41 mmol, 3.0 eq) was added in one portion and the reaction allowed to warm to −10° C. over 30 min. The reaction was then poured into saturated aqueous NH$_4$Cl and extracted with EtOAc. The combined organic extracts were washed with brine, dried (Na$_2$SO$_4$) filtered and evaporated in vacuo to give a crude residue, which was purified by column chromatography (petroleum ether:EtOAc, 100:0 to 30:1) to give the title compound as a white solid (880 mg, 85%).

LC-MS: m/z 340.0, 342.0 [M−Boc+Na]$^+$ 3-amino-4-fluoro-2,5-dimethyl-phenol (X(h))

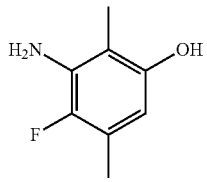

A mixture of tert-butyl N-tert-butoxycarbonyl-N-(3-bromo-6-fluoro-2,5-dimethylphenyl)carbamate (0.81 g, 1.94 mmol, 1.0 eq), Pd(dppf)Cl$_2$ (763 mg, 0.19 mmol, 0.1 eq), KOAc (571 mg, 5.82 mmol, 3.0 eq) and bis(pinacolato)diboron (591 mg, 2.33 mmol, 1.2 eq) in DMSO (10 mL) under N$_2$ was stirred at 80° C. overnight. After cooling to room temperature, the reaction was poured into water and extracted with EtOAc. The combined organic extracts were washed with water and brine, dried (Na$_2$SO$_4$), filtered and evaporated in vacuo to afford a crude residue. The residue obtained was dissolved in THF (10 mL) and the solution cooled to 0° C. H$_2$O$_2$ (30% aqueous solution, 660 mg, 5.82 mmol, 3.0 eq) was added, followed by NaOH (1M aqueous solution, 5.82 mL, 5.82 mmol, 3.0 eq) the mixture was stirred for 10 min and allowed to warm to 10° C. The pH was adjusted to pH 5~7 by addition of 3M HCl and the aqueous layer extracted with EtOAc. The combined organic extracts were washed with brine, dried (Na$_2$SO$_4$), filtered and evaporated in vacuo. The residue obtained was dissolved in MeOH (8 mL) and cooled to 0° C. HCl in dioxane (4M, 12 mL, 48 mmol, 24.7 eq) was added dropwise and the reaction mixture was allowed to warm to room temperature and stirred for 1 h. The reaction was then cooled to 0° C. and the pH adjusted to 5-6 by addition of 1M NaOH. The dioxane was removed in vacuo and the aqueous phase extracted with EtOAc. The combined organic extracts were washed with brine, dried (Na$_2$SO$_4$), filtered and evaporated in vacuo to give a crude residue, which was purified by column chromatography (petroleum ether: EtOAc, 10:1) to give the title compound as a yellow solid (157 mg, 52%).

LC-MS: m/z 156.1 [M+H]$^+$ $^1$H NMR (400 MHz, DMSO-d$_6$) δ 8.67 (s, 1H), 5.88 (d, J=6.3 Hz, 1H), 4.57 (s, 2H), 2.04 (d, J=1.9 Hz, 3H), 1.88 (s, 3H).

2-Fluoro-N-(2-fluoro-5-hydroxy-3,6-dimethyl-phenyl)-5-(3-fluorophenyl)benzamide

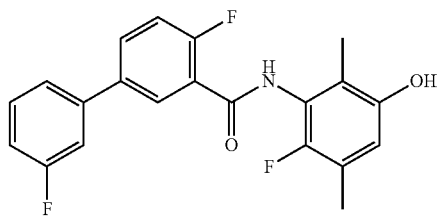

To a solution of 2-fluoro-5-(3-fluorophenyl)benzoic acid (Intermediate III(a)) (248 mg, 1.06 mmol, 1.1 eq) in CH$_2$Cl$_2$ (4 mL) and DMF (1 drop) at 0° C. was added (COCl)$_2$ (403 mg, 3.18 mmol, 3.3 eq) dropwise. The reaction mixture was stirred at room temperature for 2 h. The solvent and excess reagent were then removed under reduced pressure and the residue obtained dissolved in THF (4 mL) and added dropwise to a mixture of 3-amino-4-fluoro-2,5-dimethylphenol (X(h)) (150 mg, 0.97 mmol, 1.0 eq) and NaHCO$_3$ (407 mg, 4.85 mmol, 5.0 eq) in THF (3 mL) at 0° C. After the addition was completed, the reaction mixture was stirred at room temperature for 30 min. Water was added and the aqueous layer extracted with EtOAc. The organic extract was washed with aqueous NaHCO$_3$, water and brine, dried (Na$_2$SO$_4$), filtered and evaporated in vacuo. The residue obtained was purified by column chromatography (petroleum ether: EtOAc, 6:1 to 5:1) to give an impure product. The crude material was triturated with a mixture of petroleum ether and EtOAc (3 mL:1 mL) and the solid collected by filtration to afforded the title compound as a white solid (233 mg, 65%).

LC-MS: m/z 372.1 [M+H]$^+$ 394.1 [M+Na]$^+$

4-Fluoro-3-[[2-fluoro-5-(3-fluorophenyl)phenyl]methylamino]-2,5-dimethyl-phenol

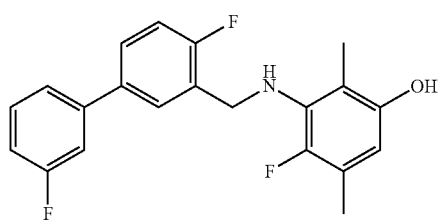 [SMILES: Cc1cc(O)c(C)c(NCc2cc(-c3cccc(F)c3)ccc2F)c1F]

To a solution of 2-fluoro-N-(2-fluoro-5-hydroxy-3,6-dimethyl-phenyl)-5-(3-fluorophenyl)benzamide (230 mg, 0.62 mmol, 1.0 eq) in THF (3 mL) at 0° C. under N$_2$ was added a solution of BH$_3$ (1M in THF, 3.7 mL, 3.7 mmol, 6.0 eq) dropwise. The reaction mixture was heated at 60° C. overnight. After cooling, the reaction was quenched by addition of water and extracted with EtOAc. The organic extract was washed with aqueous NaHCO$_3$, water and brine, dried (Na$_2$SO$_4$), filtered and evaporated in vacuo to give the title compound as a white solid (220 mg, 99%).

LC-MS: m/z 358.1 [M+H]$^+$

Isopropyl 2-[4-fluoro-3-[[2-fluoro-5-(3-fluorophenyl)phenyl]methylamino]-2,5-dimethyl-phenoxy]acetate (II(ag))

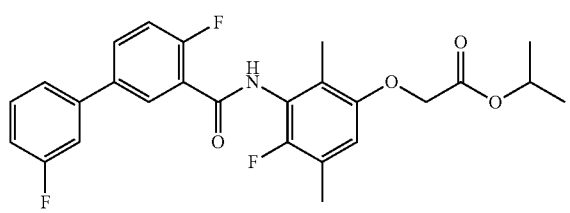 [SMILES: Cc1cc(OCC(=O)OC(C)C)c(C)c(NC(=O)c2cc(-c3cccc(F)c3)ccc2F)c1F]

To a solution of 4-fluoro-3-[[2-fluoro-5-(3-fluorophenyl)phenyl]methylamino]-2,5-dimethyl-phenol (220 mg, 0.62 mmol, 1.0 eq) in DMF (6 mL) was added Cs$_2$CO$_3$ (301 mg, 0.92 mmol, 1.5 eq) at room temperature. The reaction mixture was stirred for 30 min, then isopropyl bromoacetate (134 mg, 0.74 mmol, 1.2 eq) was added. The reaction mixture was stirred at room temperature for 1 h. TLC showed the starting material was not consumed. A further portion of Cs$_2$CO$_3$ (300 mg, 0.92 mmol, 1.5 eq) was added and the reaction stirred for 1 h, then a further portion of isopropyl bromoacetate (134 mg, 0.74 mmol, 1.2 eq) was added and the reaction stirred for 4 h. The resulting mixture was poured into water and extracted with EtOAc. The organic extract was washed with water and brine, dried (Na$_2$SO$_4$), filtered and evaporated in vacuo. The residue obtained was purified by column chromatography (petroleum ether:EtOAc, 50:1 to 20:1) to give the title compound as a colorless oil (225 mg, 80%).

LC-MS: m/z 458.2 [M+H]$^+$ $^1$H NMR (400 MHz, DMSO) δ 7.73 (dd, J=7.1, 2.3 Hz, 1H), 7.58 (ddd, J=8.2, 4.9, 2.6 Hz, 1H), 7.54-7.44 (m, 1H), 7.43-7.34 (m, 2H), 7.28-7.13 (m, 2H), 6.18 (d, J=5.7 Hz, 1H), 5.12-5.02 (m, 1H), 4.99-4.89 (m, 1H), 4.61 (s, 2H), 4.43 (d, J=7.0 Hz, 2H), 2.09-2.04 (m, 6H), 1.16 (d, J=6.3 Hz, 6H)

2-[4-Fluoro-3-[[2-fluoro-5-(3-fluorophenyl)phenyl]methylamino]-2,5-dimethyl-phenoxy]acetic acid (I(ac))

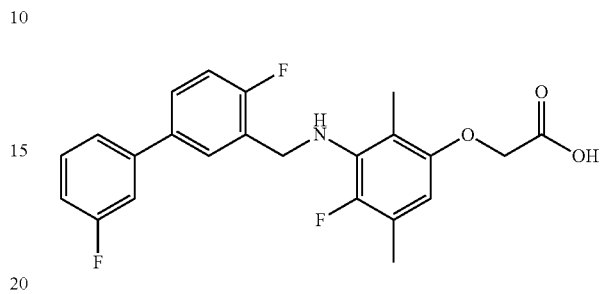

To a solution of isopropyl 2-[4-fluoro-3-[[2-fluoro-5-(3-fluorophenyl)phenyl]methyl amino]-2,5-dimethyl-phenoxy]acetate (130 mg, 0.28 mmol, 1.0 eq) in THF (2 mL) was added LiOH (2M aqueous solution, 2 mL, 4 mmol, 14 eq) at room temperature. The reaction mixture was stirred at room temperature for 2 h. Water was added and THF was removed under reduced pressure. The aqueous layer was washed with MTBE and the organic extract was discarded. The aqueous layer was adjusted to pH 3-4 by addition of 3M HCl and then extracted with EtOAc. The combined organic extracts were washed with brine, dried (Na$_2$SO$_4$), filtered and evaporated in vacuo. The crude product was recrystallized from CH$_2$Cl$_2$ (1 mL) and petroleum ether (3 mL) to give the target compound as an off-white solid (85 mg, 72%).

LC-MS: m/z 398.2 [M+H]$^+$ $^1$H NMR (400 MHz, DMSO-d$_6$) δ 12.89 (br s, 1H), 7.74 (dd, J=7.0, 2.2 Hz, 1H), 7.58 (ddd, J=7.7, 4.7, 2.3 Hz, 1H), 7.53-7.46 (m, 1H), 7.43-7.35 (m, 2H), 7.26-7.15 (m, 2H), 6.18 (d, J=5.8 Hz, 1H), 5.05 (br s, 1H), 4.55 (s, 2H), 4.43 (s, 2H), 2.07 (s, 6H) LC-MS: m/z 416.1 [M+H]$^+$

Example 30

Compound I(ad) Synthesized According to Scheme 3

2-[4-fluoro-3-[[2-fluoro-5-(3-fluorophenyl)-3-methyl-phenyl]methylamino]-2-methyl-phenoxy]acetic acid (I(ad))

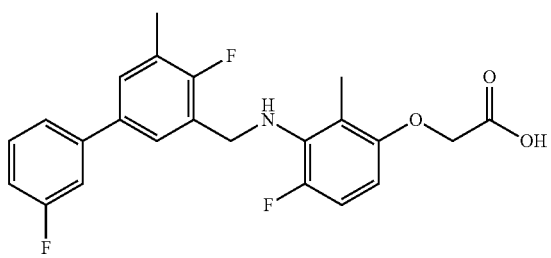

2-Fluoro-N-(6-fluoro-3-hydroxy-2-methyl-phenyl)-5-(3-fluorophenyl)-3-methyl-benzamide

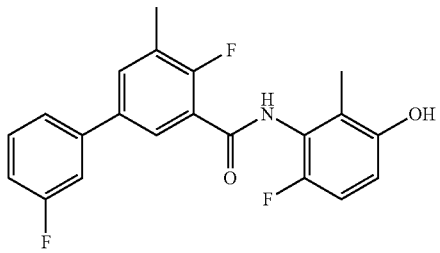 [SMILES: Cc1cc(-c2cccc(F)c2)cc(C(=O)Nc2c(F)ccc(O)c2C)c1F]

To a solution of 2-fluoro-5-(3-fluorophenyl)-3-methyl-benzoic acid (intermediate III(f)) (528 mg, 2.1 mmol, 1.0 eq), in CH$_2$Cl$_2$ (20 mL) and DMF (3 drops) was added (COCl)$_2$ (0.5 mL). The reaction was stirred at room temperature for 1 h then the solvent and excess reagent were removed under reduced pressure. The residue obtained was dissolved in THF (20 mL) and added to a mixture of 3-amino-4-fluoro-2-methylphenol (intermediate X(e)) (300 mg, 2.1 mmol, 1.0 eq) and NaHCO$_3$ (536 mg, 6.38 mmol, 3 eq) in THF (20 mL) at 0° C. After addition was completed, the reaction mixture was stirred at room temperature for 30 min. Water was added and the aqueous phase was adjusted to pH 3 by addition of diluted HCl. The aqueous solution was extracted with EtOAc and the combined organic extracts were dried (Na$_2$SO$_4$), filtered and evaporated in vacuo. The residue obtained was purified by column chromatography (petroleum ether:EtOAc, 100:1 to 1:1) to give the title compound as a white solid (420 mg, 53%).

LC-MS: m/z 372.1 [M+H]$^+$ 394.1 [M+Na]$^+$

4-Fluoro-3-[[2-fluoro-5-(3-fluorophenyl)-3-methyl-phenyl]methylamino]-2-methyl-phenol

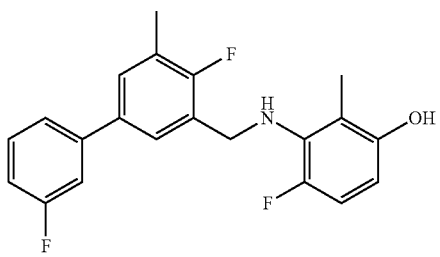 [SMILES: Cc1cc(-c2cccc(F)c2)cc(CNc2c(F)ccc(O)c2C)c1F]

To a solution of 2-fluoro-N-(6-fluoro-3-hydroxy-2-methyl-phenyl)-5-(3-fluorophenyl)-3-methyl-benzamide (404 mg, 1.1 mmol, 1.0 eq) in THF (10 mL) under N$_2$ was added a solution of BH$_3$ (1M in THF, 5.5 mL, 5.5 mmol, 5.0 eq) at room temperature. The reaction mixture was heated at 60° C. for 3 h, then cooled to room temperature and quenched with 1 M HCl. Water was added and the aqueous layer was extracted with EtOAc. The combined organic extracts were dried (Na$_2$SO$_4$), filtered and evaporated in vacuo. The crude residue obtained was purified by column chromatography (petroleum ether:EtOAc, 100:1 to 15:1) to give the title compound as a yellow oil (269 mg, 69%).

LC-MS: m/z 378.2 [M+H]$^+$

Isopropyl 2-[4-fluoro-3-[[2-fluoro-5-(3-fluorophenyl)-3-methyl-phenyl]methylamino]-2-methyl-phenoxy]acetate (II(ah))

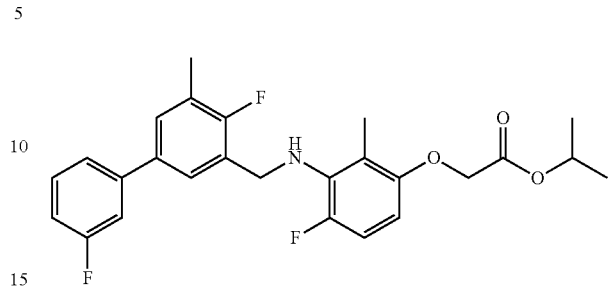

To a solution of 4-fluoro-3-[[2-fluoro-5-(3-fluorophenyl)-3-methyl-phenyl]methyl amino]-2-methyl-phenol (269 mg, 0.8 mmol, 1 eq), in 2-butanone (10 mL) was added Cs$_2$CO$_3$ (368 mg, 0.9 mmol, 1.5 eq) and isopropyl 2-bromoacetate (163.5 mg, 0.9 mmol, 1.2 eq). The reaction mixture was stirred at room temperature for 2 h, then filtered to remove the solids. The filtrate was evaporated in vacuo and the crude residue obtained purified by column chromatography (petroleum ether:EtOAc, 100:1 to 15:1) to give the title compound as a yellow oil (300 mg, 87%).

LC-MS: m/z 458.2 [M+H]$^+$ $^1$H NMR (400 MHz, DMSO) δ 7.55-7.43 (m, 3H), 7.40-7.32 (m, 2H), 7.16 (td, J=8.4, 2.1 Hz, 1H), 6.78 (dd, J=12.4, 9.0 Hz, 1H), 6.24 (dd, J=9.1, 3.6 Hz, 1H), 5.19-5.11 (m, 1H), 4.94 (hept, J=6.3 Hz, 1H), 4.63 (s, 2H), 4.44 (d, J=6.9 Hz, 2H), 2.26 (d, J=1.4 Hz, 3H), 2.12 (s, 3H), 1.15 (d, J=6.3 Hz, 6H).

2-[4-Fluoro-3-[[2-fluoro-5-(3-fluorophenyl)-3-methyl-phenyl]methylamino]-2-methyl-phenoxy]acetic acid (I(ad))

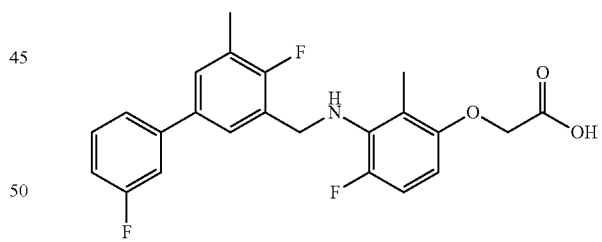

To a solution of isopropyl 2-[4-fluoro-3-[[2-fluoro-5-(3-fluorophenyl)-3-methyl-phenyl]methylamino]-2-methyl-phenoxy]acetate (150 mg, 0.33 mmol) in THF (6 mL) was added NaOH (1M aqueous solution, 4.0 mL, 4.0 mmol). The reaction mixture was stirred at room temperature for 2 h, then the THF removed under reduced pressure. The remaining aqueous solution was adjusted to pH 3-4 with diluted HCl and the solid that precipitated collected by filtration, washed with water and dried in vacuo to give the title compound as a white solid (100 mg, 74%).

LC-MS: m/z 414.1 [M–H]$^-$ $^1$H NMR (400 MHz, DMSO) δ 12.94 (br s, 1H), 7.56-7.50 (m, 1H), 7.50-7.44 (m, 2H), 7.40-7.33 (m, 2H), 7.20-7.12 (m,

1H), 6.79 (dd, J=12.3, 9.1 Hz, 1H), 6.24 (dd, J=9.0, 3.7 Hz, 1H), 5.13 (br s, 1H), 4.57 (s, 2H), 4.44 (s, 2H), 2.26 (s, 3H), 2.11 (s, 3H).

Example 31

Compound I(ae) Synthesized According to Scheme 3

2-[4-fluoro-3-[[3-(3-fluorophenyl)-5-methyl-phenyl]methylamino]-2-methyl-phenoxy]acetic acid (I(ae))

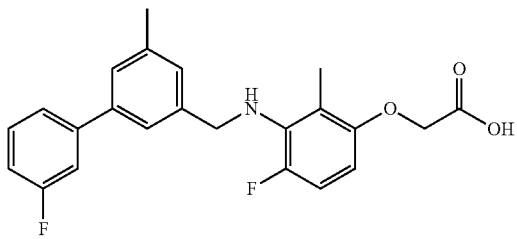 [SMILES: Cc1cc(CNc2c(F)ccc(OCC(=O)O)c2C)cc(-c2cccc(F)c2)c1]

3-Bromo-5-methylbenzoic acid

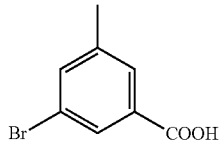

1-bromo-3,5-dimethylbenzene (15 g, 81 mmol, 1.0 eq) in a mixture of pyridine (133 mL) and H$_2$O (83 mL) was heated to 80° C. KMnO$_4$ (25.6 g, 162 mmol, 2.0 eq) was added in portions over 45 min. After the addition was completed, heating was continued at 80° C. for 1.5 h. The hot solution was then filtered, and the filtrate was acidified by addition of concentrated hydrochloric acid. The aqueous solution was extracted with EtOAc and the combined organic extracts washed with water and brine, dried (Na$_2$SO$_4$), filtered and evaporated in vacuo. The residue was purified by column chromatography (CH$_2$Cl$_2$: MeOH, 80:1 to 40:1) to give the title compound as a white solid (5.2 g, 29%)

LC-MS: m/z 212.9, 215 [M+H]$^+$
$^1$H NMR (400 MHz, MeOD) δ 7.91 (s, 1H), 7.79 (s, 1H), 7.57 (s, 1H), 2.38 (s, 3H).

3-(3-Fluorophenyl)-5-methyl-benzoic acid (III(q))

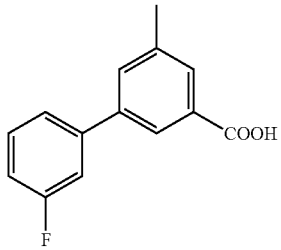 [SMILES: Cc1cc(C(=O)O)cc(-c2cccc(F)c2)c1]

To a solution of 3-bromo-5-methylbenzoic acid (3.0 g, 13.95 mmol, 1.0 eq), 3-fluorophenylboronic acid (2.34 g, 16.74 mmol, 1.2 eq) and Na$_2$CO$_3$ (5.91 g, 55.8 mmol, 4.0 eq) in a mixture of EtOH (10 mL), DMF (40 mL) and H$_2$O (10 mL) was added Pd(PPh$_3$)$_4$ (806 mg, 0.7 mmol, 0.05 eq). The mixture was stirred at 100° C. overnight. Water was added and the aqueous layer extracted with EtOAc. The organic extract was discarded and the aqueous layer was acidified to pH 4-5 by addition of 1M HCl. The aqueous layer was extracted with EtOAc and the combined organic extracts were filtered through silica gel and concentrated to give the title compound as a white solid (2.0 g, 62%)

LC-MS: m/z 229.1 [M−H]$^-$
$^1$H NMR (400 MHz, DMSO) δ 13.07 (s, 1H), 7.99 (s, 1H), 7.78 (s, 2H), 7.57-7.48 (m, 3H), 7.26-7.19 (m, 1H), 2.44 (s, 3H).

N-(6-Fluoro-3-hydroxy-2-methyl-phenyl)-3-(3-fluorophenyl)-5-methyl-benzamide

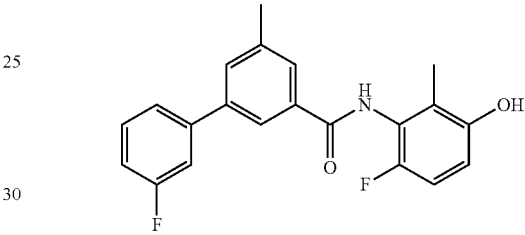

To a solution of 3-(3-fluorophenyl)-5-methyl-benzoic acid (448 mg, 1.95 mmol, 1.1 eq) in CH$_2$Cl$_2$ (10 mL) was added (COCl)$_2$ (742 mg, 5.85 mmol, 3.3 eq) and DMF (3 drops) at 0° C. The reaction mixture was stirred at room temperature for 1.5 h. The resulting mixture was concentrated in vacuo to remove the solvent and excess reagent. The solid obtained was dissolved in THF (10 mL) and added dropwise to a mixture of 3-amino-4-fluoro-2-methylphenol (intermediate X(e)) (250 mg, 1.77 mmol, 1.0 eq) and NaHCO$_3$ (744 mg, 8.86 mmol, 5.0 eq) in THF (15 mL) at 0° C. The reaction was allowed to warm to room temperature and stirred for 1 h. Water was added and the aqueous layer extracted with EtOAc. The organic extract was washed with water and brine, dried (Na$_2$SO$_4$), filtered and evaporated in vacuo. The residue obtained was purified by column chromatography (CH$_2$Cl$_2$: MeOH, 500:1 to 300:1) to give the title compound as a white solid (396 mg, 63%).

LC-MS: m/z 354.1 [M+H]$^+$ 376.1 [M+Na]$^+$

4-Fluoro-3-[[3-(3-fluorophenyl)-5-methyl-phenyl]methylamino]-2-methyl-phenol

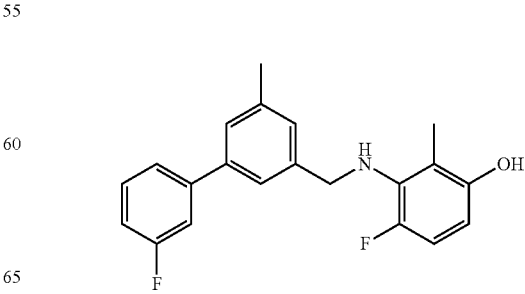

To a solution of N-(6-fluoro-3-hydroxy-2-methyl-phenyl)-3-(3-fluorophenyl)-5-methyl-benzamide (394 mg, 1.11 mmol, 1.0 eq) in THF (15 mL) under $N_2$ was added a solution of $BH_3$ (1M in THF, 6.7 mL, 6.7 mmol, 6.0 eq) dropwise The reaction mixture was heated at 60° C. overnight. After cooling, the reaction was quenched by addition of water and the aqueous layer was extracted with EtOAc. The extract was washed with water and brine, dried ($Na_2SO_4$), filtered and evaporated in vacuo. The residue obtained was purified by column chromatography (petroleum ether:EtOAc, 30:1 to 20:1) to give the title compound as a brown oil (324 mg, 86%).

LC-MS: m/z 340.2 [M+H]+ 362.1 [M+Na]+

Isopropyl 2-[4-fluoro-3-[[3-(3-fluorophenyl)-5-methyl-phenyl]methylamino]-2-methyl-phenoxy]acetate (II(ai))

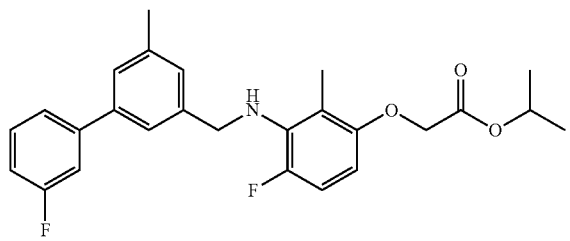

To a solution of 4-fluoro-3-[[3-(3-fluorophenyl)-5-methyl-phenyl]methylamino]-2-methyl-phenol (324 mg, 0.95 mmol, 1.0 eq) in DMF (15 mL) was added $Cs_2CO_3$ (467 mg, 1.43 mmol, 1.5 eq). The reaction mixture was stirred at room temperature for 30 min, then isopropyl bromoacetate (207 mg, 1.15 mmol, 1.2 eq) was added and stirring continued for a further 1 h. Water was added and the aqueous layer was extracted with EtOAc. The organic extract was washed with water and brine, dried ($Na_2SO_4$), filtered and evaporated in vacuo. The residue obtained was purified by column chromatography (petroleum ether:EtOAc, 50:1 to 40:1) to give the title compound as a colorless oil (317 mg, 76%).

LC-MS: m/z 440.2 [M+H]+ 462.2 [M+Na]+

$^1$H NMR (400 MHz, DMSO) δ 7.52-7.44 (m, 1H), 7.44-7.36 (m, 3H), 7.33 (s, 1H), 7.17 (td, J=8.4, 1.9 Hz, 1H), 7.13 (s, 1H), 6.77 (dd, J=12.4, 9.0 Hz, 1H), 6.21 (dd, J=9.0, 3.6 Hz, 1H), 5.22 (t, J=6.8 Hz, 1H), 4.94 (hept, J=6.2 Hz, 1H), 4.62 (s, 2H), 4.37 (d, J=6.8 Hz, 2H), 2.31 (s, 3H), 2.12 (s, 3H), 1.16 (d, J=6.3 Hz, 6H).

2-[4-Fluoro-3-[[3-(3-fluorophenyl)-5-methyl-phenyl]methylamino]-2-methyl-phenoxy]acetic acid (I(ae))

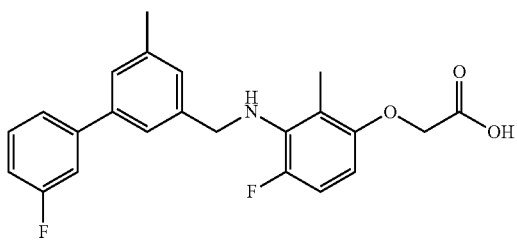 [SMILES: Cc1cc(CNc2c(F)ccc(OCC(=O)O)c2C)cc(-c2cccc(F)c2)c1]

To a solution of isopropyl 2-[4-fluoro-3-[[3-(3-fluorophenyl)-5-methyl-phenyl]methylamino]-2-methyl-phenoxy]acetate (200 mg, 0.46 mmol, 1.0 eq) in THF (10 mL) was added LiOH (2M aqueous solution, 4 mL, 8.0 mmol). The reaction mixture was stirred at room temperature for 2 h then the THF was removed in vacuo. The pH of the aqueous solution that remained was adjusted to pH 5 by addition of 3M HCl. The solid precipitate that formed was collected by filtration, washed with water and dried in vacuo to give the title compound as a yellow solid (150 mg, 83%).

LC-MS: m/z 398.2 [M+H]+

$^1$H NMR (400 MHz, DMSO) δ 7.54-7.36 (m, 4H), 7.33 (s, 1H), 7.22-7.09 (m, 2H), 6.74 (dd, J=12.3, 9.0 Hz, 1H), 6.17 (dd, J=8.9, 3.5 Hz, 1H), 5.15 (br s, 1H), 4.41 (s, 2H), 4.36 (s, 2H), 2.32 (s, 3H), 2.10 (s, 3H).

Example 32

Compound I(af) Synthesized According to Scheme 3

2-[4-fluoro-3-[[5-(3-fluorophenyl)-2-methoxy-3-methyl-phenyl]methylamino]-2-methyl-phenoxy]acetic acid (I(af))

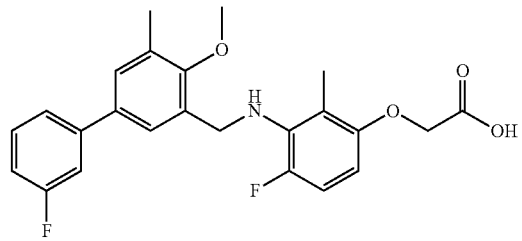 [SMILES: COc1c(C)cc(-c2cccc(F)c2)cc1CNc1c(F)ccc(OCC(=O)O)c1C]

N-(6-Fluoro-3-hydroxy-2-methyl-phenyl)-5-(3-fluorophenyl)-2-methoxy-3-methyl-benzamide

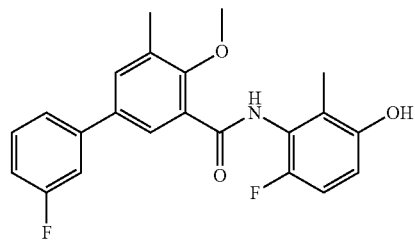 [SMILES: COc1c(C)cc(-c2cccc(F)c2)cc1C(=O)Nc1c(F)ccc(O)c1C]

To a solution of 5-(3-fluorophenyl)-2-methoxy-3-methyl-benzoic acid (intermediate III(k)) (500 mg, 1.92 mmol, 1.1 eq) in $CH_2Cl_2$ (10 mL) was added $(COCl)_2$ (731.6 mg, 5.76 mmol, 3.3 eq) at 0° C. The reaction mixture was allowed to warm to room temperature and stirred for 1 h. The resulting mixture was concentrated under reduced pressure and the residue that remained dissolved in THF (6 mL) and added to a mixture of 3-amino-4-fluoro-2-methylphenol (intermediate X(e)) (246.5 mg, 1.75 mmol, 1.0 eq) and $NaHCO_3$ (733.5 mg, 8.73 mmol, 5.0 eq) in THF (8 mL). After the addition, the reaction mixture was stirred for a further 2 h. Water was added and the aqueous layer extracted with EtOAc. The organic extract was washed with 5% $Na_2CO_3$, dried ($Na_2SO_4$), filtered and evaporated in vacuo. The residue obtained was purified by column chromatography (petroleum ether: EtOAc, 10:1 to 5:1 then CH$_2$Cl$_2$:MeOH, 20:1) to give the title compound as a white solid (540 mg, 80%).

LC-MS: m/z 384.1 [M+H]$^+$ 406.1 [M+Na]$^+$

4-Fluoro-3-[[5-(3-fluorophenyl)-2-methoxy-3-methyl-phenyl]methylamino]-2-methyl-phenol

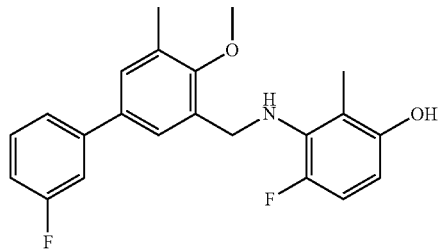 [SMILES: COc1c(C)cc(-c2cccc(F)c2)cc1CNc1c(F)ccc(O)c1C]

To a solution of N-(6-fluoro-3-hydroxy-2-methyl-phenyl)-5-(3-fluorophenyl)-2-methoxy-3-methyl-benzamide (450 mg, 1.17 mmol, 1.0 eq) in THF (6 mL) at 0° C. under N$_2$ was added a solution of BH$_3$ (1M in THF, 7.04 mL, 7.04 mmol, 6.0 eq). The reaction mixture was heated at 60° C. for 1 h. After cooling to 0° C., water was added dropwise and the aqueous layer extracted with EtOAc. The organic extract was washed with water and brine, dried (Na$_2$SO$_4$), filtered and evaporated in vacuo. The residue was purified by column chromatography (petroleum ether:EtOAc, 20:1 to 10:1) to give the title compound as a colorless oil (94 mg, 22%).

LC-MS: m/z 370.1 [M+H]$^+$ 392.1 [M+Na]$^+$

Isopropyl 2-[4-fluoro-3-[[5-(3-fluorophenyl)-2-methoxy-3-methyl-phenyl]methylamino]-2-methyl-phenoxy]acetate (II(aj))

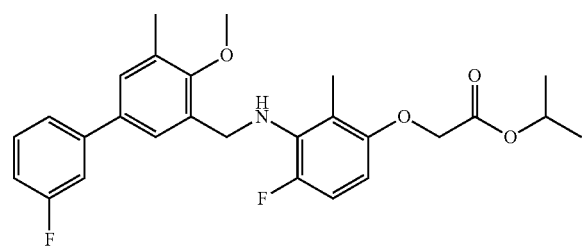 [SMILES: COc1c(C)cc(-c2cccc(F)c2)cc1CNc1c(F)ccc(OCC(=O)OC(C)C)c1C]

To a solution of 4-fluoro-3-[[5-(3-fluorophenyl)-2-methoxy-3-methyl-phenyl]methylamino]-2-methyl-phenol (94 mg, 0.25 mmol, 1.0 eq) in acetone (4 mL) at room temperature was added Cs$_2$CO$_3$ (124.4 mg, 0.38 mmol, 1.5 eq). The reaction mixture was stirred for 30 min, then isopropyl bromoacetate (55.3 mg, 1.2 mmol, 1.2 eq) was added and stirring continued for a further 2 h. Water was added and the aqueous layer extracted with EtOAc. The organic extract was washed with water and brine, dried (Na$_2$SO$_4$), filtered and evaporated in vacuo. The residue was purified by column chromatography (petroleum ether:EtOAc, 20:1) to give the title compound as a colorless oil (65 mg, 54%).

LC-MS: m/z 470.2 [M+H]$^+$ 492.2 [M+Na]$^+$ $^1$H NMR (400 MHz, DMSO) δ 7.52-7.39 (m, 3H), 7.39-7.30 (m, 2H), 7.14 (td, J=8.5, 2.3 Hz, 1H), 6.79 (dd, J=12.0, 9.1 Hz, 1H), 6.25 (dd, J=9.0, 3.6 Hz, 1H), 5.01-4.90 (m, 2H), 4.65 (s, 2H), 4.44 (s, 2H), 3.71 (s, 3H), 2.29 (s, 3H), 2.15 (s, 3H), 1.17 (d, J=6.3 Hz, 6H).

2-[4-Fluoro-3-[[5-(3-fluorophenyl)-2-methoxy-3-methyl-phenyl]methylamino]-2-methyl-phenoxy] acetic acid (I(a))

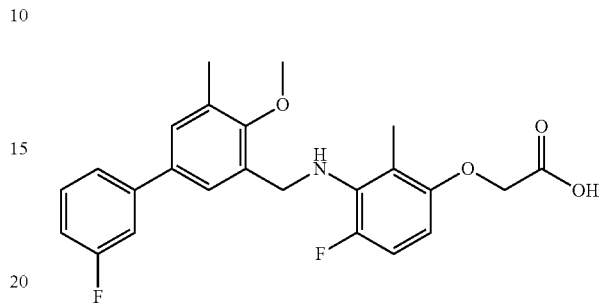

To a solution of isopropyl 2-[4-fluoro-3-[[5-(3-fluorophenyl)-2-methoxy-3-methyl-phenyl]methylamino]-2-methyl-phenoxy]acetate (64 mg, 0.2 mmol, 1.0 eq) in THF (2 mL) was added LiOH (2M aqueous solution, 2.0 mL, 4.0 mmol). The reaction mixture was stirred at room temperature for 1 h. The THF was removed and the pH of the aqueous solution that remained adjusted to pH 4-5 with diluted HCl. The aqueous layer was extracted with EtOAc, the organic extract was washed with water and brine, dried (Na$_2$SO$_4$), filtered and evaporated in vacuo to give the title compound as a white solid (30 mg, 50%).

LC-MS: m/z 428.2 [M+H]$^+$ $^1$H NMR (400 MHz, DMSO) δ 7.51-7.40 (m, 3H), 7.40-7.30 (m, 2H), 7.14 (td, J=8.7, 2.2 Hz, 1H), 6.79 (dd, J=12.4, 9.1 Hz, 1H), 6.24 (dd, J=9.1, 3.6 Hz, 1H), 4.57 (s, 2H), 4.43 (s, 2H), 3.70 (s, 3H), 2.29 (s, 3H), 2.13 (s, 3H).

Example 33

Compound I(ag) Synthesized According to Scheme 3

2-[3-[[2-fluoro-5-(3-fluorophenyl)-3-methyl-phenyl]methylamino]-2,4-dimethyl-phenoxy]acetic acid (I(ag))

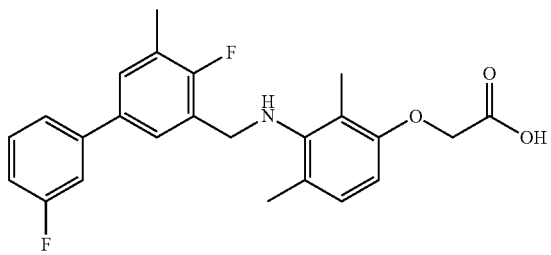 [SMILES: Cc1cc(-c2cccc(F)c2)cc(CNc2c(C)ccc(OCC(=O)O)c2C)c1F]

2-Fluoro-5-(3-fluorophenyl)-N-(3-hydroxy-2,6-dimethyl-phenyl)-3-methyl-benzamide

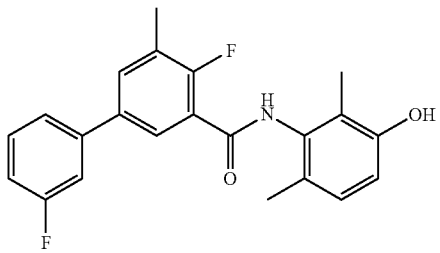

To a solution of 2-fluoro-5-(3-fluorophenyl)-3-methylbenzoic acid (intermediate III(f)) (597 mg, 2.41 mmol, 1.1 eq) in CH$_2$Cl$_2$ (15 mL) and DMF (5 drops) was added (COCl)$_2$ (916 mg, 7.22 mmol, 3.3 eq) at 0° C. The reaction mixture was stirred at room temperature for 1.5 h. The resulting mixture was concentrated under reduced pressure to remove the solvent and excess reagent and the residue obtained dissolved in THF (20 mL) and added dropwise to a solution of 3-amino-2,4-dimethylphenol (intermediate X(c)) (300 mg, 2.18 mmol, 1.0 eq) and NaHCO$_3$ (920 mg, 10.9 mmol, 5 eq) in THF (20 mL) at 0° C. After the addition was completed, the reaction mixture was stirred at room temperature for 1 h. Water was added and the aqueous layer extracted with EtOAc. The organic extract was washed with water and brine, dried (Na$_2$SO$_4$), filtered, and evaporated in vacuo. The residue was purified by column chromatography (CH$_2$Cl$_2$:MeOH, 500:1 to 300:1) to give the title compound as a white solid (270 mg, 34%).

LC-MS: m/z 368.1 [M+H]$^+$ 390.2 [M+Na]$^+$

3-[[2-Fluoro-5-(3-fluorophenyl)-3-methyl-phenyl]methylamino]-2,4-dimethyl-phenol

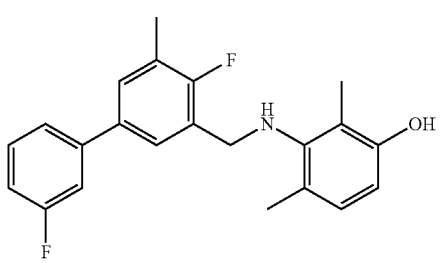 [SMILES: Cc1cc(-c2cccc(F)c2)cc(CNc2c(C)ccc(O)c2C)c1F]

To a solution of 2-fluoro-5-(3-fluorophenyl)-N-(3-hydroxy-2,6-dimethyl-phenyl)-3-methyl-benzamide (270 mg, 0.7 mmol, 1.0 eq) in THF (15 mL) was added a solution of BH$_3$ (1M in THF, 4.4 mL, 4.4 mmol, 6.0 eq) dropwise under N$_2$. The reaction mixture was heated at 60° C. overnight. After cooling, the resulting mixture was quenched by the addition of water and the aqueous layer extracted with EtOAc. The organic extract was washed with water and brine, dried (Na$_2$SO$_4$), filtered and evaporated in vacuo. The residue was purified by column chromatography (petroleum ether:EtOAc, 30:1 to 20:1) to give the title compound as a colorless oil (106 mg, 41%).

LC-MS: m/z 354.2 [M+H]$^+$

Isopropyl 2-[3-[[2-fluoro-5-(3-fluorophenyl)-3-methyl-phenyl]methylamino]-2,4-dimethyl-phenoxy]acetate (II(ak))

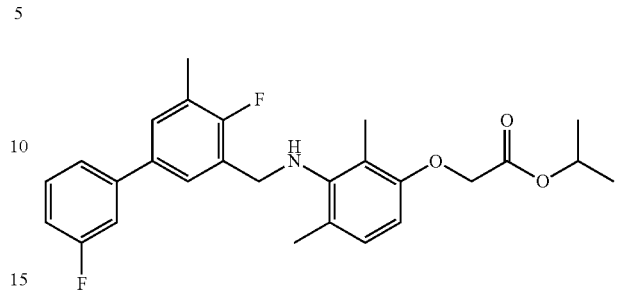

To a solution of 3-[[2-fluoro-5-(3-fluorophenyl)-3-methyl-phenyl]methylamino]-2,4-dimethyl-phenol (106 mg, 0.30 mmol, 1.0 eq) in DMF (6 mL) was added Cs$_2$CO$_3$ (147 mg, 0.45 mmol, 1.5 eq) at room temperature. The reaction mixture was stirred for 30 min, then isopropyl bromoacetate (65 mg, 0.136 mmol, 1.2 eq) was added. The reaction mixture was stirred at room temperature for 1 h. Water was added and the aqueous layer extracted with EtOAc. The organic extract was washed with water and brine, dried (Na$_2$SO$_4$), filtered and evaporated in vacuo. The residue was purified by column chromatography (petroleum ether:EtOAc, 50:1 to 40:1) to give the title compound as a colorless oil (90 mg, 66%).

LC-MS: m/z 454.2 [M+H]$^+$ 476.2 [M+Na]$^+$ $^1$H NMR (400 MHz, DMSO) δ 7.60 (dd, J=6.5, 2.2 Hz, 1H), 7.56-7.51 (m, 1H), 7.51-7.39 (m, 3H), 7.22-7.13 (m, 1H), 6.84 (d, J=8.3 Hz, 1H), 6.38 (d, J=8.3 Hz, 1H), 5.01-4.90 (m, 1H), 4.64 (s, 2H), 4.25 (t, J=7.5 Hz, 1H), 4.13 (d, J=7.3 Hz, 2H), 2.28 (d, J=1.3 Hz, 3H), 2.14 (s, 3H), 2.13 (s, 3H), 1.19 (d, J=6.3 Hz, 6H).

2-[3-[[2-Fluoro-5-(3-fluorophenyl)-3-methyl-phenyl]methylamino]-2,4-dimethyl-phenoxy]acetic acid (I(ag))

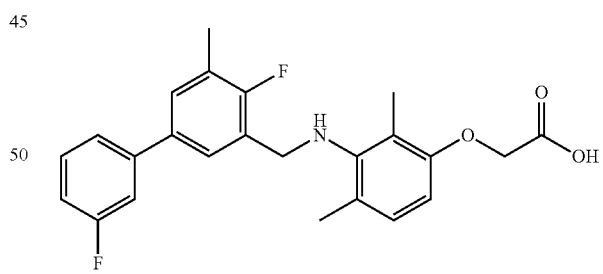

To a solution of isopropyl 2-[3-[[2-fluoro-5-(3-fluorophenyl)-3-methyl-phenyl]methyl amino]-2,4-dimethyl-phenoxy]acetate (70 mg, 0.15 mmol, 1.0 eq) in THF (5 mL) at 0° C. was added LiOH (2M aqueous solution, 2.0 mL, 4.0 mmol). The reaction mixture was allowed to warm to room temperature and stirred for 2 h. The THF was removed in vacuo and the remaining aqueous mixture diluted with water and adjusted to pH 5 by addition of 3M HCl. The solid that precipitated was collected by filtration and dried in vacuo to give the title compound as a yellow solid (40 mg, 63%).

LC-MS: m/z 412.2 [M+H]$^+$ $^1$H NMR (400 MHz, DMSO) δ 7.61 (dd, J=6.5, 2.2 Hz, 1H), 7.52 (dd, J=6.5, 2.4 Hz, 1H), 7.50-7.39 (m, 3H), 7.20-7.12 (m, 1H), 6.81 (d, J=8.3 Hz, 1H), 6.35 (d, J=8.3 Hz, 1H), 4.38 (s, 2H), 4.12 (s, 2H), 2.28 (d, J=1.2 Hz, 3H), 2.13 (s, 6H).

Example 34

Compound I(ah) Synthesized According to Scheme 3

2-[4-fluoro-3-[[3-(3-fluorophenyl)-5-hydroxy-phenyl]methylamino]-2-methyl-phenoxy]acetic acid (I(ah))

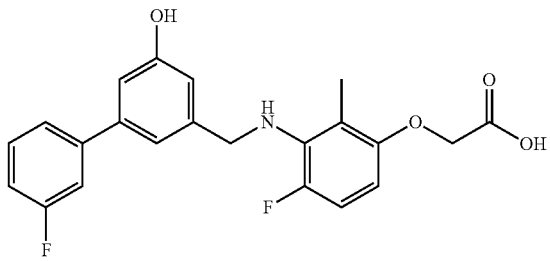

N-(6-Fluoro-3-hydroxy-2-methyl-phenyl)-3-(3-fluorophenyl)-5-methoxy-benzamide

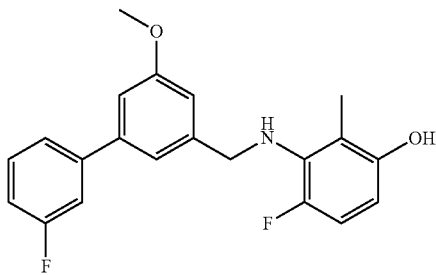 [SMILES: COc1cc(CNc2c(F)ccc(O)c2C)cc(-c2cccc(F)c2)c1]

To a solution of 3-(3-fluorophenyl)-5-methoxy-benzoic acid (524 mg, 2.1 mmol, 1.0 eq) in CH$_2$Cl$_2$ (10 mL) was added dropwise (COCl)$_2$ (810 mg, 6.4 mmol, 3 eq) at 0° C. DMF (0.1 mL) was added and the reaction mixture stirred at room temperature for 3 h. The solvent was removed under reduced pressure and the residue obtained was dissolved in THF (20 mL) and added dropwise to a mixture of 3-amino-4-fluoro-2-methyl-phenol (300 mg, 2.1 mmol, 1 eq) and K$_2$CO$_3$ (1.47 g, 10.6 mmol, 5 eq.) in THF (20 mL) at 0° C. After the addition, the reaction mixture was stirred at room temperature for 3 h. The resulting mixture was poured into water and extracted with EtOAc. The organic extract was washed with brine, dried (Na$_2$SO$_4$), filtered and evaporated in vacuo. The residue obtained was purified by column chromatography (petroleum ether:EtOAc, 20:1) to give the title compound as yellow solid (500 mg, 63%).

LC-MS: m/z 370.1 [M+H]$^+$ 392.1 [M+Na]$^+$

4-Fluoro-3-[[3-(3-fluorophenyl)-5-methoxy-phenyl]methylamino]-2-methyl-phenol

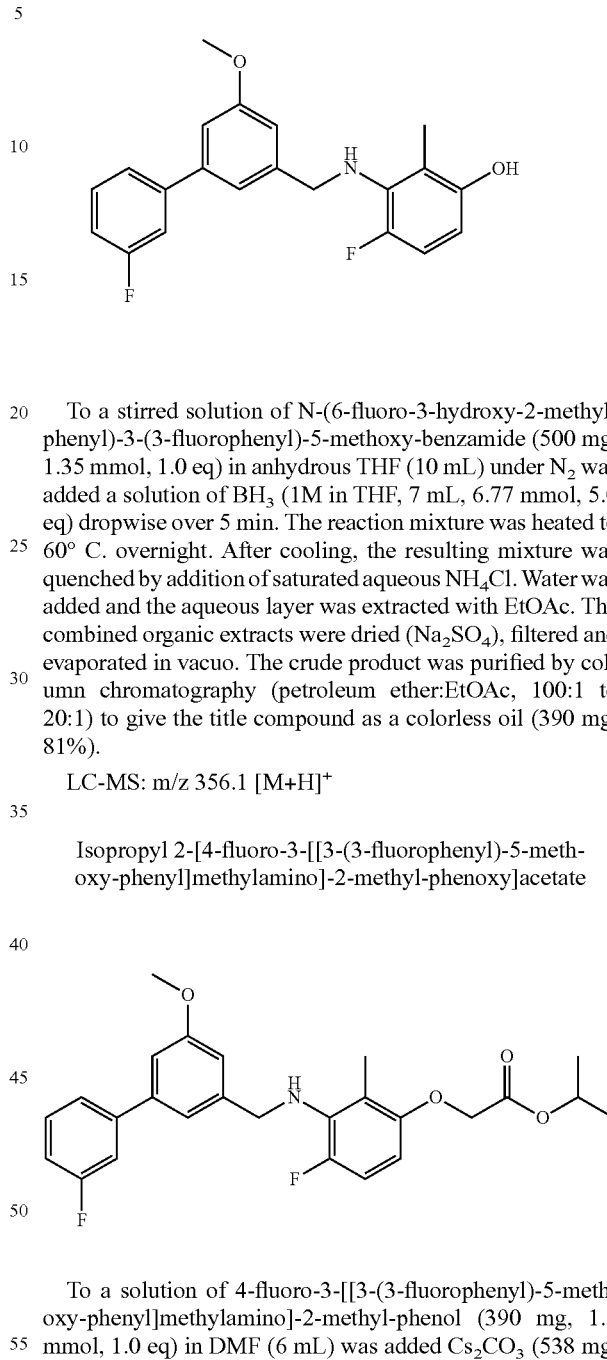

To a stirred solution of N-(6-fluoro-3-hydroxy-2-methyl-phenyl)-3-(3-fluorophenyl)-5-methoxy-benzamide (500 mg, 1.35 mmol, 1.0 eq) in anhydrous THF (10 mL) under N$_2$ was added a solution of BH$_3$ (1M in THF, 7 mL, 6.77 mmol, 5.0 eq) dropwise over 5 min. The reaction mixture was heated to 60° C. overnight. After cooling, the resulting mixture was quenched by addition of saturated aqueous NH$_4$Cl. Water was added and the aqueous layer was extracted with EtOAc. The combined organic extracts were dried (Na$_2$SO$_4$), filtered and evaporated in vacuo. The crude product was purified by column chromatography (petroleum ether:EtOAc, 100:1 to 20:1) to give the title compound as a colorless oil (390 mg, 81%).

LC-MS: m/z 356.1 [M+H]$^+$

Isopropyl 2-[4-fluoro-3-[[3-(3-fluorophenyl)-5-methoxy-phenyl]methylamino]-2-methyl-phenoxy]acetate To a solution of 4-fluoro-3-[[3-(3-fluorophenyl)-5-methoxy-phenyl]methylamino]-2-methyl-phenol (390 mg, 1.1 mmol, 1.0 eq) in DMF (6 mL) was added Cs$_2$CO$_3$ (538 mg, 1.65 mmol, 1.5 eq). The reaction was stirred 30 min, then isopropyl 2-bromoacetate (239 mg, 1.32 mmol, 1.2 eq) was added at room temperature. The reaction mixture was stirred at room temperature for a further 1 h, then water was added and the aqueous layer was extracted with EtOAc. The organic extract was washed with water and brine, dried (Na$_2$SO$_4$), filtered and evaporated in vacuo. The crude product was purified by column chromatography (petroleum ether:EtOAc, 1:0, 100:1, to 20:1) to give the title compound as a colorless oil (400 mg, 80%).

LC-MS: m/z 456.2 [M+H]$^+$, 478.2 [M+Na]$^+$

Isopropyl 2-[4-fluoro-3-[[3-(3-fluorophenyl)-5-hydroxy-phenyl]methylamino]-2-methyl-phenoxy]acetate (II(al))

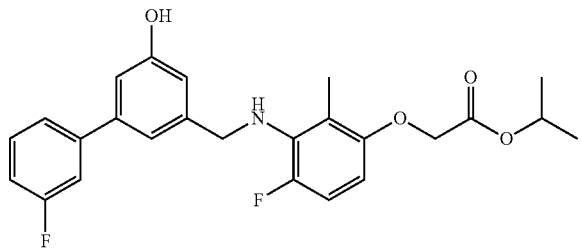

To a solution of isopropyl 2-[4-fluoro-3-[[3-(3-fluorophenyl)-5-methoxy-phenyl]methylamino]-2-methyl-phenoxy]acetate (300 mg, 0.66 mmol, 1 eq) and AlCl$_3$ (526 mg, 3.95 mmol, 6 eq) in CH$_2$Cl$_2$ (10 mL) was added ethanethiol (245 mg, 3.95 mmol, 5 eq) at 0° C. under nitrogen. The reaction mixture was stirred at room temperature for 2 h and the resulting mixture was quenched by the addition of water. The aqueous layer was extracted with EtOAc and the combined organic extracts were washed with water, dried (Na$_2$SO$_4$), filtered and evaporated in vacuo. The crude product was purified by column chromatography (petroleum ether:EtOAc, 15:1) to give the title compound as a colorless oil (120 mg, 41%).

LC-MS: m/z 442.2 [M+H]$^+$ 465.2 [M+Na]$^+$ $^1$H NMR (400 MHz, CDCl$_3$) δ 7.40-7.33 (m, 1H), 7.32-7.28 (m, 1H), 7.24-7.18 (m, 1H), 7.08 (s, 1H), 7.06-6.99 (m, 1H), 6.95-6.91 (m, 1H), 6.83-6.75 (m, 2H), 6.26 (dd, J=9.0, 3.8 Hz, 1H), 5.19-5.06 (m, 1H), 4.56 (s, 2H), 4.34 (s, 2H), 2.20 (s, 3H), 1.27 (d, J=6.3 Hz, 6H).

2-[4-Fluoro-3-[[3-(3-fluorophenyl)-5-hydroxy-phenyl]methylamino]-2-methyl-phenoxy]acetic acid (I(ah))

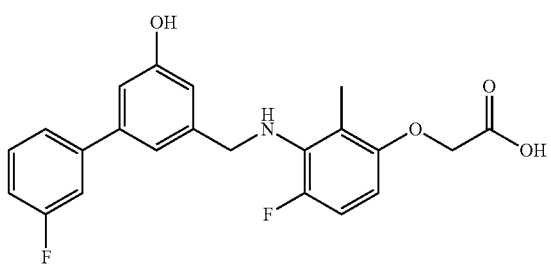 [SMILES: Cc1c(OCC(=O)O)ccc(F)c1NCc1cc(O)cc(-c2cccc(F)c2)c1]

To a solution of isopropyl 2-[4-fluoro-3-[[3-(3-fluorophenyl)-5-hydroxy-phenyl]methylamino]-2-methyl-phenoxy]acetate (90 mg, 0.2 mmol, 1 eq) in a mixture of MeOH (3 mL) and THF (3 mL) was added NaOH (1 M aqueous solution, 3 mL, 3 mmol) and the reaction was stirred at room temperature for 3 h. The MeOH and THF were removed under reduced pressure and the aqueous phase was acidified to pH 3-6 by addition of 1M HCl. The aqueous layer was extracted with EtOAc and the combined organic extracts were dried (Na$_2$SO$_4$), filtered and evaporated in vacuo to give the title compound as yellow oil (30 mg, 37%).

LC-MS: m/z 400.1 [M+H]$^+$ $^1$H NMR (400 MHz, DMSO) δ 9.52 (br s, 1H), 7.52-7.42 (m, 1H), 7.42-7.29 (m, 2H), 7.21-7.12 (m, 1H), 7.04 (s, 1H), 6.85 (s, 1H), 6.81-6.70 (m, 2H), 6.19 (dd, J=8.9, 3.5 Hz, 1H), 5.20 (br s, 1H), 4.55 (s, 2H), 4.34 (s, 2H), 2.11 (s, 3H).

Example 35

Methyl 2-[2,4-difluoro-3-[[2-fluoro-5-(3-fluorophenyl)phenyl]methylamino]phenoxy]acetate (II(c)), prepared via scheme 7

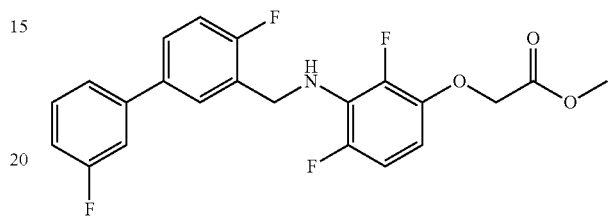

To a stirred solution of ethyl 2-[2,4-difluoro-3-[[2-fluoro-5-(3-fluorophenyl)phenyl]methylamino]phenoxy]acetate (II(a)) (290 mg, 0.7 mmol, 1.0 eq) in MeOH (30 mL) was added K$_2$CO$_3$ (28 mg, 0.2 mmol 0.3 eq). The reaction was heated at reflux overnight. The solvent was removed in vacuo and the residue obtained was diluted with water and neutralized by addition of 1M HCl. The aqueous layer was further extracted with EtOAc and the combined organic extracts were washed with brine, dried (Na$_2$SO$_4$), filtered and evaporated in vacuo. The residue was purified by chromatography (EtOAc:petroleum ether, 0:1 to 1:20) to give the title compound an oil (130 mg, 46%).

LC-MS: m/z 419.9 [M+H]$^+$ $^1$H NMR (300 MHz, DMSO-d$_6$) δ 7.73 (dd, J=7.2, 2.4 Hz, 1H), 7.66-7.56 (m, 1H), 7.54-7.44 (m, 1H), 7.43-7.36 (m, 2H), 7.24 (dd, J=9.8, 8.6 Hz, 1H), 7.23-7.13 (m, 1H), 6.80 (ddd, J=11.6, 9.3, 2.1 Hz, 1H), 6.36 (td, J=9.1, 4.6 Hz, 1H), 6.03-5.75 (m, 1H), 4.76 (s, 2H), 4.52 (d, J=7.1 Hz, 2H), 3.65 (s, 3H)

Example 36

Isopropyl 2-[2,4-difluoro-3-[[2-fluoro-5-(3-fluorophenyl)phenyl]methylamino]phenoxy]acetate (II(d)), prepared via scheme 6

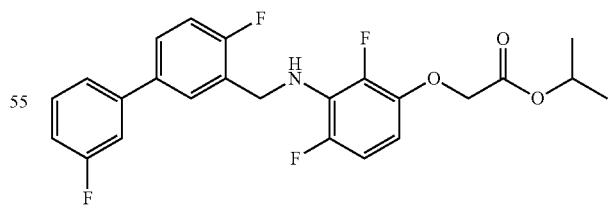

2-[2,4-Difluoro-3-[[2-fluoro-5-(3-fluorophenyl)phenyl]methylamino]phenoxy]acetic acid (I(b)) (70 mg, 0.17 mmol, 1.0 eq) was dissolved in iPrOH (5 mL). Concentrated sulphuric acid (2 drops) was added and the solution was stirred at room temperature overnight. The reaction was quenched by addition of aqueous NaHCO$_3$ and the aqueous layer was extracted with EtOAc. The combined organic extracts were dried (MgSO₄), filtered and evaporated in vacuo to give the crude product. The compound was triturated in a mixture of petroleum ether and DCM and dried under vacuum to give the title compound (II(d)) as a gummy solid (52 mg, 68%).

LC-MS: m/z 448.0 [M+H]⁺

¹H NMR (300 MHz, DMSO-d₆) δ 7.73 (dd, J=7.3, 2.3 Hz, 1H), 7.63-7.56 (m, 1H), 7.54-7.45 (m, 1H), 7.43-7.35 (m, 2H), 7.23 (dd, J=9.9, 8.6 Hz, 1H), 7.23-7.13 (m, 1H), 6.80 (ddd, J=11.6, 9.3, 2.1 Hz, 1H), 6.33 (td, J=9.1, 4.5 Hz, 1H), 5.88 (s, 1H), 4.93 (spt, J=6.3 Hz, 1H), 4.70 (s, 2H), 4.52 (d, J=7.0 Hz, 2H), 1.14 (d, J=6.2 Hz, 6H)

Example 37

Isopropyl 2-[2,4-difluoro-3-[[2-fluoro-3-(3-fluorophenyl)-5-methyl-phenyl]methylamino]phenoxy]acetate (II(f)), prepared via scheme 6

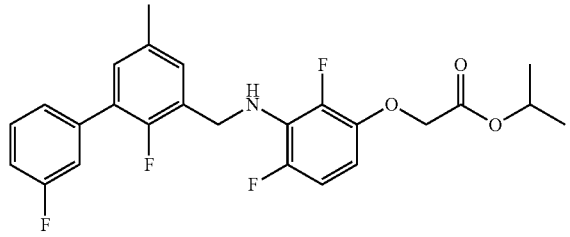 [SMILES: Cc1cc(CNc2c(F)ccc(OCC(=O)OC(C)C)c2F)c(F)c(-c2cccc(F)c2)c1]

A mixture of 2-[2,4-difluoro-3-[[2-fluoro-3-(3-fluorophenyl)-5-methyl-phenyl]methylamino]phenoxy]acetic acid (I(g)) (300 mg, 0.83 mmol, 1.0 eq) and Cs₂CO₃ (407 mg, 1.25 mmol, 1.5 eq) in DMF (5 mL) was stirred at room temperature for 1 h, then isopropyl bromoacetate (171 mg, 0.91 mmol, 1.1 eq) was added. The mixture was stirred at room temperature for 1 h. The resulting mixture was poured into water and extracted with EtOAc. The combined organic extracts were washed with water and brine, dried (Na₂SO₄), filtered and evaporated in vacuo. The residue was purified by column chromatography (EtOAc:petroleum ether, 0:1 to 1:10) to give the title compound as an oil (310 mg, 81%).

LC-MS: m/z 462.0 [M+H]⁺

¹H NMR (300 MHz, DMSO-d₆) δ 7.58-7.45 (m, 1H), 7.41-7.29 (m, 2H), 7.28-7.16 (m, 3H), 6.81 (ddd, J=11.7, 9.4, 2.1 Hz, 1H), 6.32 (td, J=9.1, 4.5 Hz, 1H), 5.91-5.77 (m, 1H), 4.95 (spt, J=6.3 Hz, 1H), 4.71 (s, 2H), 4.50 (d, J=6.9 Hz, 2H), 2.28 (s, 3H), 1.17 (d, J=6.2 Hz, 6H)

Example 38

Isopropyl 2-[3-[[2-fluoro-5-(3-fluorophenyl)phenyl]methylamino]-2,4-dimethyl-phenoxy]acetate (II(g)), prepared via scheme 6

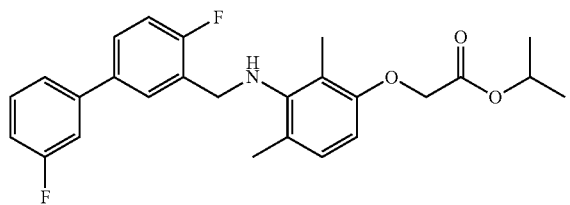 [SMILES: Cc1ccc(OCC(=O)OC(C)C)c(C)c1NCc1cc(-c2cccc(F)c2)ccc1F]

A solution of 2-[3-[[2-fluoro-5-(3-fluorophenyl)phenyl]methylamino]-2,4-dimethyl-phenoxy]acetic acid (I(j)) (120 mg, 0.3 mmol, 1 eq) and SOCl₂ (1 mL) in i-PrOH (4 mL) was heated at reflux for 2 h. The solvent was evaporated in vacuo and the residue was taken up in water and basified to pH 8 by addition of aqueous NaHCO₃. The mixture was extracted with EtOAc and the organic extract was dried (Na₂SO₄) filtered and evaporated in vacuo. The residue obtained was purified by column chromatography to give the title compound as an oil (120 mg, 90%).

LC-MS: m/z 440.1 [M+H]⁺

¹H NMR (300 MHz, DMSO-d₆) δ 7.79 (dd, J=7.2, 2.3 Hz, 1H), 7.69-7.58 (m, 1H), 7.56-7.38 (m, 3H), 7.34-7.06 (m, 2H), 6.84 (d, J=8.3 Hz, 1H), 6.37 (d, J=8.4 Hz, 1H), 5.09-4.87 (m, 1H), 4.64 (s, 2H), 4.41-4.25 (m, 1H), 4.16 (d, J=6.1 Hz, 2H), 2.12 (d, J=4.5 Hz, 6H), 1.19 (d, J=6.2 Hz, 6H)

Example 39

Isopropyl 2-[4-fluoro-3-[[2-fluoro-5-(3-fluorophenyl)phenyl]methylamino]-2-methyl-phenoxy]acetate (II(i)), prepared via scheme 3

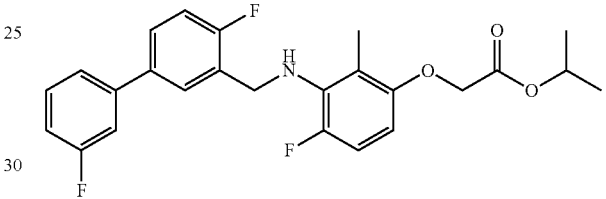

To a solution of 4-fluoro-3-[[2-fluoro-5-(3-fluorophenyl)phenyl]methylamino]-2-methyl-phenol (see example 13) (150 mg, 0.44 mmol, 1.0 eq) in DMF (2 mL) was added Cs₂CO₃ (214 mg, 0.66 mmol, 1.5 eq) and the reaction mixture was stirred for 1 h. Isopropyl 2-bromoacetate (80 mg, 0.44 mmol, 1.0 eq) was then added and the reaction was stirred for a further 1 h. The resulting mixture was poured into water and extracted with EtOAc. The organic extract was washed with water and brine, dried (Na₂SO₄), filtered and evaporated in vacuo. The residue was purified by column chromatography (EtOAc:petroleum ether, 0:1 to 1:20) to give the title compound as a colourless oil (130 mg, 80%).

LC-MS: m/z 444.1 [M+H]⁺

¹H NMR (300 MHz, DMSO-d₆) δ 7.72 (dd, J=7.2, 2.3 Hz, 1H), 7.57 (ddd, J=8.2, 5.3, 2.5 Hz, 1H), 7.53-7.43 (m, 1H), 7.42-7.33 (m, 2H), 7.29-7.11 (m, 2H), 6.78 (dd, J=12.2, 9.0 Hz, 1H), 6.24 (dd, J=9.0, 3.7 Hz, 1H), 5.53-5.06 (m, 1H), 4.94 (spt, J=1.0 Hz, 1H), 4.63 (s, 2H), 4.45 (d, J=7.0 Hz, 2H), 2.11 (s, 3H), 1.15 (d, J=6.2 Hz, 6H)

Example 40

2-Hydroxyethyl 2-[2,4-difluoro-3-[[2-fluoro-5-(3-fluorophenyl)phenyl]methylamino]phenoxy]acetate (II(j)), prepared via scheme 7

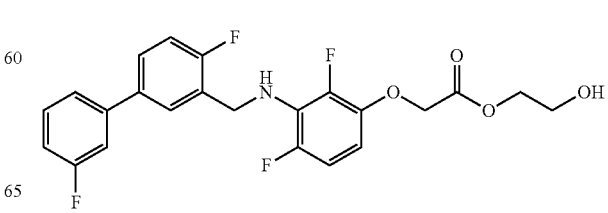

To a solution of isopropyl 2-[2,4-difluoro-3-[[2-fluoro-5-(3-fluorophenyl)phenyl]methylamino]phenoxy]acetate (II(d)) (0.63 g, 1.41 mmol, 1.0 eq) in ethylene glycol (30 mL) at room temperature was added H$_2$SO$_4$ (0.4 mL, 7.5 mmol, 5.3 eq) dropwise. The reaction mixture was stirred overnight at 10° C. then heated at 40° C. for 3 h. The reaction was then cooled to room temperature and poured into water. The aqueous layer was extracted with EtOAc and the combined organic extracts were washed with 5% Na$_2$CO$_3$, water and brine, dried (Na$_2$SO$_4$), filtered and evaporated in vacuo. The residue was purified by column chromatography (EtOAc: petroleum ether, 1:5 to 1:1) to give the title compound as an oil, which crystallised on standing to give a white solid (0.54 g, 85%).

LC-MS: m/z 450.0 [M+H]$^+$ $^1$H NMR (300 MHz, DMSO-d$_6$) δ 7.74 (dd, J=7.2, 2.2 Hz, 1H), 7.65-7.55 (m, 1H), 7.54-7.44 (m, 1H), 7.43-7.34 (m, 2H), 7.29-7.20 (m, 1H), 7.18 (dt, J=8.8, 1.6 Hz, 1H), 6.80 (ddd, J=11.6, 9.4, 2.0 Hz, 1H), 6.36 (td, J=9.1, 4.6 Hz, 1H), 5.88 (t, J=6.9 Hz, 1H), 4.84 (t, J=5.6 Hz, 1H), 4.76 (s, 2H), 4.53 (d, J=7.1 Hz, 2H), 4.11 (t, J=5.0 Hz, 2H), 3.56 (q, J=5.4 Hz, 2H)

Example 41

2-Morpholinoethyl 2-[2,4-difluoro-3-[[2-fluoro-5-(3-fluorophenyl)phenyl]methylamino]phenoxy]acetate (II(k)), prepared via scheme 6

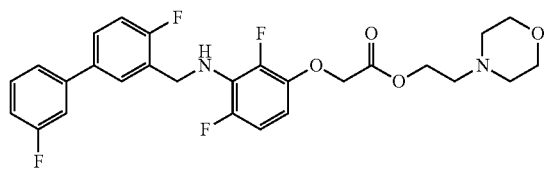 [SMILES: O=C(COc1ccc(F)c(NCc2cc(-c3cccc(F)c3)ccc2F)c1F)OCCN1CCOCC1]

A mixture of 2-[2,4-difluoro-3-[[2-fluoro-5-(3-fluorophenyl)phenyl]methylamino]phenoxy]acetic acid (I(b)) (800 mg, 1.97 mmol, 1.0 eq), 2-morpholinoethanol (284 mg, 2.17 mmol, 1.1 eq), HATU (974 mg, 2.56 mmol, 1.3 eq), and TEA (598 mg, 5.91 mmol, 3 eq) in DCM (10 mL) and DMF (10 mL) was stirred at room temperature overnight under N$_2$. The resulting mixture was poured into water and extracted with EtOAc. The organic extract was washed with brine, dried (Na$_2$SO$_4$), filtered and evaporated in vacuo and the residue purified by column chromatography, (MeOH:DCM 0:1 to 1:50) to give the title compound as a yellow oil (710 mg, 70%).

LC-MS: m/z 519.2 [M+H]$^+$ $^1$H NMR (300 MHz, DMSO-d$_6$) δ 7.74 (dd, J=2.2, 7.1 Hz, 1H), 7.64-7.55 (m, 1H), 7.54-7.44 (m, 1H), 7.43-7.33 (m, 2H), 7.29-7.19 (m, 1H), 7.22-7.12 (m, 1H), 6.94-6.67 (m, 1H), 6.35 (td, J=9.1, 4.6 Hz, 1H), 4.76 (s, 2H), 4.52 (d, J=7.1 Hz, 2H), 4.18 (t, J=5.6 Hz, 2H), 3.56-3.46 (m, 4H), 2.46 (s, 3H), 2.39-2.27 (m, 4H)

Example 42

2-[2,4-Difluoro-3-[[2-fluoro-5-(3-fluorophenyl)phenyl]methylamino]phenoxy]acetamide (II(l)), prepared via scheme 7

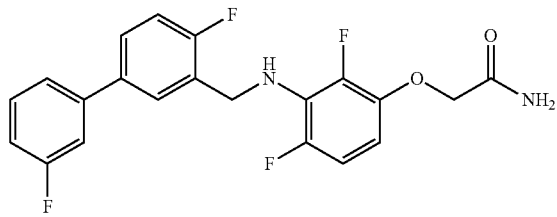 [SMILES: NC(=O)COc1ccc(F)c(NCc2cc(-c3cccc(F)c3)ccc2F)c1F]

To a mixture of isopropyl 2-[2,4-difluoro-3-[[2-fluoro-5-(3-fluorophenyl)phenyl]methylamino]phenoxy]acetate (II(d)) (1.0 g, 2.24 mmol, 1.0 eq) in dioxane (10 mL) was added NH$_3$ (35% aqueous solution, 30 mL). The reaction was then heated to 100° C. and stirred overnight. The resulting mixture was concentrated in vacuo. Water was added and the aqueous layer was extracted with EtOAc. The organic extract was washed with water and brine, dried (Na$_2$SO$_4$), filtered and evaporated in vacuo to give the title compound as a white solid (320 mg, 36%).

LC-MS: m/z 405.0 [M+H]$^+$ $^1$H NMR (300 MHz, DMSO-d$_6$) δ 7.74 (dd, J=7.1, 2.3 Hz, 1H), 7.66-7.55 (m, 1H), 7.54-7.43 (m, 1H), 7.44-7.31 (m, 4H), 7.24 (dd, J=9.7, 8.6 Hz, 1H), 7.22-7.07 (m, 1H), 6.82 (ddd, J=11.6, 9.4, 2.1 Hz, 1H), 6.32 (td, J=9.1, 4.7 Hz, 1H), 6.03-5.80 (m, 1H), 4.53 (d, J=7.1 Hz, 2H), 4.39 (s, 2H)

Example 43

2-[2,4-Difluoro-3-[[2-fluoro-5-(3-fluorophenyl)phenyl]methylamino]phenoxy]-N-ethyl-acetamide (II(m)), prepared via scheme 7

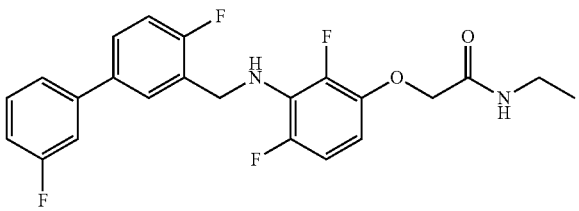

A solution of isopropyl 2-[2,4-difluoro-3-[[2-fluoro-5-(3-fluorophenyl)phenyl]methylamino]phenoxy]acetate (II(d)) (0.2 g, 0.45 mmol, 1.0 eq) in ethylamine (6 mL, 60-70% aqueous solution) was stirred at 100° C. overnight in a sealed tube. The reaction mixture was then cooled to room temperature and poured into water. The mixture was extracted with EtOAc and the combined organic extracts were washed with water and brine, dried (Na$_2$SO$_4$), filtered and evaporated in vacuo. The residue was purified by column chromatography (EtOAc:petroleum ether, 1:20 to 1:4, v/v) to give the title compound as a white solid (0.15 g, 80%).

LC-MS: m/z 433.1 [M+H]$^+$

¹H NMR (300 MHz, DMSO-d₆) δ 7.98 (t, J=5.2 Hz, 1H), 7.74 (dd, J=7.2, 2.2 Hz, 1H), 7.65-7.55 (m, 1H), 7.55-7.44 (m, 1H), 7.43-7.32 (m, 2H), 7.24 (dd, J=9.7, 8.6 Hz, 1H), 7.22-7.08 (m, 1H), 6.82 (ddd, J=11.6, 9.3, 2.0 Hz, 1H), 6.33 (td, J=9.1, 4.6 Hz, 1H), 5.88 (t, J=6.9 Hz, 1H), 4.53 (d, J=7.1 Hz, 2H), 4.40 (s, 2H), 3.19-2.89 (m, 2H), 1.00 (t, J=7.2 Hz, 3H)

Example 44

[3-Hydroxy-2,2-bis(hydroxymethyl)propyl]2-[2,4-difluoro-3-[[2-fluoro-5-(3-fluoro phenyl)phenyl]methylamino]phenoxy]acetate (II(n)), prepared via scheme 6

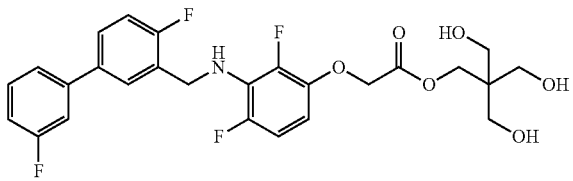 [SMILES: O=C(COc1ccc(F)c(NCc2cc(-c3cccc(F)c3)ccc2F)c1F)OCC(CO)(CO)CO]

To a stirred solution of 2-[2,4-difluoro-3-[[2-fluoro-5-(3-fluorophenyl)phenyl]methylamino]phenoxy]acetic acid (I(b)) (700 mg, 1.73 mmol, 1.0 eq) in DMF (30 mL) was added pentaerythritol (470 mg, 3.45 mmol, 2.0 eq), TEA (699 mg, 6.91 mmol, 4.0 eq) and HATU (985 mg, 2.60 mmol, 1.5 eq). The resulting mixture was stirred at room temperature overnight under N₂. The reaction was diluted with water then extracted with EtOAc. The combined organic extracts were washed with brine, dried (Na₂SO₄) and evaporated in vacuo. The residue was purified by column chromatography (DCM:MeOH=100:1-20:1) to give the title compound as a colourless oil (370 mg, 41%).

LC-MS: m/z 524.1 [M+H]⁺

¹H NMR (300 MHz, DMSO-d₆) δ 7.74 (dd, J=7.3, 2.3 Hz, 1H), 7.64-7.56 (m, 1H), 7.54-7.45 (m, 1H), 7.43-7.34 (m, 2H), 7.24 (dd, J=9.8, 8.6 Hz, 1H), 7.22-7.13 (m, 1H), 6.80 (ddd, J=11.6, 9.3, 2.1 Hz, 1H), 6.36 (td, J=9.1, 4.6 Hz, 1H), 5.96-5.81 (m, 1H), 4.73 (s, 2H), 4.52 (d, J=7.1 Hz, 2H), 4.44-4.19 (m, 3H), 4.01 (s, 2H), 3.32 (d, J=5.6 Hz, 6H)

Example 45

[3-Hydroxy-2-(hydroxymethyl)propyl]2-[2,4-difluoro-3-[[2-fluoro-5-(3-fluorophenyl)phenyl]methylamino]phenoxy]acetate (II(o)), prepared via scheme 6

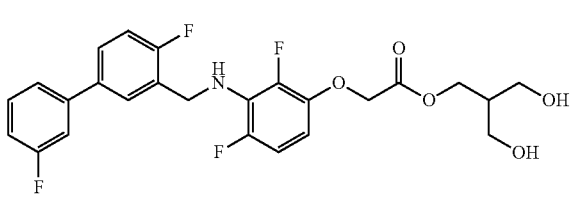 [SMILES: O=C(COc1ccc(F)c(NCc2cc(-c3cccc(F)c3)ccc2F)c1F)OCC(CO)CO]

To a stirred solution of triethyl methanetricarboxylate (700 mg, 1.73 mmol, 1.0 eq) in DMF (40 mL) was added 2-[2,4-difluoro-3-[[2-fluoro-5-(3-fluorophenyl)phenyl]methylamino]phenoxy]acetic acid (I(b)) (367 mg, 3.45 mmol, 2.0 eq), TEA (699 mg, 6.91 mmol, 4.0 eq) and HATU (985 mg, 2.60 mmol, 1.5 eq). The resulting mixture was stirred at room temperature overnight under N₂. The reaction was diluted with water then extracted with EtOAc. The combined organic extracts were washed with brine, dried (Na₂SO₄), filtered and evaporated in vacuo. The residue obtained was purified by column chromatography (DCM:MeOH=100:1-20:1) to give the title compound as a colourless oil (475 mg, 49%).

LC-MS: m/z 494.1 [M+H]⁺

¹H NMR (300 MHz, DMSO-d₆) δ 7.74 (dd, J=7.2, 2.3 Hz, 1H), 7.64-7.55 (m, 1H), 7.54-7.44 (m, 1H), 7.43-7.35 (m, 2H), 7.23 (dd, J=9.8, 8.6 Hz, 1H), 7.22-7.12 (m, 1H), 6.80 (ddd, J=11.6, 9.3, 2.1 Hz, 1H), 6.36 (td, J=9.1, 4.6 Hz, 1H), 6.07-5.80 (m, 1H), 4.75 (s, 2H), 4.54 (d, J=1.0 Hz, 2H), 4.50 (t, J=1.0 Hz, 2H), 4.11 (d, J=6.1 Hz, 2H), 3.50-3.29 (m, 4H), 1.82 (spt, J=6.0 Hz, 1H)

Example 46

1-Acetoxyethyl 2-[2,4-difluoro-3-[[2-fluoro-5-(3-fluorophenyl)phenyl]methylamino]phenoxy]acetate (II(p)), prepared via scheme 6

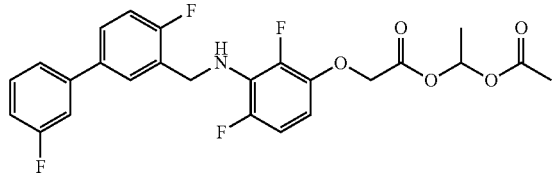 [SMILES: CC(=O)OC(C)OC(=O)COc1ccc(F)c(NCc2cc(-c3cccc(F)c3)ccc2F)c1F]

1-bromoethyl acetate (700 mg, 1.7 mmol, 1.0 eq) was dissolved in DMA (10 mL) at room temperature. K₂CO₃ (120 mg, 0.9 mmol, 0.5 mmol) was added and the mixture stirred for 90 min at 30° C. under a nitrogen atmosphere. The reaction was cooled to −5° C. and 2-[2,4-difluoro-3-[[2-fluoro-5-(3-fluorophenyl)phenyl]methylamino]phenoxy]acetic acid (I(b)) (350 mg, 2.1 mmol, 1.2 eq) was added. The reaction was warmed to 30° C. over 30 min and stirred for a further 30 min. The reaction was quenched by addition of water and extracted with ethyl acetate. The organic extract was dried (Na₂SO₄), filtered and evaporated in vacuo and the residue obtained purified by column chromatography (petroleum ether: EtOAc, 10:1) to give the title compound as a colourless oil (200 mg, 23%).

LC-MS: m/z 492.1 [M+H]¹

¹H NMR (300 MHz, DMSO-d₆) δ 7.74 (dd, J=7.2, 2.3 Hz, 1H), 7.65-7.55 (m, 1H), 7.54-7.45 (m, 1H), 7.41 (d, J=1.7 Hz, 1H), 7.39-7.29 (m, 1H), 7.23 (dd, J=9.9, 8.6 Hz, 1H), 7.22-7.12 (m, 1H), 6.88-6.74 (m, 2H), 6.35 (td, J=9.1, 4.6 Hz, 1H), 4.79 (s, 2H), 4.53 (br. s., 2H), 2.01 (s, 3H), 1.39 (d, J=5.4 Hz, 3H)

Example 47

Isopropyl 2-[2,4-difluoro-3-[[3-(3-fluorophenyl)-5-methoxy-phenyl]methylamino]phenoxy]acetate (II(q)), prepared via scheme 3

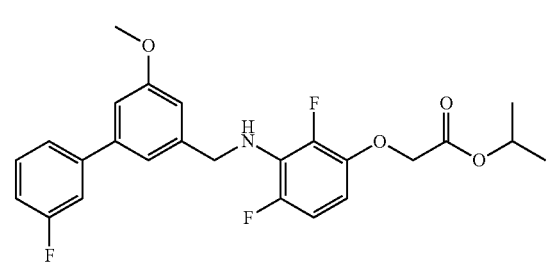 [SMILES: COc1cc(CNc2c(F)ccc(OCC(=O)OC(C)C)c2F)cc(-c2cccc(F)c2)c1]

To a solution of 2,4-difluoro-3-[[3-(3-fluorophenyl)-5-methoxy-phenyl]methylamino]phenol (see example 16) (1.0 g, 2.78 mmol, 1.0 eq) in DMF (10 mL) was added Cs$_2$CO$_3$ (1.36 g, 3.34 mmol, 1.5 eq) at room temperature. The reaction mixture was stirred for 1 h, then isopropyl 2-bromoacetate (624 mg, 3.34 mmol, 1.2 eq) was added and the reaction mixture was stirred for h. The resulting mixture was poured into water and extracted with EtOAc. The organic extract was washed with water and brine, dried (Na$_2$SO$_4$) and evaporated in vacuo. The residue obtained was purified by column chromatography, (EtOAc:petroleum ether 0:1 to 1:20) to give the title compound as a colourless oil (0.8 g, 62%).

LC-MS: m/z 460.0 [M+H]$^+$ $^1$H NMR (300 MHz, DMSO-d$_6$) δ 7.60-7.39 (m, 3H), 7.31-7.12 (m, 2H), 7.11-7.00 (m, 1H), 6.89 (s, 1H), 6.78 (ddd, J=11.7, 9.3, 2.1 Hz, 1H), 6.29 (td, J=9.1, 4.6 Hz, 1H), 6.08-5.86 (m, 1H), 4.93 (spt, J=6.3 Hz, 1H), 4.69 (s, 2H), 4.42 (d, J=7.2 Hz, 2H), 3.78 (s, 3H), 1.15 (d, J=6.2 Hz, 6H)

Example 48

Isopropyl 2-[2,4-difluoro-3-[[3-(3-fluorophenyl)-5-hydroxy-phenyl]methylamino]phenoxy]acetate (II (r))

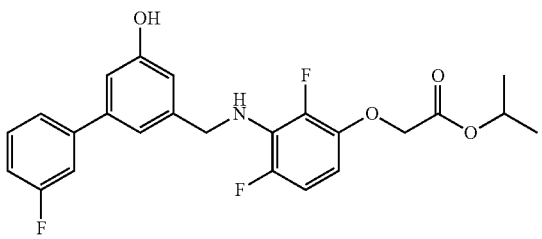 [SMILES: CC(C)OC(=O)COc1ccc(F)c(NCc2cc(O)cc(-c3cccc(F)c3)c2)c1F]

To a solution of isopropyl 2-[2,4-difluoro-3-[[3-(3-fluorophenyl)-5-methoxy-phenyl]methylamino]phenoxy]acetate (II(q)) (700 mg, 1.52 mmol, 1.0 eq) in DCM (20 mL) at 0° C. was added AlCl$_3$ (1.2 g, 9.12 mmol, 6.0 eq) and ethanethiol (566 mg, 9.12 mmol, 6.0 eq) under N$_2$. The reaction mixture was stirred at room temperature for 3 h and the resulting mixture was poured into aqueous NaHCO$_3$ and extracted with EtOAc. The organic extract was washed with water and brine, dried (Na$_2$SO$_4$), filtered and evaporated in vacuo. The residue was purified by column chromatography (EtOAc:petroleum ether, 0:1 to 1:20) to give the title compound as a yellow oil (500 mg, 74%).

LC-MS: m/z 446.0 [M+H]$^+$ $^1$H NMR (300 MHz, DMSO-d$_6$) δ 9.59 (d, J=1.3 Hz, 1H), 7.67-7.47 (m, 1H), 7.46-7.34 (m, 2H), 7.31-7.17 (m, 1H), 7.11 (s, 1H), 6.92 (d, J=1.5 Hz, 1H), 6.89-6.75 (m, 2H), 6.34 (td, J=9.0, 4.6 Hz, 1H), 6.01 (br. s., 1H), 5.01 (spt, J=1.0 Hz, 1H), 4.75 (s, 2H), 4.44 (d, J=6.8 Hz, 2H), 1.22 (d, J=6.2 Hz, 6H)

Example 49

Compound I(ai) Synthesized According to Scheme 3

2-[4-fluoro-3-[[2-fluoro-3-(3-fluorophenyl)-5-methyl-phenyl]methylamino]-2-methyl-phenoxy]acetic acid (I(ai))

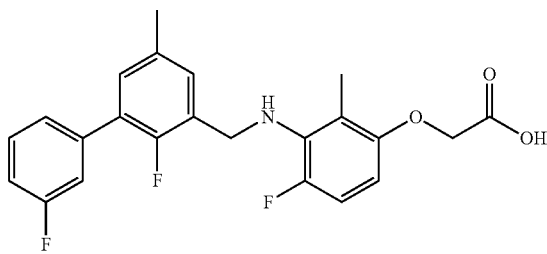

2-Fluoro-N-(6-fluoro-3-hydroxy-2-methyl-phenyl)-3-(3-fluorophenyl)-5-methyl-benzamide

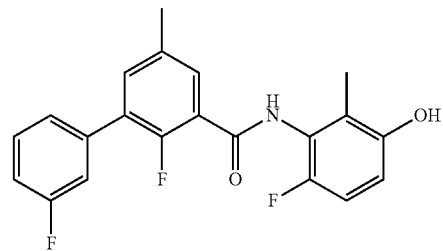 [SMILES: Cc1cc(C(=O)Nc2c(F)ccc(O)c2C)c(F)c(-c2cccc(F)c2)c1]

To a solution of 2-fluoro-3-(3-fluorophenyl)-5-methyl-benzoic acid (intermediate III(e)) (580 mg, 2.3 mmol, 1.1 eq) in CH$_2$Cl$_2$ (10 mL) at 0° C., was added oxalyl chloride (812 mg, 6.4 mmol, 3 eq) dropwise. DMF (10 drops) was added and the mixture was stirred at room temperature for 3 h. The organic solvent and excess reagent were removed under reduced pressure. The residue that remained was dissolved in THF (10 mL) and added dropwise to a mixture of 3-amino-4-fluoro-2-methylphenol (intermediate X(e)) (300 mg, 2.1 mmol, 1 eq) and K$_2$CO$_3$ (1.47 g, 10.6 mmol, 5 eq) in THF (20 mL) at 0° C. After addition was completed, the reaction was allowed to warm to room temperature and stirred for 3 h. The resulting mixture was poured into water and extracted with EtOAc. The combined organic extracts were washed with brine, dried (Na$_2$SO$_4$), filtered and evaporated in vacuo. The residue obtained was purified by column chromatography (petroleum ether:EtOAc, 100:1 to 10:1) to give the title compound as a white solid (200 mg, 25%).

LC-MS: m/z 372.1 [M+H]$^+$ 394.2 [M+Na]$^+$

4-Fluoro-3-[[2-fluoro-3-(3-fluorophenyl)-5-methyl-phenyl]methylamino]-2-methyl-phenol

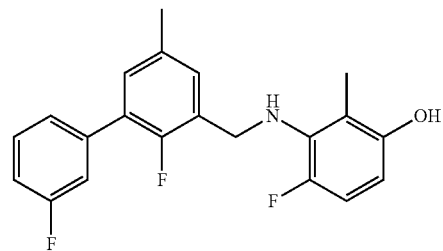

To a stirred solution of 2-fluoro-N-(6-fluoro-3-hydroxy-2-methyl-phenyl)-3-(3-fluorophenyl)-5-methyl-benzamide (200 mg, 0.54 mmol, 1.0 eq) in THF (5 mL) under nitrogen was added a solution of BH$_3$ (1M in THF, 3.0 mL, 3.0 mmol, 5.6 eq) dropwise over 5 min. the mixture was heated at 60° C. overnight, then the reaction cooled to room temperature and quenched by addition of aqueous NH$_4$Cl. The reaction was further diluted with water and the aqueous layer was extracted with EtOAc. The combined organic extracts were dried (Na$_2$SO$_4$), filtered and evaporated in vacuo. The residue obtained was purified by column chromatography (petroleum ether:EtOAc, 100:1 to 25:1) to give the title compound as a colorless oil (180 mg, 93%).

LC-MS: m/z 358.1 [M+H]$^+$

Isopropyl 2-[4-fluoro-3-[[2-fluoro-3-(3-fluorophenyl)-5-methyl-phenyl]methylamino]-2-methyl-phenoxy]acetate (II(am))

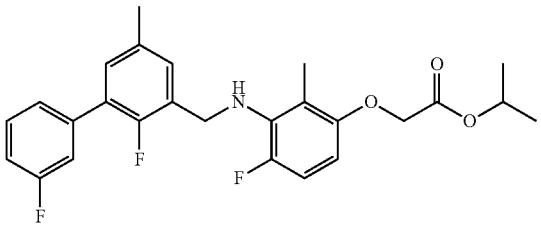 [SMILES: Cc1cc(CNc2c(F)ccc(OCC(=O)OC(C)C)c2C)c(F)c(-c2cccc(F)c2)c1]

To a solution of 4-fluoro-3-[[2-fluoro-3-(3-fluorophenyl)-5-methyl-phenyl]methylamino]-2-methyl-phenol (180 mg, 0.5 mmol, 1.0 eq) in DMF (3 mL) was added Cs$_2$CO$_3$ (246 mg, 0.75 mmol, 1.5 eq). The reaction was stirred for 30 min at room temperature then isopropyl 2-bromoacetate (99 mg, 0.55 mmol, 1.1 eq) was added. The reaction was stirred a further h then diluted with water and extracted with EtOAc. The organic extract was washed with brine, dried (Na$_2$SO$_4$), filtered and evaporated in vacuo. The residue obtained was purified by column chromatography (petroleum ether: EtOAc, 1:0 to 25:1) to give the title compound as a colorless oil (100 mg, 43%).

LC-MS: m/z 458.2 [M+H]$^+$ 480.2 [M+Na]$^+$ $^1$H NMR (400 MHz, CDCl$_3$) δ 7.43-7.35 (m, 1H), 7.29 (dd, J=7.7, 1.0 Hz, 1H), 7.25-7.20 (m, 1H), 7.15-7.09 (m, 2H), 7.09-7.02 (m, 1H), 6.78 (dd, J=11.1, 9.1 Hz, 1H), 6.25 (dd, J=8.9, 3.8 Hz, 1H), 5.17-5.07 (m, 1H), 4.53 (s, 2H), 4.40 (s, 2H), 2.32 (s, 3H), 2.21 (s, 3H), 1.25 (d, J=6.2 Hz, 6H).

2-[4-Fluoro-3-[[2-fluoro-3-(3-fluorophenyl)-5-methyl-phenyl]methylamino]-2-methyl-phenoxy]acetic acid (I(ai))

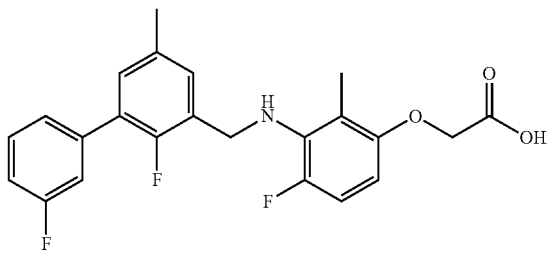 [SMILES: Cc1cc(CNc2c(F)ccc(OCC(=O)O)c2C)c(F)c(-c2cccc(F)c2)c1]

To a stirred solution of isopropyl 2-[4-fluoro-3-[[2-fluoro-3-(3-fluorophenyl)-5-methyl-phenyl]methylamino]-2-methyl-phenoxy]acetate (100 mg, 0.22 mmol, 1.0 eq) in a mixture of THF (10 mL) and H$_2$O (10 mL) was added NaOH (17 mg, 0.44 mmol, 2.0 eq). The reaction was stirred for 2 h then acidified to pH 4 by addition of 1M HCl. The aqueous layer was extracted with EtOAc and the combined organic extracts were washed with brine, dried (Na$_2$SO$_4$), filtered and evaporated in vacuo. The residue obtained was purified by column chromatography (CH$_2$Cl$_2$:MeOH, 20:1) to give a partially purified material. Further purification by preparative HPLC provided the title compound as yellow solid (9 mg, 10%).

LC-MS: m/z 416.1 [M+H]$^+$ 430.2 [M+Na]$^+$ $^1$H NMR (400 MHz, MeOD) δ 7.47-7.40 (m, 1H), 7.28 (dd, J=7.8, 0.9 Hz, 1H), 7.22-7.13 (m, 3H), 7.13-7.05 (m, 1H), 6.84 (dd, J=11.2, 9.1 Hz, 1H), 6.47 (dd, J=9.0, 3.9 Hz, 1H), 4.62 (s, 2H), 4.45 (s, 2H), 2.30 (s, 3H), 2.19 (s, 3H).

Example 50

Compound I(aj) Synthesized According to Scheme 3

2-[3-[[3-(3-fluorophenyl)-5-methyl-phenyl]methylamino]-2,4-dimethyl-phenoxy]acetic acid (I(aj))

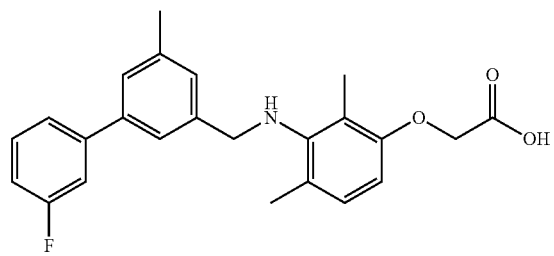

3-(3-Fluorophenyl)-N-(3-hydroxy-2,6-dimethylphenyl)-5-methyl-benzamide

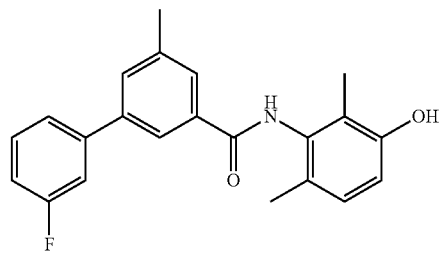

To a solution of 3-(3-fluorophenyl)-5-methyl-benzoic acid (300 mg, 1.30 mmol, 1.1 eq) (III(q)) in CH$_2$Cl$_2$ (10 mL) was added (COCl)$_2$ (610 mg, 4.81 mmol, 3.3 eq) and DMF (5 drops). The reaction mixture was stirred at room temperature for 2 h. The resulting mixture was concentrated under reduced pressure to remove the solvent and excess reagent. The residue obtained was dissolved in THF (10 mL) and added dropwise to a mixture of 3-amino-2,4-dimethylphenol (intermediate X(c)) (163 mg, 1.18 mmol, 1.0 eq) and NaHCO$_3$ (612 mg, 7.30 mmol, 5.0 eq) in THF (20 mL) at 0° C. After addition was completed, the reaction mixture was allowed to warm to room temperature and stirred for 1 h. The resulting mixture was poured into water and extracted with EtOAc. The combined organic extracts were washed with water and brine, dried (Na$_2$SO$_4$), filtered, and evaporated in vacuo. The crude product obtained was purified by column chromatography (CH$_2$Cl$_2$: MeOH, 500:1 to 300:1) to give the title compound as a white solid (290 mg, 57%).

LC-MS: m/z 350.2 [M+H]$^+$ 372.1 [M+Na]$^+$

3-[[3-(3-Fluorophenyl)-5-methyl-phenyl]methylamino]-2,4-dimethyl-phenol

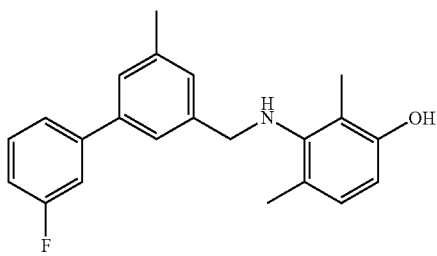 [SMILES: Cc1cc(CNc2c(C)ccc(O)c2C)cc(-c2cccc(F)c2)c1]

To a solution of 3-(3-fluorophenyl)-N-(3-hydroxy-2,6-dimethyl-phenyl)-5-methyl-benzamide (288 mg, 0.82 mmol, 1.0 eq) in THF (10 mL) under N$_2$ was added a solution of BH$_3$ (1M in THF, 5.0 mL, 5.0 mmol, 6.0 eq) at 0° C. The reaction mixture was heated at 60° C. overnight. After cooling, the resulting mixture was quenched with water and extracted with EtOAc. The combined organic extracts were washed with water and brine, dried (Na$_2$SO$_4$), filtered and evaporated in vacuo. The residue was purified by column chromatography (petroleum ether: EtOAc, 50:1 to 20:1) to give the title compound as a colorless oil (168 mg, 61%).

LC-MS: m/z 336.2 [M+H]$^+$ 358.1 [M+Na]$^+$

Isopropyl 2-[3-[[3-(3-fluorophenyl)-5-methyl-phenyl]methylamino]-2,4-dimethyl-phenoxy]acetate (II(an))

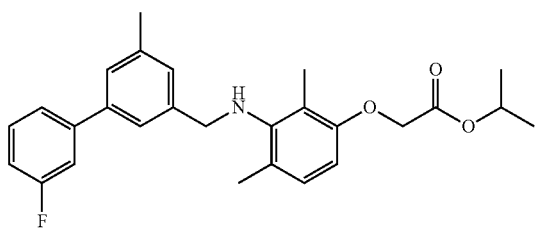 [SMILES: Cc1cc(CNc2c(C)ccc(OCC(=O)OC(C)C)c2C)cc(-c2cccc(F)c2)c1]

To a solution of 3-[[3-(3-fluorophenyl)-5-methyl-phenyl]methylamino]-2,4-dimethyl-phenol (168 mg, 0.50 mmol, 1.0 eq) in DMF (10 mL) was added Cs$_2$CO$_3$ (245 mg, 0.75 mmol, 1.5 eq). The reaction mixture was stirred at room temperature for 30 min then isopropyl bromoacetate (109 mg, 0.6 mmol, 1.2 eq) was added. The reaction mixture was stirred at room temperature for a further 1 h then poured into water and extracted with EtOAc. The combined organic extracts were washed with water and brine, dried (Na$_2$SO$_4$), filtered and evaporated in vacuo. The residue was purified by column chromatography (petroleum ether: EtOAc, 40:1 to 30:1) to give the title compound as a colorless oil (151 mg, 69%).

LC-MS: m/z 436.2 [M+H]$^+$ 458.2 [M+Na]$^+$ $^1$H NMR (400 MHz, DMSO) δ 7.53-7.34 (m, 5H), 7.21-7.13 (m, 2H), 6.83 (d, J=8.5 Hz, 1H), 6.35 (d, J=8.4 Hz, 1H), 5.02-4.90 (m, 1H), 4.64 (s, 2H), 4.30 (br t, J=7.4 Hz, 1H), 4.09 (d, J=6.7 Hz, 2H), 2.34 (s, 3H), 2.14 (s, 3H), 2.12 (s, 3H), 1.19 (d, J=6.3 Hz, 6H).

2-[3-[[3-(3-Fluorophenyl)-5-methyl-phenyl]methylamino]-2,4-dimethyl-phenoxy]acetic acid (I(aj))

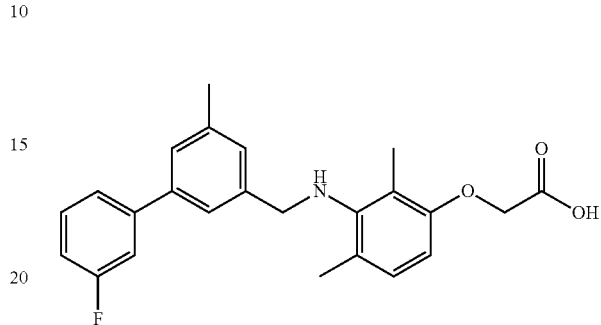

To a solution of isopropyl 2-[3-[[3-(3-fluorophenyl)-5-methyl-phenyl]methylamino]-2,4-dimethyl-phenoxy]acetate (114 mg, 0.26 mmol, 1.0 eq) in THF (10 mL) at 0° C. was added LiOH (2M aqueous solution, 4 mL, 8 mmol). The reaction mixture was allowed to warm to room temperature and stirred overnight. The THF was removed under reduced pressure and the aqueous solution that remained was diluted with water and adjusted to pH 4-6 by the addition of dilute HCl. The solid precipitate that formed was collected by filtration, washed with water and dried in vacuo to give title compound as a yellow solid (70 mg, 68%).

LC-MS: m/z 394.1 [M+H]$^+$ $^1$H NMR (400 MHz, DMSO) δ 7.52-7.35 (m, 5H), 7.21-7.12 (m, 2H), 6.80 (d, J=8.3 Hz, 1H), 6.32 (d, J=8.3 Hz, 1H), 4.35 (s, 2H), 4.07 (s, 2H), 2.34 (s, 3H), 2.13 (s, 3H), 2.12 (s, 3H).

Example 51

Compound I(ak) Synthesized According to Scheme 3

2-[3-[[5-(3-Fluorophenyl)-2,3-dimethyl-phenyl]methylamino]-2,4-dimethyl-phenoxy]acetic acid (I(ak))

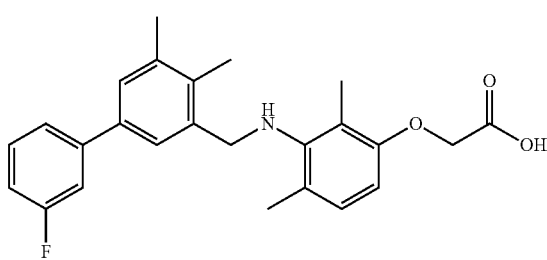

5-(3-Fluorophenyl)-N-(3-hydroxy-2,6-dimethyl-phenyl)-2,3-dimethyl-benzamide

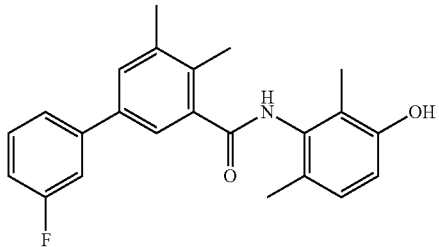 [SMILES: Cc1cc(-c2cccc(F)c2)cc(C(=O)Nc2c(C)ccc(O)c2C)c1C]

To a solution of 5-(3-fluorophenyl)-2,3-dimethyl-benzoic acid (intermediate III(m)) (0.4 g, 1.6 mmol, 1.0 eq) in CH$_2$Cl$_2$ (15 mL) was added (COCl)$_2$ (0.62 g, 4.9 mmol, 3.0 eq) and DMF (0.01 mL). The reaction mixture was stirred at room temperature for 1.5 h, then the solvent and excess reagent were removed under reduced pressure. The residue obtained was dissolved in THF (20 mL) and added dropwise to a mixture of 3-amino-2,4-dimethylphenol (intermediate X(c)) (260 mg, 1.9 mmol, 1.2 eq) and K$_2$CO$_3$ (0.9 g, 6.5 mmol, 4.0 eq) in THF (20 mL) at 0° C. The reaction mixture was stirred at room temperature for 1 h, then poured into water and extracted with EtOAc. The combined organic extracts were washed with water and brine, dried (Na$_2$SO$_4$), filtered and evaporated in vacuo. The residue was purified by column chromatography (petroleum ether: EtOAc, 15:1 to 3:1) to give the title compound as a colorless oil (300 mg, 51%)

LC-MS: m/z 363.2 [M+H]$^+$

3-[[5-(3-Fluorophenyl)-2,3-dimethyl-phenyl]methylamino]-2,4-dimethyl-phenol

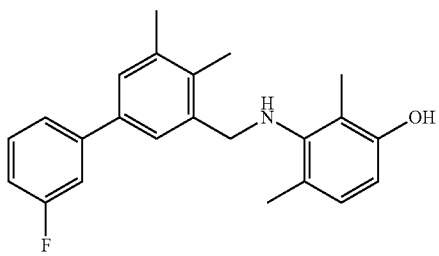 [SMILES: Cc1cc(-c2cccc(F)c2)cc(CNc2c(C)ccc(O)c2C)c1C]

To a solution of 5-(3-fluorophenyl)-N-(3-hydroxy-2,6-dimethyl-phenyl)-2,3-dimethyl-benzamide (300 mg, 0.82 mmol, 1.0 eq) in THF (10 mL) under N$_2$ was added a solution of BH$_3$ (1M in THF, 4.1 mL, 4.1 mmol, 5.0 eq) dropwise at 0° C. The reaction mixture was heated at 60° C. overnight. After cooling, the reaction was quenched by addition of water and the aqueous layer extracted with EtOAc. The organic extract was washed with water and brine, dried (Na$_2$SO$_4$), filtered and evaporated in vacuo. The residue was purified by column chromatography (petroleum ether: EtOAc, 30:1 to 20:1) to give the title compound as a colorless oil (90 mg, 32%).

LC-MS: m/z 350.2 [M+H]$^+$

Isopropyl 2-[3-[[5-(3-fluorophenyl)-2,3-dimethyl-phenyl]methylamino]-2,4-dimethyl-phenoxy]acetate (II(ao))

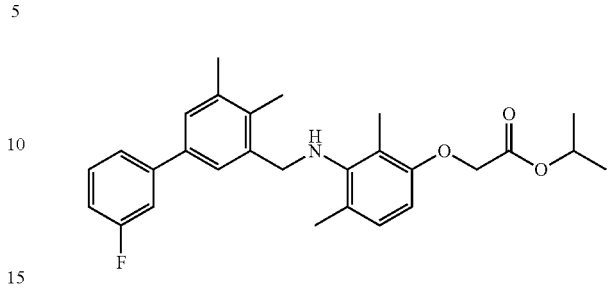

To a solution 3-[[5-(3-fluorophenyl)-2,3-dimethyl-phenyl]methylamino]-2,4-dimethyl-phenol (87.5 mg, 0.25 mmol, 1.0 eq) in DMF (10 mL) was added Cs$_2$CO$_3$ (0.16 g, 0.51 mmol, 2.0 eq). The reaction mixture was stirred at room temperature for 30 min then isopropyl bromoacetate (56 mg, 0.3 mmol, 1.2 eq) was added and the reaction stirred for a further 1 h. The resulting mixture was poured into water and extracted with EtOAc. The organic extract was washed with water and brine, dried (Na$_2$SO$_4$), filtered and evaporated in vacuo. The residue was purified by column chromatography (petroleum ether: EtOAc, 100:1 to 30:1) to give the title compound as a colorless oil (80 mg, 69%).

LC-MS: m/z 450.2 [M+H]$^+$ $^1$H NMR (400 MHz, DMSO) δ 7.58 (d, J=1.5 Hz, 1H), 7.52-7.41 (m, 3H), 7.20-7.09 (m, 1H), 6.86 (d, J=8.3 Hz, 1H), 6.39 (d, J=8.3 Hz, 1H), 5.06-4.89 (m, 1H), 4.65 (s, 2H), 4.08 (d, J=5.7 Hz, 2H), 3.99 (br s, 1H), 2.32 (s, 3H), 2.20 (s, 3H), 2.13 (s, 3H), 2.12 (s, 3H), 1.20 (d, J=6.3 Hz, 6H).

2-[3-[[5-(3-Fluorophenyl)-2,3-dimethyl-phenyl]methylamino]-2,4-dimethyl-phenoxy]acetic acid (I(ak))

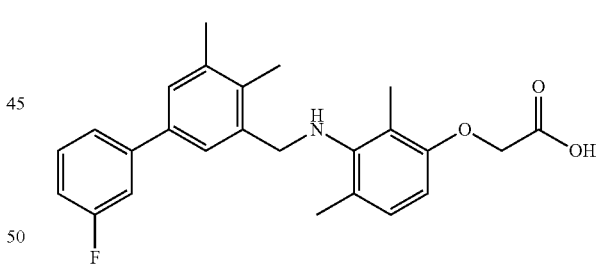

To a solution of isopropyl 2-[3-[[5-(3-fluorophenyl)-2,3-dimethyl-phenyl]methylamino]-2,4-dimethyl-phenoxy]acetate (80 mg, 0.17 mmol, 1.0 eq) in a mixture of THF (5 mL) and MeOH (5 mL) was added NaOH (2M aqueous solution, 3 mL, 6.0 mmol) at 0° C. The reaction mixture was allowed to warm to room temperature and stirred for 2 h. The organic solvent was removed in vacuo and the remaining aqueous solution diluted with water and acidified to pH 4-6 with diluted HCl. The solid precipitate that formed was collected by filtration, washed with water and dried in vacuo to give the title compound as a white solid (20 mg, 27%).

LC-MS: m/z 406.2 [M−H]$^-$ $^1$H NMR (400 MHz, MeOD) δ 7.45-7.36 (m, 2H), 7.36-7.31 (m, 2H), 7.26-7.20 (m, 1H), 7.06-6.99 (m, 1H), 6.96 (d,

J=8.4 Hz, 1H), 6.58 (d, J=8.4 Hz, 1H), 4.62 (s, 2H), 4.30 (s, 2H), 2.35 (s, 3H), 2.24 (s, 3H), 2.19 (s, 3H), 2.14 (s, 3H).

Example 52

Compound I(al) Synthesized According to Scheme 3

2-[3-[[5-(3-fluorophenyl)-2-methoxy-3-methyl-phenyl]methylamino]-2,4-dimethyl-phenoxy]acetic acid (I(al))

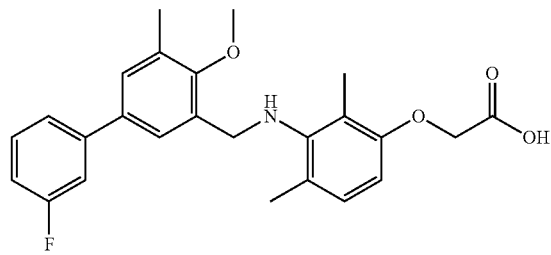

5-(3-Fluorophenyl)-N-(3-hydroxy-2,6-dimethyl-phenyl)-2-methoxy-3-methyl-benzamide

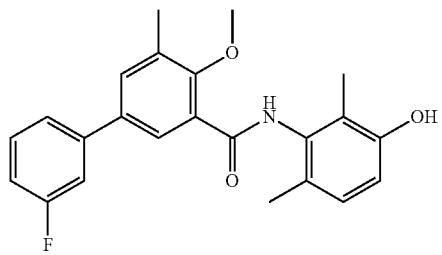 [SMILES: COc1c(C)cc(-c2cccc(F)c2)cc1C(=O)Nc1c(C)ccc(O)c1C]

To a solution of 5-(3-fluorophenyl)-2-methoxy-3-methyl-benzoic acid (intermediate III(k)) (400 mg, 1.5 mmol, 1.1 eq) in CH$_2$Cl$_2$ (8 mL) was added (COCl)$_2$ (585 mg, 4.6 mmol, 3.3 eq) and DMF (3 drops). The reaction mixture was stirred at room temperature for 1 h. The resulting mixture was concentrated under reduced pressure to remove the solvent and excess reagent and the residue obtained was dissolved in THF (8 mL) and added dropwise to a solution of 3-amino-2,4-dimethylphenol (intermediate X(c)) (192 mg, 1.4 mmol, 1.0 eq) and NaHCO$_3$ (587 mg, 7.0 mmol, 5.0 eq) in THF (6 mL) at 0° C. After the addition was complete the reaction mixture was allowed to warm to room temperature and was stirred for 2 h. The resulting mixture was poured into water and extracted with EtOAc. The combined organic extracts were washed with water and brine, dried (Na$_2$SO$_4$), filtered and evaporated in vacuo. The residue obtained was purified by column chromatography (petroleum ether: EtOAc, 10:1 to 5:1, then DCM: MeOH, 20:1) to give the title compound as a yellow solid (436 mg 82%).

LC-MS: m/z 380.2 [M+H]$^+$

3-[[5-(3-Fluorophenyl)-2-methoxy-3-methyl-phenyl]methylamino]-2,4-dimethyl-phenol

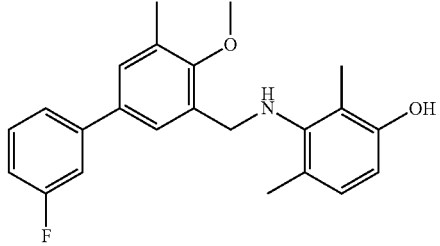 [SMILES: COc1c(C)cc(-c2cccc(F)c2)cc1CNc1c(C)ccc(O)c1C]

To a solution of 5-(3-fluorophenyl)-N-(3-hydroxy-2,6-dimethyl-phenyl)-2-methoxy-3-methyl-benzamide (270 mg, 0.71 mmol, 1.0 eq) in THF (5 mL) at 0° C. under N$_2$ was added a solution of BH$_3$ (1M in THF, 1.07 mL, 1.07 mmol, 1.5 eq) dropwise. The reaction mixture was heated at 60° C. for 4 h, then cooled and quenched with water. The aqueous layer was extracted with EtOAc and the combined organic extracts were washed with water and brine, dried (Na$_2$SO$_4$), filtered and evaporated in vacuo. The residue obtained was purified by column chromatography (petroleum ether:EtOAc 30:1 to 20:1) to give the title compound as a yellow oil (115 mg, 44%)

LC-MS: m/z 366.2 [M+H]$^+$

Isopropyl 2-[3-[[5-(3-fluorophenyl)-2-methoxy-3-methyl-phenyl]methylamino]-2,4-dimethyl-phenoxy] acetate (II(ap))

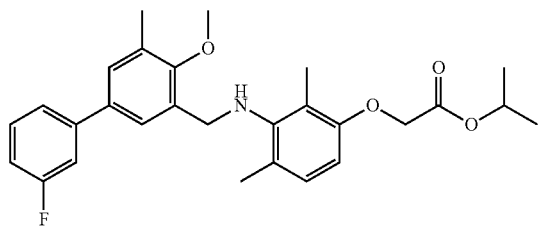

To a solution of 3-[[5-(3-fluorophenyl)-2-methoxy-3-methyl-phenyl]methylamino]-2,4-dimethyl-phenol (115 mg, 0.31 mmol, 1.0 eq) in acetone (4 mL) was added Cs$_2$CO$_3$ (154 mg, 0.47 mmol, 1.5 eq). The reaction mixture was stirred for 30 min at room temperature then isopropyl bromoacetate (68.4 mg, 0.38 mmol, 1.2 eq) was added. The reaction mixture was stirred at room temperature for a further 2 h then poured into water and extracted with EtOAc. The combined organic extracts were washed with water and brine, dried (Na$_2$SO$_4$), filtered and evaporated in vacuo. The residue was purified by column chromatography (petroleum ether:EtOAc 30:1 to 20:1) to give the title compound as a colorless oil (155 mg, 100%).

LC-MS: m/z 466.2 [M+H]$^+$ 488.2 [M+Na]$^+$ $^1$H NMR (400 MHz, DMSO) δ 7.59 (d, J=2.0 Hz, 1H), 7.52-7.37 (m, 4H), 7.20-7.10 (m, 1H), 6.85 (d, J=8.4 Hz, 1H), 6.37 (d, J=8.4 Hz, 1H), 5.01-4.89 (m, 1H), 4.65 (s, 2H), 4.21-4.14 (m, 1H), 4.11 (d, J=6.5 Hz, 2H), 3.68 (s, 3H), 2.31 (s, 3H), 2.15 (s, 6H), 1.19 (d, J=6.2 Hz, 6H).

2-[3-[[5-(3-Fluorophenyl)-2-methoxy-3-methyl-phenyl]methylamino]-2,4-dimethyl-phenoxy]acetic acid (I(al))

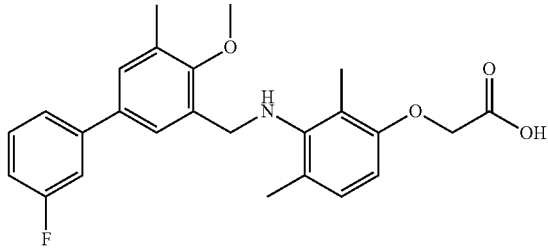

To a solution of isopropyl 2-[3-[[5-(3-fluorophenyl)-2-methoxy-3-methyl-phenyl]methylamino]-2,4-dimethyl-phenoxy]acetate (155 mg, 0.33 mmol, 1.0 eq) in THF (4 mL) was added LiOH (2M aqueous solution, 4 mL, 8 mmol). The reaction mixture was stirred at room temperature for 2 h then the THF was removed under reduced pressure. The aqueous solution that remained was diluted with water and the pH adjusted to 4-6 with diluted HCl. The solid precipitate that formed was collected by filtration, washed with water and dried in vacuo to give a partially purified product. This material was further purified by preparative HPLC to give the title compound as a yellow solid (30 mg, 21%).

LC-MS: m/z 424.2 [M+H]$^+$ $^1$H NMR (400 MHz, DMSO) δ 7.66 (s, 1H), 7.55 (s, 1H), 7.54-7.41 (m, 3H), 7.17 (t, J=8.3 Hz, 1H), 6.96 (d, J=8.1 Hz, 1H), 6.55 (s, 1H), 4.64 (s, 2H), 4.22 (s, 2H), 3.72 (s, 3H), 2.33 (s, 3H), 2.24 (s, 3H), 2.21 (s, 3H).

Example 53

Compound I(am) Synthesized According to Scheme 3

2-[3-[[2-Fluoro-3-(3-fluorophenyl)-5-methyl-phenyl]methylamino]-2,4-dimethyl-phenoxy]acetic acid (I(am))

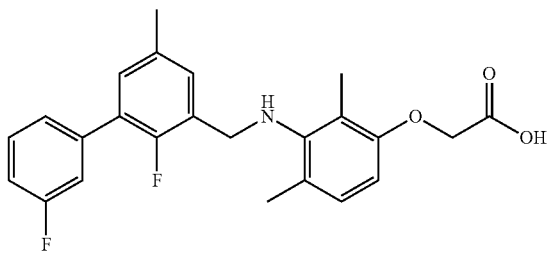 [SMILES: Cc1cc(CNc2c(C)ccc(OCC(=O)O)c2C)c(F)c(-c2cccc(F)c2)c1]

2-Fluoro-3-(3-fluorophenyl)-N-(3-hydroxy-2,6-dimethyl-phenyl)-5-methyl-benzamide

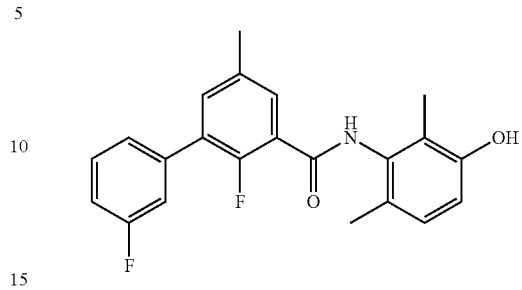

To a solution of 2-fluoro-3-(3-fluorophenyl)-5-methyl-benzoic acid (intermediate III(e)) (597 mg, 2.4 mmol, 1.1 eq) in CH$_2$Cl$_2$ (15 mL) was added (COCl)$_2$ (916 mg, 7.2 mmol, 3.3 eq) and DMF (5 drops). The reaction mixture was stirred at room temperature for 2 h, then the solvent and excess reagent were removed under reduced pressure. The residue obtained was dissolved in THF (20 mL) and added dropwise to a mixture of 3-amino-2,4-dimethylphenol (intermediate X(c)) (300 mg, 2.2 mmol, 1.0 eq) and NaHCO$_3$ (920 mg, 10.9 mmol, 5.0 eq) in THF (20 mL) at 0° C. After the addition was completed, the reaction was allowed to warm to room temperature and stirred for a further 1 h. The reaction was then poured into water and extracted with EtOAc. The combined organic layers were washed with water and brine, dried (Na$_2$SO$_4$), filtered, and evaporated in vacuo. The residue obtained was purified by column chromatography (CH$_2$Cl$_2$: MeOH, 500:1 to 300:1) to give the title compound as a white solid (588 mg, 73%).

LC-MS: m/z 368.1 [M+H]$^+$

3-[[2-Fluoro-3-(3-fluorophenyl)-5-methyl-phenyl]methylamino]-2,4-dimethyl-phenol

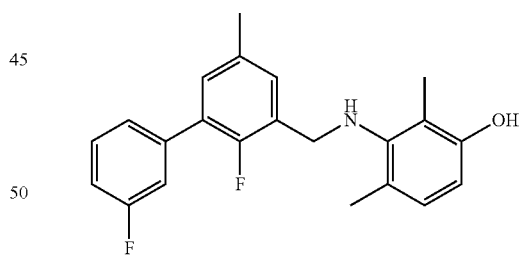

To a solution of 2-fluoro-3-(3-fluorophenyl)-N-(3-hydroxy-2,6-dimethyl-phenyl)-5-methyl-benzamide (588 mg, 1.6 mmol, 1.0 eq) in THF (10 mL) at 0° C. under N$_2$ was added a solution of BH$_3$ (1M in THF, 9.6 mL, 9.6 mmol, 6.0 eq) dropwise. The reaction mixture was heated at 60° C. overnight. The reaction was cooled to room temperature, quenched with H$_2$O and extracted with EtOAc. The combined organic layers were washed with water and brine, dried (Na$_2$SO$_4$), filtered and evaporated in vacuo. The residue obtained was purified by column chromatography (petroleum ether:EtOAc, 50:1 to 20:1) to give the title compound as white solid (220 mg, 39%)

LC-MS: m/z 354.1 [M+H]$^+$

Isopropyl 2-[3-[[2-fluoro-3-(3-fluorophenyl)-5-methyl-phenyl]methylamino]-2,4-dimethyl-phenoxy]acetate (II(bb))

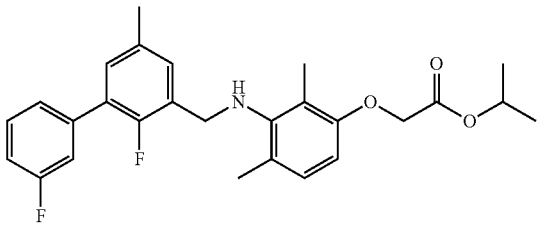 [SMILES: Cc1cc(CNc2c(C)ccc(OCC(=O)OC(C)C)c2C)c(F)c(-c2cccc(F)c2)c1]

To a solution of 3-[[2-fluoro-3-(3-fluorophenyl)-5-methyl-phenyl]methylamino]-2,4-dimethyl-phenol (114 mg, 0.32 mmol, 1.0 eq) in DMF (10 mL) was added Cs₂CO₃ (158 mg, 0.48 mmol, 1.5 eq). The reaction mixture was stirred at room temperature for 30 min the isopropyl bromoacetate (70 mg, 0.39 mmol, 1.2 eq) was added. The reaction mixture was stirred a further 1 h then poured into water and extracted with EtOAc. The combined organic layers were washed with water and brine, dried (Na₂SO₄), filtered and evaporated in vacuo. The residue was purified by column chromatography (petroleum ether:EtOAc, 30:1 to 20:1) to give the title compound as colorless oil (108 mg, 76%).

$^1$H NMR (400 MHz, DMSO) δ 7.51 (td, J=8.1, 6.4 Hz, 1H), 7.37-7.28 (m, 3H), 7.27-7.19 (m, 2H), 6.84 (d, J=8.3 Hz, 1H), 6.37 (d, J=8.4 Hz, 1H), 4.96 (hept, J=6.3 Hz, 1H), 4.65 (s, 2H), 4.17 (br t, J=7.5 Hz, 1H), 4.09 (d, J=6.3 Hz, 2H), 2.31 (s, 3H), 2.14 (br s, 6H), 1.19 (d, J=6.3 Hz, 6H).

2-[3-[[2-Fluoro-3-(3-fluorophenyl)-5-methyl-phenyl]methylamino]-2,4-dimethyl-phenoxy]acetic acid

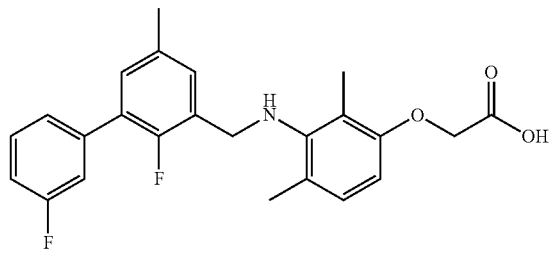 [SMILES: Cc1cc(CNc2c(C)ccc(OCC(=O)O)c2C)c(F)c(-c2cccc(F)c2)c1]

To a solution of isopropyl 2-[3-[[2-fluoro-3-(3-fluorophenyl)-5-methyl-phenyl]methylamino]-2,4-dimethyl-phenoxy]acetate (80 mg, 0.18 mmol, 1.0 eq) in THF (8 mL) at 0° C. was added LiOH (2M aqueous solution, 4 mL, 8.0 mmol). The reaction mixture was allowed to warm to room temperature and stirred overnight. The THF was removed and the remaining aqueous solution was diluted with water. The pH was adjusted to pH 4-6 by addition of diluted HCl. The solid precipitate that formed was collected by filtration, washed with water and dried in vacuo to give target compound as a yellow solid (30 mg, 41%).

LC-MS: m/z 412.1 [M+H]⁺

$^1$H NMR (400 MHz, DMSO) δ 7.57-7.48 (m, 1H), 7.44-7.35 (m, 2H), 7.35-7.28 (m, 2H), 7.28-7.22 (m, 1H), 7.00 (d, J=8.7 Hz, 1H), 6.72-6.62 (m, 1H), 4.67 (s, 2H), 4.31 (s, 2H), 2.34 (s, 3H), 2.25 (s, 3H), 2.20 (s, 3H).

Example 54

Compound I(an) Synthesized According to Scheme 5

2-[2-cyano-4-fluoro-3-[[2-fluoro-5-(3-fluorophenyl)phenyl]methylamino]phenoxy]acetic acid (I(an))

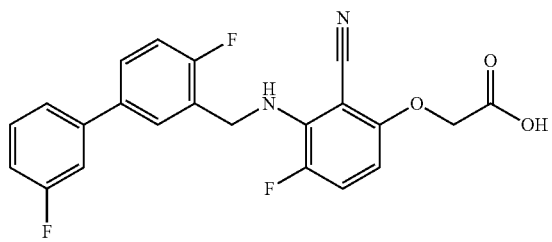 [SMILES: N#Cc1c(OCC(=O)O)ccc(F)c1NCc1cc(-c2cccc(F)c2)ccc1F]

2-Cyano-6-fluoro-3-methoxy-benzoic acid

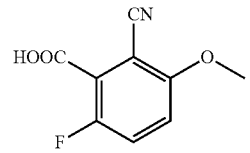

To a solution of N,N-diisopropylamine (5.6 mL, 39.7 mmol, 1.2 eq) in THF (100 mL) at −78° C. was added n-BuLi (2.5M in hexanes, 15.9 mL, 39.7 mmol, 1.2 eq) dropwise. The mixture was stirred for 30 min at −78° C., then a solution of 5-fluoro-2-methoxy-benzonitrile (5.0 g, 33.1 mmol, 1.0 eq) in THF (20 mL) was added. The resulting mixture was stirred for a further 1.5 h at −78° C. then CO₂ was bubbled into the mixture for 30 min. The reaction was quenched by addition of saturated aqueous NH₄Cl and water and the resulting solution acidified to pH 4 with 3M HCl. The aqueous layer was extracted with EtOAc and the combined organic extracts were washed with brine, dried (Na₂SO₄) filtered and evaporated in vacuo. The residue obtained was triturated with 2-methoxy-2-methylpropane (20 mL) to give title compound as an off-white solid (3.5 g, 54%).

LC-MS: m/z 196.1 [M+H]⁺ 218.0 [M+Na]⁺

2-Amino-3-fluoro-6-methoxy-benzonitrile

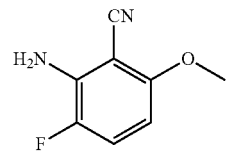

To a stirred solution of 2-cyano-6-fluoro-3-methoxy-benzoic acid (2 g, 10.3 mmol, 1.0 eq) in THF (40 mL) were added Et₃N (3.6 mL, 25.8 mmol, 2.5 eq) and DPPA (2.97 g, 10.8 mmol, 1.05 eq). The reaction was stirred at room temperature 3 h then water (10 mL) was added and the mixture was heated at reflux for 2 h. The THF was removed in vacuo and the aqueous solution diluted with water and extracted with EtOAc. The combined organic extracts were washed with brine, dried ($Na_2SO_4$), filtered and evaporated in vacuo. The residue obtained was purified by column chromatography (petroleum ether:EtOAc, 5:1) to give the title compound as an off-white solid (900 mg, 53%).

LC-MS: m/z 167.0 [M+H]$^+$ $^1$H NMR (400 MHz, CDCl$_3$) δ 7.06 (dd, J=10.7, 9.0 Hz, 1H), 6.10 (dd, J=9.0, 3.3 Hz, 1H), 4.49 (br s, 2H), 3.84 (s, 3H).

5-Bromo-2-fluoro-benzaldehyde

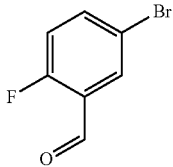

To a solution of N,N-diisopropylamine (8.87 mL, 62.9 mmol, 1.1 eq) in dry THF (80 mL) at −78° C. was added n-BuLi (2.5M in hexane, 27.5 mL, 68.5 mmol, 1.2 eq). The resulting mixture was stirred for 30 min then 1-bromo-4-fluoro-benzene (10 g, 57.1 mmol, 1 eq) in dry THF (20 mL) was added. The resultant mixture was stirred at −78° C. for 2 h then methyl formate (3.8 g, 62.9 mmol, 1.1 eq) was added and the reaction was stirred a further 30 min at −78° C. The reaction was allowed to warm to room temperature and stirred a further 1 h. The reaction was then diluted with water (100 mL), and the aqueous layer was extracted with EtOAc. The combined organic extracts were washed with brine, dried ($Na_2SO_4$), filtered and evaporated in vacuo. The residue obtained was purified by column chromatography (petroleum ether:EtOAc, 20:1) to give the title compound as a yellow oil (6.25 g, 54%).

$^1$H NMR (400 MHz, CDCl$_3$) δ 10.29 (s, 1H), 7.97 (dd, J=6.1, 2.6 Hz, 1H), 7.70 (ddd, J=8.8, 4.7, 2.6 Hz, 1H), 7.09 (dd, J=9.6, 8.9 Hz, 1H).

2-Fluoro-5-(3-fluorophenyl)benzaldehyde

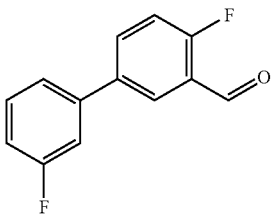 [SMILES: O=Cc1cc(-c2cccc(F)c2)ccc1F]

To a stirred mixture of 5-bromo-2-fluoro-benzaldehyde (3.0 g, 14.8 mmol, 1 eq), (3-fluorophenyl)boronic acid (2.48 g, 17.7 mmol, 1.2 eq) and $K_2CO_3$ (4.13 g, 44.4 mmol, 3 eq) in a mixture of EtOH (30 mL), DMF (30 mL) and water (10 mL) under $N_2$ was added Pd(PPh$_3$)$_4$ (1.71 g, 1.48 mmol, 0.1 eq). The reaction was heated at 100° C. for 3 h, then filtered through Celite. The filtrate was diluted with water and extracted with EtOAc. The combined organic extracts were washed with water and brine, dried ($Na_2SO_4$), filtered and evaporated in vacuo. The residue obtained was purified by column chromatography (petroleum ether:EtOAc, 300:1) to give the title compound as a yellow oil (1.1 g, 34%).

$^1$H NMR (400 MHz, CDCl$_3$) δ 10.38 (s, 1H), 8.03 (dd, J=6.5, 2.5 Hz, 1H), 7.77 (ddd, J=8.6, 5.0, 2.6 Hz, 1H), 7.43-7.35 (m, 1H), 7.33-7.29 (m, 1H), 7.25-7.20 (m, 2H), 7.05 (tdd, J=8.4, 2.5, 1.0 Hz, 1H).

3-Fluoro-2-[[2-fluoro-5-(3-fluorophenyl)phenyl]methylamino]-6-methoxy-benzonitrile

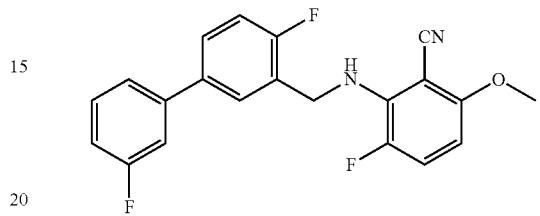

To a solution of 2-fluoro-5-(3-fluorophenyl)benzaldehyde (505 mg, 2.32 mmol, 1.2 eq) and 2-amino-3-fluoro-6-methoxy-benzonitrile (320 mg, 1.93 mmol, 1 eq) in toluene (30 mL) was added 4 Å molecular sieves (10 g). The mixture was heated at reflux for 4 h, then filtered to remove the molecular sieves. The filtrate was concentrated and the residue obtained was dissolved in methanol (30 mL). NaBH$_4$ (109.6 mg, 2.9 mmol, 1.5 eq) was added and the reaction stirred for 2 h at room temperature. The reaction was quenched by addition of water, and the aqueous layer was extracted with EtOAc. The combined organic extracts were washed with brine, dried ($Na_2SO_4$), filtered and evaporated in vacuo. The residue obtained was purified by column chromatography (petroleum ether:EtOAc, 50:1) to give the title compound as an off-white solid (610 mg, 72%).

LC-MS: m/z 368.9 [M+H]$^+$, 390.9 [M+Na]$^+$ $^1$H NMR (400 MHz, CDCl$_3$) δ 7.57 (dd, J=7.0, 2.3 Hz, 1H), 7.46 (ddd, J=8.3, 4.9, 2.4 Hz, 1H), 7.42-7.35 (m, 1H), 7.32-7.27 (m, 1H), 7.23-7.18 (m, 1H), 7.14 (dd, J=9.6, 8.6 Hz, 1H), 7.10-7.00 (m, 2H), 6.15 (dd, J=9.0, 3.2 Hz, 1H), 4.82 (d, J=6.6 Hz, 2H), 4.69 (br s, 1H), 3.84 (s, 3H).

3-Fluoro-2-[[2-fluoro-5-(3-fluorophenyl)phenyl]methylamino]-6-hydroxy-benzonitrile

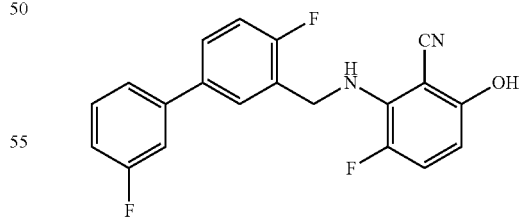

To a solution of 3-fluoro-2-[[2-fluoro-5-(3-fluorophenyl)phenyl]methylamino]-6-methoxy-benzonitrile (560 mg, 1.5 mmol, 1 eq) in CH$_2$Cl$_2$ (30 mL) was added BBr$_3$ (1.14 g, 4.5 mmol, 3 eq) and the reaction was stirred overnight. The mixture was then poured into water, and the aqueous layer was extracted with EtOAc. The combined organic extracts were washed with brine, dried ($Na_2SO_4$), filtered and evaporated in vacuo. The residue obtained was purified by column chroma- Isopropyl 2-[2-cyano-4-fluoro-3-[[2-fluoro-5-(3-fluorophenyl)phenyl]methylamino]phenoxy]acetate (II(ar))

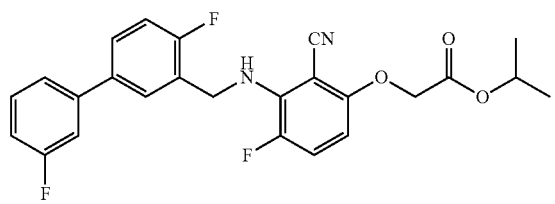

To a solution of 3-fluoro-2-[[2-fluoro-5-(3-fluorophenyl)phenyl]methylamino]-6-hydroxy-benzonitrile (360 mg, 1.0 mmol, 1 eq) in acetone was added Cs$_2$CO$_3$ (651.6 mg, 2.0 mmol, 2 eq). The reaction was stirred for 30 min at room temperature then isopropyl 2-bromoacetate (221 mg, 1.2 mmol, 1.2 eq) was added. The reaction was stirred for a further 2 h, then quenched with water and the aqueous layer was extracted with EtOAc. The combined organic extracts were washed with brine, dried (Na$_2$SO$_4$), filtered, and evaporated in vacuo. The residue obtained was purified by column chromatography (petroleum ether:EtOAc, 50:1 to 10:1) to give the title compound as a colorless oil (270 mg, 59%).

LC-MS: m/z 455.1 [M+H]$^+$ 477.1 [M+Na]$^+$ $^1$H NMR (400 MHz, CDCl$_3$) δ 7.58 (dd, J=7.0, 2.3 Hz, 1H), 7.46 (ddd, J=8.5, 4.9, 2.4 Hz, 1H), 7.42-7.35 (m, 1H), 7.32-7.27 (m, 1H), 7.24-7.18 (m, 1H), 7.14 (dd, J=9.6, 8.6 Hz, 1H), 7.07-6.99 (m, 2H), 6.02 (dd, J=9.0, 3.1 Hz, 1H), 5.15-5.04 (m, 1H), 4.83 (d, J=4.8 Hz, 2H), 4.73 (br s, 1H), 4.63 (s, 2H), 1.24 (d, J=6.3 Hz, 6H).

2-[2-Cyano-4-fluoro-3-[[2-fluoro-5-(3-fluorophenyl)phenyl]methylamino]phenoxy]acetic acid (I(an))

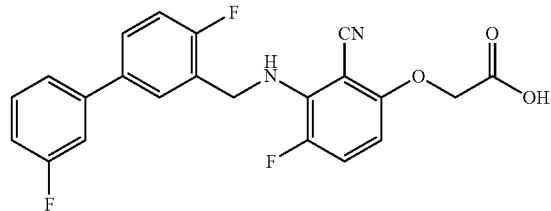 [SMILES: N#Cc1c(OCC(=O)O)ccc(F)c1NCc1cc(-c2cccc(F)c2)ccc1F]

To a solution of isopropyl 2-[2-cyano-4-fluoro-3-[[2-fluoro-5-(3-fluorophenyl)phenyl]methylamino]phenoxy]acetate (220 mg, 0.48 mmol, 1 eq) in a mixture of THF (10 mL) and water (10 mL) was added LiOH (20 mg, 0.96 mmol, 2 eq). The reaction was stirred for 3 h then the THF removed in vacuo. The aqueous solution that remained was acidified to pH 4 with 3M HCl and the aqueous layer was extracted with EtOAc. The combined organic extracts were washed with brine, dried (Na$_2$SO$_4$), filtered and evaporated in vacuo. The residue obtained was triturated with a mixture of 2-methoxy-2-methylpropane (5 mL) and petroleum ether (20 mL) to give the desired product as an off-white solid (110 mg, 56%).

LC-MS: m/z 413.1 [M+H]$^+$ 435.1 [M+Na]$^+$ $^1$H NMR (400 MHz, DMSO) δ 7.69 (dd, J=7.1, 2.1 Hz, 1H), 7.66-7.59 (m, 1H), 7.54-7.45 (m, 1H), 7.44-7.38 (m, 2H), 7.31-7.22 (m, 2H), 7.22-7.15 (m, 1H), 6.62 (td, J=6.7, 2.7 Hz, 1H), 6.21 (dd, J=9.1, 3.0 Hz, 1H), 4.83-4.68 (m, 4H).

Example 55

Compound I(ao) Synthesized According to Scheme 3

2-[3-[[3-(3-fluorophenyl)-5-hydroxy-phenyl]methylamino]-2,4-dimethyl-phenoxy]acetic acid (I(ao))

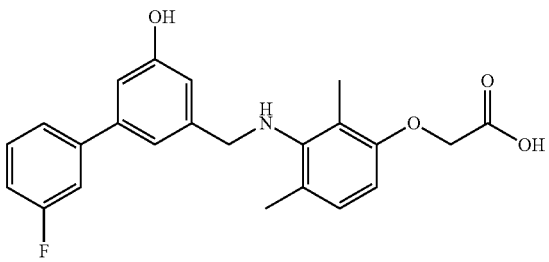

3-(3-Fluorophenyl)-N-(3-hydroxy-2,6-dimethylphenyl)-5-methoxy-benzamide

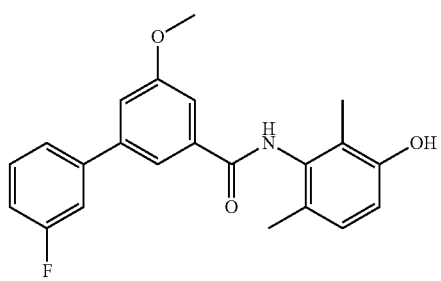 [SMILES: COc1cc(C(=O)Nc2c(C)ccc(O)c2C)cc(-c2cccc(F)c2)c1]

To a solution of 3-(3-fluorophenyl)-5-methoxy-benzoic acid (intermediate III(i)) (1.4 g, 5.7 mmol, 1.0 eq) in CH$_2$Cl$_2$ (15 mL) were added (COCl)$_2$ (2.2 g, 17.3 mmol, 3.0 eq) and DMF (0.01 mL). The reaction mixture was stirred at room temperature for 1.5 h then the solvent and excess reagent removed under reduced pressure. The residue obtained was dissolved in THF (20 mL) and added dropwise to a solution of 3-amino-2,4-dimethylphenol (intermediate X(c)) (791 mg, 5.77 mmol, 1.0 eq) in THF (20 mL) at 0° C. The solution was allowed to warm to room temperature and stirred for 1 h. The reaction mixture was poured into water and extracted with EtOAc. The combined organic extracts were washed with water and brine, dried (Na$_2$SO$_4$), filtered and evaporated in vacuo. The residue obtained was purified by column chromatography (petroleum ether: EtOAc, 100:1 to 1:1) to give the title compound as a white solid (1.2 g, 57%).

LC-MS: m/z 365.4 [M+H]$^+$

3-[[3-(3-Fluorophenyl)-5-methoxy-phenyl]methylamino]-2,4-dimethyl-phenol

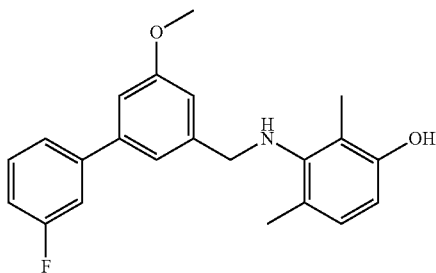 [SMILES: COc1cc(CNc2c(C)ccc(O)c2C)cc(-c2cccc(F)c2)c1]

To a solution of 3-(3-fluorophenyl)-N-(3-hydroxy-2,6-dimethyl-phenyl)-5-methoxy-benzamide (1.2 g, 3.3 mmol, 1.0 eq) in THF (50 mL) at 0° C. under $N_2$ was added a solution of $BH_3$ (1M in THF, 16.0 mL, 16.0 mmol, 5.0 eq) dropwise. The reaction mixture was heated at 60° C. overnight then cooled to room temperature and quenched with water. The aqueous layer was extracted with EtOAc and the combined organic extracts were washed with water and brine, dried ($Na_2SO_4$), filtered and evaporated in vacuo. The residue obtained was purified by column chromatography (petroleum ether:EtOAc, 100:1 to 5:1) to give the title compound as a colorless oil (700 mg, 60%).

LC-MS: m/z 351.4 [M+1].

Isopropyl 2-[3-[[3-(3-fluorophenyl)-5-methoxy-phenyl]methylamino]-2,4-dimethyl-phenoxy]acetate (II(at))

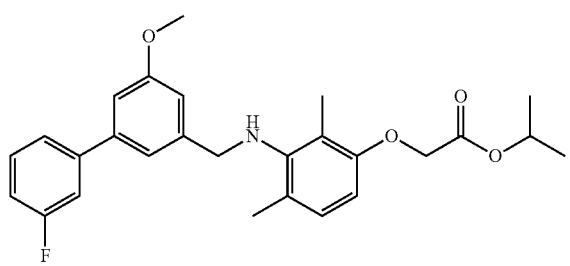 [SMILES: COc1cc(CNc2c(C)ccc(OCC(=O)OC(C)C)c2C)cc(-c2cccc(F)c2)c1]

To a solution of 3-[[3-(3-fluorophenyl)-5-methoxy-phenyl]methylamino]-2,4-dimethyl-phenol (700 mg, 2.0 mmol, 1.0 eq) in 2-butanone (4 mL) was added $Cs_2CO_3$ (973 mg, 3 mmol, 1.5 eq). The reaction mixture was stirred for 30 min then isopropyl bromoacetate (432 mg, 2.4 mmol, 1.2 eq) was added. The reaction mixture was stirred at room temperature for a further 1 h then poured into water and extracted with EtOAc. The combined organic extracts were washed with water and brine, dried ($Na_2SO_4$), filtered and evaporated in vacuo. The residue was purified by column chromatography (petroleum ether:EtOAc, 100:0 to 30:1) to give the title compound as a colorless oil (570 mg, 63%).

LC-MS: m/z 451.5 [M+H]$^+$ $^1$H NMR (400 MHz, DMSO) δ 7.53-7.41 (m, 3H), 7.23-7.15 (m, 2H), 7.08 (s, 1H), 6.92 (s, 1H), 6.82 (d, J=8.4 Hz, 1H), 6.34 (d, J=8.3 Hz, 1H), 4.96 (hept, J=6.3 Hz, 1H), 4.64 (s, 2H), 4.38 (br t, J=7.1 Hz, 1H), 4.11 (d, J=5.2 Hz, 2H), 3.78 (s, 3H), 2.14 (s, 3H), 2.12 (s, 3H), 1.19 (d, J=6.3 Hz, 6H).

Isopropyl 2-[3-[[3-(3-fluorophenyl)-5-hydroxy-phenyl]methylamino]-2,4-dimethyl-phenoxy]acetate (II(as))

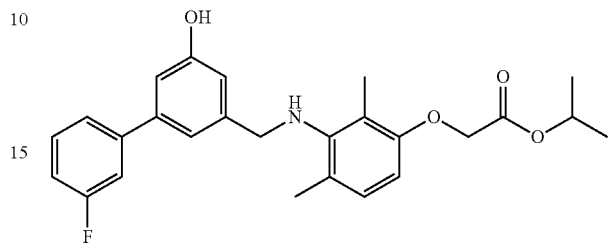

To a solution of isopropyl 2-[3-[[3-(3-fluorophenyl)-5-methoxy-phenyl]methylamino]-2,4-dimethyl-phenoxy]acetate (390 mg, 0.9 mmol, 1.0 eq) in $CH_2Cl_2$ (10 mL) at 0° C. was added dropwise ethyl mercaptan (321 mg, 5.2 mmol, 6.0 eq) and $AlCl_3$ (690 mg, 5.2 mmol, 6.0 eq). The reaction mixture was stirred at room temperature for 1 h then poured into water and extracted with EtOAc. The organic extract was washed with water and brine, dried ($Na_2SO_4$), filtered and evaporated in vacuo. The residue obtained was purified by column chromatography (petroleum ether: EtOAc, 100:1 to 10:1) to give the title compound as a white solid (200 g, 53%).

LC-MS: m/z 437.5 [M+H]$^+$ $^1$H NMR (400 MHz, DMSO) δ 9.54 (s, 1H), 7.54-7.43 (m, 1H), 7.39 (d, J=7.9 Hz, 1H), 7.37-7.32 (m, 1H), 7.17 (td, J=8.3, 1.8 Hz, 1H), 7.06 (s, 1H), 6.89 (s, 1H), 6.83 (d, J=8.4 Hz, 1H), 6.80 (s, 1H), 6.34 (d, J=8.3 Hz, 1H), 5.02-4.90 (m, 1H), 4.63 (s, 2H), 4.28 (br t, J=6.9 Hz, 1H), 4.05 (d, J=6.6 Hz, 2H), 2.14 (s, 3H), 2.13 (s, 3H), 1.19 (d, J=6.3 Hz, 6H).

2-[3-[[3-(3-Fluorophenyl)-5-hydroxy-phenyl]methylamino]-2,4-dimethyl-phenoxy]acetic acid (I(ao))

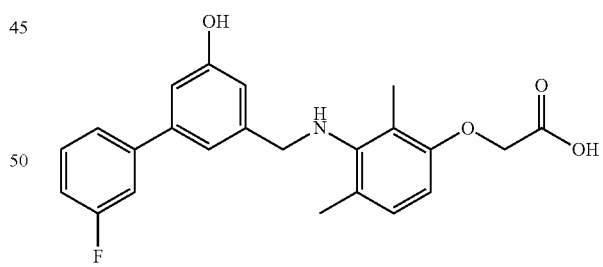

To a solution of isopropyl 2-[3-[[3-(3-fluorophenyl)-5-hydroxy-phenyl]methylamino]-2,4-dimethyl-phenoxy]acetate (100 mg, 0.22 mmol, 1.0 eq) in THF (10 mL) at 0° C. was added NaOH (1M aqueous solution, 3 mL, 3 mmol). The reaction mixture was stirred at room temperature overnight then the THF was removed under reduced pressure. The remaining aqueous solution was poured into water and adjusted to pH 4-6 by addition of diluted HCl. The solid that precipitated was collected by filtration, washed with water and dried in vacuo to give the title compound as a yellow solid (60 mg, 66%).

LC-MS: m/z 409.5 [M−H]$^−$

¹H NMR (400 MHz, DMSO) δ 9.60 (br s, 1H), 7.53-7.44 (m, 1H), 7.43-7.32 (m, 2H), 7.18 (td, J=8.3, 2.3 Hz, 1H), 7.08 (s, 1H), 6.93 (s, 1H), 6.90-6.84 (m, 1H), 6.82 (s, 1H), 6.44 (br s, 1H), 4.60 (s, 2H), 4.11 (br s, 2H), 2.16 (s, 6H).

Example 56

Compound I(ap) Synthesized According to Scheme 3

2-[3-[[3-(3-fluorophenyl)-5-methoxy-phenyl]methylamino]-2,4-dimethyl-phenoxy]acetic acid (I(ap))

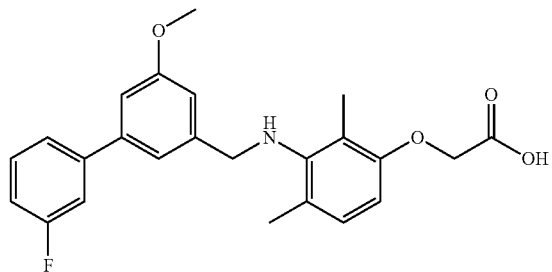

To a solution of isopropyl 2-[3-[[3-(3-fluorophenyl)-5-methoxy-phenyl]methylamino]-2,4-dimethyl-phenoxy]acetate (II(at)) (100 mg, 0.22 mmol, 1.0 eq) in THF (10 mL) was added NaOH (1M aqueous solution, 3.0 mL, 3.0 mmol). The reaction mixture was stirred at room temperature for 2 h, then the THF was removed under reduced pressure. The remaining aqueous solution was adjusted to pH 3-4 by the addition of diluted HCl. The solid that precipitated was collected by filtration, washed with water and dried in vacuo to give the title compound as a yellow solid (60 mg, 66%).

LC-MS: m/z 409.5 [M–H]⁻

¹H NMR (400 MHz, DMSO) δ 7.55-7.42 (m, 3H), 7.27-7.11 (m, 3H), 6.99-6.88 (m, 2H), 6.54 (br s, 1H), 4.63 (s, 2H), 4.24 (br s, 2H), 3.79 (s, 3H), 2.17 (s, 6H).

Example 57

Compound I(aq) Synthesized According to Scheme 3

2-[3-[[5-(3,4-difluorophenyl)-2,3-dimethyl-phenyl]methylamino]-2,4-difluoro-phenoxy]acetic acid (I(aq))

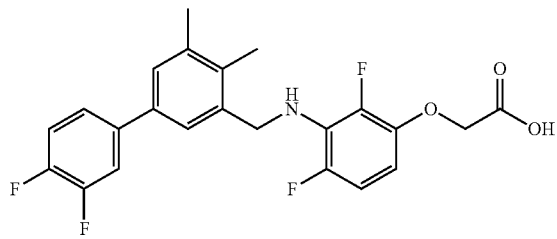

5-(3,4-Difluorophenyl)-2,3-dimethyl-benzoic acid (III(s))

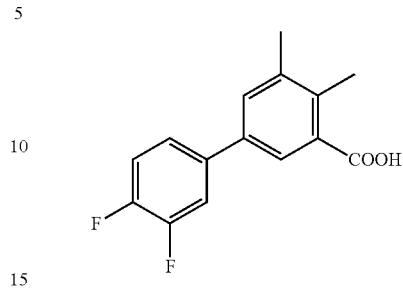

To a mixture of 5-bromo-2,3-dimethyl-benzoic acid (500 mg, 2.18 mmol, 1.0 eq), (3,4-difluorophenyl)boronic acid (378.6 mg, 2.40 mmol, 1.1 eq) and Na₂CO₃ (693 mg, 6.54 mmol, 3.0 eq) in a mixture of EtOH (2.5 mL), DMF (10 mL) and H₂O (2.5 mL) was added Pd(PPh₃)₄ (126 mg, 0.11 mmol, 0.05 eq) under nitrogen. The mixture was stirred at 100° C. overnight. After cooling to room temperature, water was added and the diluted reaction mixture filtered through celite. The aqueous layer was extracted with EtOAc and the organic extract was discarded. The remaining aqueous layer was acidified to pH 2 by addition of 3M HCl. The resulting mixture was extracted with EtOAc and the combined organic extracts were washed with water and brine, dried (Na₂SO₄), filtered and evaporated in vacuo to give the title compound as a white solid (400 mg, 70%).

LC-MS: m/z 261.1 [M–H]⁻

¹H NMR (400 MHz, DMSO) δ 7.84-7.74 (m, 2H), 7.68 (s, 1H), 7.57-7.46 (m, 2H), 2.41 (s, 3H), 2.37 (d, J=8.7 Hz, 3H).

N-(2,6-Difluoro-3-hydroxy-phenyl)-5-(3,4-difluorophenyl)-2,3-dimethyl-benzamide

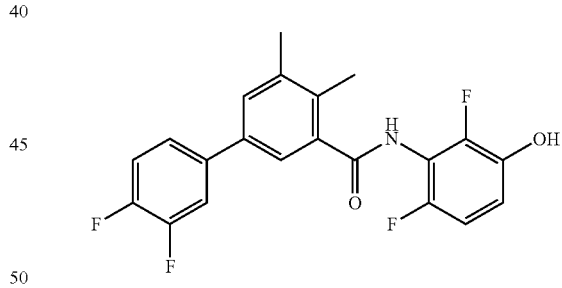

To a solution of 5-(3,4-difluorophenyl)-2,3-dimethyl-benzoic acid (395 mg, 1.51 mmol, 1.1 eq) in CH₂Cl₂ (5 mL) was added (COCl)₂ (521.6 mg, 4.11 mmol, 3.0 eq) dropwise at 0° C. DMF (10 mg, 0.14 mmol, 0.1 eq) was added and the reaction mixture was stirred at room temperature for 2 h. The resulting mixture was concentrated under reduced pressure to remove the solvent and excess reagent. The residue obtained was dissolved in THF (4 mL) and added dropwise to a mixture of 3-amino-2,4-difluoro-phenol (intermediate X(a)) (198 mg, 1.37 mmol, 1.0 eq) and NaHCO₃ (575 mg, 6.85 mmol, 5.0 eq) in THF (4 mL) at 0° C. After addition was completed the reaction mixture was stirred at room temperature for 30 min. Water was added and the aqueous layer extracted with EtOAc. The combined organic extracts were washed with saturated NaHCO₃, water and brine, dried (Na₂SO₄), filtered and evaporated in vacuo. The residue was purified by column chromatography (petroleum ether:EtOAc, 10:1 to 4:1) to give the title compound as a white solid (100 mg, 19%).

LC-MS: m/z 388.3 [M−H]⁻

3-[[5-(3,4-Difluorophenyl)-2,3-dimethyl-phenyl]methylamino]-2,4-difluoro-phenol

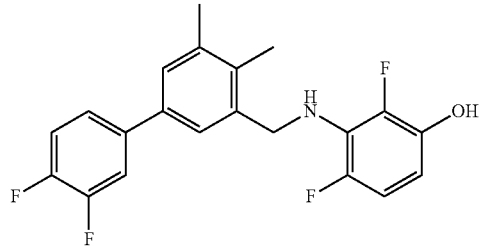 [SMILES: Cc1cc(-c2ccc(F)c(F)c2)cc(CNc2c(F)ccc(O)c2F)c1C]

To a solution of N-(2,6-difluoro-3-hydroxy-phenyl)-5-(3,4-difluorophenyl)-2,3-dimethyl-benzamide (90 mg, 0.23 mmol, 1.0 eq) in THF (1.5 mL) under $N_2$ was added dropwise a solution of $BH_3$ (1M in THF, 1.03 mL, 1.03 mmol, 4.6 eq) at 0° C. The reaction mixture was heated at 60° C. overnight then cooled and the reaction quenched with water. The aqueous layer was extracted with EtOAc and the combined organic extracts were washed with brine, dried ($Na_2SO_4$), filtered and evaporated in vacuo. The residue obtained was purified by column chromatography (petroleum ether: EtOAc, 30:1 to 15:1) to give the title compound as a colorless oil (70 mg, 81%).

LC-MS: m/z 376.1 [M+H]⁺

Isopropyl 2-[3-[[5-(3,4-difluorophenyl)-2,3-dimethyl-phenyl]methylamino]-2,4-difluoro-phenoxy]acetate (II(au))

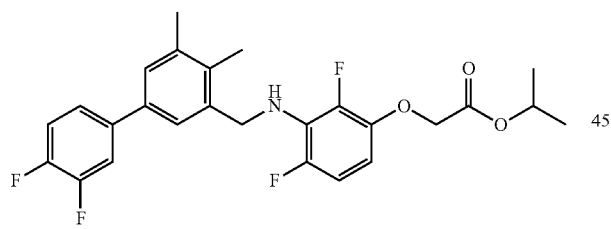

To a solution of 3-[[5-(3,4-difluorophenyl)-2,3-dimethyl-phenyl]methylamino]-2,4-difluoro-phenol (70 mg, 0.19 mmol, 1.0 eq) in acetone (2 mL) was added $Cs_2CO_3$ (90 mg, 0.28 mmol, 1.5 eq) at room temperature. The reaction mixture was stirred for 10 min then isopropyl bromoacetate (40 mg, 0.22 mmol, 1.2 eq) was added. The reaction mixture was stirred at room temperature for a further 30 min then water was added and the aqueous layer was extracted with EtOAc. The combined organic extracts were washed with brine, dried ($Na_2SO_4$), filtered and evaporated in vacuo. The residue was purified by column chromatography (petroleum ether: EtOAc, 100:0 to 20:1) to give the title compound as a colorless oil (73 mg, 82%).

LC-MS: m/z 498.2 [M+H]⁺

¹H NMR (400 MHz, DMSO) δ 7.58 (ddd, J=12.3, 7.8, 2.2 Hz, 1H), 7.48 (dt, J=10.6, 8.6 Hz, 1H), 7.43-7.35 (m, 3H), 6.81 (ddd, J=11.5, 9.3, 2.0 Hz, 1H), 6.31 (td, J=9.1, 4.5 Hz, 1H), 5.61 (br s, 1H), 5.00-4.87 (m, 1H), 4.70 (s, 2H), 4.47 (d, J=5.1 Hz, 2H), 2.30 (s, 3H), 2.21 (s, 3H), 1.15 (d, J=6.3 Hz, 6H).

2-[3-[[5-(3,4-Difluorophenyl)-2,3-dimethyl-phenyl]methylamino]-2,4-difluoro-phenoxy]acetic acid (I(aq))

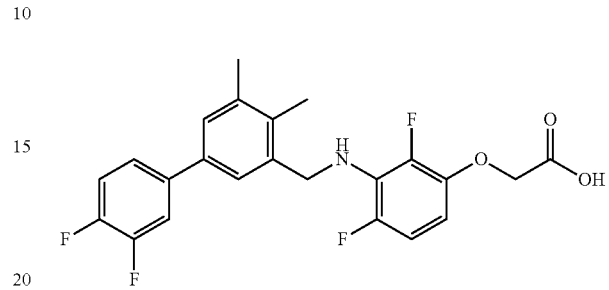

To a solution of isopropyl 2-[3-[[5-(3,4-difluorophenyl)-2,3-dimethyl-phenyl]methylamino]-2,4-difluoro-phenoxy]acetate (70 mg, 0.15 mmol, 1.0 eq) in a mixture of THF (1.5 mL) and MeOH (0.5 mL) was added LiOH (2M aqueous solution, 1.5 mL, 3.0 mmol). The reaction was stirred at room temperature for 1 h then the organic solvent was removed under reduced pressure. The remaining aqueous solution was diluted with water and the solution acidified to pH 4-5 with 3M HCl. The mixture was extracted with EtOAc and the combined organic extracts were washed with water and brine, dried ($Na_2SO_4$), filtered and evaporated in vacuo to give the title compound as a white solid (63 mg, 99%).

LC-MS: m/z 434.1 [M+H]⁺

¹H NMR (400 MHz, DMSO) δ 7.60 (ddd, J=12.3, 7.8, 2.1 Hz, 1H), 7.48 (dt, J=10.4, 8.6 Hz, 1H), 7.43 (s, 1H), 7.41-7.34 (m, 2H), 6.82-6.68 (m, 1H), 6.20 (br s, 1H), 5.41 (br s, 1H), 4.45 (d, J=6.5 Hz, 2H), 4.23 (br s, 2H), 2.30 (s, 3H), 2.21 (s, 3H).

Example 58

Compound I(ar) Synthesized According to Scheme 3

2-[3-[[5-(3,5-Difluorophenyl)-2,3-dimethyl-phenyl]methylamino]-2,4-difluoro-phenoxy]acetic acid (I(ar))

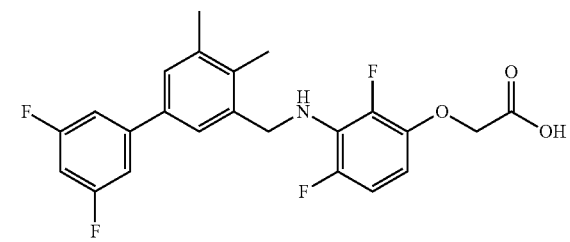 [SMILES: Cc1cc(-c2cc(F)cc(F)c2)cc(CNc2c(F)ccc(OCC(=O)O)c2F)c1C]

5-(3,5-Difluorophenyl)-2,3-dimethyl-benzoic acid (III(t))

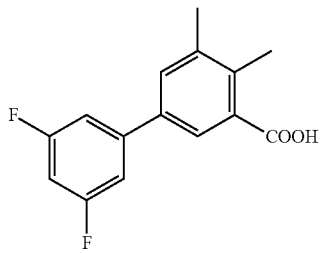 [SMILES: Cc1cc(-c2cc(F)cc(F)c2)cc(C(=O)O)c1C]

To a solution of 5-bromo-2,3-dimethylbenzoic acid (500 mg, 2.18 mmol, 1.0 eq), (3,5-difluorophenyl)boronic acid (414 mg, 2.62 mmol, 1.2 eq) and $Na_2CO_3$ (925 mg, 8.73 mmol, 4.0 eq) in a mixture of EtOH (5 mL), DMF (20 mL) and water (5 mL) was added $Pd(PPh_3)_4$ (252 mg, 0.22 mmol, 0.1 eq) under nitrogen. The mixture was stirred at 100° C. overnight. Water was added and the mixture acidified to pH 3 by addition of 3M HCl. The aqueous layer was extracted with EtOAc and the combined organic extracts were washed with water and brine, dried ($Na_2SO_4$), filtered and evaporated in vacuo. The residue was purified by column chromatography ($CH_2Cl_2$:MeOH, 300:1 to 200:1) to give the title compound as a white solid (184 mg, 32%).

LC-MS: m/z 261.1 [M−H]$^-$ $^1$H NMR (400 MHz, DMSO) δ 12.99 (br s), 7.82 (s), 7.74 (s), 7.44 (d, J=7.1 Hz), 7.27-7.17 (m), 2.41 (s), 2.36 (s).

N-(2,6-Difluoro-3-hydroxy-phenyl)-5-(3,5-difluorophenyl)-2,3-dimethyl-benzamide

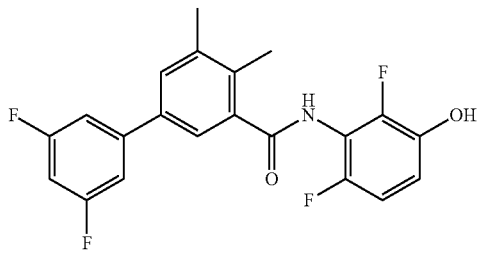 [SMILES: Cc1cc(-c2cc(F)cc(F)c2)cc(C(=O)Nc2c(F)ccc(O)c2F)c1C]

To a solution of 5-(3,5-difluorophenyl)-2,3-dimethyl-benzoic acid (240 mg, 0.92 mmol, 1.1 eq) in $CH_2Cl_2$ (12 mL) was added $(COCl)_2$ (348 mg, 2.75 mmol, 3.3 eq) and DMF (5 drops). The reaction mixture was stirred at room temperature for 1.5 h, then concentrated under reduced pressure to remove the organic solvent and excess reagent. The residue obtained was dissolved in THF (10 mL) and added dropwise to a solution of 3-amino-2,4-difluorophenol (intermediate X(a)) (121 mg, 0.83 mmol, 1.0 eq) and $NaHCO_3$ (386 mg, 4.6 mmol, 5.0 eq) in THF (10 mL) at 0° C. After the addition, the reaction mixture was stirred at room temperature for 1 h. The resulting mixture was diluted with water and extracted with EtOAc. The organic extract was washed with water and brine, dried ($Na_2SO_4$), filtered and evaporated in vacuo. The residue was purified by column chromatography ($CH_2Cl_2$:MeOH, 500:1 to 200:1) to give the title compound as a yellow solid (50 mg, 15%).

LC-MS: m/z 390.1 [M+H]$^+$ 412.1 [M+Na]$^+$

3-[[5-(3,5-Difluorophenyl)-2,3-dimethyl-phenyl]methylamino]-2,4-difluoro-phenol

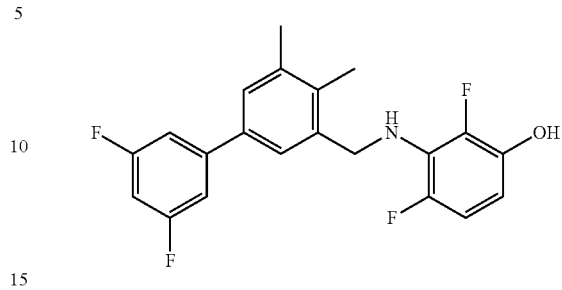

To a solution of N-(2,6-difluoro-3-hydroxy-phenyl)-5-(3,5-difluorophenyl)-2,3-dimethyl-benzamide (46 mg, 0.12 mmol, 1.0 eq) in THF (5 mL) under $N_2$ was added dropwise a solution of $BH_3$ (1M in THF, 0.72 mL, 0.72 mmol, 6.0 eq). The reaction mixture was heated at 60° C. overnight. After cooling, the resulting mixture was quenched with water and extracted with EtOAc. The organic extract was washed with water and brine, dried ($Na_2SO_4$), filtered and evaporated in vacuo. The residue was purified by column chromatography (petroleum ether:EtOAc, 40:1 to 20:1) to give the title compound as a colorless oil (20 mg, 45%).

LC-MS: m/z 376.2 [M+H]$^+$

Isopropyl 2-[3-[[5-(3,5-difluorophenyl)-2,3-dimethyl-phenyl]methylamino]-2,4-difluoro-phenoxy]acetate (II(av))

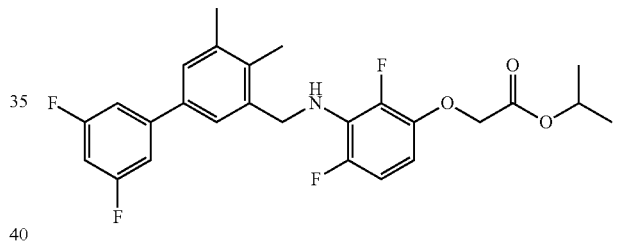

To a solution of 3-[[5-(3,5-difluorophenyl)-2,3-dimethyl-phenyl]methylamino]-2,4-difluoro-phenol (20 mg, 0.05 mmol, 1.0 eq) in DMF (3 mL) was added $Cs_2CO_3$ (26 mg, 0.075 mmol, 1.5 eq). The mixture was stirred at room temperature for 30 min then isopropyl bromoacetate (11 mg, 0.06 mmol, 1.2 eq) was added. The reaction mixture was stirred at room temperature for a further 1 h then diluted with water and extracted with EtOAc. The combined organic extracts were washed with water and brine, dried ($Na_2SO_4$), filtered and evaporated in vacuo. The residue was purified by column chromatography (petroleum ether:EtOAc, 30:1) to give the title compound as a colorless oil (23 mg, 92%).

LC-MS: m/z 476.1 [M+H]$^+$

2-[3-[[5-(3,5-Difluorophenyl)-2,3-dimethyl-phenyl]methylamino]-2,4-difluoro-phenoxy]acetic acid (I(ar))

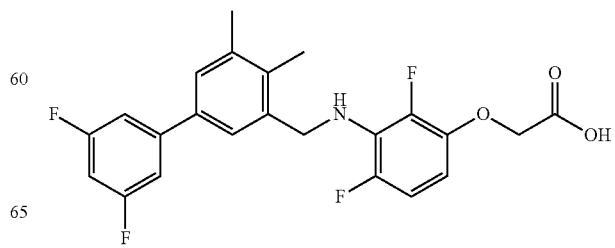

To a solution of isopropyl 2-[3-[[5-(3,5-difluorophenyl)-2,3-dimethyl-phenyl]methylamino]-2,4-difluoro-phenoxy]acetate (23 mg, 0.048 mmol, 1.0 eq) in THF (3 mL) at 0° C. was added LiOH (2M aqueous solution, 1 mL, 2.0 mmol). The reaction mixture was allowed to warm to room temperature and stirred overnight. The THF was removed under reduced pressure and the remaining aqueous solution was adjusted to pH 3 by addition of 3M HCl. The resulting mixture was extracted with EtOAc and the combined organic extracts were washed with water and brine, dried ($Na_2SO_4$), filtered and concentrated in vacuo to give the title compound as a yellow solid (20 mg, 95%).

LC-MS: m/z 434.1 $[M+H]^+$ 456.1 $[M+Na]^+$ $^1$H NMR (400 MHz, DMSO) δ 7.48 (s, 1H), 7.45 (s, 1H), 7.32-7.23 (m, 2H), 7.17 (tt, J=9.3, 2.3 Hz, 1H), 6.81 (ddd, J=11.5, 9.3, 2.1 Hz, 1H), 6.32 (td, J=9.1, 4.6 Hz, 1H), 5.56 (br s, 1H), 4.63 (s, 2H), 4.48 (d, J=6.6 Hz, 2H), 2.31 (s, 3H), 2.22 (s, 3H).

Example 59

Compound I(as) Synthesized According to Scheme 5

(R,S)-2-[2,4-difluoro-3-[1-[2-fluoro-5-(3-fluorophenyl)phenyl]ethylamino]phenoxy]acetic acid (I(as))

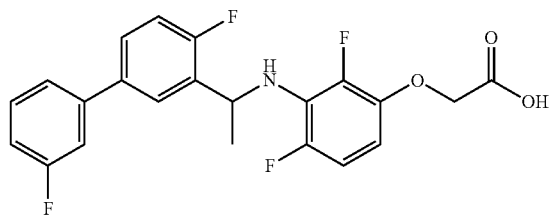 [SMILES: CC(Nc1c(F)ccc(OCC(=O)O)c1F)c1cc(-c2cccc(F)c2)ccc1F]

2-Fluoro-5-(3-fluorophenyl)-N-methoxy-N-methyl-benzamide

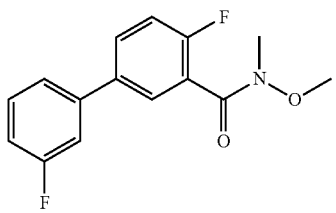 [SMILES: CON(C)C(=O)c1cc(-c2cccc(F)c2)ccc1F]

To a solution of 2-fluoro-5-(3-fluorophenyl)benzoic acid (intermediate III(a)) (2 g, 8.5 mmol, 1.0 eq) and N-methoxymethanamine hydrochloride (916 mg, 9.4 mmol, 1.1 eq) in DMF (20 mL) was added triethylamine (3.6 mL, 25.6 mmol, 3.0 eq) at 0° C. HOBt (1.51 g, 11.1 mmol, 1.3 eq) and EDC (2.13 g, 11.1 mmol, 1.3 eq) were added and the solution was stirred for 2 days. Water was added and the aqueous layer was extracted with EtOAc. The organic extracts were washed with water and brine, dried ($Na_2SO_4$), filtered and evaporated in vacuo. The residue obtained was purified by column chromatography (petroleum ether: EtOAc, 20:1 to 10:1 then $CH_2Cl_2$) to give the title compound as a colorless oil (2.03 g, 85%).

LC-MS: m/z 278.1 $[M+H]^+$ 300.1 $[M+Na]^+$

1-[2-Fluoro-5-(3-fluorophenyl)phenyl]ethanone

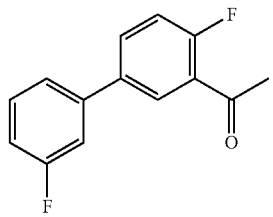 [SMILES: CC(=O)c1cc(-c2cccc(F)c2)ccc1F]

To a solution of 2-fluoro-5-(3-fluorophenyl)-N-methoxy-N-methyl-benzamide (1.8 g, 6.5 mmol, 1.0 eq) in THF (14 mL) at −20° C. was added MeMgBr (3.2 mL, 9.7 mmol, 1.5 eq). The mixture was stirred at 0° C. for 2 h then water was added and the aqueous layer was extracted with EtOAc. The combined organic extracts were washed with brine, dried ($Na_2SO_4$), filtered and evaporated in vacuo. The residue obtained was purified by column chromatography (petroleum ether: EtOAc, 20:1 to 10:1) to give the title compound as a white solid (1.3 g, 86%).

LC-MS: m/z 233.1 $[M+H]^+$ 255.1 $[M+Na]^+$ 2,4-Difluoro-3-[(E)-1-[2-fluoro-5-(3-fluorophenyl)phenyl]ethylideneamino]phenol

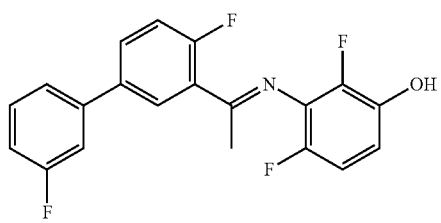 [SMILES: C/C(=N\c1c(F)ccc(O)c1F)c1cc(-c2cccc(F)c2)ccc1F]

To a mixture of compound I-[2-fluoro-5-(3-fluorophenyl)phenyl]ethanone (500 mg, 2.1 mmol, 1 eq) and 3-amino-2,4-difluorophenol (intermediate X(a)) (375 mg, 2.5 mmol, 1 eq) in toluene (50 mL) was added 4 Å molecule sieves (30 grains) and $AlCl_3$ (28 mg, 0.21 mmol, 0.1 eq). The reaction was heated at reflux overnight, the sieves were removed by filtration and the filtrate evaporated under reduced pressure. The residue obtained was purified by column chromatography (petroleum ether: EtOAc, 25:1) to give the title compound as a colorless oil (500 mg, 66%).

LC-MS: m/z 360.1 $[M+H]^+$ 382.1 $[M+Na]^+$ (R,S)-2,4-Difluoro-3-[1-[2-fluoro-5-(3-fluorophenyl)phenyl]ethylamino]phenol

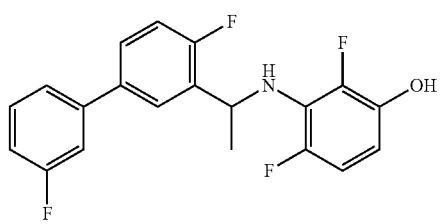 [SMILES: CC(Nc1c(F)ccc(O)c1F)c1cc(-c2cccc(F)c2)ccc1F]

2,4-difluoro-3-[(E)-1-[2-fluoro-5-(3-fluorophenyl)phenyl]ethylideneamino]phenol (300 mg, 0.8 mmol, 1.0 eq) was dissolved in THF (20 mL) and a solution of BH$_3$ (1M in THF, 3.2 mL, 3.2 mmol, 4.0 eq) was added dropwise. The solution was then heated at 60° C. overnight. The reaction was quenched with methanol and the solvent was removed in vacuo. The residue obtained was purified by column chromatography (petroleum ether:EtOAc, 15:1) with a second batch of the same reaction (50 mg scale) to give the title compound as a colorless oil (320 mg, 91%).

LC-MS: m/z 362.1 [M+H]$^+$ 384.1 [M+Na]$^+$ (R,S)-Isopropyl 2-[2,4-difluoro-3-[1-[2-fluoro-5-(3-fluorophenyl)phenyl]ethylamino]phenoxy]acetate (II(aw))

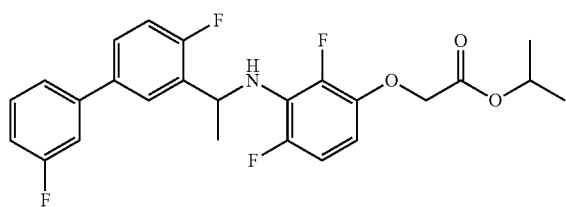 [SMILES: CC(C)OC(=O)COc1ccc(F)c(NC(C)c2cc(-c3cccc(F)c3)ccc2F)c1F]

To a solution of (R,S)-2,4-difluoro-3-[1-[2-fluoro-5-(3-fluorophenyl)phenyl]ethylamino]phenol (320 mg, 0.88 mmol, 1 eq) in DMF (20 mL) was added K$_2$CO$_3$ (486 mg, 1.1 mmol, 4 eq) and the mixture stirred for 30 min. Isopropyl bromoacetate (190 mg, 1.1 mmol, 1.2 eq) was added dropwise to the reaction and the mixture stirred overnight. The reaction was diluted with water and extracted with EtOAc. The organic extract was washed with water and brine, dried (Na$_2$SO$_4$), filtered and evaporated in vacuo. The residue obtained was purified by column chromatography (petroleum ether:EtOAc, 50:1) to give the title compound as a colorless oil (380 mg, 93%).

LC-MS: m/z 484.1 [M+Na]$^+$ $^1$H NMR (400 MHz, CDCl$_3$) δ 7.46 (dd, J=7.1, 2.3 Hz), 7.41-7.34 (m), 7.25 (d, J=8.3 Hz), 7.20-7.14 (m), 7.07 (dd, J=10.3, 8.6 Hz), 7.04-6.99 (m), 6.65 (ddd, J=11.2, 9.2, 2.2 Hz), 6.25 (td, J=9.0, 4.7 Hz), 5.21-5.13 (m), 5.13-5.04 (m), 4.53 (s), 4.13 (br d, J=9.6 Hz), 1.62 (d, J=6.7 Hz), 1.22 (d, J=6.3 Hz).

(R,S)-2-[2,4-Difluoro-3-[1-[2-fluoro-5-(3-fluorophenyl)phenyl]ethylamino]phenoxy]acetic acid (I(as))

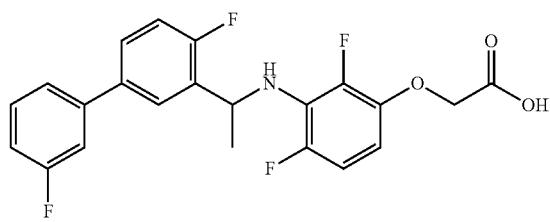 [SMILES: CC(Nc1c(F)ccc(OCC(=O)O)c1F)c1cc(-c2cccc(F)c2)ccc1F]

To a solution of (R,S)-isopropyl 2-[2,4-difluoro-3-[1-[2-fluoro-5-(3-fluorophenyl)phenyl]ethylamino]phenoxy]acetate (130 mg, 0.28 mmol, 1 eq) in THF (10 mL) was added a solution of LiOH.H2O (24 mg, 0.56 mmol, 2 eq) in H$_2$O (10 mL) and the mixture was stirred overnight at room temperature. The solution was acidified to pH 1 by addition of 1N HCl and the aqueous layer was extracted with EtOAc. The combined organic extracts were washed with brine, dried (Na$_2$SO$_4$), filtered and evaporated in vacuo to give the title compound as a yellow solid (85 mg, 72%).

LC-MS: m/z 420.1 [M+H]$^+$ 442.1 [M+Na]$^+$ $^1$H NMR (400 MHz, CDCl$_3$) δ 7.44 (dd, J=7.1, 2.2 Hz, 1H), 7.41-7.31 (m, 2H), 7.23 (d, J=7.8 Hz, 1H), 7.18-7.11 (m, 1H), 7.10-6.97 (m, 2H), 6.70-6.61 (m, 1H), 6.25 (td, J=8.9, 4.6 Hz, 1H), 5.15 (q, J=6.6 Hz, 1H), 4.58 (s, 2H), 1.61 (d, J=6.8 Hz, 3H).

Example 60

Compound I(at) Synthesized According to Scheme 3

2-[4-fluoro-3-[[5-(3-fluorophenyl)-2,3-dimethylphenyl]methylamino]-2-methyl-phenoxy]acetic acid (I(at))

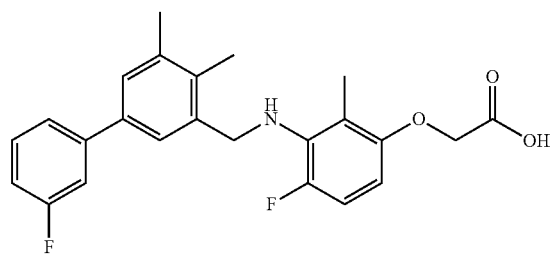

N-(6-Fluoro-3-hydroxy-2-methyl-phenyl)-5-(3-fluorophenyl)-2,3-dimethyl-benzamide

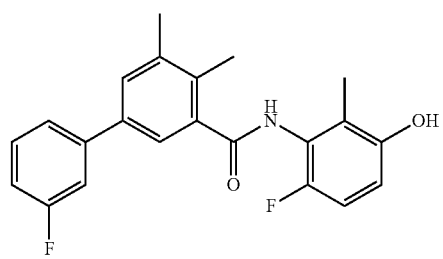

To a solution of 5-(3-fluorophenyl)-2,3-dimethyl-benzoic acid (intermediate III(m)) (500 mg, 2.0 mmol, 1.0 eq) in CH$_2$Cl$_2$ (10 mL) at 0° C. was added oxalyl chloride (770 mg, 6.1 mmol, 3.0 eq) and DMF (0.1 mL) and the reaction was stirred for 1 h. The solvent and excess reagent were removed under reduced pressure and the residue obtained was dissolved in THF (10 mL) and added to a mixture of 3-amino-4-fluoro-2-methyl-phenol (intermediate X(e)) (280 mg, 2.0 mmol, 1.0 eq) and Na$_2$CO$_3$ (860 mg, 8.1 mmol, 4.0 eq) in THF (10 mL) at 0° C. The reaction was stirred for 3 h, then filtered and concentrated in vacuo. The residue obtained was purified by column chromatography (petroleum ether: EtOAc, 400:1 to 4:3) to give the title compound as a brown solid (300 mg, 40%).

LC-MS: m/z 368.2 [M+H]$^+$ 390.2 [M+Na]$^+$

4-Fluoro-3-[[5-(3-fluorophenyl)-2,3-dimethyl-phenyl]methylamino]-2-methyl-phenol

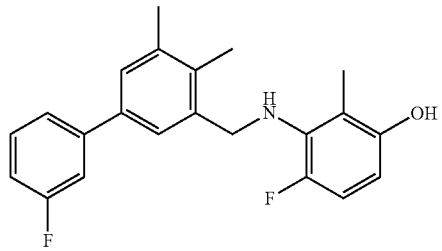

To a solution of N-(6-fluoro-3-hydroxy-2-methyl-phenyl)-5-(3-fluorophenyl)-2,3-dimethyl-benzamide (290 mg, 0.78 mmol, 1.0 eq) in THF (10 mL) was added a solution of $BH_3$ (1M in THF, 5 mL, 5.0 mmol, 6.4 eq) under nitrogen. The mixture was heated at 60° C. overnight then the reaction quenched by addition of methanol. The mixture was evaporated in vacuo and the residue obtained purified by column chromatography (petroleum ether:EtOAc, 400:1 to 20:1) to give the title compound as a pale red oil (230 mg, 85%).

LC-MS: m/z 376.1 [M+Na]$^+$

Isopropyl 2-[4-fluoro-3-[[5-(3-fluorophenyl)-2,3-dimethyl-phenyl]methylamino]-2-methyl-phenoxy]acetate (II(ax))

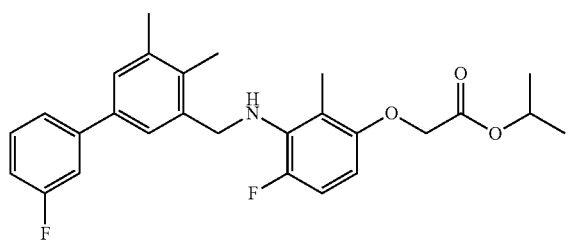

To a solution of 4-fluoro-3-[[5-(3-fluorophenyl)-2,3-dimethyl-phenyl]methylamino]-2-methyl-phenol (230 mg, 0.65 mmol, 1.0 eq) in DMF (5 mL) was added $Cs_2CO_3$ (420 mg, 1.3 mmol, 2.0 eq) and isopropyl 2-bromoacetate (140 mg, 0.78 mmol, 1.2 eq). The reaction was stirred at room temperature for 1 h then water and EtOAc were added. The aqueous layer was extracted with EtOAc and the combined organic extracts were dried ($Na_2SO_4$), filtered and evaporated in vacuo. The residue obtained was purified by column chromatography (petroleum ether:EtOAc, 400:1 to 40:7) to give the title compound as a colorless oil (180 mg, 62%).

LC-MS: m/z 454.2 [M+H]$^+$ 476.2 [M+Na]$^+$ $^1$H NMR (400 MHz, DMSO) δ 7.50-7.42 (m, 2H), 7.42-7.32 (m, 3H), 7.17-7.10 (m, 1H), 6.80 (dd, J=12.3, 9.0 Hz, 1H), 6.25 (dd, J=9.0, 3.6 Hz, 1H), 5.00-4.89 (m, 1H), 4.89-4.82 (m, 1H), 4.64 (s, 2H), 4.40 (d, J=6.3 Hz, 2H), 2.31 (s, 3H), 2.21 (s, 3H), 2.12 (s, 3H), 1.17 (d, J=6.2 Hz, 6H).

2-[4-fluoro-3-[[5-(3-fluorophenyl)-2,3-dimethyl-phenyl]methylamino]-2-methyl-phenoxy]acetic acid (I(at))

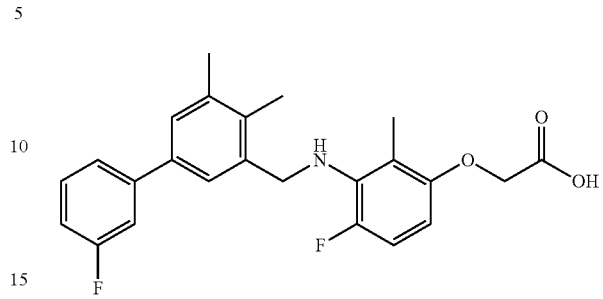

To a solution of isopropyl 2-[4-fluoro-3-[[5-(3-fluorophenyl)-2,3-dimethyl-phenyl]methylamino]-2-methyl-phenoxy]acetate (80 mg, 0.17 mmol, 1.0 eq) in a mixture of THF (5 mL) and MeOH (5 mL) was added NaOH (2M aqueous solution, 5 mL, 10 mmol). The reaction was stirred for 3 h then the organic solvent was removed under reduced pressure. The remaining aqueous solution was adjusted to pH 5 with diluted HCl and the mixture extracted with EtOAc. The combined organic extracts were dried ($Na_2SO_4$), filtered and evaporated in vacuo. The residue obtained was purified by column chromatography ($CH_2Cl_2$:MeOH, 400:1 to 4:1) to give the title compound as a white solid (74 mg, 97%).

LC-MS: m/z 410.2 [M−H]$^-$ $^1$H NMR (400 MHz, DMSO) δ 7.52 (s, 1H), 7.50-7.35 (m, 4H), 7.14 (app t, J=7.7 Hz, 1H), 6.97-6.88 (m, 1H), 6.48 (dd, J=8.9, 3.3 Hz, 1H), 4.63 (s, 2H), 4.46 (s, 2H), 2.29 (s, 3H), 2.15 (s, 3H), 2.13 (s, 3H).

Example 61

Compound I(au) Synthesized According to Scheme 3

2-[3-[(2,3-dimethyl-5-phenyl-phenyl)methylamino]-2,4-difluoro-phenoxy]acetic acid (I(au))

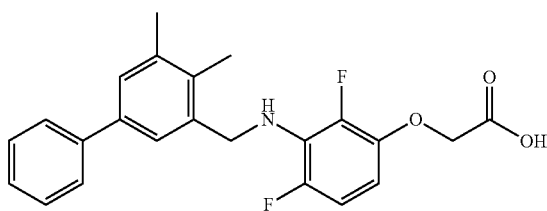 [SMILES: Cc1cc(-c2ccccc2)cc(CNc2c(F)ccc(OCC(=O)O)c2F)c1C]

2,3-Dimethyl-5-phenyl-benzoic acid (III(u))

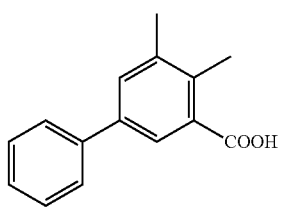 [SMILES: Cc1cc(-c2ccccc2)cc(C(=O)O)c1C]

To a solution of 5-bromo-2,3-dimethyl-benzoic acid (690 mg, 3.0 mmol, 1.0 eq), phenylboronic acid (404 mg, 3.3 mmol, 1.1 eq) and Na$_2$CO$_3$ (958 mg, 9.0 mmol, 3.0 eq) in a mixture of EtOH (5 mL), DMF (20 mL) and water (5 mL) was added Pd(PPh$_3$)$_4$ (0.17 g, 0.15 mmol, 0.05 eq). The reaction was heated at 100° C. overnight then diluted with EtOAc and filtered through celite. The aqueous layer was acidified to pH 4-5 with diluted HCl and extracted with EtOAc. The combined organic extracts were washed with water and brine, dried (Na$_2$SO$_4$), filtered and evaporated in vacuo. The residue obtained was purified by column chromatography (petroleum ether:EtOAc, 10:1 then CH$_2$Cl$_2$:MeOH, 400:0 to 20:1) to give the title compound as a white solid (315 mg, 46%).

LC-MS: m/z 225.1 [M−H]$^-$

N-(2,6-Difluoro-3-hydroxy-phenyl)-2,3-dimethyl-5-phenyl-benzamide

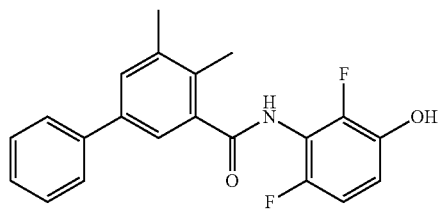 [SMILES: Cc1cc(-c2ccccc2)cc(C(=O)Nc2c(F)ccc(O)c2F)c1C]

To a solution of 2,3-dimethyl-5-phenyl-benzoic acid (315 mg, 1.4 mmol, 1.1 eq) in CH$_2$Cl$_2$ (10 mL) was added oxalyl chloride (530 mg, 4.2 mmol, 3.3 eq) at 0° C. The reaction was allowed to warm to room temperature and stirred for 1 h. The solvent and excess reagent were removed under reduced pressure and the residue that remained dissolved in THF (10 mL) and added dropwise to a mixture of 3-amino-2,4-difluoro-phenol (intermediate X(a)) (184 mg, 1.3 mmol, 1.0 eq) and NaHCO$_3$ (532 mg, 6.3 mmol, 5.0 eq) in THF (8 mL) at 0° C. The reaction was stirred at room temperature for 2 h, water was added and the aqueous layer was extracted with EtOAc. The combined organic extracts were washed with water and brine, dried (Na$_2$SO$_4$), filtered, and evaporated in vacuo. The residue was purified by column chromatography (petroleum ether:EtOAc, 20:1 to 10:1, then CH$_2$Cl$_2$:MeOH, 500:1 to 100:1) to give the title compound as a yellow solid (220 mg, 49%).

LC-MS: m/z 354.1[M+H]$^+$ 376.1 [M+Na]$^+$

3-[(2,3-Dimethyl-5-phenyl-phenyl)methylamino]-2,4-difluoro-phenol

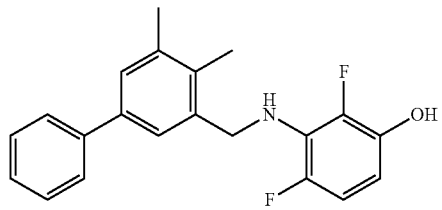 [SMILES: Cc1cc(-c2ccccc2)cc(CNc2c(F)ccc(O)c2F)c1C]

To a solution of N-(2,6-difluoro-3-hydroxy-phenyl)-2,3-dimethyl-5-phenyl-benzamide (210 mg, 0.6 mmol, 1.0 eq) in THF (4 mL) at 0° C. was added dropwise a solution of BH$_3$ (1M in THF, 3.6 mL, 3.6 mmol, 6.0 eq). The reaction mixture was heated at 60° C. for 5 h, then cooled and quenched by addition of water. The aqueous layer was extracted with EtOAc and the combined organic extracts were washed with water and brine, dried (Na$_2$SO$_4$), filtered and evaporated in vacuo. The residue obtained was purified by column chromatography (petroleum ether:EtOAc, 100:0 to 10:1) to give the title compound as colorless oil (120 mg, 60%).

LC-MS: m/z 362.1 [M+Na]$^+$

Isopropyl 2-[3-[(2,3-dimethyl-5-phenyl-phenyl)methylamino]-2,4-difluoro-phenoxy]acetate (II(ay))

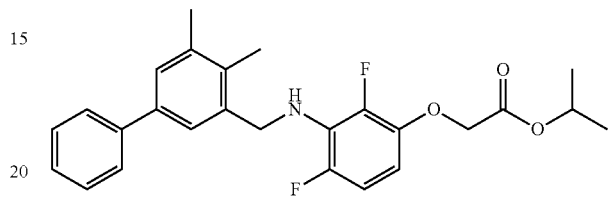

To a solution of 3-[(2,3-dimethyl-5-phenyl-phenyl)methylamino]-2,4-difluoro-phenol (120 mg, 0.4 mmol, 1.0 eq) in acetone (4 mL) was added Cs$_2$CO$_3$ (173 mg, 0.5 mmol, 1.5 eq) and the reaction was stirred at room temperature for 30 min. Isopropyl bromoacetate (76 mg, 0.42 mmol, 1.2 eq) was added and the reaction was stirred at room temperature for 1 h. Water was added and the aqueous layer was extracted with EtOAc. The combined organic extracts were washed with water and brine, dried (Na$_2$SO$_4$), filtered and evaporated in vacuo. The residue obtained was purified by column chromatography (petroleum ether:EtOAc, 20:1) to give the title compound as a colorless oil (117 mg, 75%).

LC-MS: m/z 462.2 [M+Na]$^+$ $^1$H NMR (400 MHz, DMSO) δ 7.55-7.49 (m, 2H), 7.45-7.37 (m, 3H), 7.36-7.27 (m, 2H), 6.80 (ddd, J=11.6, 9.2, 2.1 Hz, 1H), 6.30 (td, J=9.1, 4.5 Hz, 1H), 5.65 (br s, 1H), 5.00-4.88 (m, 1H), 4.70 (s, 2H), 4.48 (d, J=6.2 Hz, 2H), 2.31 (s, 3H), 2.21 (s, 3H), 1.15 (d, J=6.3 Hz, 6H).

2-[3-[(2,3-Dimethyl-5-phenyl-phenyl)methylamino]-2,4-difluoro-phenoxy]acetic acid (I(au))

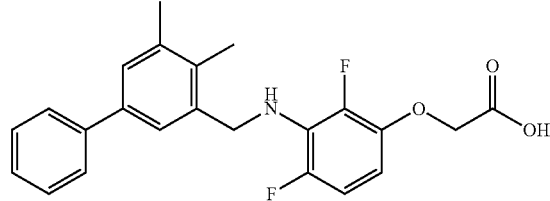 [SMILES: Cc1cc(-c2ccccc2)cc(CNc2c(F)ccc(OCC(=O)O)c2F)c1C]

To a solution of isopropyl 2-[3-[(2,3-dimethyl-5-phenyl-phenyl)methylamino]-2,4-difluoro-phenoxy]acetate (110 mg, 0.25 mmol, 1.0 eq) in THF (4 mL) was added LiOH (52 mg, 1.2 mmol, 5 eq) and water (3 mL) and the reaction mixture stirred at room temperature for 1 h. The THF was removed under reduced pressure and the remaining aqueous solution was adjusted to pH 4-5 by addition of 1M HCl. The mixture was extracted with EtOAc and the combined organic extracts washed with water and brine, dried (Na$_2$SO$_4$), filtered and evaporated in vacuo to give the title compound as a yellow oil (80 mg, 80%).

LC-MS: m/z 398.2 [M+H]$^+$ 420.1 [M+Na]$^+$ $^1$H NMR (400 MHz, DMSO) δ 13.02 (br s, 1H), 7.57-7.49 (m, 2H), 7.47-7.38 (m, 3H), 7.37-7.27 (m, 2H), 6.81 (ddd, J=11.5, 9.3, 2.0 Hz, 1H), 6.31 (td, J=9.1, 4.5 Hz, 1H), 5.62 (br s, 1H), 4.65 (s, 2H), 4.49 (d, J=6.1 Hz, 2H), 2.32 (s, 3H), 2.22 (s, 3H).

The following compounds according to the invention were made according to scheme 3 in a similar manner to the compounds described above.

22° C. with 0.5 nM [$^3$H]PGE$_2$ ligand in the absence or presence of the test compound in a buffer containing 10 mM MES/KOH (pH 6.0), 10 mM MgCl$_2$ and 1 mM EDTA.

TABLE 3

| Compound number | Structure | LC-MS $^1$H NMR |
|---|---|---|
| I(av) | 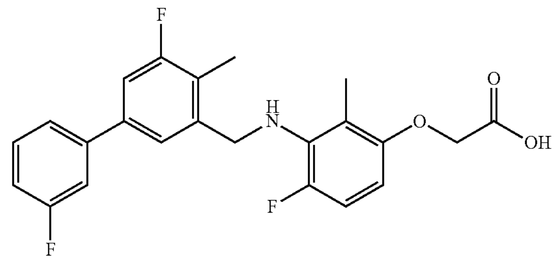 | m/z 416.2 [M + H]$^+$ $^1$H NMR (400 MHz, DMSO) δ 7.54-7.37 (m, 5H), 7.23-7.14 (m, 1H), 6.80 (dd, J = 12.3, 9.0 Hz, 1H), 6.26 (dd, J = 9.0, 3.6 Hz, 1H), 5.01 (br s, 1H), 4.57 (s, 2H), 4.40 (s, 2H), 2.21 (d, J = 1.3 Hz, 3H), 2.12 (s, 3H). |
| I(aw) | 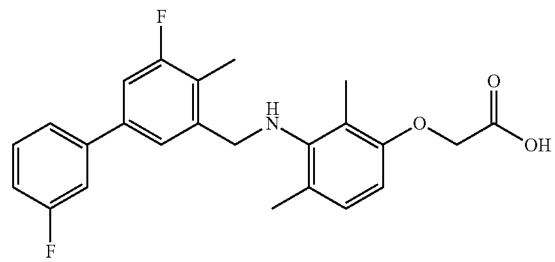 [SMILES: Cc1ccc(OCC(=O)O)c(C)c1NCc1cc(-c2cccc(F)c2)cc(F)c1C] | m/z 412.2 [M + H]$^+$ $^1$H NMR (400 MHz, DMSO) δ 7.64 (d, J = 1.4 Hz, 1H), 7.56-7.47 (m, 3H), 7.44 (dd, J = 11.0, 1.6 Hz, 1H), 7.25-7.16 (m, 1H), 6.81 (d, J = 8.4 Hz, 1H), 6.35 (d, J = 8.3 Hz, 1H), 4.24 (s, 2H), 4.07 (s, 2H), 2.18 (d, J = 1.5 Hz, 3H), 2.10 (s, 6H). |
| II(az) | 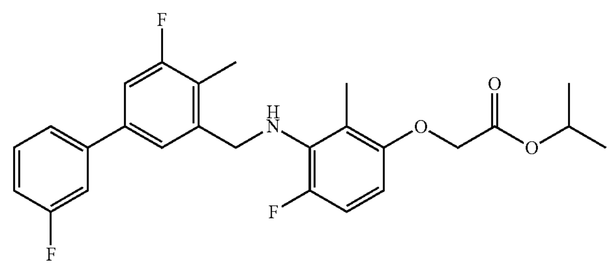 | m/z 458.2 [M + H]$^+$ 480.2 [M + Na]$^+$ $^1$H NMR (400 MHz, DMSO) δ 7.53-7.36 (m, 5H), 7.18 (td, J = 7.9, 1.3 Hz, 1H), 6.80 (dd, J = 12.3, 9.0 Hz, 1H), 6.26 (dd, J = 9.0, 3.7 Hz, 1H), 5.08-5.00 (m, 1H), 5.00-4.89 (m, 1H), 4.64 (s, 2H), 4.41 (d, J = 6.8 Hz, 2H), 2.21 (d, J = 1.6 Hz, 3H), 2.12 (s, 3H), 1.16 (d, J = 6.3 Hz, 6H). |
| II(ba) | 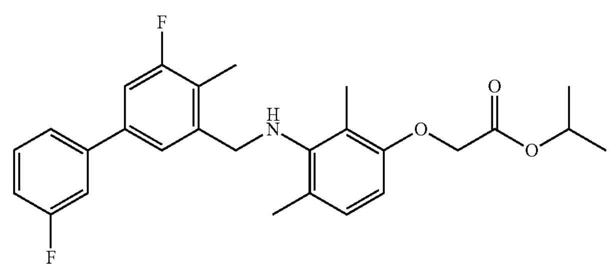 | m/z 454.2 [M + H]$^+$ 476.2 [M + Na]$^+$ $^1$H NMR (400 MHz, CDCl$_3$) δ 7.42 (br s, 1H), 7.41-7.36 (m, 1H), 7.35-7.30 (m, 1H), 7.25-7.16 (m, 2H), 7.08-7.00 (m, 1H), 6.93 (d, J = 8.3 Hz, 1H), 6.40 (d, J = 8.3 Hz, 1H), 5.14 (hept, J = 6.2 Hz, 1H), 4.58 (s, 2H), 4.15 (s, 2H), 2.28 (d, J = 1.9 Hz, 3H), 2.27 (s, 3H), 2.19 (s, 3H), 1.28 (d, J = 6.3 Hz, 6H). |

Tests

Compounds according to the table 4 were subjected to pharmacological tests for determining their agonist effect on EP2 receptors. Tests involved measuring the in vitro activity of the compounds of the invention on EP2 receptors.

Test 1: Binding Assays

Test 1.1: Human Prostanoid EP$_4$ Receptor Binding Assay

Protocol

Cell membrane homogenate from Human embryonic kidney HEK-293(T) cells expressing recombinant human prostanoid EP$_4$ receptor was used to perform Prostanoid receptor radioligand binding assays.

The competition reaction was initiated by incubation of membrane protein homogenate (20 μg protein) for 120 min at Non-specific binding was determined in the presence of 10 μM PGE$_2$ (the corresponding non-radioactive prostanoid). Affinity of the compound binding to hEP4 receptor was measured by displacement of the radiolabeled ligand in the presence of varying doses of tested compound.

Incubations were terminated by rapid filtration under vacuum through glass fiber filters (GF/B, Packard) presoaked with 0.3% PEI and washed several times with ice-cold 50 mM Tris-HCl using a 96-sample cell harvester (Unifilter, Packard).

The filters were dried and the residual radioactivity bound to the individual filters determined with addition of scintillation cocktail (Microscint 0, Packard) by a scintillation counter (Topcount, Packard).

The results were expressed as a percent inhibition of the control radioligand specific binding.

The standard reference compound PGE$_2$, was tested in at several concentrations to obtain a competition curve to determined IC$_{50}$.

Analysis and Expression of Results

The specific ligand binding to the receptors is defined as the difference between the total binding and the nonspecific binding determined in the presence of an excess of unlabelled ligand. The results are expressed as a percent of control specific binding ((measured specific binding/control specific binding)×100) obtained in the presence of the test compounds. The IC50 values (concentration causing a half-maximal inhibition of control specific binding) and Hill coefficients (nH) were determined by non-linear regression analysis of the competition curves generated with mean replicate values using Hill equation curve fitting (Y=D+[(A−D)/(1+(C/C50)nH)], where Y=specific binding, D=minimum specific binding, A=maximum specific binding, C=compound concentration, C50=IC50, and nH=slope factor). This analysis was performed using a software developed at Cerep (Hill software) and validated by comparison with data generated by the commercial software SigmaPlot® 4.0 for Windows® (© 1997 by SPSS Inc.). The inhibition constants (Ki) were calculated using the Cheng Prusoff equation (Ki=IC50/(1+(L/KD)), where L=concentration of radioligand in the assay, and KD=affinity of the radioligand for the receptor). A scatchard plot is used to determine the Kd.

Test 1.2: Human Prostanoid EP$_2$ Receptor Cellular Functional Assay

Protocol

Human CHO cells expressing the recombinant human prostanoid EP$_2$ receptor were suspended in assay medium (HBSS buffer (Invitrogen) containing 20 mM HEPES (pH7.4) and 500 μM isobutyl-methylxanthine IBMX) and plated out to yield approximately 1×10$^4$ cells/well in a 96-well. Following this, cells were incubated with agonists for 30 min in the presence of the test compounds. For stimulated control measurements, separate assay wells contain 10 μM PGE$_2$ (control specific agonist). All incubations were carried out at 37° C. in a 5% CO$_2$ atmosphere. Following incubation, the amount of cAMP in each well was determined by HTRF method. The cells are lysed and the fluorescence acceptor (D2-labeled cAMP) and fluorescence donor (anti-cAMP antibody labeled with europium cryptate) are added. After 60 min at room temperature, the fluorescence transfer is measured at λ ex=337 nm and λ em=620 and 665 nm using a microplate reader (Rubystar, BMG).

The cAMP concentration is determined by dividing the signal measured at 665 nm by that measured at 620 nm (ratio).

The standard reference agonist PGE$_2$ was tested at several concentrations to generate a concentration-response curve to determined EC$_{50}$.

Analysis and Expression of Results

The results are expressed as a percent of control specific agonist response ((measured specific response/control specific agonist response)×100) obtained in the presence of the test compounds. The EC50 values (concentration producing a half-maximal specific response) were determined by non-linear regression analysis of the concentration-response curves generated with mean replicate values using Hill equation curve fitting (Y=D+[(A−D)/(1+(C/C50)nH)], where Y=specific response, D=minimum specific response, A=maximum specific response, C=compound concentration, and C50=EC50 and nH=slope factor). This analysis was performed using a software developed at Cerep (Hill software) and validated by comparison with data generated by the commercial software SigmaPlot® 4.0 for Windows® (© 1997 by SPSS Inc.).

TABLE 4

| Compound number | In vitro functional assay EP2 (h) EC$_{50}$ (nM) | % response | In vitro potency EP4 (h) IC$_{50}$ (nM) |
|---|---|---|---|
| I(a) | 110 | 74% | NC |
| I(b) | 28 | 82% | NC |
| I(c) | 69 | 66% | NC |
| I(d) | 35 | 74% | NC |
| I(e) | 160 | 65% | NC |
| I(f) | 160 | 61% | NC |
| I(g) | 55 | 80% | NC |
| I(h) | 13 | 88% | NC |
| I(i) | 99 | 73% | NC |
| I(j) | 26 | 80% | NC |
| I(k) | 73 | 77% | >300 |
| I(l) | 24 | 76% | NC |
| I(m) | 10 | 89% | NC |
| I(n) | 52 | 86% | NC |
| I(o) | 34 | 74% | NC |
| I(p) | 17 | 70% | NC |
| I(q) | 18 | 70% | NC |
| I(r) | 45 | 78% | >300 |
| I(s) | 17 | 72% | NC |
| I(t) | 17 | 73% | NC |
| I(u) | 9 | 78% | NC |
| I(v) | 2 | 85% | NC |
| I(w) | 14 | 40% | NC |
| I(x) | 27 | 45% | NC |
| I(y) | 130 | 62% | NC |
| I(z) | 4 | 53% | NC |
| I(aa) | 3 | 97% | >300 |
| I(ab) | 50 | 105% | NC |
| I(ac) | 18 | 117% | NC |
| I(ad) | 2 | 101% | >300 |
| I(ae) | 3 | 83% | NC |
| I(af) | 5 | 70% | NC |
| I(ag) | <1 | 85% | >300 |
| I(ah) | 8 | 74% | NC |
| I(ai) | 35 | 80% | NC |
| I(aj) | 7 | 79% | NC |
| I(ak) | 2 | 113% | >300 |
| I(al) | 0.9 | 70% | >300 |
| I(am) | 3 | 87% | NC |
| I(an) | 9 | 91% | NC |
| I(ao) | 1 | 76% | NC |
| I(ap) | 3 | 89% | NC |
| I(aq) | 2 | 31% | NC |
| I(ar) | 8 | 130% | NC |
| I(as) | 11 | 107% | NC |
| I(at) | 6 | 91% | >300 |
| I(au) | 15 | 81% | NC |
| I(av) | 5 | 97% | NC |
| I(aw) | 3 | 80% | >300 |
| II(d) | >300 | 44% | |
| I(as) (+ isomer)* | 18 | 124% | NC |
| CP-544326 | 46 | 72% | NC |

*Isolated by prep chiral HPLC using the following conditions: Column: Chiralcel OJ-H 5 μm; Dimension: 2 × 25 cm; Mobile phase: CO2 90% MeOH 10%; Flow rate 55 ml/min; Pressure = 100 bars; Column = 35° C.; Detection: 254 nm. [α]$_D$ = +171 +/− 3
NC: not calculable CP-544326 corresponds to the acid of taprenepag.

Taprenepag is a prodrug which was until recently in Phase II for the treatment of glaucoma.

It is apparent from the results above that compounds above are very potent and very selective EP2 agonists.

Test 2: Solubility

Solubility of the test materials was evaluated on n=1 trial, following the procedure below:

2.5 mg of each compound for solubility testing were dissolved in 5 mL of the diluent, an initial concentration of 500 ug/mL. The mixture was first vortexed for 15 seconds to allow a good wetting of the API, then sonicated for 5 minutes to promote solubilisation. The vortex/sonication cycle was repeated 3 times. The suspension was stirred at room temperature using a magnetic stirrer at 300 rpm. This mixture is observed at 4 h, 24 h and 48 h to determine if the test compound has dissolved. At each time point if the compound is completely solubilised a further 5 mg of the test compound is added and the process repeated.

When no more test compound will dissolve in the diluent, an aliquot of 0.5 mL of the suspension was withdrawn and centrifuged 3×2 min at 13400 rpm. The supernatant for HPLC quantification was filtered using 0.2 µm Pall Aerodisc Nylon 13 mm membrane and quantified by comparing to the calibration curve, using the method: column: Nucleodur C18 ISIS 3 µm 4.6×125 mm, Mobile Phase (CH3COOH 0.05% in H2O and ACN), Flow rate: 1 ml/min, Wavelength: λ=240 nm (IIa and IIc) or 240 nM (IId), Injected volume: 10 µl, Gradient of concentration: from 30% B to 100% B in 6 min.

TABLE 5

| Compound | Solubility at equilibrium (µg/mL) |
|---|---|
| PF-04217329 | 542 |
| II(a) | 8117 |
| II(c) | 6780 |
| II(d) | 711 |

PF-04217329 corresponds to the prodrug: taprenepag.

It is apparent from the results above that prodrugs of the invention are more soluble than taprenepag.

Test 3: In Vivo Activity of Compounds According to the Invention:
Test 3.1: Monkey
Laser-Induced Hypertensive Cynomolgus Monkey Ten adult female cynomolgus monkeys, each weighing 3-5 kg, in which glaucoma had been induced unilaterally by diode laser photocoagulation of the mid-trabecular meshwork, were used in this study.

Intraocular pressure (IOP) was measured at 0 hr (before drug administration) and then hourly until 6 hrs after drug administration on one baseline day, one vehicle-treatment day, and treatment days 1, 3, and 5 with 0.01% of compound II(d).

Compound II(d) was tested in two groups of 4 monkeys for a total of 8 monkeys. Following one baseline day (untreated) and one vehicle-treatment day (50 µl (25 µl×2), drop of vehicle to the glaucomatous eye at 9:30 (a 50 µl drop (25 µl×2) of compound (II(d)) were topically applied to the glaucomatous eye only once daily at 9:30 am for 5 consecutive days.

Slit-lamp examination for the detection of aqueous humor flare and cells was performed in a dark room before drug administration and at 1, 3 and 5 hrs after dosing on baseline day and at the same times on treatment days 1, 3 and 5.

Two-tailed paired and unpaired t test and the ANOVA test were used for statistical analysis.

Results are presented in FIG. 1, and show that the overall IOP is reduced by 22% after a daily administration over 5 days.

It is therefore apparent that the compounds of the invention are potent and efficacious agonists on EP2 receptors and are selective over EP4 receptors.

It is therefore apparent that the compounds of the invention have an agonist activity for EP2 receptors. The compounds according to the invention can therefore be used for preparing medicaments, especially medicaments which are agonists of EP2 receptors.

Accordingly, in another of its aspects, the invention provides medicaments which comprise a prodrug of formula (II), or a drug of formula (I), or an addition salt thereof with a pharmaceutically acceptable organic base or inorganic cation, or else a co-crystal or a solvate (to be adapted on a case-by-case basis) of the compound of formula (I) or (II).

These medicaments are employed therapeutically, especially in the treatment [and the prevention] of Glaucoma, or ocular hypertension. Glaucoma, according to the present invention, as to be understood as absolute glaucoma, congenital glaucoma, traumatic glaucoma due to birth injury, but also primary open-angle glaucoma, including capsular with pseudoexfoliation of lens, chronic simple, low-tension, pigmentary.

Glaucoma also includes Primary angle-closure glaucoma, which comprises both primary and residual stage of angle closure glaucoma, in its acute, chronic or intermittent forms. It also includes Glaucoma secondary to eye trauma, Glaucoma secondary to eye inflammation, Glaucoma secondary to other eye disorders, Glaucoma secondary to drugs, other Glaucoma as well as unspecified Glaucoma.

According to another of its aspects, the present invention relates to pharmaceutical compositions comprising as active principle a compound according to the invention. In an aspect, the compound according to the invention is a compound of formula (I) or one of its prodrugs. In another aspect, the compounds according to the invention are compounds of formula II. These pharmaceutical compositions comprise an effective dose of at least one compound according to the invention, or one of its prodrugs, and also at least one pharmaceutically acceptable excipient.

The said excipients are selected, in accordance with the pharmaceutical form and method of administration desired, from the customary excipients, which are known to a person skilled in the art.

In the pharmaceutical compositions of the present invention for oral, sublingual, subcutaneous, intramuscular, intravenous, topical, local, intra-tracheal, intranasal, transdermal, intraocular or rectal administration, the active principle of formula (I) above, or one of its prodrugs, may be administered in a unit administration form, in a mixture with conventional pharmaceutical excipients, to animals and to human beings for the prophylaxis and/or treatment of the above disorders or diseases.

The unit administration appropriate forms include oral forms such as tablets, soft or hard gel capsules, powders, granules and oral solutions or suspensions, sublingual, buccal, intratracheal, intra-ocular and intranasal administration forms, forms for inhalative, topical, transdermal, subcutaneous, intra-muscular or intravenous administration, rectal administration forms and implants. For topical application it is possible to use the compounds or their prodrugs according to the invention in creams, gels, ointments, eye drops or lotions.

As an example, a unit administration form of a compound according to the invention in eye drop form may comprise the following components:
Compound according to the invention: 1% w/v
Dimethyl sufoxide+PVP K-30: 1% w/v
Benzalkonium chloride: 0.01-0.02% w/v
Ededate disodium: 0.005-0.1% w/v
Boric acid: quantity sufficient (QS) to buffer capacity
Sodium borate: NMT 0.5%
Sodium chloride: QS to osmolality 308 mOsm/kg
Polysorbate 80 0.1-3%
HPMC 4000 cps 0.45-1%
HCl/NaOH QS to pH 5-6
Purified water QS to required volume Drugs and prodrugs according to the present invention can also be given in combination, and in particular, as a non limitative list, in combination with beta-blockers, prostaglandins, sympathomimetic collyres, inhibitors of carbonic anhydrase, or parasympathomimetic collyres, for example.

Suitable beta blockers include timolol, Alprenolol, Bucindolol, Carteolol, Carvedilol, Labetalol, Nadolol, Oxprenolol, Penbutolol, Pindolol, Propranolol, Sotalol, Eucommia bark (herb), Acebutolol, Atenolol, Betaxolol, Bisoprolol, Celiprolol, Esmolol, Metoprolol, Nebivolol, Butaxamine, ICI-118, 551, or SR 59230A.

Suitable prostaglandins include, for example latanoprost, bimatoprost, travoprost or tafluprost.

Suitable sympathomimetic eye-drops include for example brimonidine (Alphagan), apraclonidine (Iopidine), dipivefrin (Propine, AKPro), and epinephrine (Eppy, Glaucon, Epinal, Epifrin).

Suitable inhibitors of carbonic anhydrase include Acetazolamide, Methazolamide, Dorzolamide, or Topiramate, for example.

Suitable parasympathomimetic collyres include pilocarpine.

The present invention, according to another of its aspects, also provides a method of treating the pathologies indicated above, which comprises administering to a patient an effective dose of a compound according to the invention, or one of its prodrugs.

The invention claimed is:

1. A compound of formula (I) or formula (II), wherein the compound of formula (II) is a prodrug of the compound of formula (I):

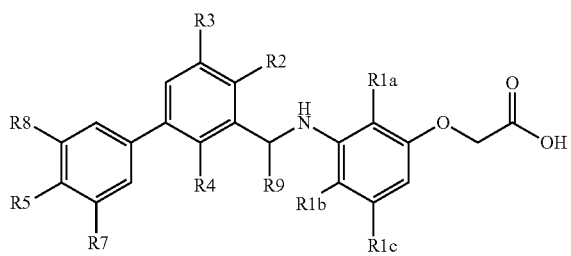

(I)

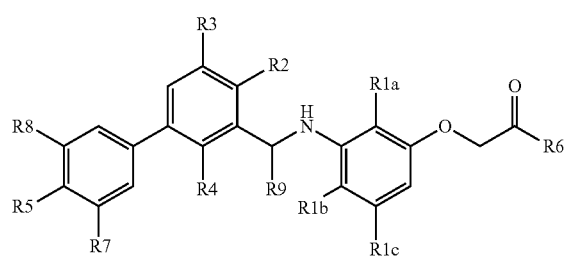

(II)

wherein
R1a represents H, a halogen, a $(C_1-C_6)$alkyl or a CN;
R1b represents H, a halogen or a $(C_1-C_6)$alkyl;
R1c represents H or a $(C_1-C_6)$alkyl;
R2 represents H, a halogen, an OH, an O—$(C_1-C_6)$alkyl or a $(C_1-C_6)$alkyl;
R3 represents H, a halogen, a $(C_1-C_6)$alkyl, an OH, an O—$(C_1-C_6)$alkyl, a $CONH_2$ or a CN;
R4 represents H, a halogen or a $(C_1-C_6)$alkyl;
R5 represents H or F;
R6 represents an O—$(C_1-C_6)$alkyl, an O—$(C_1-C_6)$alkyl-heterocycloalkyl, an $NH_2$, an NH—$(C_1-C_6)$alkyl, an O—$(C_1-C_6)$alkyl optionally substituted by one to three hydroxyl groups, or an O—$(C_1-C_6)$alkyl—O—CO($C_1$-$C_6$)alkyl);
R7 represents H or F;
R8 represents H or F; and
R9 represents H or a $(C_1-C_6)$alkyl,
or an enantiomer thereof.

2. The compound according to claim 1, in which compounds are not:
2-[2,4-difluoro-3-[[2-fluoro-3-(3-fluorophenyl)phenyl]methylamino]phenoxy]acetic acid;
2-[2,4-difluoro-3-[[3-(3-fluorophenyl)-2-methyl-phenyl]methylamino]phenoxy]acetic acid;
2-[2-fluoro-3-[[2-fluoro-5-(3-fluorophenyl)phenyl]methylamino]phenoxy]acetic acid;
2-[4-fluoro-3-[[2-fluoro-5-(3-fluorophenyl)phenyl]methylamino]phenoxy]acetic acid;
2-[2,4-difluoro-3-[[5-(3-fluorophenyl)-2-methoxy-phenyl]methylamino]phenoxy]acetic acid;
2-[2,4-difluoro-3-[[5-(3-fluorophenyl)-2-hydroxy-phenyl]methylamino]phenoxy]acetic acid;
2-[2,4-difluoro-3-[[3-(3-fluorophenyl)-2,5-dimethyl-phenyl]methylamino]phenoxy]acetic acid;
2-[2,4-difluoro-3-[[5-fluoro-3-(3-fluorophenyl)-2-methylphenyl]methylamino]phenoxy]acetic acid;
2-[2,4-difluoro-3-[[2-fluoro-3-(3-fluorophenyl)-6-hydroxy-phenyl]methylamino]phenoxy]acetic acid;
2-[2,4-difluoro-3-[[2-fluoro-3-(3-fluorophenyl)-6-methoxy-phenyl]methylamino]phenoxy]acetic acid;
2-[2,4-difluoro-3-[[3-(3-fluorophenyl)-5-isopropyl-phenyl]methylamino]phenoxy]acetic acid;
2-[3-[[3-ethyl-5-(3-fluorophenyl)phenyl]methylamino]-2,4-difluoro-phenoxy]acetic acid;
2-[2-ethyl-4-fluoro-3-[[2-fluoro-5-(3-fluorophenyl)phenyl]methylamino]phenoxy]acetic acid;
2-[4-fluoro-3-[[2-fluoro-5-(3-fluorophenyl)phenyl]methylamino]-2-isopropyl-phenoxy]acetic acid;
2-[2,4-difluoro-3-[[2-fluoro-5-(4-fluorophenyl)phenyl]methylamino]phenoxy]acetic acid;
2-[2,4-difluoro-3-[(2-fluoro-5-phenyl-phenyl)methylamino]phenoxy]acetic acid;
2-[2,4-difluoro-3-[[2-fluoro-3-(3-fluorophenyl)-6-methyl-phenyl]methylamino]phenoxy]acetic acid;
2-[3-[[5-(3-fluorophenyl)-2,3-dimethyl-phenyl]methylamino]phenoxy]acetic acid;
2-[4-fluoro-3-[[5-(3-fluorophenyl)-2,3-dimethyl-phenyl]methylamino]phenoxy]acetic acid;
2-[3-[[2-fluoro-5-(3-fluorophenyl)-3-methyl-phenyl]methylamino]phenoxy]acetic acid;
or an enantiomer thereof.

3. The compound according to claim 1, selected from the group consisting of:
I(ai): 2-[4-fluoro-3-[[2-fluoro-3-(3-fluorophenyl)-5-methyl-phenyl]methylamino]-2-methyl-phenoxy]acetic acid;
I(aj): 2-[3-[[3-(3-fluorophenyl)-5-methyl-phenyl]methylamino]-2,4-dimethyl-phenoxy]acetic acid;
I(ak): 2-[3-[[5-(3-fluorophenyl)-2,3-dimethyl-phenyl]methylamino]-2,4-dimethyl-phenoxy]acetic acid;
I(al): 2-[3-[[5-(3-fluorophenyl)-2-methoxy-3-methyl-phenyl]methylamino]-2,4-dimethyl-phenoxy]acetic acid;
I(am): 2-[3-[[2-Fluoro-3-(3-fluorophenyl)-5-methyl-phenyl]methylamino]-2,4-dimethyl-phenoxy]acetic acid;

I(an): 2-[2-cyano-4-fluoro-3-[[2-fluoro-5-(3-fluorophenyl)phenyl]methylamino]phenoxy]acetic acid;
I(ao): 2-[3-[[3-(3-fluorophenyl)-5-hydroxy-phenyl]methylamino]-2,4-dimethyl-phenoxy]acetic acid;
I(ap): 2-[3-[[3-(3-fluorophenyl)-5-methoxy-phenyl]methylamino]-2,4-dimethyl-phenoxy]acetic acid;
I(aq): 2-[3-[[5-(3,4-difluorophenyl)-2,3-dimethyl-phenyl]methylamino]-2,4-difluoro-phenoxy]acetic acid;
I(ar): 2-[3-[[5-(3,5-difluorophenyl)-2,3-dimethyl-phenyl]methylamino]-2,4-difluoro-phenoxy]acetic acid;
I(as): 2-[2,4-difluoro-3-[1-[2-fluoro-5-(3-fluorophenyl)phenyl]ethylamino]phenoxy]acetic acid;
I(at): 2-[4-fluoro-3-[[5-(3-fluorophenyl)-2,3-dimethyl-phenyl]methylamino]-2-methyl-phenoxy]acetic acid;
I(au): 2-[3-[(2,3-dimethyl-5-phenyl-phenyl)methylamino]-2,4-difluoro-phenoxy]acetic acid;
I(av): 2-[4-fluoro-3-[[3-fluoro-5-(3-fluorophenyl)-2-methyl-phenyl]methylamino]-2-methyl-phenoxy]acetic acid; and
I(aw): 2-[3-[[3-fluoro-5-(3-fluorophenyl)-2-methyl-phenyl]methylamino]-2,4-dimethyl-phenoxy]acetic acid;
or an enantiomer thereof.

4. The compound according to claim 1, selected from the group consisting of:
I(h): 2-[2,4-difluoro-3-[[2-fluoro-5-(3-fluorophenyl)-3-methyl-phenyl]methylamino]phenoxy]acetic acid;
I(i): 2-[2-fluoro-3-[[2-fluoro-5-(3-fluorophenyl)phenyl]methylamino]-4-methyl-phenoxy]acetic acid;
I(j): 2-[3-[[2-fluoro-5-(3-fluorophenyl)phenyl]methylamino]-2,4-dimethyl-phenoxy]acetic acid;
I(k): 2-[4-chloro-2-fluoro-3-[[2-fluoro-5-(3-fluorophenyl)phenyl]methylamino]phenoxy]acetic acid;
I(l): 2-[3-[[2-chloro-5-(3-fluorophenyl)phenyl]methylamino]-2,4-difluoro-phenoxy]acetic acid;
I(m): 2-[4-fluoro-3-[[2-fluoro-5-(3-fluorophenyl)phenyl]methylamino]-2-methyl-phenoxy]acetic acid;
I(n): 2-[2,4-difluoro-3-[[3-fluoro-5-(3-fluorophenyl)phenyl]methylamino]phenoxy]acetic acid;
I(o): 2-[2-chloro-4-fluoro-3-[[2-fluoro-5-(3-fluorophenyl)phenyl]methylamino]phenoxy]acetic acid;
I(p): 2-[2,4-difluoro-3-[[3-(3-fluorophenyl)-5-hydroxy-phenyl]methylamino]phenoxy]acetic acid;
I(q): 2-[2,4-difluoro-3-[[3-(3-fluorophenyl)-5-methoxy-phenyl]methylamino]phenoxy]acetic acid;
I(r): 2-[2,4-dichloro-3-[[2-fluoro-5-(3-fluorophenyl)phenyl]methylamino]phenoxy]acetic acid;
I(s): 2-[3-[[2,6-difluoro-3-(3-fluorophenyl)phenyl]methylamino]-2,4-difluoro-phenoxy]acetic acid;
I(t): 2-[2,4-difluoro-3-[[5-(3-fluorophenyl)-2-methoxy-3-methyl-phenyl]methylamino]phenoxy]acetic acid;
I(u): 2-[2,4-difluoro-3-[[5-(3-fluorophenyl)-2-hydroxy-3-methyl-phenyl]methylamino]phenoxy]acetic acid;
I(v): 2-[2,4-difluoro-3-[[5-(3-fluorophenyl)-2,3-dimethyl-phenyl]methylamino]phenoxy]acetic acid;
I(w): 2-[3-[[5-(3,4-difluorophenyl)-2-fluoro-phenyl]methylamino]-2,4-difluoro-phenoxy]acetic acid;
I(x): 2-[3-[[3-cyano-5-(3-fluorophenyl)phenyl]methylamino]-2,4-difluoro-phenoxy]acetic acid;
I(y): 2-[2,4-difluoro-3-[[6-fluoro-3-(3-fluorophenyl)-2-methyl-phenyl]methylamino]phenoxy]acetic acid;
I(z): 2-[3-[[3-carbamoyl-5-(3-fluorophenyl)phenyl]methylamino]-2,4-difluoro-phenoxy]acetic acid;
I(aa): 2-[2,4-difluoro-3-[[3-fluoro-5-(3-fluorophenyl)-2-methyl-phenyl]methylamino]phenoxy]acetic acid;
I(ab): 2-[2,4-difluoro-3-[[2-fluoro-5-(3-fluorophenyl)phenyl]methylamino]-5-methyl-phenoxy]acetic acid;
I(ac): 2-[4-fluoro-3-[[2-fluoro-5-(3-fluorophenyl)phenyl]methylamino]-2,5-dimethyl-phenoxy]acetic acid;
I(ad): 2-[4-fluoro-3-[[2-fluoro-5-(3-fluorophenyl)-3-methyl-phenyl]methylamino]-2-methyl-phenoxy]acetic acid;
I(ae): 2-[4-fluoro-3-[[3-(3-fluorophenyl)-5-methyl-phenyl]methylamino]-2-methyl-phenoxy]acetic acid;
I(af): 2-[4-fluoro-3-[[5-(3-fluorophenyl)-2-methoxy-3-methyl-phenyl]methylamino]-2-methyl-phenoxy]acetic acid;
I(ag): 2-[3-[[2-fluoro-5-(3-fluorophenyl)-3-methyl-phenyl]methylamino]-2,4-dimethyl-phenoxy]acetic acid; and
I(ah): 2-[4-fluoro-3-[[3-(3-fluorophenyl)-5-hydroxy-phenyl]methylamino]-2-methyl-phenoxy]acetic acid.

5. The compound according to claim 1, selected from the group consisting of:
I(a): 2-[3-[[2-fluoro-5-(3-fluorophenyl)phenyl]methylamino]phenoxy]acetic acid;
I(b): 2-[2,4-difluoro-3-[[2-fluoro-5-(3-fluorophenyl)phenyl]methylamino]phenoxy]acetic acid;
I(c): 2-[2,4-difluoro-3-[[5-(3-fluorophenyl)-2-methyl-phenyl]methylamino]phenoxy]acetic acid;
I(d): 2-[2,4-difluoro-3-[[3-(3-fluorophenyl)-5-methyl-phenyl]methylamino]phenoxy]acetic acid;
I(e): 2-[2,4-difluoro-3-[[3-(3-fluorophenyl)phenyl]methylamino]phenoxy]acetic acid;
I(f): 2-[2,4-difluoro-3-[[2-fluoro-3-(3-fluorophenyl)-5-hydroxy-phenyl]methylamino]phenoxy]acetic acid; and
I(g): 2-[2,4-difluoro-3-[[2-fluoro-3-(3-fluorophenyl)-5-methylphenyl]methylamino]phenoxy]acetic acid.

6. The compound according to claim 1, where the compound is 2-[2,4-difluoro-3-[[2-fluoro-5-(3-fluorophenyl)phenyl]methylamino]phenoxy]acetic acid.

7. The compound according to claim 1, wherein the compound is a compound of formula (II):

or an enantiomer thereof.

8. The compound according to claim 7, selected from the group consisting of:
II(s): ethyl 2-[3-[[2-fluoro-5-(3-fluorophenyl)phenyl]methylamino]phenoxy]acetate;
II(t): ethyl 2-[2,4-difluoro-3-[[5-(3-fluorophenyl)-2-methyl-phenyl]methylamino]phenoxy]acetate;
II(u): ethyl 2-[2,4-difluoro-3-[[3-(3-fluorophenyl)phenyl]methylamino]phenoxy]acetate;
II(v): ethyl 2-[2,4-difluoro-3-[[2-fluoro-3-(3-fluorophenyl)-5-hydroxy-phenyl]methylamino]phenoxy]acetate;
II(w): ethyl 2-[2,4-difluoro-3-[[2-fluoro-3-(3-fluorophenyl)-5-methyl-phenyl]methylamino]phenoxy]acetate;
II(x): ethyl 2-[2-fluoro-3-[[2-fluoro-5-(3-fluorophenyl)phenyl]methylamino]-4-methyl-phenoxy]acetate;

II(y): ethyl 2-[4-fluoro-3-[[2-fluoro-5-(3-fluorophenyl)phenyl]methylamino]-2-methyl-phenoxy]acetate;

II(z): ethyl 2-[2,4-difluoro-3-[[3-fluoro-5-(3-fluorophenyl)phenyl]methylamino]phenoxy]acetate;

II(aa): ethyl 2-[2-chloro-4-fluoro-3-[[2-fluoro-5-(3-fluorophenyl)phenyl]methylamino]phenoxy]acetate;

II(ab): ethyl 2-[2,4-difluoro-3-[[3-(3-fluorophenyl)-5-methoxy-phenyl]methylamino]phenoxy]acetate;

II(ac): ethyl 2-[3-[[2,6-difluoro-3-(3-fluorophenyl)phenyl]methylamino]-2,4-difluoro-phenoxy]acetate;

II(ad): ethyl 2-[2,4-difluoro-3-[[5-(3-fluorophenyl)-2-hydroxy-3-methyl-phenyl]methylamino]phenoxy]acetate;

II(ae): isopropyl 2-[2,4-difluoro-3-[[3-fluoro-5-(3-fluorophenyl)-2-methyl-phenyl]methylamino]phenoxy]acetate;

II(af): isopropyl 2-[2,4-difluoro-3-[[2-fluoro-5-(3-fluorophenyl)phenyl]methylamino]-5-methyl-phenoxy]acetate;

II(ag): isopropyl 2-[4-fluoro-3-[[2-fluoro-5-(3-fluorophenyl)phenyl]methylamino]-2,5-dimethyl-phenoxy]acetate;

II(ah): isopropyl 2-[4-fluoro-3-[[2-fluoro-5-(3-fluorophenyl)-3-methyl-phenyl]methylamino]-2-methyl-phenoxy]acetate;

II(ai): isopropyl 2-[4-fluoro-3-[[3-(3-fluorophenyl)-5-methyl-phenyl]methylamino]-2-methyl-phenoxy]acetate;

II(aj): isopropyl 2-[4-fluoro-3-[[5-(3-fluorophenyl)-2-methoxy-3-methyl-phenyl]methylamino]-2-methyl-phenoxy]acetate;

II(ak): isopropyl 2-[3-[[2-fluoro-5-(3-fluorophenyl)-3-methyl-phenyl]methylamino]-2,4-dimethyl-phenoxy]acetate;

II(al): isopropyl 2-[4-fluoro-3-[[3-(3-fluorophenyl)-5-hydroxy-phenyl]methylamino]-2-methyl-phenoxy]acetate;

II(am): isopropyl 2-[4-fluoro-3-[[2-fluoro-3-(3-fluorophenyl)-5-methyl-phenyl]methylamino]-2-methyl-phenoxy]acetate;

II(an): isopropyl 2-[3-[[3-(3-fluorophenyl)-5-methyl-phenyl]methylamino]-2,4-dimethyl-phenoxy]acetate;

II(ao): isopropyl 2-[3-[[5-(3-fluorophenyl)-2,3-dimethyl-phenyl]methylamino]-2,4-dimethyl-phenoxy]acetate;

II(ap): isopropyl 2-[3-[[5-(3-fluorophenyl)-2-methoxy-3-methyl-phenyl]methylamino]-2,4-dimethyl-phenoxy]acetate;

II(aq): isopropyl 2-[3-[[2-fluoro-5-(3-fluorophenyl)-3-methyl-phenyl]methylamino]-2,4-dimethyl-phenoxy]acetate;

II(ar): isopropyl 2-[2-cyano-4-fluoro-3-[[2-fluoro-5-(3-fluorophenyl)phenyl]methylamino]phenoxy]acetate;

II(as): isopropyl 2-[3-[[3-(3-fluorophenyl)-5-hydroxy-phenyl]methylamino]-2,4-dimethyl-phenoxy]acetate;

II(at): isopropyl 2-[3-[[3-(3-fluorophenyl)-5-methoxy-phenyl]methylamino]-2,4-dimethyl-phenoxy]acetate;

II(au): isopropyl 2-[3-[[5-(3,4-difluorophenyl)-2,3-dimethyl-phenyl]methylamino]-2,4-difluoro-phenoxy]acetate;

II(av): isopropyl 2-[3-[[5-(3,5-difluorophenyl)-2,-dimethyl-phenyl]methylamino]-2,4-difluoro-phenoxy]acetate;

II(aw): isopropyl 2-[2,4-difluoro-3-[1-[2-fluoro-5-(3-fluorophenyl)phenyl]ethylamino]phenoxy]acetate;

II(ax): isopropyl 2-[4-fluoro-3-[[5-(3-fluorophenyl)-2,3-dimethyl-phenyl]methylamino]-2-methyl-phenoxy]acetate;

II(ay): isopropyl 2-[3-[(2,3-dimethyl-5-phenyl-phenyl)methylamino]-2,4-difluoro-phenoxy]acetate;

II(az): isopropyl 2-[4-fluoro-3-[[3-fluoro-5-(3-fluorophenyl)-2-methyl-phenyl]methylamino]-2-methyl-phenoxy]acetate;

II(ba): isopropyl 2-[3-[[3-fluoro-5-(3-fluorophenyl)-2-methyl-phenyl]methylamino]-2,4-dimethyl-phenoxy]acetate; and II(bb): isopropyl 2-[3-[[2-fluoro-3-(3-fluorophenyl)-5-methyl-phenyl]methylamino]-2,4-dimethyl-phenoxy]acetate;

or an enantiomer thereof.

9. The compound according to claim 7, selected from the group consisting of:

II(b): ethyl 2-[2,4-difluoro-3-[[3-(3-fluorophenyl)-5-hydroxy-phenyl]methylamino]phenoxy] acetate;

II(e): isopropyl 2-[2,4-difluoro-3-[[3-(3-fluorophenyl)-5-methyl-phenyl]methylamino]phenoxy]acetate;

II(f): isopropyl 2-[2,4-difluoro-3-[[2-fluoro-3-(3-fluorophenyl)-5-methyl-phenyl]methylamino]phenoxy]acetate;

II(g): isopropyl 2-[3-[[2-fluoro-5-(3-fluorophenyl)phenyl]methylamino]-2,4-dimethyl-phenoxy]acetate;

II(h): ethyl 2-[2,4-difluoro-3-[[2-fluoro-5-(3-fluorophenyl)-3-methyl-phenyl]methylamino]phenoxy]acetate;

II(i): isopropyl 2-[4-fluoro-3-[[2-fluoro-5-(3-fluorophenyl)phenyl]methylamino]-2-methyl-phenoxy]acetate;

II(j): 2-hydroxyethyl 2-[2,4-difluoro-3-[[2-fluoro-5-(3-fluorophenyl)phenyl]methylamino]phenoxy]acetate;

II(k): 2-morpholinoethyl 2-[2,4-difluoro-3-[[2-fluoro-5-(3-fluorophenyl)phenyl]methylamino]phenoxy]acetate;

II(l): 2-[2,4-difluoro-3-[[2-fluoro-5-(3-fluorophenyl)phenyl]methylamino]phenoxy]acetamide;

II(m): 2-[2,4-difluoro-3-[[2-fluoro-5-(3-fluorophenyl)phenyl]methylamino]phenoxy]-N-ethyl-acetamide;

II(n): [3-hydroxy-2,2-bis(hydroxymethyl)propyl]2-[2,4-difluoro-3-[[2-fluoro-5-(3-fluorophenyl)phenyl]methylamino]phenoxy]acetate;

II(o): [3-hydroxy-2-(hydroxymethyl)propyl]2-[2,4-difluoro-3-[[2-fluoro-5-(3-fluorophenyl)phenyl]methylamino]phenoxy]acetate;

II(p): 1-acetoxyethyl 2-[2,4-difluoro-3-[[2-fluoro-5-(3-fluorophenyl)phenyl]methylamino]phenoxy]acetate;

II(q): isopropyl 2-[2,4-difluoro-3-[[3-(3-fluorophenyl)-5-methoxy-phenyl]methylamino]phenoxy]acetate; and II(r): isopropyl 2-[2,4-difluoro-3-[[3-(3-fluorophenyl)-5-hydroxy-phenyl]methylamino]phenoxy]acetate.

10. The compound according to claim 7, selected from the group consisting of:

II(a): ethyl 2-[2,4-difluoro-3-[[2-fluoro-5-(3-fluorophenyl)phenyl]methylamino]phenoxy]acetate;

II(c): methyl 2-[2,4-difluoro-3-[[2-fluoro-5-(3-fluorophenyl)phenyl]methylamino]phenoxy]acetate; and II(d): isopropyl 2-[2,4-difluoro-3-[[2-fluoro-5-(3-fluorophenyl)phenyl]methylamino]phenoxy]acetate.

11. The compound according to claim 7, where the compound is isopropyl 2-[2,4-difluoro-3-[[2-fluoro-5-(3-fluorophenyl)phenyl]methylamino]phenoxy]acetate.

12. The compound according to claim 1, wherein the compound is a compound of formula (I), or enantiomer thereof.

13. The compound according to claim 1, wherein the compound is a compound of formula (II):

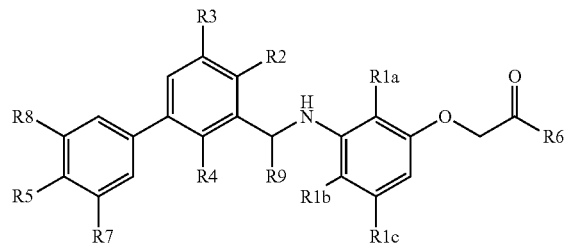

wherein

R1a represents F;
R1b represents F;
R1c represents H;
R2 represents F;
R3 represents H;
R4 represents H;
R5 represents H;
R7 represents F;
R8 represents H; and
R9 represents H;
or an enantiomer thereof.

14. A pharmaceutical composition, comprising the compound, or enantiomer thereof, according to claim 1, and also at least one pharmaceutically acceptable excipient.

15. A pharmaceutical composition comprising the compound, or enantiomer thereof, according to claim 7, and at least one pharmaceutically acceptable excipient.

16. A pharmaceutical composition comprising the compound of claim 6, and at least one pharmaceutically acceptable excipient.

17. A pharmaceutical composition comprising the compound of claim 11, and at least one pharmaceutically acceptable excipient.

18. A pharmaceutical composition comprising the compound, or an enantiomer thereof, according to claim 12, and at least one pharmaceutically acceptable excipient.

19. A pharmaceutical composition comprising the compound, or an enantiomer thereof, according to claim 13, and at least one pharmaceutically acceptable excipient.

20. A combination comprising the compound, or enantiomer thereof, according to claim 1 with beta-blockers, prostaglandins, sympathomimetic collyres, inhibitors of carbonic anhydrase, or parasympathomimetic collyres.

21. A process for preparing a compound, or an enantiomer thereof, according to claim 1, comprising reducing a compound of formula (XI):

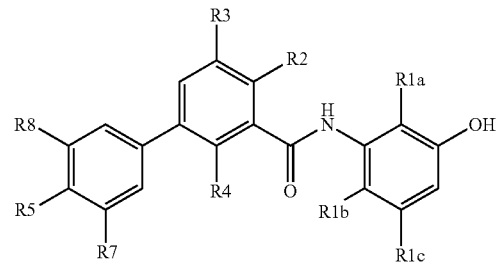

to give a compound of formula (IX);

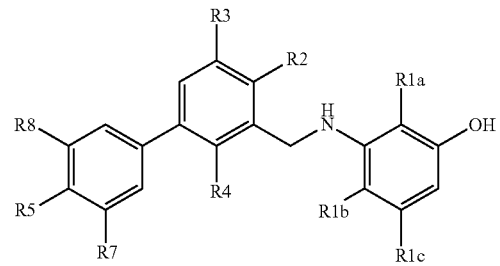

reacting the compound of formula (IX) with "BrCH$_2$COR6 to give a compound of formula (II), or an enantiomer thereof,

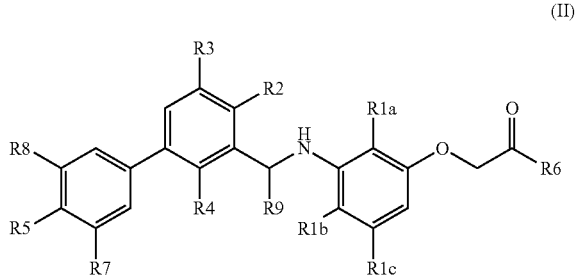

in which R1a, R1b, R1c, R2, R3, R4, R5, R6, R7, and R8 are as defined in claim 1, and wherein R9 is H; and optionally saponifying the compound of formula (II) to give a compound of formula (I), or an enantiomer thereof:

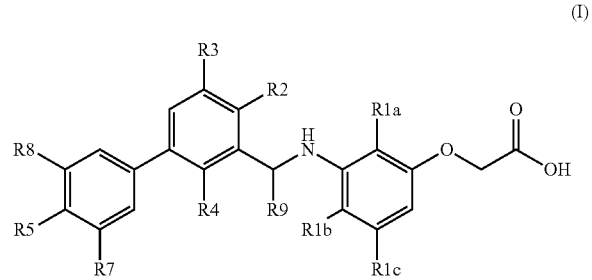

in which R1a, R1b, R1c, R2, R3, R4, R5, R7, and R8 are as defined in claim 1, and wherein R9 is H.

22. The process of claim 21, wherein the saponification step is performed.

23. The process of claim 21, wherein the saponification step is not performed.

24. A process for preparing a compound according to claim 1, or an enantiomer thereof, comprising reacting a compound of formula (IX), or an enantiomer thereof,

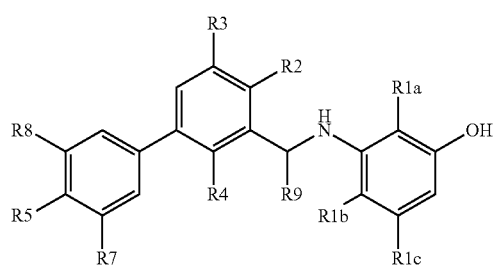

(IX)

with $BrCH_2COR6$ to give a compound of formula (II), or an enantiomer thereof,

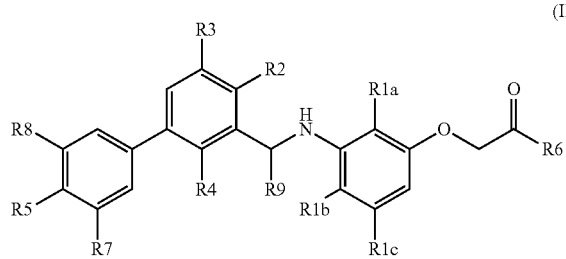

(II)

in which R1a, R1b, R1c, R2, R3, R4, R5, R6, R7, R8, and R9 are as defined in claim 1; and, optionally saponifying the compound of formula (II) to give a compound of formula (I), or an enantiomer thereof,

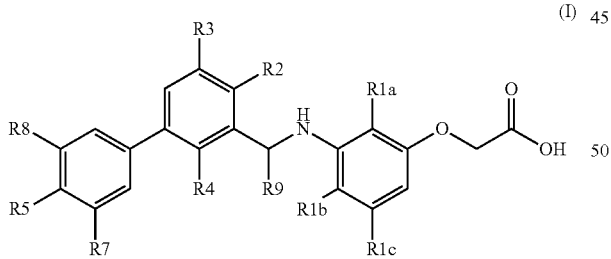

(I)

in which R1a, R1b, R1c, R2, R3, R4, R5, R7, R8, and R9 are as defined in claim 1.

25. The process of claim 24, wherein the saponification step is performed.

26. The process of claim 24, wherein the saponification step is not performed.

27. A process for preparing a compound according to claim 1, or an enantiomer thereof, comprising
saponifying a compound of formula (II), or an enantiomer thereof,

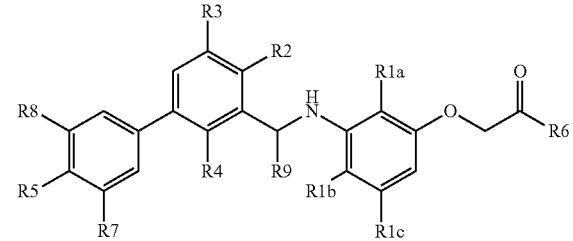

(II)

to give a compound of formula (I), or an enantiomer thereof,

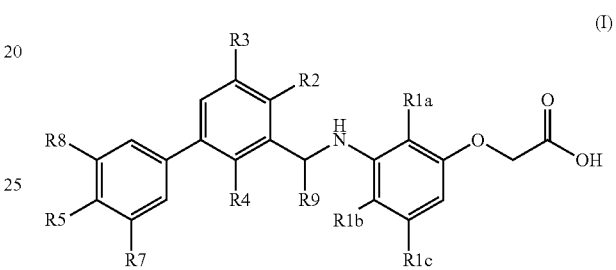

(I)

in which R1a, R1b, R1c, R2, R3, R4, R5, R6, R7, R8, and R9 are as defined in claim 1.

28. A process for preparing a compound according to claim 1, or an enantiomer thereof, comprising converting a compound of formula (I), or an enantiomer thereof,

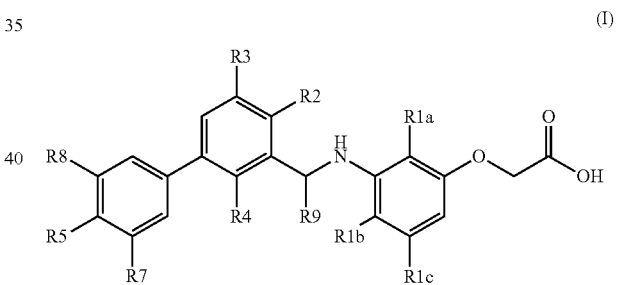

(I)

into the corresponding ester or amide to give the compound of formula (II), or enantiomer thereof,

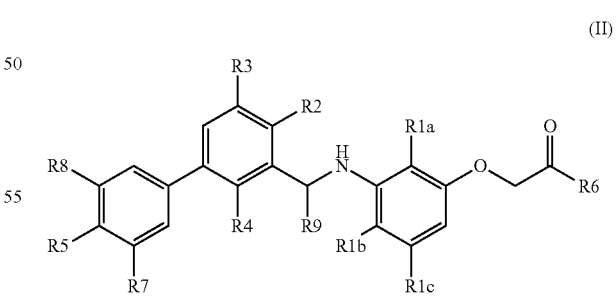

(II)

in which R1a, R1b, R1c, R2, R3, R4, R5, R6, R7, R8, and R9 are as defined in claim 1.

* * * * *